United States Patent
Jacobs et al.

(10) Patent No.: US 9,493,489 B2
(45) Date of Patent: Nov. 15, 2016

(54) BORON-CONTAINING SMALL MOLECULES AS ANTI-PROTOZOAL AGENTS

(75) Inventors: Robert Jacobs, Wake Forest, NC (US); Matthew Orr, Raleigh, NC (US); Stephen Wring, South Boston, MA (US); Daitao Chen, Raleigh, NC (US); Huchen Zhou, Shanghai (CN); Dazhong Ding, Hanzhong (CN); Yiqing Feng, State College, PA (US); Long Yi, Yugan (CN); Vincent S. Hernandez, Watsonville, CA (US); Yong-Kang Zhang, San Jose, CA (US); Jacob J. Plattner, Orinda, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 982 days.

(21) Appl. No.: 13/062,450

(22) PCT Filed: Oct. 15, 2009

(86) PCT No.: PCT/US2009/060914
§ 371 (c)(1),
(2), (4) Date: Apr. 19, 2011

(87) PCT Pub. No.: WO2010/045503
PCT Pub. Date: Apr. 22, 2010

(65) Prior Publication Data
US 2011/0207702 A1 Aug. 25, 2011

Related U.S. Application Data

(60) Provisional application No. 61/105,759, filed on Oct. 15, 2008, provisional application No. 61/105,763, filed on Oct. 15, 2008, provisional application No. 61/110,907, filed on Nov. 3, 2008, provisional (Continued)

(51) Int. Cl.
*A61K 31/69* (2006.01)
*C07F 5/02* (2006.01)

(52) U.S. Cl.
CPC ............... *C07F 5/025* (2013.01); *A61K 31/69* (2013.01)

(58) Field of Classification Search
CPC ............................. C07F 5/025; A61K 31/69
USPC ........ 544/69, 229; 549/213; 514/64; 546/13; 435/258.1; 558/384; 564/8; 548/110
See application file for complete search history.

(56) References Cited

U.S. PATENT DOCUMENTS 2,260,336 A  10/1941  Prescott et al.
3,873,279 A   3/1975  Singer (Continued)

FOREIGN PATENT DOCUMENTS

EP  1 444 981 A1  8/2004
WO  WO 95/033754  5/1995

(Continued)

OTHER PUBLICATIONS

Akama T, et al., "Discovery and structure-activity study of a novel benzoxaborole anti-inflammatory agent (AN2728) for the potential topical treatment of psoriasis and atopic dermatitis," *Bioorganic & Medicinal Chemistry Letter 19* (2009) 2129-2132.

(Continued)

*Primary Examiner* — T. Victor Oh
(74) *Attorney, Agent, or Firm* — Morgan, Lewis & Bockius LLP

(57) ABSTRACT

This invention provides, among other things, novel compounds useful for treating protozoal infections, pharmaceutical compositions containing such compounds, as well as combinations of these compounds with at least one additional therapeutically effective agent.

57 Claims, 10 Drawing Sheets

Related U.S. Application Data application No. 61/119,956, filed on Dec. 4, 2008, provisional application No. 61/148,241, filed on Jan. 29, 2009, provisional application No. 61/162,321, filed on Mar. 22, 2009, provisional application No. 61/162,325, filed on Mar. 22, 2009.

(56) References Cited

U.S. PATENT DOCUMENTS

| | | | |
|---|---|---|---|
| 4,602,011 | A | 7/1986 | West et al. |
| 4,716,035 | A | 12/1987 | Sampathkumar |
| 4,766,113 | A | 8/1988 | West et al. |
| 4,894,220 | A | 1/1990 | Nabi et al. |
| 5,348,947 | A | 9/1994 | Patel et al. |
| 5,348,948 | A | 9/1994 | Patel et al. |
| 5,591,731 | A | 1/1997 | Kennedy et al. |
| 5,668,258 | A | 9/1997 | Stolowitz |
| 5,688,928 | A | 11/1997 | Stolowitz |
| 5,831,045 | A | 11/1998 | Stolowitz et al. |
| 5,880,188 | A | 3/1999 | Austin et al. |
| 5,962,498 | A | 10/1999 | Driedger et al. |
| 6,083,903 | A | 7/2000 | Adams et al. |
| 6,306,628 | B1 | 10/2001 | Rothschild et al. |
| 6,369,098 | B1 | 4/2002 | Pershadsingh et al. |
| 6,800,645 | B1 | 10/2004 | Cox et al. |
| 6,833,274 | B2 * | 12/2004 | Lawrence et al. ............ 436/128 |
| 6,855,848 | B2 | 2/2005 | Scherer et al. |
| 7,169,603 | B2 | 1/2007 | Hedley et al. |
| 7,217,701 | B2 | 5/2007 | Mikoshiba et al. |
| 7,390,806 | B2 | 6/2008 | Lee et al. |
| 7,465,836 | B2 | 12/2008 | Lee et al. |
| 7,582,621 | B2 | 9/2009 | Baker et al. |
| 7,652,000 | B2 | 1/2010 | Perry et al. |
| 7,767,657 | B2 | 8/2010 | Baker et al. |
| 7,816,344 | B2 | 10/2010 | Baker et al. |
| 7,888,356 | B2 | 2/2011 | Lee et al. |
| 8,039,450 | B2 | 10/2011 | Akama et al. |
| 8,039,451 | B2 | 10/2011 | Baker et al. |
| 8,106,031 | B2 | 1/2012 | Lee et al. |
| 8,168,614 | B2 | 5/2012 | Baker et al. |
| 8,343,944 | B2 | 1/2013 | Xia et al. |
| 8,440,642 | B2 | 5/2013 | Baker et al. |
| 8,461,134 | B2 | 6/2013 | Hernandez et al. |
| 8,461,135 | B2 | 6/2013 | Akama et al. |
| 8,461,336 | B2 | 6/2013 | Zhou et al. |
| 8,470,803 | B2 | 6/2013 | Akama et al. |
| 8,501,712 | B2 | 8/2013 | Baker et al. |
| 2002/0028831 | A1 | 3/2002 | Manley |
| 2002/0161230 | A1 | 10/2002 | Meudt et al. |
| 2003/0032673 | A1 | 2/2003 | Nagy |
| 2004/0224923 | A1 | 11/2004 | Lee et al. |
| 2005/0054644 | A1 | 3/2005 | Lee et al. |
| 2005/0125852 | A1 | 6/2005 | Caenepeel et al. |
| 2006/0009386 | A1 | 1/2006 | Stossel et al. |
| 2006/0222671 | A1 | 10/2006 | Weidner |
| 2006/0234981 | A1 | 10/2006 | Baker et al. |
| 2007/0155699 | A1 | 7/2007 | Baker et al. |
| 2007/0286822 | A1 | 12/2007 | Sanders et al. |
| 2007/0293457 | A1 | 12/2007 | Baker et al. |
| 2009/0227541 | A1 | 9/2009 | Baker et al. |
| 2010/0256092 | A1 | 10/2010 | Xia et al. |
| 2011/0124597 | A1 | 5/2011 | Hernandez et al. |
| 2011/0190235 | A1 * | 8/2011 | Chen et al. .................. 514/64 |
| 2011/0207701 | A1 | 8/2011 | Zhou et al. |

FOREIGN PATENT DOCUMENTS

| | | |
|---|---|---|
| WO | WO 98/12206 A1 | 3/1998 |
| WO | 0969531 | 1/2000 |
| WO | WO 0044387 A1 | 8/2000 |
| WO | WO 00/75142 A2 | 12/2000 |
| WO | 1155698 A1 | 11/2001 |
| WO | WO 0244184 | 6/2002 |
| WO | WO 03033002 A1 | 4/2003 |
| WO | WO 030059916 A2 | 7/2003 |
| WO | WO 20040056322 A2 | 7/2004 |
| WO | WO 2005013892 A3 | 2/2005 |
| WO | WO 2006007384 | 1/2006 |
| WO | wo 2006062731 A1 | 6/2006 |
| WO | WO 2006079843 A1 | 8/2006 |
| WO | WO 2006089067 A2 | 8/2006 |
| WO | WO 2007022437 A2 | 2/2007 |
| WO | WO 2007078340 A2 | 7/2007 |
| WO | WO 2007095638 A2 | 8/2007 |
| WO | WO 2007146965 A2 | 12/2007 |
| WO | WO 2008157726 A1 | 12/2008 |
| WO | WO 2009111676 A2 | 9/2009 |
| WO | WO 2009140309 A2 | 11/2009 |
| WO | WO 2010028005 A | 3/2010 |
| WO | WO 2010045503 A | 4/2010 |
| WO | WO 2010045505 A1 | 4/2010 |

OTHER PUBLICATIONS

Baker SJ, et al., "Therapeutic potential of boron-containing compounds," *Future Med. Chem.* (2009) 1(7), 1275-1288.

Freund, et al. A Novel Oxaborole, AN 3520, Shows Efficacy Against Human African Trypanosomiasis (HAT) In Vitro and In Vivo, Including Promise in a Murine CNS Model of *T. brucei* infection. American Society of Tropical Medicine and Hygiene, Dec. 7-11, 2008, new Orleans, LA.

Luan, et al., "Inhibition of Experimental Periodontitis by a Topical Boron-based Antimicrobial," *J Dent Res* 87(2): 148-152 (2008).

Seiradake E, et al., "Crystal Structures of the Human and Fungal Cytosolic Leucyl-tRNA Synthetase Editing Domains: A Structural Basis for the Rational Design of Antifungal Benzoxaboroles," *Journal of Molecular Biology* 390 (2009) 196-207.

Xie, et al., "A New Class of Benzoxaborole-based Potent Antitrypanosomal Agents: Probing the Effect of Different Linage Groups on Trypanosoma brucei Growth Inhibition", American Society of Tropical Medicine and Hygiene, Dec. 7-11, 2008, new Orleans, LA.

"AN2718 has Broad Spectrum Antifungal Activity Necessary for the Topical Treatment of Skin and Nail Fungal Infections", Scientific Presentation at the American Academy of Dermatology Annual Meeting, San Francisco, CA Mar. 6-10, 2009.

"AN2728 Demonstrates Significant Effiacy in Three Phase Ib Psoriasis Microplaque Trials" Scientific Presentation at the American Academy of Dermatology Annual Meeting, San Francisco, CA Mar. 6-10, 2009.

AN2728 Demonstrates Significant Safety and Efficacy in a Phase IIa Double Blind Trial in Plaque Type Psoriasis, The American Academy of Dermatology Annual Meeting, Mar. 6-10, 2009, San Francisco, CA.

"AN2728 Ointment, a Novel Oxaborole with Anti-Inflammatory Activity, Demonstrates Safety and Significant Efficacy in a Phase Ib Psoriasis Plaque Test", Scientific Presentation at Montagna Symposium on Biology of Skin, Gleneden Beach, OR, Oct. 2-6, 2008.

"AN2898 Inhibitis Cytokines Relevant to Topical Treatment of Psoriasis and Atopic Dermatitis", Scientific Presentation at the American Academy of Dermatology Annual Meeting, San Francisco, CA Mar. 6-10, 2009.

AN2920 A Novel Oxaborole, Shows In Vitro and In Vivo Activity Against *Trypanosoma brucei*, American Society of Tropical Medicine and Hygiene, Dec. 7-11, 2008, new Orleans, LA.

"Discovery of Novel Boron Containing Compounds as Dual Inhibitors of TNF-α and IL-23 Release," World Congress of Inflammation, Jul. 6-10, 2009, Tokyo, Japan.

"Lead Optimization Investigation of Oxaboroles for the Treatment of Human African Trypanosomiasis," American Chemical Society, Aug. 16-20, 2009, Washington, DC.

"Novel Boron-Containing Small Molecules Demonstrate Potent Activity Against Malaria Parasites with Excellent Drug-like Properties." The American Society of Tropical Medicine and Hygiene, Nov. 20, 2009. Washington, DC.

"Novel Boron-Containing Small Molecules as Potential Therapeutics Against Human Lymphatic Filariasis," The American Society of Tropical Medicine and Hygiene, Nov. 20, 2009, Washington, DC.

(56) References Cited

OTHER PUBLICATIONS

"Novel Cyclic Boronates as HCV NS3/4A Protease Inhibitors,"7th Annual Congress of International Drug Discovery Science and Technology, Oct. 22-25, 2009, Shanghai, China.

"Novel Oxaborole 6-Carboxamides Demonstrate Potential for Treatment of CNS-Stage Human African Trypanosomiasis," Key Stone Symposium, Mar. 22-26, 2009, Breckenridge, CO.

"Structure-Activity Studies of AN2728 and AN2898, Novel Oxaborole Compounds with Anti-Inflammatory Activity", Scientific Presentation at the International Investigative Dermatology Conference, Kyoto, Japan, May 14-18, 2008.

"Structure-Activity Studies led to the Discovery of AN2898 in Developement for Topical Treatment of Psoriasis and Atopic Dermatitis", Scientific Presentation at the American Academy of Dermatology Annual Meeting, San Francisco, CA Mar. 6-10, 2009.

"Structure-Activity Studies Led To The Discovery Of AN2898 In Developement For Topical Treatment Of Psoriasis And Atopic Dermatitis," Society for Investigative Dermatology Annual Meeting, May 6-9, 2009, Montreal, Canada.

F1-1223a: In Vitro Activity and In Vivo Efficacy of (S)-3-(aminomethyl)benzo[c] [1,2]oxaborol-1(3H)-ol (ABX): A Gram-negative Antimicrobial, Interscience Conference on Antimicrobial Agents and Chemothertherapy Conference, Sep. 12-15, 2009, San Francisco.

Austin, et al., "Oxaboroles and Salts and their Use of Biocides for Plastics", CAS, vol. 124, pp. 234-024, (1996).

Bailey, et al., "Boron-Containing Antibacterial Agenst: Effect on Growth and Morphology of Bacteria Under Various Culture Conditions," Antimicrobial Agents and Chemotherapy, 17(04):549-553, (Apr. 1980).

Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).

Baker, et al., "Progress on New Therapeutics for Fungal Nail Infections", Annual Reports in Medicinal Chemistry, vol. 40: pp. 323-335, (2005).

Bessis, N., "Gene Therapy for Rheumatoid Arthritis," J. Gene Med, vol. 4: pp. 581-591 (2002).

Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).

Caims, et al., "Derivatives of 1,4-Xylene-2,5-diboronic acid and 1,4-xylene-2-boronic acid", J. Org. Chem. vol. 29; pp. 2810-2812, (1964).

Chander, et al. "Prevalence of Fungal Corneal Ulcers in Northern India", Infections, vol. 22, No. 3: pp. 207-209, (1994).

Chemical Abstracts Registry Number 845302-09-2, Entered STN Mar. 11, 2005.

Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).

Dale, et al., "Substituted Styrenes VIII Syntheses and some Reactions of the Vinylbenzeneboronic Acids" J. Org. Chem. vol. 27; pp. 2598-2603, (1962).

Denis, "Pharmacology 1104 Lecture: Drug Classifications & Characteristics of Antimicrobials" (2003).

Farfan, et al., "Through-Bond Modulation on N-B Ring Formation Shown by NMR and X-Ray Diffraction Studies or Borate Derivatives of Pyridyl Alcohois," J. Chem. Soc. Perkin Trans., vol. 2; pp. 527-532 (1992).

Ferrer, Targeting Aminocytl-tRNA Synthetases for the Treatment of Fungal Infections, Drug News Perspective, vol. 19, No. 6; pp. 347-348, (Jul./Aug. 2006).

Fungicide: Definition from Answer.com, (1998).

Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).

Guo-Zheng et al., "Single Site Transarylation of 2,2'-Dimetalized-1,1'-Binaphthyl to Aminocloroborates and Synthesis of 2-Binaphthyl Boron Compounds," Youji Huaxue/Organic Chemistry, Science Press, vol. 16, No. 02; pp. 139-144, (1996) (English Abstract).

Haynes, et al., "Arylboronic Acids VIII, Reactions of boronphthalide" J. Org. Chem. vol. 29, No. 11; pp. 3229-3233, (1964).

Hauck, et al., "Preparation and Anticonvulsant Activity of Some Arydialkkylsuccinimides" Research Lab of Parke Davis Co. (1967).

He, et al., "Small-Molecule Inhibition of TNF-alpha", Science, vol. 310, No. 5750; pp. 1022-1025, (Nov. 11, 2005).

Lampe, et al., "Synthesis and Protien Kinase Inhibitory Activity of Balanol Analogues with Modified Benzophenone Subunits", J. Med. Chem., vol. 45; pp. 2624-2643, (2002).

Lennarz, et al., "Arylboronic Acids. IV. Reactions of Boronophthalide" J. Am. Chem. Soc. vol, 82; pp. 2172-2175, (1960).

Li, et al., "An Improved Protocol for Preparation of 3-Pyridyl- and Some Arylboronic Acids", J. Org. Chem., vol. 67; pp. 5394-5397, (2002).

Koster, et al., "Cyclisierugen von Bor-Stickstoff-Verbindugen in der Hietz" Liebigs Ann, Chem., vol. 720; pp. 23-31, (1968).

Koster, et al., "Boron Compounds, XXXIX. Alkenoxy(diorgany)boranes Substituted at the Alkeonxy Group from 2-methylacrolein and triorganylboranes," Justus Liebigs Annalen Der Chemie, No. 06; pp. 1116-1134, (1976).

McMillin, et al., "Systemic Aspects of Psoriasis: An Intergrative Model Based on Intestinal Etiology", Int. Med. vol. 2, Issue 2/3, (1999).

Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).

Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).

Mudran, "Drug Delivery to the Nail Following Topical Application", International Journal of Pharmaceutics, vol. 236: pp. 1-26, (2002).

Patani, et al., "Bioterrorism: A Rational Approach to Drug Design", Chem. Rev., vol. 96; pp. 3147-3176 (1996).

Qin, et al., "Luminescent Organoboron Quinolate Polymers," Journal of the American Chemical Society, vol. 126, No. 22; pp. 7015-7018, (Jun. 9, 2004).

Rock, et al., "An Antifungal Agents Inhibits Aminoacyl-tRNA Synthetase by Trapping tRNA in the Editing Site", Science, vol. 316, No. 5832; pp. 1759-1761, (Jun. 22, 2007).

Snyder, et al. "Common Bacteria Whose Susceptibility to Antimicrobials in no longer Predictable" J. Med. Liban, vol. 48 No. 4; pp. 208-214, (2000).

Sugar, et al., "Comparison of Three Methods of Antifungal Susceptibility Testing with the Proposed NCCLS Standard Broth Macrodilution Assay: Lack of Effect of Phenol Red" Diagn. Microbiol. Infect. Dis. vol. 21; pp. 129-133, (1995).

Tabuchi, et al., "Anticoccidial Activity of some Azacyclo Organoborinates," Heterocycles, vol. 60, No. 01; pp. 177-182, (2003).

Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).

Trujillo, et al., "X-Ray Crystallographic Study of Boroxazolidones, Obtained from L-ornithine, L-methionine, Kainic acid and 2,6-pyridinedicarboxylic acid", Journal of Organometallic Chemistry, vol. 571; pp. 21-29, (1998).

Tschampel, et al., "Arylboronic Acids. VII, Some Reactions to o-Formybenzeneboronic Acids", J Org. Chem. vol. 29, No. 8: pp. 2168-2172, (1964).

(56) References Cited

OTHER PUBLICATIONS

Turner, et al., Current Pharmaceuticai Design, vol. 2; pp. 209-224 (1996).
Vippagunta, "Crystalline Solids", Advanced Drug Delivery Reviews, vol. 48; pp. 3-26, (2001).
Wang, et al., "Expression, Purification and Characterization of Human cAMP-Specific Phosphodiesterase (PDE4) Subtypes A, B, C, and D)", Biochemical and Biophysical Research Communications, vol. 234; pp. 320-324, (1997).
Ye, et al., "Convenient and Versatile Syntheis of formyl-substituted Benzoxaboroles", Tetrahedron, vol. 65; pp. 8738-8744, (2009).
Zhdankin, et al., "Synthesis and Structure of Benzoboroxles: Novel Organboron Heterocycles," Tetrahedron Letters, vol. 40; pp. 6705-6708, (1999).
Zhou, et al., "Hemodextrin: a Self-assembled Cyclodextrin-Porphyrin Construct That Binds Dioxygen," Biophysical Chemistry, 105:639-648 (2003).
Zhou, at al, "Structure-activity Studies on a Library of Potent Calix[4]arene-based PDGF Antagonists that Inhibit PDGF-stimulated PDGFR Tyrosine Phosphorylation," Org. Biomol. Chem., 4:2376-2386 (2006).
Zhou, et al., "Pattern Recognition of Proteins Based on an Array of Functionalized Porphyrins," J. Am. Chem. Soc., 128:2421-2425 (2006).
Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990). (English Abstract).

\* cited by examiner

FIGURE 1A

| Example Number | T.b.brucei S427 IC50 (ug/mL) | T.b.brucei STIB 795 IC50 (uM) | T. cruzi C2C4 IC50 (ug/mL) | T. cruzi CL2 IC50 (uM) | T.b. gambiense 108R IC50 (ug/mL) | T.b. gambiense 40R IC50 (ug/mL) | T.b. gambiense DAL 1402 IC50 (ug/mL) | T.b. gambiense DRANI IC50 (ug/mL) | T.b. gambiense ITMAP 141267 IC50 (ug/mL) | T. b. rhodesiense STIB900 IC50 (ug/mL) | L. donovani axenic IC50 (ug/mL) | L. donovani macrophage IC50 (ug/mL) |
|---|---|---|---|---|---|---|---|---|---|---|---|---|
| H1 | 0.04 | | 0.22 | | 0.03 | 0.03 | 0.01 | 0.02 | 0.02 | 0.04 | 0.05 | 2.28 |
| H2 | 0.05 | | | | | | | | | | | |
| H3 | 0.06 | | | | | | | | | | | |
| H4 | 0.03 | | | | | | | | | | | |
| H5 | 0.05 | | | | | | | | | | | |
| H6 | 0.07 | | 1.11 | | | | | | | | | |
| H7 | 0.02 | | | | 0.02 | 0.02 | 0.01 | 0.02 | 0.01 | 0.03 | | |
| H8 | 0.04 | | | | | | | | | | | |
| H9 | 0.15 | 0.12 | 0.78 | | 0.06 | 0.07 | 0.03 | 0.06 | 0.05 | 0.06 | 0.23 | 5.66 |
| H10 | 0.04 | | | | | | | | | | | |
| H11 | 0.07 | | 0.34 | | 0.25 | 0.19 | 0.09 | 0.22 | 0.17 | 0.20 | 0.08 | 4.73 |
| H12 | 0.03 | | | | | | | | | | | |
| H13 | 0.04 | | | | | | | | | | | |
| H14 | 0.05 | | | | 0.02 | 0.03 | 0.01 | 0.02 | 0.02 | 0.04 | | |
| H15 | 0.05 | | | | | | | | | | | |
| H16 | 0.05 | | | | | | | | | | | |
| H17 | 0.04 | | | | | | | | | | | |
| H18 | 0.07 | | | | | | | | | | | |
| H19 | 0.06 | | 0.23 | | 0.03 | 0.04 | 0.02 | 0.04 | 0.02 | 0.04 | 0.07 | 0.74 |
| H20 | 0.05 | | | | | | | | | | | |
| H21 | 0.06 | | | | | | | | | | | |
| H22 | 0.06 | | | | | | | | | | | |
| H23 | 0.05 | | | | | | | | | | | |
| H24 | 0.06 | | | | | | | | | | | |
| H25 | 0.06 | | | | | | | | | | | |
| H26 | 0.05 | | | | | | | | | | | |
| H27 | 0.28 | | | | | | | | | | | |
| H28 | 0.07 | | | | | | | | | | | |
| H29 | 0.04 | | | | | | | | | | | |
| H30 | 0.03 | | | 0.31 | 0.06 | 0.05 | 0.03 | 0.06 | 0.04 | 0.06 | 0.12 | 4.31 |

FIGURE 1B

| Example Number | L. infantum macrophage IC50 (uM) | P. falciparum IC50 (ug/mL) |
|---|---|---|
| H1 | | 0.22 |
| H2 | | |
| H3 | | |
| H4 | | |
| H5 | | |
| H6 | | |
| H7 | | |
| H8 | | |
| H9 | 64.00 | 0.39 |
| H10 | | |
| H11 | | 4.25 |
| H12 | | |
| H13 | | |
| H14 | | |
| H15 | | |
| H16 | | |
| H17 | | |
| H18 | | |
| H19 | | 1.11 |
| H20 | | |
| H21 | | |
| H22 | | |
| H23 | | |
| H24 | | |
| H25 | | |
| H26 | | |
| H27 | | |
| H28 | | |
| H29 | | |
| H30 | | 3.79 |

FIGURE 1C

| Example Number | T.b.brucei S427 IC50 (ug/mL) | T.b.brucei STIB 795 IC50 (uM) | T. cruzi C2C4 IC50 (ug/mL) | T. cruzi CL2 IC50 (uM) | T.b. gambiense 108R IC50 (ug/mL) | T.b. gambiense 40R IC50 (ug/mL) | T. b. gambiense DAL 1402 IC50 (ug/mL) | T. b. gambiense DRANI IC50 (ug/mL) | T. b. gambiense ITMAP 141267 IC50 (ug/mL) | T. b. rhodesiense STIB900 IC50 (ug/mL) | L. donovani axenic IC50 (ug/mL) | L. donovani macrophage IC50 (ug/mL) |
|---|---|---|---|---|---|---|---|---|---|---|---|---|
| H31 | 0.02 | | | | | | | | | | | |
| H32 | 0.08 | | | | | | | | | | | |
| H33 | 0.03 | | | | | | | | | | | |
| H35 | 0.02 | | | | | | | | | | | |
| H36 | 0.03 | | | | | | | | | | | |
| H37 | 0.02 | | 0.29 | | 0.03 | 0.04 | 0.02 | 0.05 | 0.03 | 0.05 | 0.07 | 5.49 |
| H38 | 0.03 | | | | | | | | | | | |
| H40 | | 0.25 | | 0.62 | | | | | | 0.40 | | |
| H42 | 1.05 | | | | | | | | | | | |
| H43 | 0.04 | | | | | | | | | | | |
| H44 | 0.07 | | | | | | | | | | | |
| H45 | 0.03 | | | | | | | | | | | |
| H46 | 0.05 | | | | | | | | | | | |
| H47 | 0.04 | | | | | | | | | | | |
| H48 | 0.03 | | | | | | | | | | | |
| H49 | 0.16 | | | | | | | | | | | |
| H51 | 0.07 | | | | | | | | | | | |
| H52 | 1.87 | | | | | | | | | | | |
| H53 | 0.02 | | | | | | | | | | | |
| H54 | 0.05 | | | | | | | | | | | |
| H55 | 0.02 | | | | | | | | | | | |
| H56 | 0.03 | | | | | | | | | | | |
| H57 | 0.68 | | | | | | | | | | | |
| H58 | 0.25 | | | | | | | | | | | |
| H59 | 0.29 | | | | | | | | | | | |
| H60 | 0.82 | | | | | | | | | | | |
| H61 | 0.05 | | | | | | | | | | | |
| H62 | 0.04 | | | | | | | | | | | |
| H63 | 0.02 | | | | | | | | | | | |
| H64 | 0.02 | | | | | 0.02 | 0.02 | 0.01 | 0.02 | 0.02 | 0.03 | |

FIGURE 1D

| Example Number | L. infantum macrophage IC50 (uM) | P. falciparum IC50 (ug/mL) |
|---|---|---|
| H31 | | |
| H32 | | |
| H33 | | |
| H35 | | |
| H36 | | |
| H37 | | 5.00 |
| H38 | | |
| H40 | 5.06 | |
| H42 | | |
| H43 | | |
| H44 | | |
| H45 | | |
| H46 | | |
| H47 | | |
| H48 | | |
| H49 | | |
| H51 | | |
| H52 | | |
| H53 | | |
| H54 | | |
| H55 | | |
| H56 | | |
| H57 | | |
| H58 | | |
| H59 | | |
| H60 | | |
| H61 | | |
| H62 | | |
| H63 | | |
| H64 | | |

FIGURE 1E

| Example Number | T.b.brucei S427 IC50 (ug/mL) | T.b.brucei STIB 795 IC50 (uM) | T. cruzi C2C4 IC50 (ug/mL) | T. cruzi CL2 IC50 (uM) | T.b. gambiense 108R IC50 (ug/mL) | T.b. gambiense 40R IC50 (ug/mL) | T. b. gambiense DAL 1402 IC50 (ug/mL) | T. b. gambiense DRANI IC50 (ug/mL) | T. b. gambiense ITMAP 141267 IC50 (ug/mL) | T. b. rhodesiense STIB900 IC50 (ug/mL) | L. donovani axenic IC50 (ug/mL) | L. donovani macrophage IC50 (ug/mL) |
|---|---|---|---|---|---|---|---|---|---|---|---|---|
| H65 | 0.03 | | | | | | | | | | | |
| H66 | 0.01 | | 0.09 | | | | | | | 0.04 | 0.03 | 9.87 |
| H67 | 0.02 | | | | | | | | | | | |
| H68 | 0.03 | | | | | | | | | | | |
| H70 | 0.09 | | | | | | | | | | | |
| H72 | 0.15 | | | | | | | | | | | |
| H73 | 0.04 | | | | | | | | | | | |
| H74 | 0.03 | | | | | | | | | | | |
| H78 | 0.91 | | | | | | | | | | | |
| H79 | 2.22 | | | | | | | | | | | |
| H80 | 0.08 | | | | | | | | | | | |
| H81 | 0.06 | | | | | | | | | | | |
| H82 | 0.13 | | | | | | | | | | | |
| H83 | 0.07 | | | | | | | | | | | |
| H84 | 0.46 | | | | | | | | | | | |
| H85 | 0.16 | | | | | | | | | | | |
| H86 | 0.19 | | | | | | | | | | | |
| H87 | 0.33 | | | | | | | | | | | |
| H88 | 0.71 | | | | | | | | | | | |
| H89 | 0.07 | | | | | | | | | | | |
| H90 | 0.19 | | | | | | | | | | | |
| H91 | 0.18 | | | | | | | | | | | |
| H92 | 0.09 | | | | | | | | | | | |
| H93 | 0.07 | | | | | | | | | | | |
| H94 | 0.14 | | | | | | | | | | | |
| H95 | 0.08 | | | | | | | | | | | |
| H96 | 0.07 | | | | | | | | | | | |
| H98 | 0.79 | 1.60 | | 64.00 | | | | | | 5.41 | | |
| H99 | 0.44 | | | 39.83 | | | | | | 2.06 | | |
| H100 | 0.12 | 0.25 | | 0.64 | 0.10 | 0.11 | 0.05 | 0.09 | 0.06 | 0.13 | | |

FIGURE 1F

| Example Number | L. infantum macrophage IC50 (uM) | P. falciparum IC50 (ug/mL) |
|---|---|---|
| H65 | | |
| H66 | | 3.21 |
| H67 | | |
| H68 | | |
| H70 | | |
| H72 | | |
| H73 | | |
| H74 | | |
| H78 | | |
| H79 | | |
| H80 | | |
| H81 | | |
| H82 | | |
| H83 | | |
| H84 | | |
| H85 | | |
| H86 | | |
| H87 | | |
| H88 | | |
| H89 | | |
| H90 | | |
| H91 | | |
| H92 | | |
| H93 | | |
| H94 | | |
| H95 | | |
| H96 | | |
| H98 | 64.00 | |
| H99 | 64.00 | |
| H100 | 10.77 | |

FIGURE 1G

| Example Number | T.b.brucei S427 IC50 (ug/mL) | T.b.brucei STIB 795 IC50 (uM) | T. cruzi C2C4 IC50 (ug/mL) | T. cruzi CL2 IC50 (uM) | T.b. gambiense 108R IC50 (ug/mL) | T.b. gambiense 40R IC50 (ug/mL) | T. b. gambiense DAL 1402 IC50 (ug/mL) | T. b. gambiense DRANI IC50 (ug/mL) | T. b. gambiense ITMAP 141267 IC50 (ug/mL) | T. b. rhodesiense STIB900 IC50 (ug/mL) | L. donovani axenic IC50 (ug/mL) | L. donovani macrophage IC50 (ug/mL) |
|---|---|---|---|---|---|---|---|---|---|---|---|---|
| H101 | 0.20 | 0.25 |  | 0.55 |  |  |  |  |  | 0.45 |  |  |
| H102 | 0.18 | 0.34 |  | 2.32 |  |  |  |  |  | 0.50 |  |  |
| H103 | 0.15 |  |  |  |  |  |  |  |  |  |  |  |
| H104 | 0.12 | 0.25 |  | 1.40 |  |  |  |  |  | 0.30 |  |  |
| H105 | 0.58 | 0.46 |  | 4.27 |  |  |  |  |  | 0.51 |  |  |
| H106 | 0.16 |  |  |  |  |  |  |  |  |  |  |  |
| H107 | 0.71 | 0.36 |  | 2.73 |  |  |  |  |  | 0.50 |  |  |
| H108 | 0.11 | 0.26 |  | 0.57 |  |  |  |  |  | 0.25 |  |  |
| H109 | 0.49 | 0.48 |  | 19.61 |  |  |  |  |  | 0.57 |  |  |
| H111 | 1.00 | 64.00 |  | 64.00 |  |  |  |  |  | 64.00 |  |  |
| H114 | 0.29 | 0.32 |  | 2.18 |  |  |  |  |  | 0.44 |  |  |
| H116 | 0.98 | 0.25 |  | 2.29 |  |  |  |  |  | 0.49 |  |  |
| H119 | 0.52 | 0.44 |  | 5.72 |  |  |  |  |  | 0.53 |  |  |
| H121 | 0.25 | 0.25 |  | 0.88 |  |  |  |  |  | 0.39 |  |  |
| H124 | 0.51 | 0.11 |  | 0.67 |  |  |  |  |  | 0.25 |  |  |
| H125 | 0.28 |  |  |  |  |  |  |  |  |  |  |  |
| H126 | 0.04 |  | 2.90 |  | 0.05 | 0.05 | 0.03 | 0.06 | 0.05 | 0.09 | 0.10 | 2.12 |
| H127 | 1.21 |  |  |  |  |  |  |  |  |  |  |  |
| H128 | 0.02 | 0.32 | 0.23 |  |  |  |  |  |  | 0.03 | 0.10 |  |
| H129 | 0.17 |  |  |  |  |  |  |  |  |  |  |  |
| H130 | 0.33 |  |  |  |  |  |  |  |  |  |  |  |
| H131 | 0.16 | 0.26 |  | 10.62 |  |  |  |  |  | 0.45 |  |  |
| H132 | 0.15 | 0.33 |  | 9.13 |  |  |  |  |  | 0.36 |  |  |
| H133 | 1.62 | 2.04 |  | 64.00 |  |  |  |  |  | 2.61 |  |  |
| H134 | 1.30 | 0.62 |  | 32.00 |  |  |  |  |  | 0.94 |  |  |
| H135 | 0.35 | 0.32 |  | 32.00 |  |  |  |  |  | 0.32 |  |  |
| H136 | 0.32 | 0.32 |  | 4.79 |  |  |  |  |  | 0.45 |  |  |
| H137 | 2.02 | 0.95 |  | 32.00 |  |  |  |  |  | 0.86 |  |  |
| H138 | 1.66 | 0.37 |  | 32.00 |  |  |  |  |  | 0.84 |  |  |
| H139 | 0.17 | 0.50 |  | 8.87 |  |  |  |  |  | 0.48 |  | 100.00 |

FIGURE 1H

| Example Number | L. infantum macrophage IC50 (uM) | P. falciparum IC50 (ug/mL) |
| --- | --- | --- |
| H101 | 6.96 | |
| H102 | 64.00 | |
| H103 | | |
| H104 | 2.69 | |
| H105 | 64.00 | |
| H106 | | |
| H107 | 64.00 | |
| H108 | 6.35 | |
| H109 | 8.11 | |
| H111 | 64.00 | |
| H114 | 8.11 | |
| H116 | 34.56 | |
| H119 | 64.00 | |
| H121 | 64.00 | |
| H124 | 34.56 | |
| H125 | | |
| H126 | | 3.31 |
| H127 | | |
| H128 | 28.51 | 1.41 |
| H129 | | |
| H130 | | |
| H131 | 50.80 | |
| H132 | 50.80 | |
| H133 | 64.00 | |
| H134 | 64.00 | |
| H135 | 26.99 | |
| H136 | 64.00 | |
| H137 | 64.00 | |
| H138 | 64.00 | |
| H139 | 64.00 | |

FIGURE 1I

| Example Number | T.b.brucei S427 IC50 (ug/mL) | T.b.brucei STIB 795 IC50 (uM) | T. cruzi C2C4 IC50 (ug/mL) | T. cruzi CL2 IC50 (uM) | T.b. gambiense 108R IC50 (ug/mL) | T.b. gambiense 40R IC50 (ug/mL) | T. b. gambiense DAL 1402 IC50 (ug/mL) | T. b. gambiense DRANI IC50 (ug/mL) | T. b. gambiense ITMAP 141267 IC50 (ug/mL) | T. b. rhodesiense STIB900 IC50 (ug/mL) | L. donovani axenic IC50 (ug/mL) | L. donovani macrophage IC50 (ug/mL) |
|---|---|---|---|---|---|---|---|---|---|---|---|---|
| H140 | 0.59 | 1.31 | | 64.00 | | | | | | 2.91 | | |
| H141 | 0.03 | 0.32 | | 0.32 | | | | | | 0.14 | | |
| H142 | 0.47 | 0.42 | | 10.49 | | | | | | 0.77 | | |
| H143 | 0.32 | | | | | | | | | | | |
| H144 | 0.35 | | | 6.35 | | | | | | 0.67 | 2.15 | |
| H145 | 0.12 | | | 1.12 | | | | | | 0.17 | 0.19 | 3.00 |
| H146 | 0.14 | | | | | | | | | | | |
| H147 | 0.13 | | | 1.60 | | | | | | 0.14 | 0.20 | 2.34 |
| H148 | 0.03 | | | 0.23 | | | | | | 0.11 | 0.23 | 2.23 |
| H149 | 0.09 | | | | | | | | | | | |
| H150 | 0.20 | | | | | | | | | | | |
| H151 | 0.17 | | | | | | | | | | | |
| H152 | 0.05 | | | | | | | | | | | |
| H153 | 0.14 | | | | | | | | | | | |
| H154 | 0.21 | | | | | | | | | | | |

FIGURE 1J

| Example Number | L. infantum macrophage IC50 (uM) | P. falciparum IC50 (ug/mL) |
|---|---|---|
| H140 | | |
| H141 | 0.95 | |
| H142 | 64.00 | |
| H143 | | |
| H144 | | 2.91 |
| H145 | | 0.12 |
| H146 | | |
| H147 | | 0.33 |
| H148 | | 0.44 |
| H149 | | |
| H150 | | |
| H151 | | |
| H152 | | |
| H153 | | |
| H154 | | |

BORON-CONTAINING SMALL MOLECULES AS ANTI-PROTOZOAL AGENTS

CROSS-REFERENCES TO RELATED APPLICATIONS

This application is a National Stage of filed International Patent Application Serial No. PCT/US2009/060914 filed Oct. 15, 2009 and published as WO 2010/045503 A1, which claims the benefit of U.S. Provisional Pat. App. No. 61/105,759, filed Oct. 15, 2008, U.S. Provisional Pat. App. No. 61/105,763, filed Oct. 15, 2008, U.S. Provisional Pat. App. No. 61/110,907, filed Nov. 3, 2008, U.S. Provisional Pat. App. No. 61/119,956, filed Dec. 4, 2008, U.S. Provisional Pat. App. No. 61/148,241, filed Jan. 29, 2009, U.S. Provisional Pat. App. No. 61/162,321, filed Mar. 22, 2009 and U.S. Provisional Pat. App. No. 61/162,325, filed Mar. 22, 2009 each of which is incorporated by reference in its entirety for all purposes.

BACKGROUND OF THE INVENTION

The global rise of protozoa resistant to antimicrobials in general, poses a major threat. Deployment of massive quantities of antimicrobial agents into the ecosphere during the past 60 years has introduced a powerful selective pressure for the emergence and spread of antimicrobial-resistant pathogens. Thus, there is a need to discover new broad spectrum antimicrobials, such as antiprotozoals, useful in combating microorganisms, especially those with multi-drug-resistance.

Boron-containing molecules, such as oxaboroles, useful as antimicrobials have been described previously, such as in U.S. Pat. Pubs. US20060234981 and US20070155699. Generally speaking, an oxaborole has the following structure and substituent numbering system:

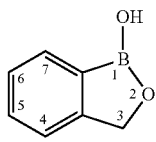

It has now been discovered that certain classes of oxaboroles which are surprisingly effective antiprotozoals. This, and other uses of these oxaboroles are described herein.

SUMMARY OF THE INVENTION

This invention provides, among other things, novel compounds useful for treating protozoa infections, pharmaceutical compositions containing such compounds, as well as combinations of these compounds with at least one additional therapeutically effective agent.

BRIEF DESCRIPTION OF THE DRAWING

FIG. 1 displays biological data for the compounds of the invention.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: aq. is aqueous; AcOH is acetic acid; ACTBr is cetyltrimethylammonium bromide; $B_2pin_2$-bis(pinacolato)diboron; Boc is tert-butoxy carbonyl; $Boc_2O$-di-tert-butyl dicarbonate; BzOOH-benzoyl peroxide; $Cs_2CO_3$ is cesium carbonate; DABCO is 1,4-diazabicyclo[2.2.2]octane; DCM is dichloromethane or methylene chloride; DIAD is diisopropyl azodicarboxylate; DIEA is diisopropylethylamine; N,N-Diisopropylethylamine is DIPEA; DMAP is 4-(dimethylamino)pyridine; DME is 1,2-dimethoxyethane; DMF is N,N-dimethylformamide; DMSO is dimethylsulfoxide; eq. is equivalent; EtOAc is ethyl acetate; EtOH is ethanol; $Et_2O$ is diethyl ether; EDCI-N-(3-dimethylaminopropyl)-N'-ethylcarbodiimide hydrochloride; m-CPBA-3-chloroperoxybenzoic acid; equiv-equivalent; h is hours; HATU is O-(7-azabenzotriazol-1-yl)-N,N,N',N'-tetramethyluronium hexafluorophosphate; HCl is hydrochloric acid; HPLC is high pressure liquid chromatography; ISCO Companion is automated flash chromatography equipment with fraction analysis by UV absorption available from Presearch; KOAc is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN is acetonitrile; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; $NH_4Cl$ is ammonium chloride; $N_2$ is nitrogen; NMM-N-methylmorpholine; n-BuLi is n-butyllithium; overnight is O/N; $PdCl_2(pddf)$ is 1,1'-Bis(diphenylphosphino) ferrocene]dichloro palladium (II); PrOH is 1-propanol; iPrOH is 2-propanol; $POCl_3$ is phosphorus chloride oxide; RT or rt is room temperature; TFA is trifluoroacetic acid; $Tf_2O$ is trifluoromethanesulfonic anhydride; THF is tetrahydrofuran; THP-tetrahydropyranyl; TMSI is trimethylsilyl iodide; $H_2O$ is water; Ac—acetyl; PTSA—para-toluene sulfonic acid; Pyr.—Pyridine; Cbz—benzyloxycarbonyl; PMB—p-methoxybenzyl; DHP—dihydropyran; CSA—camphor sulfonic acid; CTAB—cetyltrimethylammonium bromide; sat.—saturated; Cy—cyclohexyl; Ph—phenyl; Ar—aryl.

"Compound of the invention," as used herein refers to the compounds discussed herein, salts (e.g. pharmaceutically acceptable salts), prodrugs, solvates and hydrates of these compounds.

"Combination of the invention," as used herein refers to the compounds and antiprotozoals discussed herein as well as acids, bases, salt forms (such as pharmaceutically acceptable salts), prodrugs, solvates and hydrates of these compounds and antiprotozoals.

"Boron containing compounds", as used herein, refers to the compounds of the invention that contain boron as part of their chemical formula.

MIC, or minimum inhibitory concentration, is the point where the compound stops more than 50% of cell growth, preferably 60% of cell growth, preferably 70% of cell growth, preferably 80% of cell growth, preferably 90% of cell growth, relative to an untreated control.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to a radical of a molecule that is attached to the remainder of the molecule.

The symbol $\sim\!\!\sim\!\!\sim$, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—, —S(O)—CH$_3$, —CH$_2$—CH$_2$—S(O)$_2$—CH$_3$, —CH═CH—O—CH$_3$, —CH$_2$—CH═N—OCH$_3$, and —CH═CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, dioxaborolane, dioxaborinane and dioxaborepane. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above.

Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR''''—C(NR'R"R''')=NR'''', —NR''''—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to (2 m'+1), where m' is the total number of carbon atoms in such radical. R', R", R''', R'''' and R''''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''', R'''' and R''''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR''''—C(NR'R"R''')=NR'''', —NR''''—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', R'''' and R''''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''', R'''' and R''''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "Cosmetically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

"Cosmetically effective" refers to a material that, when applied to the skin, nail, hair, claw or hoof, produces a desired cosmetic result locally at the place of application of an active ingredient in the material.

The term "pharmaceutically acceptable salt" is meant to include a salt of a compound of the invention which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the present invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the present invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the present invention. The graphic representations of racemic, ambiscalemic and scalemic or enantiomerically pure compounds used herein are taken from Maehr, *J. Chem. Ed.* 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the present invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal skin, nail, hair, claw or hoof using a diffusion cell apparatus. A diffusion cell is described by Merritt et al. Diffusion Apparatus for Skin Penetration, *J of Controlled Release*, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to a broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical composition administered to a subject via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more "patient friendly," by minimizing the frequency (e.g., once daily) or route of dosing (e.g., oral), or to improve the taste or odor if given orally, or to minimize pain if given parenterally.

In some embodiments, the prodrugs are chemically more stable than the active drug, thereby improving formulation and delivery of the parent drug, compared to the drug alone.

Prodrugs for carboxylic acid analogs of the invention may include a variety of esters. In an exemplary embodiment, the pharmaceutical compositions of the invention include a carboxylic acid ester. In an exemplary embodiment, the prodrug is suitable for treatment/prevention of those diseases and conditions that require the drug molecule to cross the blood brain barrier. In an exemplary embodiment, the prodrug enters the brain, where it is converted into the active form of the drug molecule. In one embodiment, a prodrug is used to enable an active drug molecule to reach the inside of the eye after topical application of the prodrug to the eye. Additionally, a prodrug can be converted to its parent compound by chemical or biochemical methods in an ex vivo environment. For example, a prodrug can be slowly converted to its parent compound when placed in a transdermal patch reservoir with a suitable enzyme or chemical reagent.

"Antibiotic", as used herein, is a compound which can kill or inhibit the growth of bacteria. The term antibiotic is broad enough to encompass acids, bases, salt forms (such as pharmaceutically acceptable salts), prodrugs, solvates and hydrates of the antibiotic compound.

"Antiprotozoal" or "antiprotozoa", as used herein, is a compound which can kill or inhibit the growth of protozoa. The term antiprotozoal or antiprotozoa is broad enough to encompass acids, bases, salt forms (such as pharmaceutically acceptable salts), prodrugs, solvates and hydrates of the antiprotozoal or antiprotozoa compound.

The term "microbial infection" or "infection by a microorganism" refers to any infection of a host by an infectious agent including, but not limited to, viruses, bacteria, mycobacteria, fungus and parasites (see, e.g., Harrison's Principles of Internal Medicine, pp. 93-98 (Wilson et al., eds., 12th ed. 1991); Williams et al., *J. of Medicinal Chem.* 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an enzyme, such as a beta-lactamase or a leucyl t-RNA synthetase.

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Boron is able to form dative bonds (or coordination bonds) with oxygen, sulfur or nitrogen under some circumstances in this invention. Dative bonds are usually weaker than covalent bonds. In situations where a boron atom is covalently bonded to at least one oxygen, sulfur or nitrogen, and is at the same time datively bonded to an oxygen, sulfur or nitrogen, respectively, the dative bond and covalent bond between the boron and the two identical heteroatoms can interconvert or be in the form of a resonance hybrid. There is potential uncertainty surrounding the exact nature and extent of electron sharing in these situations. The structures supplied are not intended to include any and all possible bonding scenarios between boron and the atom to which it is bound. Non limiting examples of these bonds are as follows:

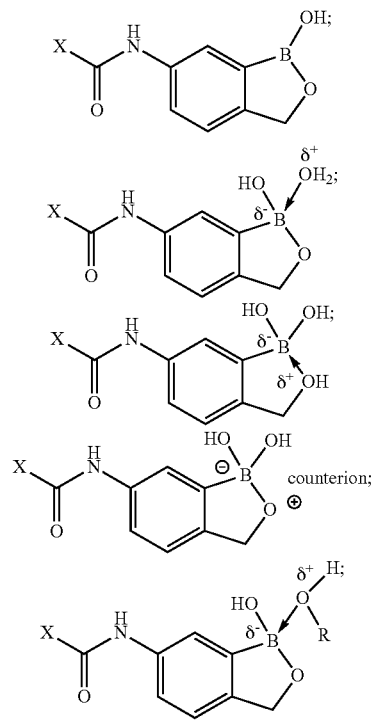

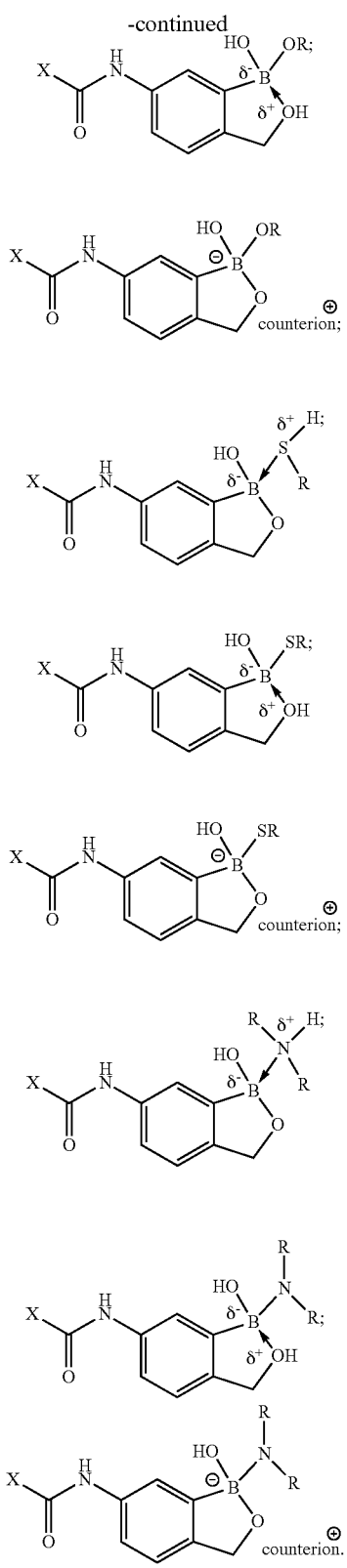

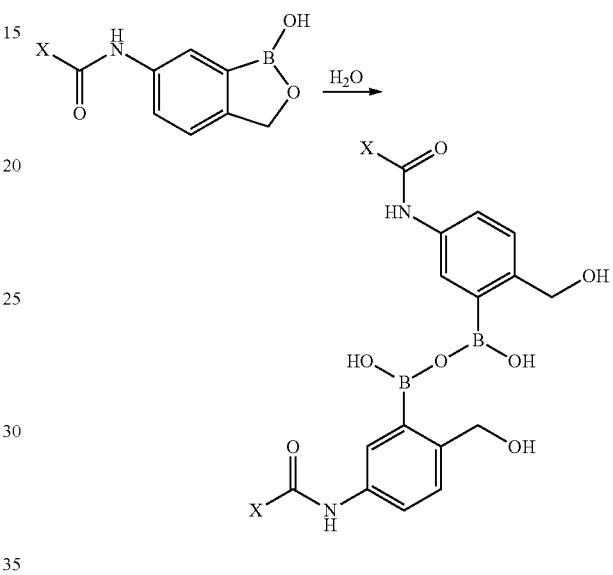

the oxygens. Due to the negative charge, a positively charged counterion may associate with this compound, thus forming a salt. Examples of positively charged counterions include $H^+$, $H_3O^+$, calcium, sodium, ammonium, potassium. The salts of these compounds are implicitly contained in descriptions of these compounds.

The present invention also encompasses compounds that are poly- or multi-valent species, including, for example, species such as dimers, trimers, tetramers and higher homologs of the compounds of use in the invention or reactive analogues thereof. For example, dimers can form under the following conditions:

The present invention also encompasses compounds that are anhydrides of the cyclic boronic esters are synthesized by subjecting these compounds to dehydrating conditions. Examples of these anhydrides are provided below:

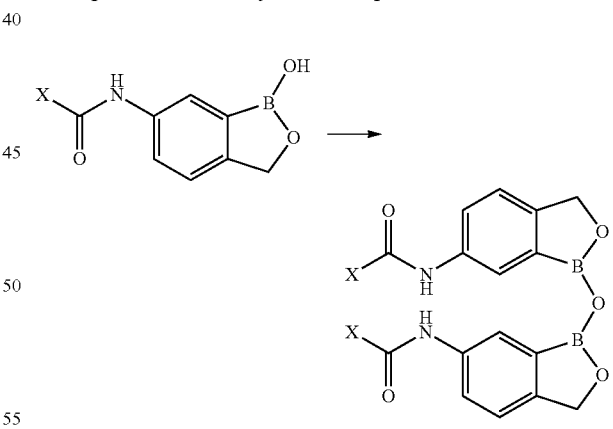

Trimers of the compounds of the invention are also produced. For example, trimers of acyclic boronic esters can be formed as follows:

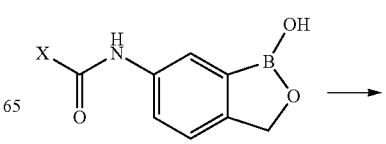

The compounds comprising a boron bonded to a carbon and three heteroatoms (such as three oxygens described in this section) can optionally contain a fully negatively charged boron or partially negatively charged boron, due to the nature of the dative bond between the boron and one of

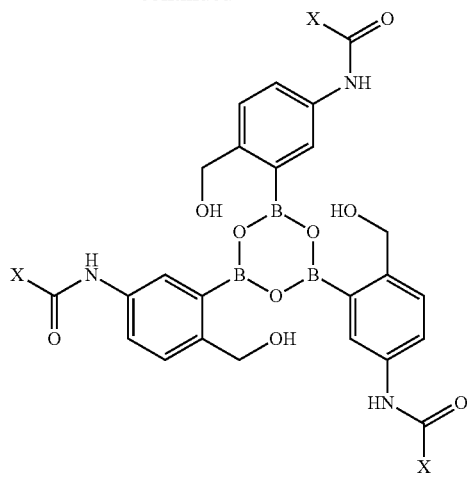

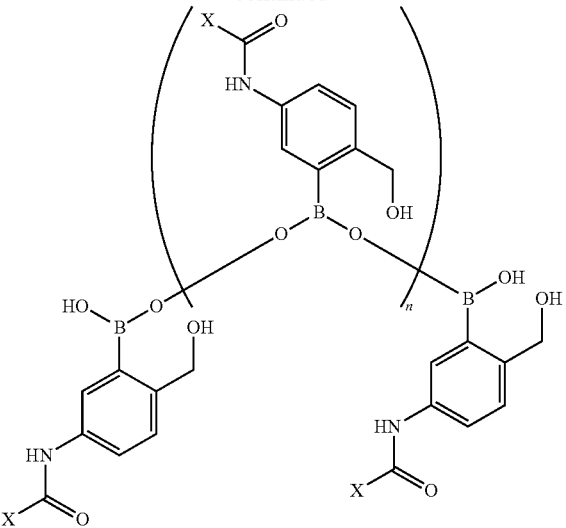

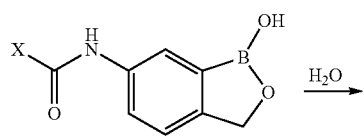

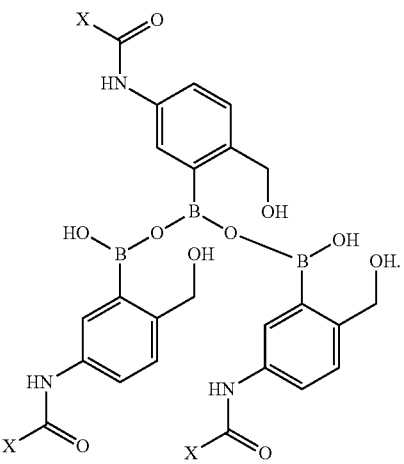

Polymers of the compounds of the invention are also produced through the removal of certain protecting groups in strong acid. For example, trimers can be formed as follows:

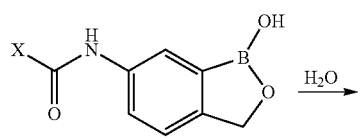

Also of use in the present invention are compounds that are poly- or multi-valent species, including, for example, species such as dimers, trimers, tetramers and higher homologs of the compounds of use in the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of use in the invention). Moreover, the framework can be derivatized with a single species of the invention or more than one species of the invention.

Moreover, the present invention includes the use of compounds within the motif set forth in the formulae contained herein, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to replace a hydroxyl group with a diol, or an amine with a quaternary amine, hydroxy amine or similar more water-soluble moiety. In a preferred embodiment, additional water solubility is imparted by substitution at a site not essential for the activity towards the editing domain of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

II. Introduction

The present invention provides novel boron compounds. The novel compounds, as well as pharmaceutical compositions containing such compounds or combinations of these compounds with at least one additional therapeutically effective agent, can be used for, among other things, treating protozoal infections.

III. The Compounds

III. a) Cyclic Boronic Esters

In one aspect, the invention provides a compound of the invention. In an exemplary embodiment, the invention is a compound described herein. In an exemplary embodiment, the invention is a compound according to a formula described herein.

In an exemplary embodiment, the compound of the invention has the following structure:

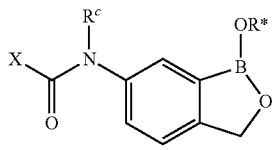

wherein X is selected from the group consisting of substituted phenyl, substituted or unsubstituted phenylalkyl, substituted or unsubstituted heteroaryl and unsubstituted cycloalkyl, $R^c$ is H or unsubstituted alkyl and R* is H or a negative charge, or a salt thereof. In an exemplary embodiment, $R^c$ is H. In an exemplary embodiment, $R^c$ is methyl. In an exemplary embodiment, $R^c$ is ethyl. In an exemplary embodiment, $R^c$ is unsubstituted $C_3$ alkyl. In an exemplary embodiment, X is substituted phenyl. In an exemplary embodiment, X is substituted phenyl which is not monosubstituted with unsubstituted alkyl. In an exemplary embodiment, X is substituted phenyl which is not monosubstituted with halosubstituted alkyl. In an exemplary embodiment, X is phenyl, substituted with at least one member selected from the group consisting of: halogen, cyano, nitro, OR, SR, NRR, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl, wherein each R is independently selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In an exemplary embodiment, X is phenyl, substituted with at least one or more of the substituents described herein. In an exemplary embodiment, X is heteroaryl, optionally substituted with at least one or more of the substituents described herein: In an exemplary embodiment, X is phenyl, substituted with at least one member selected from the group consisting of halogen, cyano, nitro, OR, SR, NRR, unsubstituted alkyl, halosubstituted alkyl, unsubstituted alkoxy, alkyl substituted amidyl, substituted or unsubstituted cycloalkyl, substituted or unsubstituted heterocycloalkyl, substituted or unsubstituted aryl and substituted or unsubstituted heteroaryl, wherein each R is independently selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In an exemplary embodiment, X is not a phenyl which is monosubstituted with unsubstituted alkyl. In an exemplary embodiment, X is not a phenyl which is monosubstituted with halosubstituted alkyl. In an exemplary embodiment, X is not a phenyl which is only substituted with halogens.

In an exemplary embodiment, the compound of the invention has the following structure:

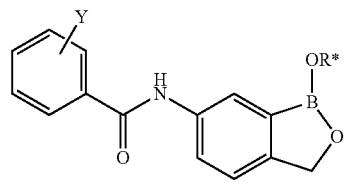

wherein Y is selected from the group consisting of halogen, halo-substituted $C_1$-$C_6$ alkyl and unsubstituted $C_1$-$C_6$ alkyl; and R* is selected from the group consisting of H, a negative charge and a positively charged counterion, or a salt thereof. In an exemplary embodiment, Y is an unsubstituted $C_3$ alkyl. In an exemplary embodiment, Y is an unsubstituted $C_4$ alkyl. In an exemplary embodiment, Y is an unsubstituted $C_5$ alkyl. In an exemplary embodiment, Y is an unsubstituted $C_6$ alkyl. In an exemplary embodiment, Y is selected from the group consisting of methyl, ethyl, propyl, butyl, pentyl and hexyl. In an exemplary embodiment, Y is selected from the group consisting of cyclopropyl, cyclobutyl, cyclopentyl and cyclohexyl. In an exemplary embodiment, Y is halo-substituted $C_1$-$C_6$ alkyl. In an exemplary embodiment, Y is $C_1$-$C_6$ alkyl, substituted with one halogen. In an exemplary embodiment, Y is $C_1$-$C_6$ alkyl, substituted with two halogens. In an exemplary embodiment, Y is $C_1$-$C_6$ alkyl, substituted with three halogens. In an exemplary embodiment, Y is $C_1$-$C_6$ alkyl, substituted with four halogens. In an exemplary embodiment, Y is $C_1$-$C_6$ alkyl, substituted with one fluorine. In an exemplary embodiment, Y is $C_1$-$C_6$ alkyl, substituted with two fluorines. In an exemplary embodiment, Y is $C_1$-$C_6$ alkyl, substituted with three fluorines. In an exemplary embodiment, Y is $C_1$-$C_6$ alkyl, substituted with four fluorines. In an exemplary embodiment, Y is $C_1$-$C_6$ alkyl, substituted with one chlorine. In an exemplary embodiment, Y is $C_1$-$C_6$ alkyl, substituted with two chlorines. In an exemplary embodiment, Y is $C_1$-$C_6$ alkyl, substituted with three chlorines. In an exemplary embodiment, Y is $C_1$-$C_6$ alkyl, substituted with four chlorines. In an exemplary embodiment, Y is $C_1$-$C_6$ alkyl, substituted with a combination of two different halogens. In an exemplary embodiment, Y is $C_1$-$C_6$ alkyl, substituted with at least one fluorine and at least one chlorine. In an exemplary embodiment, Y is $C_1$-$C_6$ alkyl, substituted with at least one fluorine and at least one bromine. In an exemplary embodiment, Y is $C_1$-$C_6$ alkyl, substituted with at least one chlorine and at least one bromine. In an exemplary embodiment, Y is fluoro-substituted $C_1$-$C_6$ alkyl. In an exemplary embodiment, Y is trifluoro-substituted $C_1$-$C_6$ alkyl. In an exemplary embodiment, the compound of the invention has a structure which is selected from the group consisting of:

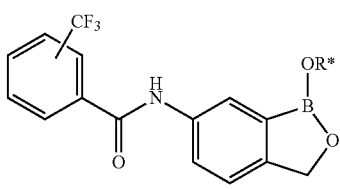

wherein R* is selected from the group consisting of H, a negative charge and a positively charged counterion, or a salt thereof. In another exemplary embodiment, R* is H.

In an exemplary embodiment, the compound of the invention has a structure which is selected from the group consisting of:

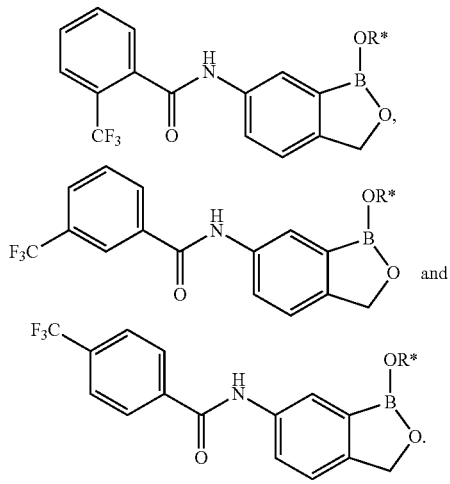

In an exemplary embodiment, the compound has the following structure:

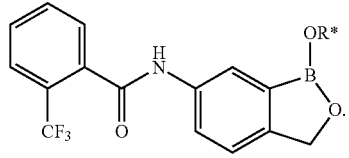

In an exemplary embodiment, the compound of the invention has a structure which is selected from the group consisting of:

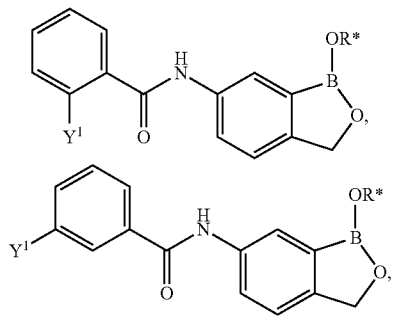

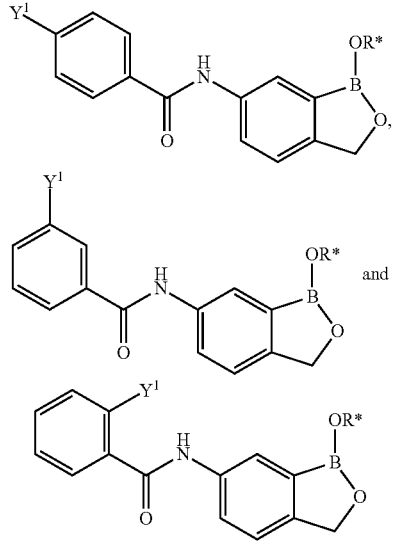

wherein $Y^1$ is a halogen, R* is H or a negative charge. In another exemplary embodiment, R* is H. In an exemplary embodiment, the compound is H4 or H5 or H6 or H7 or H8 or H9 or H10, or a salt thereof.

In an exemplary embodiment, the compound of the invention has a structure which is selected from the group consisting of:

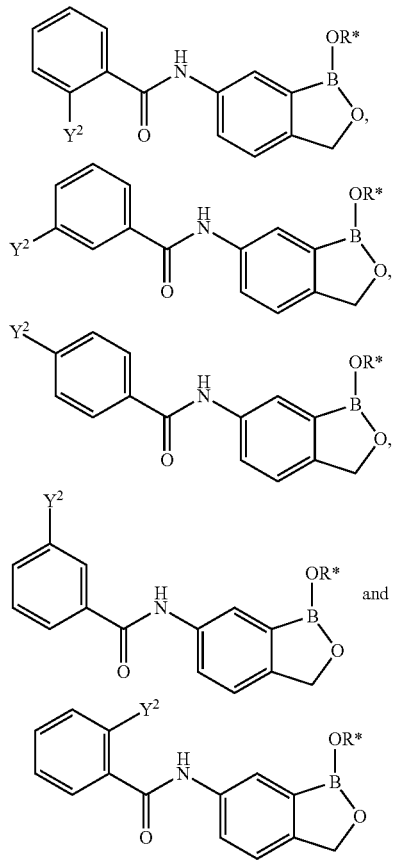

wherein $Y^2$ is unsubstituted alkyl, R* is H or a negative charge. In another exemplary embodiment, R* is H. In an exemplary embodiment, $Y^2$ is unsubstituted $C_1$ alkyl. In an exemplary embodiment, $Y^2$ is unsubstituted $C_2$ alkyl. In an exemplary embodiment, $Y^2$ is unsubstituted $C_3$ alkyl. In an exemplary embodiment, $Y^2$ is unsubstituted n-propyl or isopropyl. In an exemplary embodiment, $Y^2$ is unsubstituted $C_4$ alkyl. In an exemplary embodiment, $Y^2$ is n-butyl or sec-butyl or iso-butyl or tert-butyl. In an exemplary embodiment, $Y^2$ is unsubstituted $C_5$ alkyl. In an exemplary embodiment, $Y^2$ is unsubstituted $C_6$ alkyl. In an exemplary embodiment, the compound is H28 or H29 or H30 or H31 or H32 or H33, or a salt thereof.

In an exemplary embodiment, the compound of the invention has a structure which is selected from the group consisting of:

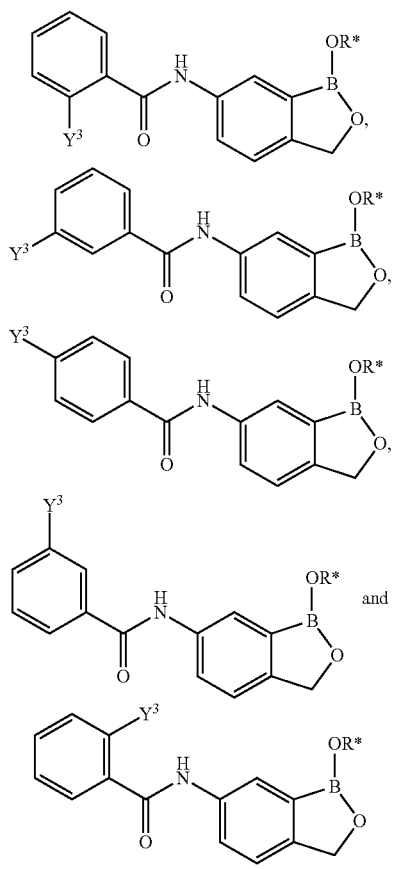

wherein $Y^3$ is unsubstituted alkoxy, R* is H or a negative charge. In another exemplary embodiment, R* is H. In an exemplary embodiment, $Y^3$ is unsubstituted $C_1$ alkoxy. In an exemplary embodiment, $Y^3$ is unsubstituted $C_2$ alkoxy. In an exemplary embodiment, $Y^3$ is unsubstituted $C_3$ alkoxy. In an exemplary embodiment, $Y^3$ is n-propoxy. In an exemplary embodiment, $Y^3$ is isopropoxy. In an exemplary embodiment, $Y^3$ is unsubstituted $C_4$ alkoxy. In an exemplary embodiment, $Y^3$ is unsubstituted $C_5$ alkoxy. In an exemplary embodiment, $Y^3$ is unsubstituted $C_6$ alkoxy. In an exemplary embodiment, the compound is H35 or H36 or H37 or H31 or H32 or H33, or a salt thereof.

In an exemplary embodiment, the compound of the invention has a structure which is selected from the group consisting of:

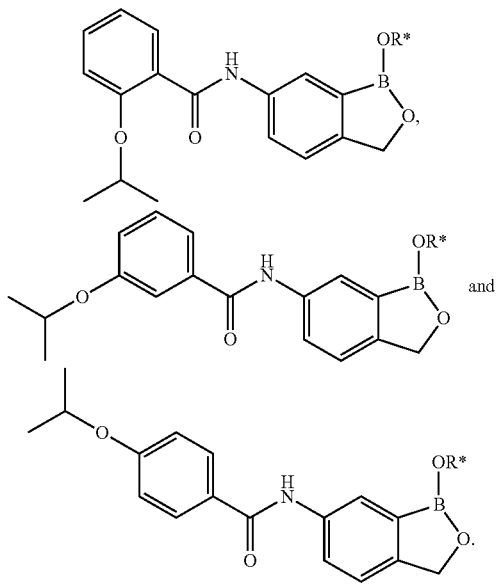

In an exemplary embodiment, the compound of the invention has a structure which is selected from the group consisting of:

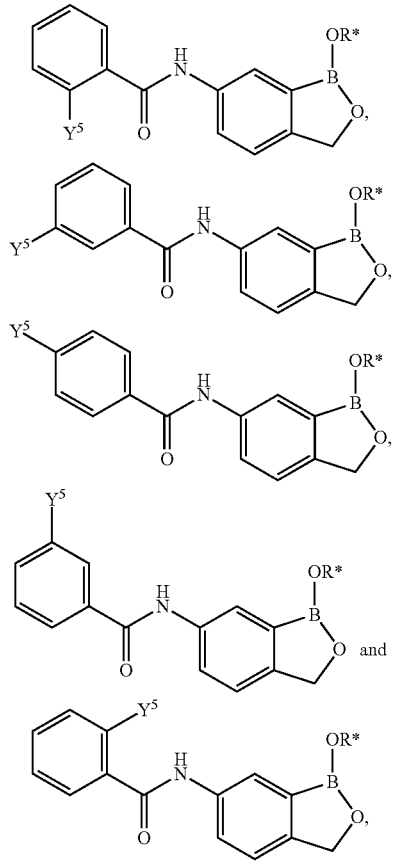

wherein $Y^5$ is halosubstituted alkoxy, R* is H or a negative charge. In another exemplary embodiment, R* is H. In an exemplary embodiment, $Y^5$ is halosubstituted $C_1$ alkoxy. In an exemplary embodiment, $Y^5$ is halosubstituted $C_2$ alkoxy.

In an exemplary embodiment, $Y^5$ is halosubstituted $C_3$ alkoxy. In an exemplary embodiment, $Y^5$ is halosubstituted $C_4$ alkoxy. In an exemplary embodiment, $Y^5$ is halosubstituted $C_5$ alkoxy. In an exemplary embodiment, $Y^5$ is halosubstituted $C_6$ alkoxy. In an exemplary embodiment, $Y^5$ is fluoro-substituted $C_1$-$C_6$ alkoxy. In an exemplary embodiment, $Y^5$ is substituted with one or two or three halogens. In an exemplary embodiment, $Y^5$ is trifluoro-substituted $C_1$-$C_6$ alkoxy. In an exemplary embodiment, $Y^5$ is trifluoromethoxy.

In an exemplary embodiment, the compound of the invention has a structure which is selected from the group consisting of:

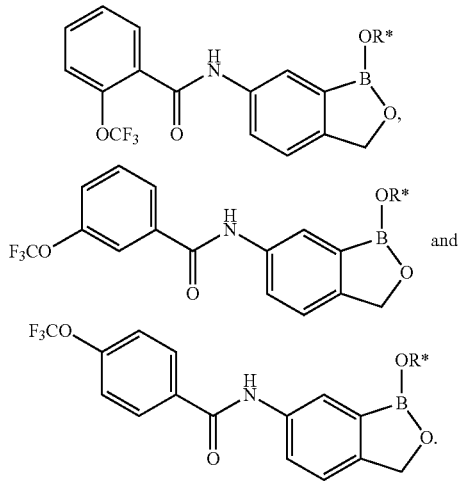

In an exemplary embodiment, the compound of the invention has a structure which is selected from the group consisting of:

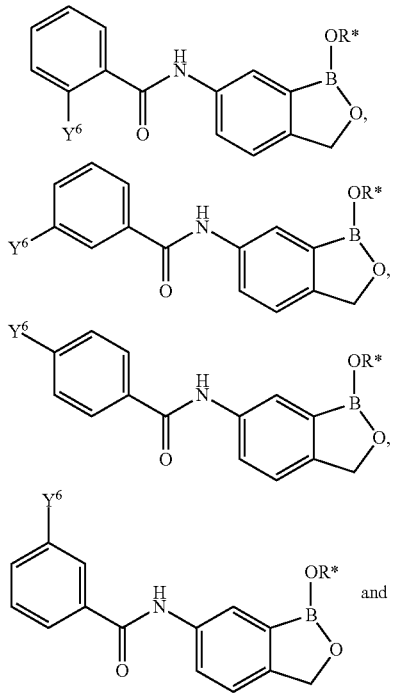

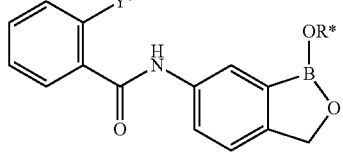

wherein $Y^6$ is halosubstituted alkylthio, R* is H or a negative charge. In another exemplary embodiment, R* is H. In an exemplary embodiment, $Y^6$ is halosubstituted $C_1$ alkylthio. In an exemplary embodiment, $Y^6$ is halosubstituted $C_2$ alkylthio. In an exemplary embodiment, $Y^6$ is halosubstituted $C_3$ alkylthio. In an exemplary embodiment, $Y^6$ is halosubstituted $C_4$ alkylthio. In an exemplary embodiment, $Y^6$ is halosubstituted $C_5$ alkylthio. In an exemplary embodiment, $Y^6$ is halosubstituted $C_6$ alkylthio. In an exemplary embodiment, $Y^6$ is fluoro-substituted $C_1$-$C_6$ alkylthio. In an exemplary embodiment, $Y^6$ is substituted with one or two or three halogens. In an exemplary embodiment, $Y^6$ is trifluoro-substituted $C_1$-$C_6$ alkylthio. In an exemplary embodiment, $Y^5$ is trifluoromethylthio.

In an exemplary embodiment, the compound of the invention is selected from the group consisting of:

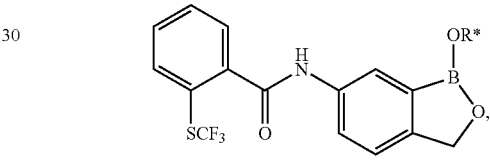

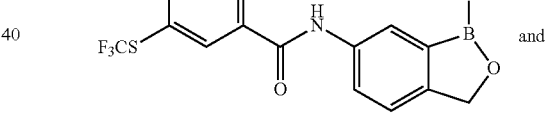

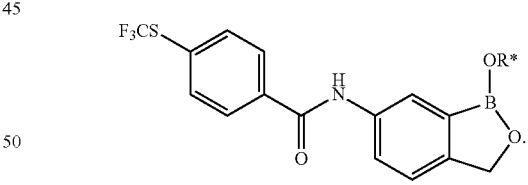

In an exemplary embodiment, the compound of the invention is:

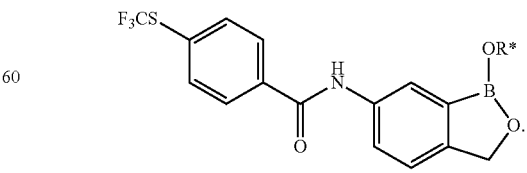

In an exemplary embodiment, the compound of the invention has a structure according to the following formula:

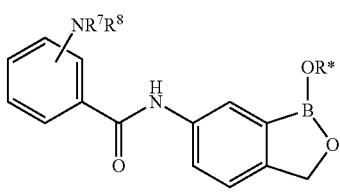

wherein $R^7$ is unsubstituted alkyl and $R^8$ is unsubstituted alkyl and $R^*$ is as described herein, or a salt thereof.

In an exemplary embodiment, the compound of the invention has a structure which is selected from the group consisting of:

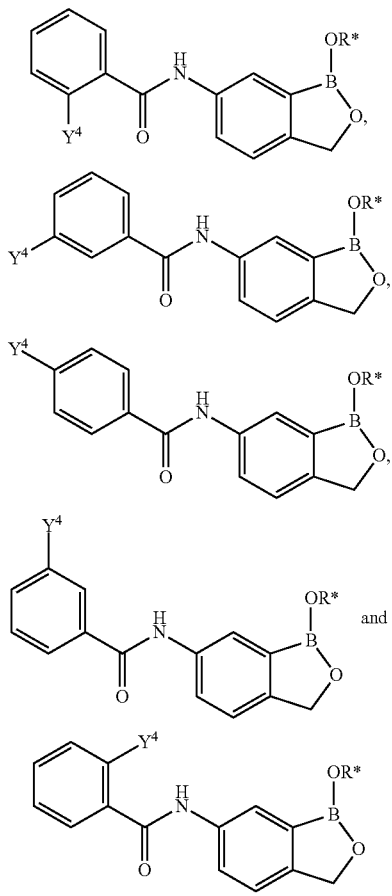

wherein $Y^4$ is —NHC(O)$R^4$, wherein $R^4$ is unsubstituted alkyl, $R^*$ is H or a negative charge. In another exemplary embodiment, $R^*$ is H. In an exemplary embodiment, $R^4$ is unsubstituted $C_1$ alkyl. In an exemplary embodiment, $R^4$ is unsubstituted $C_2$ alkyl. In an exemplary embodiment, $R^4$ is unsubstituted $C_3$ alkyl. In an exemplary embodiment, $R^4$ is unsubstituted $C_4$ alkyl. In an exemplary embodiment, $R^4$ is unsubstituted $C_5$ alkyl. In an exemplary embodiment, $R^4$ is unsubstituted $C_6$ alkyl. In an exemplary embodiment, the compound of the invention is H51, or a salt thereof.

In an exemplary embodiment, the compound of the invention has a structure which is selected from the group consisting of:

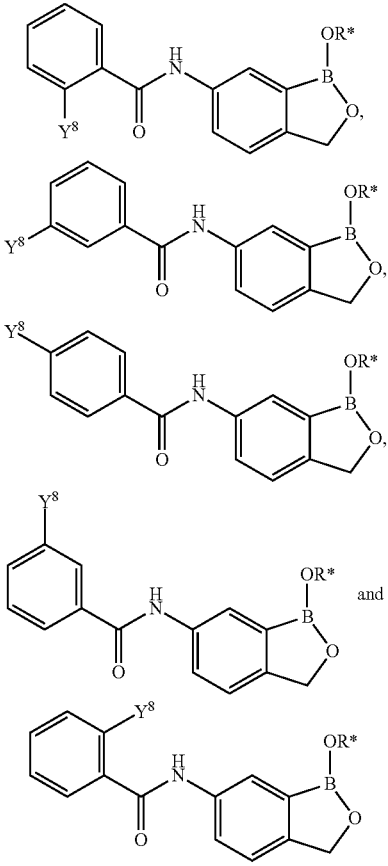

wherein $Y^8$ is —S(O)$_2$NHCHNR$^7$R$^8$, wherein $R^7$ is unsubstituted alkyl, $R^8$ is unsubstituted alkyl, $R^*$ is H or a negative charge. In another exemplary embodiment, $R^*$ is H. In an exemplary embodiment, $R^7$ is unsubstituted $C_1$ alkyl and $R^8$ is unsubstituted alkyl. In an exemplary embodiment, $R^7$ is unsubstituted $C_2$ alkyl and $R^8$ is unsubstituted alkyl. In an exemplary embodiment, $R^7$ is unsubstituted $C_3$ alkyl and $R^8$ is unsubstituted alkyl. In an exemplary embodiment, $R^7$ is unsubstituted $C_4$ alkyl and $R^8$ is unsubstituted alkyl. In an exemplary embodiment, $R^7$ is unsubstituted $C_5$ alkyl and $R^8$ is unsubstituted alkyl. In an exemplary embodiment, $R^7$ is unsubstituted $C_6$ alkyl and $R^8$ is unsubstituted alkyl. In an exemplary embodiment, $Y^8$ is —S(O)$_2$NHCHN(CH$_3$)$_2$.

In an exemplary embodiment, the compound of the invention has a structure according to the following formula:

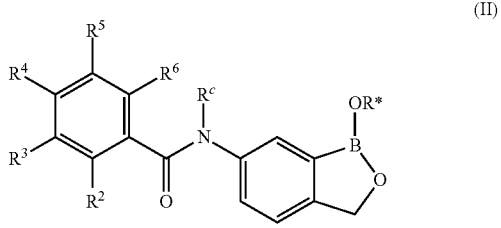

(II)

wherein $R^*$ is H or a negative charge, $R^c$ is as described herein and $R^2$, $R^3$, $R^4$, $R^5$ and $R^6$ are according to the entries in the following table, or a salt thereof

| | R² | R³ | R⁴ | R⁵ | R⁶ |
|---|---|---|---|---|---|
| 1 | F | H | H | H | H |
| 2 | H | F | H | H | H |
| 3 | H | H | F | H | H |
| 4 | H | H | H | F | H |
| 5 | H | H | H | H | F |
| 6 | Cl | H | H | H | H |
| 7 | H | Cl | H | H | H |
| 8 | H | H | Cl | H | H |
| 9 | H | H | H | Cl | H |
| 10 | H | H | H | H | Cl |
| 11 | Br | H | H | H | H |
| 12 | H | Br | H | H | H |
| 13 | H | H | Br | H | H |
| 14 | H | H | H | Br | H |
| 15 | H | H | H | H | Br |
| 16 | I | H | H | H | H |
| 17 | H | I | H | H | H |
| 18 | H | H | I | H | H |
| 19 | H | H | H | I | H |
| 20 | H | H | H | H | I |
| 21 | CN | H | H | H | H |
| 22 | H | CN | H | H | H |
| 23 | H | H | CN | H | H |
| 24 | H | H | H | CN | H |
| 25 | H | H | H | H | CN |
| 26 | NO₂ | H | H | H | H |
| 27 | H | NO₂ | H | H | H |
| 28 | H | H | NO₂ | H | H |
| 29 | H | H | H | NO₂ | H |
| 30 | H | H | H | H | NO₂ |
| 31 | Ph | H | H | H | H |
| 32 | H | Ph | H | H | H |
| 33 | H | H | Ph | H | H |
| 34 | H | H | H | Ph | H |
| 35 | H | H | H | H | Ph |
| 36 | —CH3 | H | H | H | H |
| 37 | H | —CH3 | H | H | H |
| 38 | H | H | —CH3 | H | H |
| 39 | H | H | H | —CH3 | H |
| 40 | H | H | H | H | —CH3 |
| 41 | —CH₂CH₃ | H | H | H | H |
| 42 | H | —CH₂CH₃ | H | H | H |
| 43 | H | H | —CH₂CH₃ | H | H |
| 44 | H | H | H | —CH₂CH₃ | H |
| 45 | H | H | H | H | —CH₂CH₃ |
| 46 | —CF₃ | H | H | H | H |
| 47 | H | —CF₃ | H | H | H |
| 48 | H | H | —CF₃ | H | H |
| 49 | H | H | H | —CF₃ | H |
| 50 | H | H | H | H | —CF₃ |
| 51 | —OCH₃ | H | H | H | H |
| 52 | H | —OCH₃ | H | H | H |
| 53 | H | H | —OCH₃ | H | H |
| 54 | H | H | H | —OCH₃ | H |
| 55 | H | H | H | H | —OCH₃ |
| 56 | —OCH₂CH₃ | H | H | H | H |
| 57 | H | —OCH₂CH₃ | H | H | H |
| 58 | H | H | —OCH₂CH₃ | H | H |
| 59 | H | H | H | —OCH₂CH₃ | H |
| 60 | H | H | H | H | —OCH₂CH₃ |
| 61 | —OCH(CH₃)₂ | H | H | H | H |
| 62 | H | —OCH(CH₃)₂ | H | H | H |
| 63 | H | H | —OCH(CH₃)₂ | H | H |
| 64 | H | H | H | —OCH(CH₃)₂ | H |
| 65 | H | H | H | H | —OCH(CH₃)₂ |
| 66 | —NR⁷R⁸ | H | H | H | H |
| 67 | H | —NR⁷R⁸ | H | H | H |
| 68 | H | H | —NR⁷R⁸ | H | H |
| 69 | H | H | H | —NR⁷R⁸ | H |
| 70 | H | H | H | H | —NR⁷R⁸ |
| 71 | —NH₂ | H | H | H | H |
| 72 | H | —NH₂ | H | H | H |
| 73 | H | H | —NH₂ | H | H |
| 74 | H | H | H | —NH₂ | H |
| 75 | H | H | H | H | —NH₂ |
| 76 | —N(CH₃)R⁸ | H | H | H | H |
| 77 | H | —N(CH₃)R⁸ | H | H | H |
| 78 | H | H | —N(CH₃)R⁸ | H | H |
| 79 | H | H | H | —N(CH₃)R⁸ | H |

-continued

| | R² | R³ | R⁴ | R⁵ | R⁶ |
|---|---|---|---|---|---|
| 80 | H | H | H | H | —N(CH₃)R⁸ |
| 81 | —N(CH₃)₂ | H | H | H | H |
| 82 | H | —N(CH₃)₂ | H | H | H |
| 83 | H | H | —N(CH₃)₂ | H | H |
| 84 | H | H | H | —N(CH₃)₂ | H |
| 85 | H | H | H | H | —N(CH₃)₂ |
| 86 | —NHC(O)CH₃ | H | H | H | H |
| 87 | H | —NHC(O)CH₃ | H | H | H |
| 88 | H | H | —NHC(O)CH₃ | H | H |
| 89 | H | H | H | —NHC(O)CH₃ | H |
| 90 | H | H | H | H | —NHC(O)CH₃ |

In an exemplary embodiment, for any of the entries in the above table, $R^c$ is H. In an exemplary embodiment, for any of the entries in the above table, $R^c$ is methyl. In an exemplary embodiment, for any of the entries in the above table, $R^c$ is ethyl. In an exemplary embodiment, for any of the entries in the above table, $R^c$ is propyl.

In an exemplary embodiment, the compound has a structure according to the following formula:

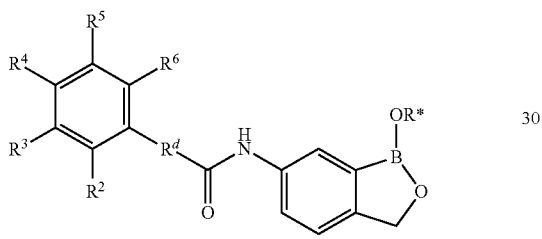

wherein R* is H or a negative charge, $R^d$ is $C_1$-$C_6$ unsubstituted alkylene and R², R³, R⁴, R⁵ and R⁶ are according to the entries in the following table, or a salt thereof

| | R² | R³ | R⁴ | R⁵ | R⁶ |
|---|---|---|---|---|---|
| 91 | H | H | H | H | H |
| 92 | F | H | H | H | H |
| 93 | H | F | H | H | H |
| 94 | H | H | F | H | H |
| 95 | H | H | H | F | H |
| 96 | H | H | H | H | F |
| 97 | Cl | H | H | H | H |
| 98 | H | Cl | H | H | H |
| 99 | H | H | Cl | H | H |
| 100 | H | H | H | Cl | H |
| 101 | H | H | H | H | Cl |
| 102 | Br | H | H | H | H |
| 103 | H | Br | H | H | H |
| 104 | H | H | Br | H | H |
| 105 | H | H | H | Br | H |
| 106 | H | H | H | H | Br |
| 107 | I | H | H | H | H |
| 108 | H | I | H | H | H |
| 109 | H | H | I | H | H |
| 110 | H | H | H | I | H |
| 111 | H | H | H | H | I |
| 112 | CN | H | H | H | H |
| 113 | H | CN | H | H | H |
| 114 | H | H | CN | H | H |
| 115 | H | H | H | CN | H |
| 116 | H | H | H | H | CN |
| 117 | NO₂ | H | H | H | H |
| 118 | H | NO₂ | H | H | H |
| 119 | H | H | NO₂ | H | H |

-continued

| | R² | R³ | R⁴ | R⁵ | R⁶ |
|---|---|---|---|---|---|
| 120 | H | H | H | NO₂ | H |
| 121 | H | H | H | H | NO₂ |
| 122 | Ph | H | H | H | H |
| 123 | H | Ph | H | H | H |
| 124 | H | H | Ph | H | H |
| 125 | H | H | H | Ph | H |
| 126 | H | H | H | H | Ph |
| 127 | —CH₃ | H | H | H | H |
| 128 | H | —CH₃ | H | H | H |
| 129 | H | H | —CH₃ | H | H |
| 130 | H | H | H | —CH₃ | H |
| 131 | H | H | H | H | —CH₃ |
| 132 | —CH₂CH₃ | H | H | H | H |
| 133 | H | —CH₂CH₃ | H | H | H |
| 134 | H | H | —CH₂CH₃ | H | H |
| 135 | H | H | H | —CH₂CH₃ | H |
| 136 | H | H | H | H | —CH₂CH₃ |
| 137 | —CF₃ | H | H | H | H |
| 138 | H | —CF₃ | H | H | H |
| 139 | H | H | —CF₃ | H | H |
| 140 | H | H | H | —CF₃ | H |
| 141 | H | H | H | H | —CF₃ |
| 142 | —OCH₃ | H | H | H | H |
| 143 | H | —OCH₃ | H | H | H |
| 144 | H | H | —OCH₃ | H | H |
| 145 | H | H | H | —OCH₃ | H |
| 146 | H | H | H | H | —OCH₃ |
| 147 | —OCH₂CH₃ | H | H | H | H |
| 148 | H | —OCH₂CH₃ | H | H | H |
| 149 | H | H | —OCH₂CH₃ | H | H |
| 150 | H | H | H | —OCH₂CH₃ | H |
| 151 | H | H | H | H | —OCH₂CH₃ |
| 152 | —OCH(CH₃)₂ | H | H | H | H |
| 153 | H | —OCH(CH₃)₂ | H | H | H |
| 154 | H | H | —OCH(CH₃)₂ | H | H |
| 155 | H | H | H | —OCH(CH₃)₂ | H |
| 156 | H | H | H | H | —OCH(CH₃)₂ |
| 157 | —NR⁷R⁸ | H | H | H | H |
| 158 | H | —NR⁷R⁸ | H | H | H |
| 159 | H | H | —NR⁷R⁸ | H | H |
| 160 | H | H | H | —NR⁷R⁸ | H |
| 161 | H | H | H | H | —NR⁷R⁸ |
| 162 | —NH₂ | H | H | H | H |
| 163 | H | —NH₂ | H | H | H |
| 164 | H | H | —NH₂ | H | H |
| 165 | H | H | H | —NH₂ | H |
| 166 | H | H | H | H | —NH₂ |
| 167 | —N(CH₃)R⁸ | H | H | H | H |
| 168 | H | —N(CH₃)R⁸ | H | H | H |
| 169 | H | H | —N(CH₃)R⁸ | H | H |
| 170 | H | H | H | —N(CH₃)R⁸ | H |
| 171 | H | H | H | H | —N(CH₃)R⁸ |
| 172 | —N(CH₃)₂ | H | H | H | H |
| 173 | H | —N(CH₃)₂ | H | H | H |
| 174 | H | H | —N(CH₃)₂ | H | H |
| 175 | H | H | H | —N(CH₃)₂ | H |
| 176 | H | H | H | H | —N(CH₃)₂ |
| 177 | —NHC(O)CH₃ | H | H | H | H |
| 178 | H | —NHC(O)CH₃ | H | H | H |
| 179 | H | H | —NHC(O)CH₃ | H | H |
| 180 | H | H | H | —NHC(O)CH₃ | H |
| 181 | H | H | H | H | —NHC(O)CH₃ |

In an exemplary embodiment, for any of the entries in the above table, $R^d$ is methylene. In an exemplary embodiment, for any of the entries in the above table, $R^d$ is ethylene. In an exemplary embodiment, for any of the entries in the above table, $R^d$ is propylene. In an exemplary embodiment, for any of the entries in the above table, $R^d$ is ethyl substituted methylene.

In an exemplary embodiment, the compound of the invention has a structure which is selected from the group consisting of:

or a salt thereof.

In an exemplary embodiment, the compound of the invention has a structure according to the following formula:

wherein $Z^5$ is unsubstituted pyrimidinyl or unsubstituted pyrazinyl or unsubstituted pyridazinyl. In an exemplary embodiment, the compound of the invention has a structure which is selected from the group consisting of:

or a salt thereof. In an exemplary embodiment, the compound is H75 or a salt thereof.

In an exemplary embodiment, the compound of the invention has a structure according to the following formula:

wherein $Z^6$ is halosubstituted pyridazinyl. In an exemplary embodiment, $Z^6$ is pyridazinyl, substituted with one halogen. In an exemplary embodiment, $Z^6$ is pyridazinyl, substituted with two halogens. In an exemplary embodiment, $Z^6$ is pyridazinyl, substituted with two chlorines. In an exemplary embodiment, the compound of the invention has a structure which is:

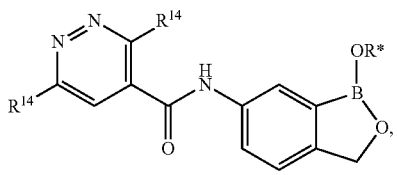

wherein each R[14] is chlorine or fluorine, or a salt thereof. In an exemplary embodiment, each R[14] is chlorine. In an exemplary embodiment, the compound is H76 or a salt thereof.

In an exemplary embodiment, the compound of the invention has a structure according to the following formula:

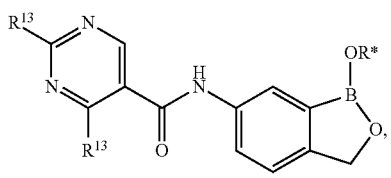

wherein each R[13] is independently selected from the group selected from H, —SH and —OH. In an exemplary embodiment, each R[13] is —SH or —OH. In an exemplary embodiment, the compound is H77 or a salt thereof.

In an exemplary embodiment, the compound of the invention has a structure according to the following formula:

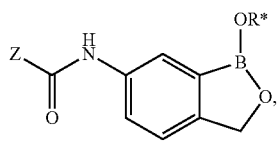

wherein Z is thiophenyl. In an exemplary embodiment, the compound of the invention has a structure which is:

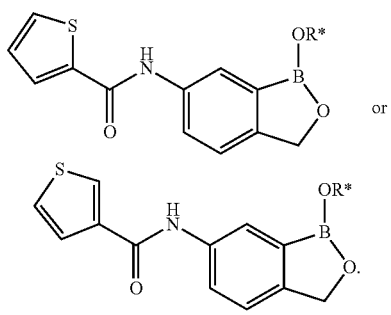

In an exemplary embodiment, the compound of the invention has a structure according to the following formula:

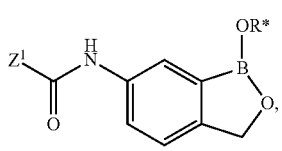

wherein $Z^1$ is unsubstituted alkylthiophenyl. In an exemplary embodiment, the compound of the invention has a structure which is

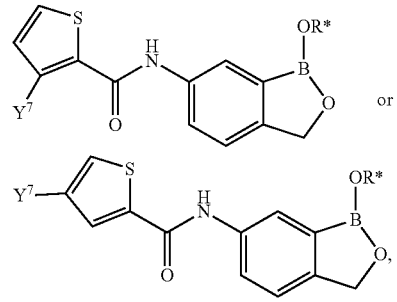

wherein $Y^7$ is unsubstituted alkyl, R* is H or a negative charge. In another exemplary embodiment, R* is H. In an exemplary embodiment, $Y^7$ is unsubstituted $C_1$ alkyl. In an exemplary embodiment, $Y^7$ is unsubstituted $C_2$ alkyl. In an exemplary embodiment, $Y^7$ is unsubstituted $C_3$ alkyl. In an exemplary embodiment, $Y^7$ is unsubstituted $C_4$ alkyl. In an exemplary embodiment, $Y^7$ is unsubstituted $C_5$ alkyl. In an exemplary embodiment, $Y^7$ is unsubstituted $C_6$ alkyl.

In an exemplary embodiment, the compound is H64 or H65 or a salt thereof.

In an exemplary embodiment, the compound of the invention has a structure according to the following formula:

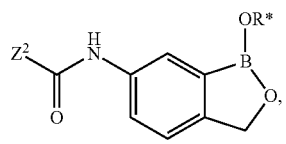

wherein $Z^2$ is unsubstituted benzothiophenyl. In an exemplary embodiment, the compound of the invention is H66 or a salt thereof.

In an exemplary embodiment, the compound of the invention has a structure according to the following formula:

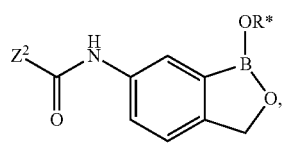

wherein $Z^2$ is halosubstituted benzothiophenyl. In an exemplary embodiment, $Z^2$ is benzothiophenyl substituted with chloro. In an exemplary embodiment, $Z^2$ is benzothiophenyl substituted with fluoro. In an exemplary embodiment, $Z^2$ is benzothiophenyl substituted with one halogen. In an exemplary embodiment, $Z^2$ is benzothiophenyl substituted with two halogens. In an exemplary embodiment, $Z^2$ is benzothiophenyl substituted with two fluorines. In an exemplary embodiment, $Z^2$ is benzothiophenyl substituted with two chlorines. In an exemplary embodiment, $Z^2$ is benzothiophenyl substituted with a fluorine and a chlorine. In an exemplary embodiment, the compound of the invention is:

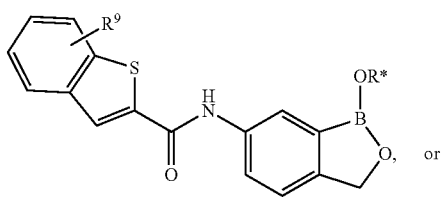

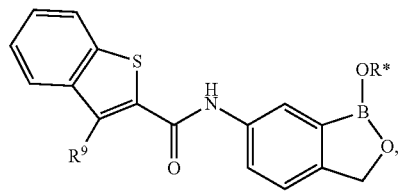

wherein R⁹ is halogen. In an exemplary embodiment, the compound of the invention is:

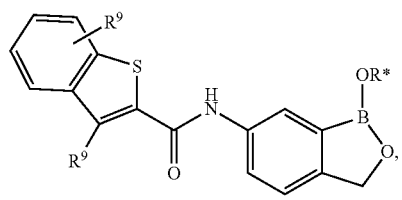

wherein each R⁹ is an independently selected halogen. In an exemplary embodiment, the compound of the invention is H67 or H68 or a salt thereof.

In an exemplary embodiment, the compound of the invention has a structure according to the following formula:

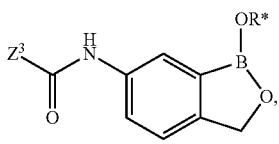

wherein $Z^3$ is unsubstituted oxazolyl. In an exemplary embodiment, the compound of the invention has a structure which is

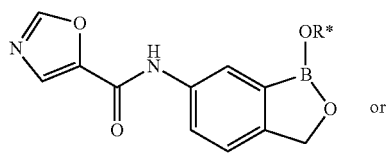

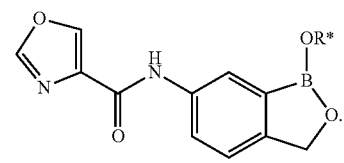

In an exemplary embodiment, the compound of the invention has a structure according to the following formula:

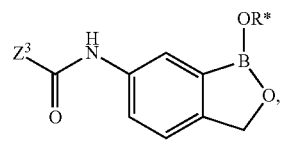

wherein $Z^3$ is unsubstituted alkyl oxazolyl. In an exemplary embodiment, the compound of the invention has a structure which is

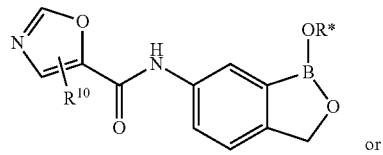

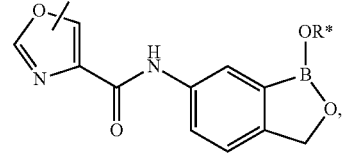

wherein $R^{10}$ is unsubstituted alkyl. In an exemplary embodiment, the compound of the invention has a structure according to the following formula:

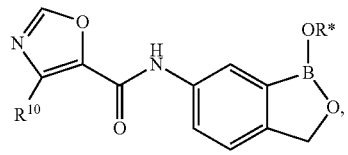

wherein $R^{10}$ is unsubstituted alkyl. In an exemplary embodiment, $R^{10}$ is $C_1$ or $C_2$ or $C_3$ or $C_4$ or $C_5$ or $C_6$ alkyl. In an exemplary embodiment, the compound is H71 or a salt thereof.

In an exemplary embodiment, the compound of the invention has a structure according to the following formula:

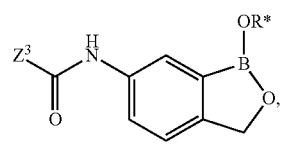

wherein $Z^3$ is unsubstituted isoxazolyl. In an exemplary embodiment, the compound of the invention has a structure which is

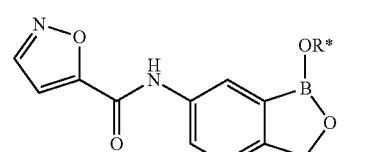

or

-continued

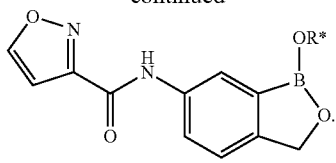

In an exemplary embodiment, the compound of the invention has a structure according to the following formula:

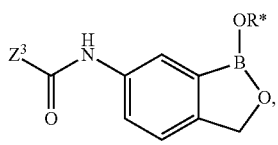

wherein $Z^3$ is unsubstituted alkyl isoxazolyl. In an exemplary embodiment, the compound of the invention has a structure which is

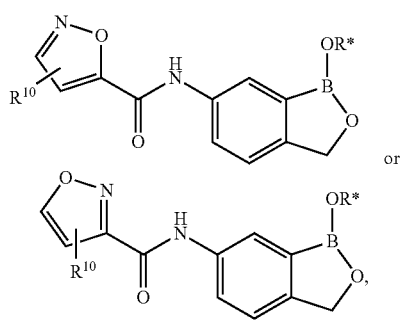

wherein $R^{10}$ is unsubstituted $C_1$-$C_6$ alkyl. In an exemplary embodiment, the compound of the invention has a structure according to the following formula:

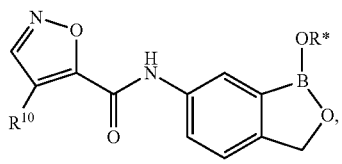

wherein $R^{10}$ is unsubstituted alkyl. In an exemplary embodiment, $R^{10}$ is unsubstituted $C_1$ alkyl. In an exemplary embodiment, $R^{10}$ is unsubstituted $C_2$ alkyl. In an exemplary embodiment, $R^{10}$ is unsubstituted $C_3$ alkyl. In an exemplary embodiment, $R^{10}$ is unsubstituted $C_4$ alkyl. In an exemplary embodiment, $R^{10}$ is unsubstituted $C_5$ alkyl. In an exemplary embodiment, $R^{10}$ is unsubstituted $C_6$ alkyl.

In an exemplary embodiment, the compound of the invention has a structure according to the following formula:

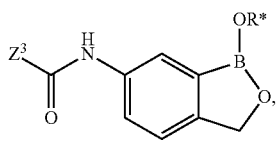

wherein $Z^3$ is unsubstituted thiazolyl. In an exemplary embodiment, the compound of the invention has a structure which is

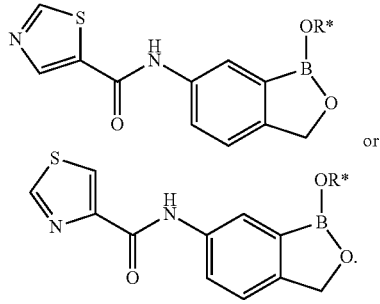

In an exemplary embodiment, the compound of the invention has a structure according to the following formula:

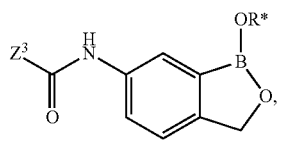

wherein $Z^3$ is unsubstituted alkyl thiazolyl. In an exemplary embodiment, the compound of the invention has a structure which is:

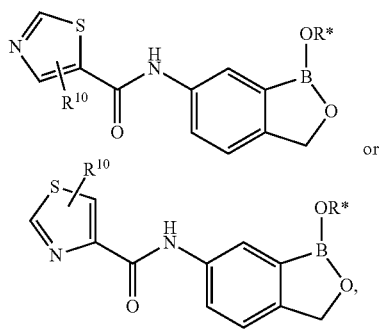

wherein $R^{10}$ is unsubstituted alkyl. In an exemplary embodiment, the compound of the invention has a structure which is:

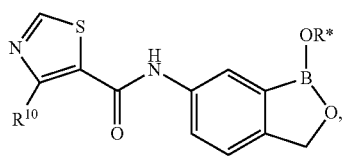

wherein $R^{10}$ is unsubstituted alkyl. In an exemplary embodiment, $R^{10}$ is $C_1$ or $C_2$ or $C_3$ or $C_4$ or $C_5$ or $C_6$ alkyl. In an exemplary embodiment, the compound is H72 or a salt thereof.

In an exemplary embodiment, the compound of the invention has a structure according to the following formula:

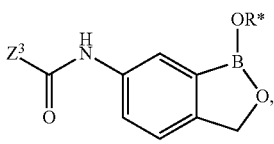

wherein $Z^3$ is unsubstituted pyrazolyl. In an exemplary embodiment, the compound of the invention has a structure which is

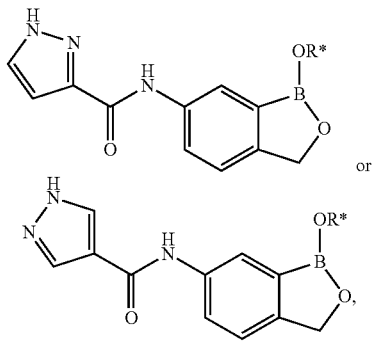

or

In an exemplary embodiment, the compound of the invention has a structure according to the following formula:

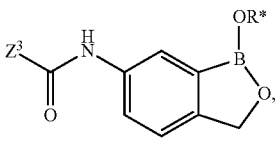

wherein $Z^3$ is selected from the group consisting of unsubstituted alkyl pyrrolyl, unsubstituted phenyl pyrrolyl and unsubstituted phenyl (unsubstituted alkyl)pyrrolyl. In an exemplary embodiment, the compound of the invention has a structure which is:

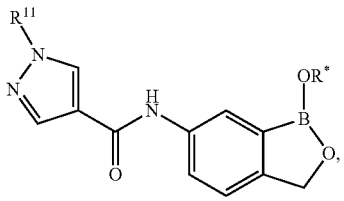

wherein each $R^{11}$ is independently selected from unsubstituted $C_1$-$C_6$ alkyl or phenyl. In an exemplary embodiment, the compound of the invention has a structure which is

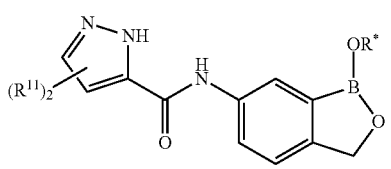

or

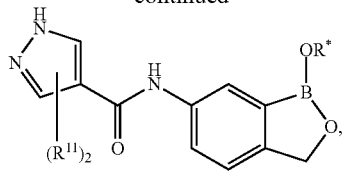

wherein each $R^{11}$ is independently selected from unsubstituted $C_1$-$C_6$ alkyl or phenyl. In an exemplary embodiment, the compound of the invention has a structure which is

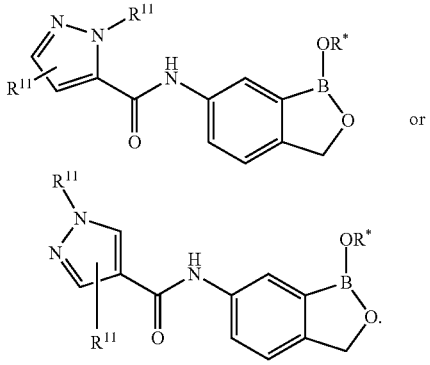

or

In an exemplary embodiment, $R^{11}$ is unsubstituted $C_1$ alkyl.
In an exemplary embodiment, $R^{11}$ is unsubstituted $C_2$ alkyl.
In an exemplary embodiment, $R^{11}$ is unsubstituted $C_3$ alkyl.
In an exemplary embodiment, $R^{11}$ is unsubstituted $C_4$ alkyl.
In an exemplary embodiment, $R^{11}$ is unsubstituted $C_5$ alkyl.
In an exemplary embodiment, $R^{11}$ is unsubstituted $C_6$ alkyl.
In an exemplary embodiment, $R^{11}$ is unsubstituted phenyl.
In an exemplary embodiment, the compound of the invention has a structure according to the following formula:

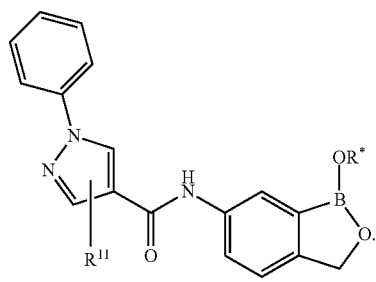

In an exemplary embodiment, the compound of the invention is H73 or a salt thereof. In an exemplary embodiment, the compound of the invention is H74 or a salt thereof.
In an exemplary embodiment, the compound of the invention has a structure according to the following formula:

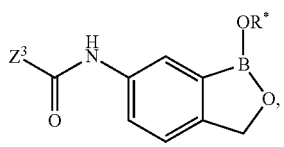

wherein $Z^3$ is unsubstituted furanyl. In an exemplary embodiment, the compound is:

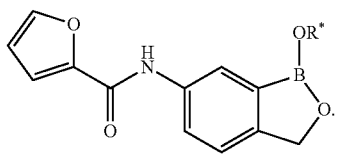

In an exemplary embodiment, the compound of the invention has a structure according to the following formula:

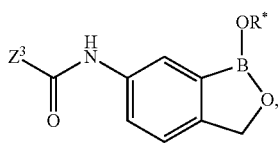

wherein $Z^3$ is unsubstituted alkylfuranyl. In an exemplary embodiment, the compound of the invention is:

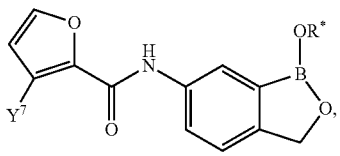

wherein $Y^7$ is unsubstituted alkyl, R* is a member selected from H and a negative charge. In another exemplary embodiment, R* is H. In an exemplary embodiment, $Y^7$ is unsubstituted $C_1$ alkyl. In an exemplary embodiment, $Y^7$ is unsubstituted $C_2$ alkyl. In an exemplary embodiment, $Y^7$ is unsubstituted $C_3$ alkyl. In an exemplary embodiment, $Y^7$ is unsubstituted $C_4$ alkyl. In an exemplary embodiment, $Y^7$ is unsubstituted $C_5$ alkyl. In an exemplary embodiment, $Y^7$ is unsubstituted $C_6$ alkyl. In an exemplary embodiment, the compound of the invention is H62 or a salt thereof.

In an exemplary embodiment, the compound of the invention has a structure according to the following formula:

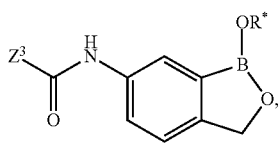

wherein $Z^3$ is unsubstituted pyrrole. In an exemplary embodiment, the compound is:

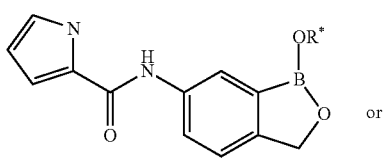

or a salt thereof.

In an exemplary embodiment, the compound of the invention has a structure according to the following formula:

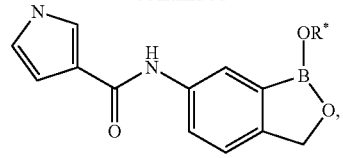

wherein $Z^3$ is unsubstituted alkyl pyrrole. In an exemplary embodiment, the compound is:

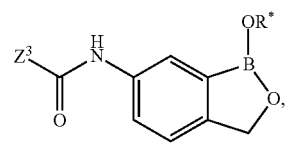

wherein $R^{10}$ is unsubstituted alkyl, or a salt thereof. In an exemplary embodiment, the compound is:

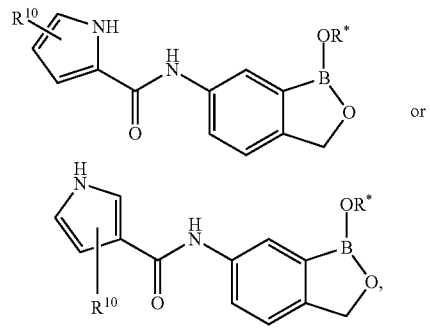

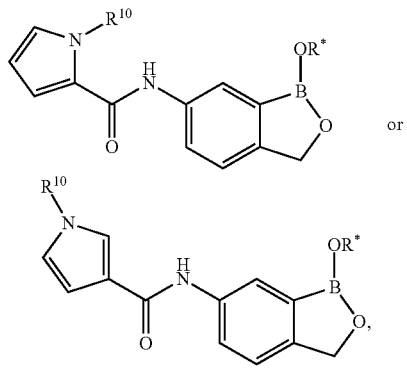

wherein $R^{10}$ is unsubstituted alkyl, or a salt thereof. In an exemplary embodiment, $R^{10}$ is unsubstituted $C_1$ alkyl. In an exemplary embodiment, $R^{10}$ is unsubstituted $C_2$ alkyl. In an exemplary embodiment, $R^{10}$ is unsubstituted $C_3$ alkyl. In an exemplary embodiment, $R^{10}$ is unsubstituted $C_4$ alkyl. In an exemplary embodiment, $R^{10}$ is unsubstituted $C_5$ alkyl. In an exemplary embodiment, $R^{10}$ is unsubstituted $C_6$ alkyl. In an exemplary embodiment, the compound is H69 or a salt thereof.

In an exemplary embodiment, the compound of the invention has a structure which is selected from the group consisting of

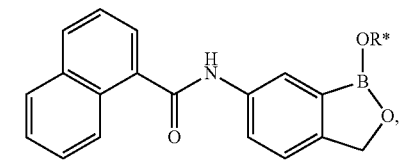

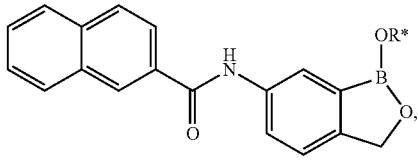

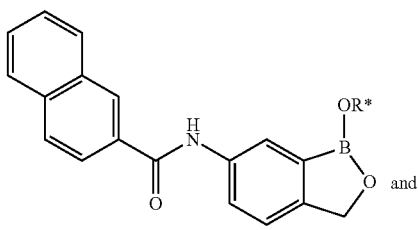

and

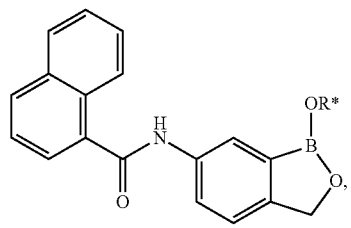

or a salt thereof.

In an exemplary embodiment, the compound of the invention has a structure which is selected from the group consisting of

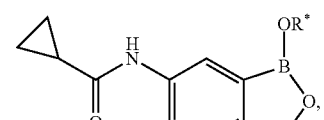

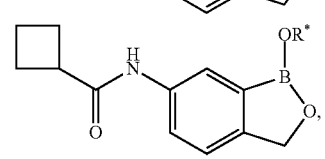

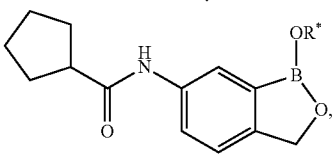

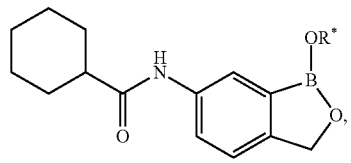

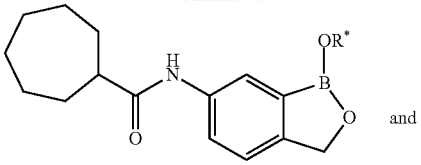

and

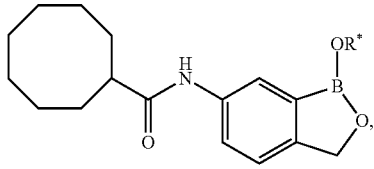

or a salt thereof.

In an exemplary embodiment, the compound of the invention has a structure according to the following formula:

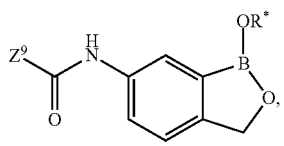

wherein $Z^9$ is unsubstituted alkyl. In an exemplary embodiment, $Z^9$ is unsubstituted $C_1$ or $C_2$ or $C_3$ or $C_4$ or $C_5$ or $C_6$ alkyl. In an exemplary embodiment, $Z^9$ is methyl. In an exemplary embodiment, $Z^9$ is unsubstituted $C_4$ alkyl. In an exemplary embodiment, $Z^9$ is n-butyl or sec-butyl or isobutyl or tert-butyl. In an exemplary embodiment, $Z^9$ is tert-butyl.

In an exemplary embodiment, the compound of the invention has a structure according to the following formula:

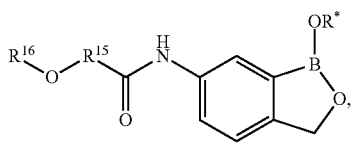

wherein $R^{15}$ is unsubstituted alkyl and $R^{16}$ is H or phenyl substituted alkyl. In an exemplary embodiment, $R^{15}$ is unsubstituted $C_1$ or $C_2$ or $C_3$ or $C_4$ or $C_5$ or $C_6$ alkyl. In an exemplary embodiment, $R^{15}$ is unsubstituted $C_3$ alkyl. In an exemplary embodiment, $R^{16}$ is benzyl.

In an exemplary embodiment, the compound of the invention has a structure according to the following formula:

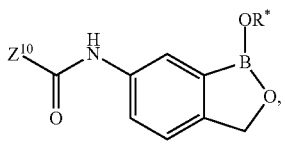

wherein $Z^{10}$ is hydroxy-substituted alkyl. In an exemplary embodiment, $Z^{10}$ is hydroxysubstituted $C_1$ or $C_2$ or $C_3$ or $C_4$ or $C_5$ or $C_6$ alkyl.

In an exemplary embodiment, the compound of the invention has a structure according to the following formula:

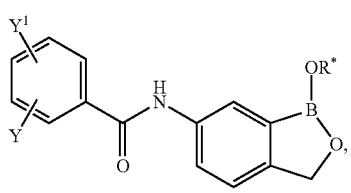

wherein $Y^1$ is a halogen, Y is halo-substituted alkyl, R* is H or a negative charge. In an exemplary embodiment, Y is halo-substituted $C_1$-$C_6$ alkyl. In another exemplary embodiment, R* is H. In an exemplary embodiment, Y is fluoro-substituted $C_1$-$C_6$ alkyl, and $Y^1$ is as described herein. In an exemplary embodiment, Y is trifluoro-substituted $C_1$-$C_6$ alkyl, $Y^1$ is as described herein. In an exemplary embodiment, Y is $C_1$-$C_6$ alkyl, substituted with one halogen, $Y^1$ is as described herein. In an exemplary embodiment, Y is $C_1$-$C_6$ alkyl, substituted with two halogens, $Y^1$ is as described herein. In an exemplary embodiment, Y is $C_1$-$C_6$ alkyl, substituted with three halogens, $Y^1$ is as described herein. In an exemplary embodiment, Y is $C_1$-$C_6$ alkyl, substituted with four halogens, $Y^1$ is as described herein. In an exemplary embodiment, Y is $C_1$-$C_6$ alkyl, substituted with one fluorine, $Y^1$ is as described herein. In an exemplary embodiment, Y is $C_1$-$C_6$ alkyl, substituted with two fluorines, $Y^1$ is as described herein. In an exemplary embodiment, Y is $C_1$-$C_6$ alkyl, substituted with three fluorines, $Y^1$ is as described herein. In an exemplary embodiment, Y is $C_1$-$C_6$ alkyl, substituted with four fluorines, $Y^1$ is as described herein. In an exemplary embodiment, Y is $C_1$-$C_6$ alkyl, substituted with one chlorine, $Y^1$ is as described herein. In an exemplary embodiment, Y is $C_1$-$C_6$ alkyl, substituted with two chlorines, $Y^1$ is as described herein. In an exemplary embodiment, Y is $C_1$-$C_6$ alkyl, substituted with three chlorines, $Y^1$ is as described herein. In an exemplary embodiment, Y is $C_1$-$C_6$ alkyl, substituted with four chlorines, $Y^1$ is as described herein. In an exemplary embodiment, Y is $C_1$-$C_6$ alkyl, substituted with a combination of two different halogens, $Y^1$ is as described herein. In an exemplary embodiment, Y is $C_1$-$C_6$ alkyl, substituted with at least one fluorine and at least one chlorine, $Y^1$ is as described herein. In an exemplary embodiment, Y is $C_1$-$C_6$ alkyl, substituted with at least one fluorine and at least one bromine, $Y^1$ is as described herein. In an exemplary embodiment, Y is $C_1$-$C_6$ alkyl, substituted with at least one chlorine and at least one bromine, $Y^1$ is as described herein. In an exemplary embodiment, Y is fluoro-substituted $C_1$-$C_6$ alkyl, and $Y^1$ is chloro. In an exemplary embodiment, Y is trifluoro-substituted $C_1$-$C_6$ alkyl, $Y^1$ is chloro. In an exemplary embodiment, Y is fluoro-substituted $C_1$-$C_6$ alkyl, and $Y^1$ is fluoro. In an exemplary embodiment, Y is trifluoro-substituted $C_1$-$C_6$ alkyl, $Y^1$ is fluoro. In an exemplary embodiment, Y is fluoro-substituted $C_1$-$C_6$ alkyl, and $Y^1$ is bromo. In an exemplary embodiment, the compound of the invention has a structure which is:

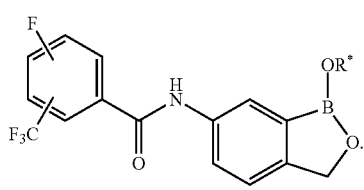

In an exemplary embodiment, the compound of the invention has a structure which is:

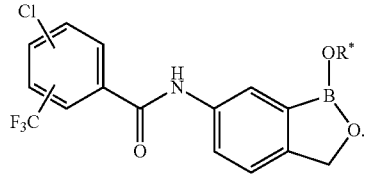

In an exemplary embodiment, the compound of the invention has a structure which is:

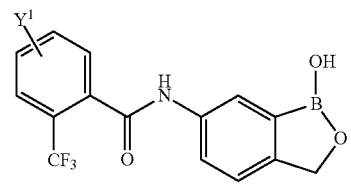

wherein $Y^1$ is as described herein.

In an exemplary embodiment, the compound of the invention has a structure which is:

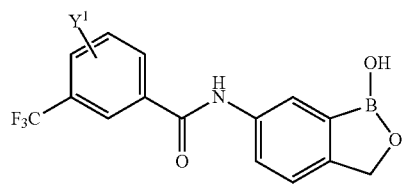

wherein $Y^1$ is as described herein.

In an exemplary embodiment, the compound of the invention has a structure which is:

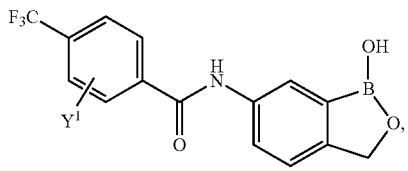

wherein $Y^1$ is as described herein.

In an exemplary embodiment, the compound of the invention has a structure which is:

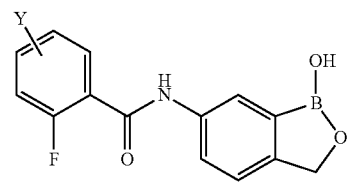

wherein Y is as described herein.

In an exemplary embodiment, the compound of the invention has a structure which is:

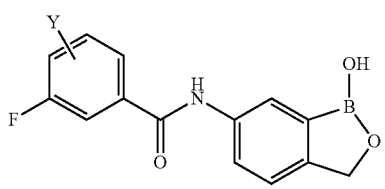

wherein Y is as described herein.
In an exemplary embodiment, the compound of the invention has a structure which is:

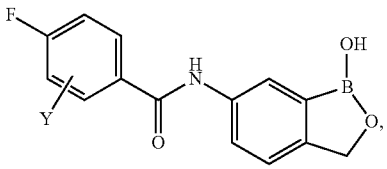

wherein Y is as described herein.
In an exemplary embodiment, the compound of the invention has a structure which is:

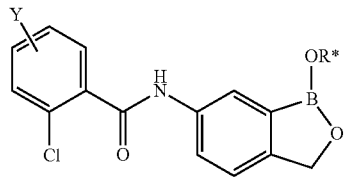

wherein Y is as described herein.
In an exemplary embodiment, the compound of the invention has a structure which is:

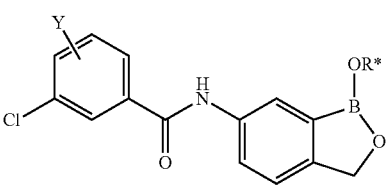

wherein Y is as described herein.
In an exemplary embodiment, the compound of the invention has a structure which is:

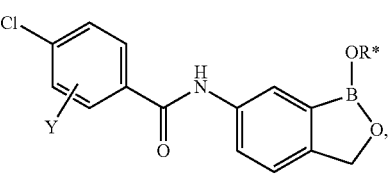

wherein Y is as described herein.
In an exemplary embodiment, the compound of the invention has a structure which is H17 or a salt thereof. In an exemplary embodiment, the compound of the invention has a structure which is H18 or a salt thereof. In an exemplary embodiment, the compound of the invention has a structure which is H19 or a salt thereof. In an exemplary embodiment, the compound of the invention has a structure which is H20 or a salt thereof. In an exemplary embodiment, the compound of the invention has a structure which is H21 or a salt thereof. In an exemplary embodiment, the compound of the invention has a structure which is H22 or a salt thereof. In an exemplary embodiment, the compound of the invention has a structure which is H23 or a salt thereof.

In an exemplary embodiment, the compound has a structure according to the following formula:

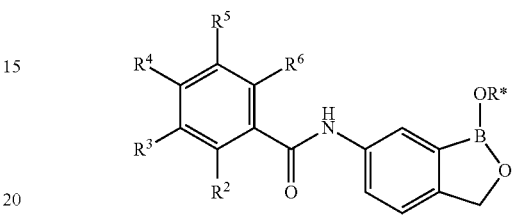

wherein R* is H or a negative charge, and $R^2$, $R^3$, $R^4$, $R^5$ and $R^6$ are according to the entries in the following table, or a salt thereof.

| | $R^2$ | $R^3$ | $R^4$ | $R^5$ | $R^6$ |
|---|---|---|---|---|---|
| 182 | $CF_3$ | F | H | H | H |
| 183 | $CF_3$ | H | F | H | H |
| 184 | $CF_3$ | H | H | F | H |
| 185 | $CF_3$ | H | H | H | F |
| 186 | F | $CF_3$ | H | H | H |
| 187 | H | $CF_3$ | F | H | H |
| 188 | H | $CF_3$ | H | F | H |
| 189 | H | $CF_3$ | H | H | F |
| 190 | F | H | $CF_3$ | H | H |
| 191 | H | F | $CF_3$ | H | H |
| 192 | H | H | $CF_3$ | F | H |
| 193 | H | H | $CF_3$ | H | F |
| 194 | F | H | H | $CF_3$ | H |
| 195 | H | F | H | $CF_3$ | H |
| 196 | H | H | F | $CF_3$ | H |
| 197 | H | H | H | $CF_3$ | F |
| 198 | F | H | H | H | $CF_3$ |
| 199 | H | F | H | H | $CF_3$ |
| 200 | H | H | F | H | $CF_3$ |
| 201 | H | H | H | F | $CF_3$ |
| 202 | $CF_3$ | Cl | H | H | H |
| 203 | $CF_3$ | H | Cl | H | H |
| 204 | $CF_3$ | H | H | Cl | H |
| 205 | $CF_3$ | H | H | H | Cl |
| 206 | Cl | $CF_3$ | H | H | H |
| 207 | H | $CF_3$ | Cl | H | H |
| 208 | H | $CF_3$ | H | Cl | H |
| 209 | H | $CF_3$ | H | H | Cl |
| 210 | Cl | H | $CF_3$ | H | H |
| 211 | H | Cl | $CF_3$ | H | H |
| 212 | H | H | $CF_3$ | Cl | H |
| 213 | H | H | $CF_3$ | H | Cl |
| 214 | Cl | H | H | $CF_3$ | H |
| 215 | H | Cl | H | $CF_3$ | H |
| 216 | H | H | Cl | $CF_3$ | H |
| 217 | H | H | H | $CF_3$ | Cl |
| 218 | Cl | H | H | H | $CF_3$ |
| 219 | H | Cl | H | H | $CF_3$ |
| 220 | H | H | Cl | H | $CF_3$ |
| 221 | H | H | H | Cl | $CF_3$ |
| 222 | $CF_3$ | $CF_3$ | H | H | H |
| 223 | $CF_3$ | H | $CF_3$ | H | H |
| 224 | $CF_3$ | H | H | $CF_3$ | H |
| 225 | $CF_3$ | H | H | H | $CF_3$ |
| 226 | H | $CF_3$ | $CF_3$ | H | H |
| 227 | H | $CF_3$ | H | $CF_3$ | H |
| 228 | H | $CF_3$ | H | H | $CF_3$ |

| | R² | R³ | R⁴ | R⁵ | R⁶ |
|---|---|---|---|---|---|
| 229 | H | H | CF₃ | CF₃ | H |
| 230 | H | H | CF₃ | H | CF₃ |
| 231 | H | H | H | CF₃ | CF₃ |
| 232 | F | F | H | H | H |
| 233 | F | H | F | H | H |
| 234 | F | H | H | F | H |
| 235 | F | H | H | H | F |
| 236 | H | F | F | H | H |
| 237 | H | F | H | F | H |
| 238 | H | F | H | H | F |
| 239 | H | H | F | F | H |
| 240 | H | H | F | H | F |
| 241 | H | H | H | F | F |
| 242 | Cl | Cl | H | H | H |
| 243 | Cl | H | Cl | H | H |
| 244 | Cl | H | H | Cl | H |
| 245 | Cl | H | H | H | Cl |
| 246 | H | Cl | Cl | H | H |
| 247 | H | Cl | H | Cl | H |
| 248 | H | Cl | H | H | Cl |
| 249 | H | H | Cl | Cl | H |
| 250 | H | H | Cl | H | Cl |
| 251 | H | H | H | Cl | Cl |
| 252 | F | Cl | H | H | H |
| 253 | F | H | Cl | H | H |
| 254 | F | H | H | Cl | H |
| 255 | F | H | H | H | Cl |
| 256 | H | F | Cl | H | H |
| 257 | H | F | H | Cl | H |
| 258 | H | F | H | H | Cl |
| 259 | H | H | F | Cl | H |
| 260 | H | H | F | H | Cl |
| 261 | H | H | H | F | Cl |
| 262 | Cl | F | H | H | H |
| 263 | Cl | H | F | H | H |
| 264 | Cl | H | H | F | H |
| 265 | Cl | H | H | H | F |
| 266 | H | Cl | F | H | H |
| 267 | H | Cl | H | F | H |
| 268 | H | Cl | H | H | F |
| 269 | H | H | Cl | F | H |
| 270 | H | H | Cl | H | F |
| 271 | H | H | H | Cl | F |
| 272 | —CH₃ | —CH₃ | H | H | H |
| 273 | —CH₃ | H | —CH₃ | H | H |
| 274 | —CH₃ | H | H | —CH₃ | H |
| 275 | —CH₃ | H | H | H | —CH₃ |
| 276 | H | —CH₃ | —CH₃ | H | H |
| 277 | H | —CH₃ | H | —CH₃ | H |
| 278 | H | —CH₃ | H | H | —CH₃ |
| 279 | H | H | —CH₃ | —CH₃ | H |
| 280 | H | H | —CH₃ | H | —CH₃ |
| 281 | H | H | H | —CH₃ | —CH₃ |
| 282 | —Y³ | —CH₃ | H | H | H |
| 283 | —Y³ | H | —CH₃ | H | H |
| 284 | —Y³ | H | H | —CH₃ | H |
| 285 | —Y³ | H | H | H | —CH₃ |
| 286 | H | —Y³ | —CH₃ | H | H |
| 287 | H | —Y³ | H | —CH₃ | H |
| 288 | H | —Y³ | H | H | —CH₃ |
| 289 | H | H | —Y³ | —CH₃ | H |
| 290 | H | H | —Y³ | H | —CH₃ |
| 291 | H | H | H | —Y³ | —CH₃ |
| 292 | —CH₃ | —Y³ | H | H | H |
| 293 | —CH₃ | H | —Y³ | H | H |
| 294 | —CH₃ | H | H | —Y³ | H |
| 295 | —CH₃ | H | H | H | —Y³ |
| 296 | H | —CH₃ | —Y³ | H | H |
| 297 | H | —CH₃ | H | —Y³ | H |
| 298 | H | —CH₃ | H | H | —Y³ |
| 299 | H | H | —CH₃ | —Y³ | H |
| 300 | H | H | —CH₃ | H | —Y³ |
| 301 | H | H | H | —CH₃ | —Y³ |
| 302 | —Y² | —OCH₃ | H | H | H |
| 303 | —Y² | H | —OCH₃ | H | H |
| 304 | —Y² | H | H | —OCH₃ | H |
| 305 | —Y² | H | H | H | —OCH₃ |
| 306 | H | —Y² | —OCH₃ | H | H |
| 307 | H | —Y² | H | —OCH₃ | H |
| 308 | H | —Y² | H | H | —OCH₃ |
| 309 | H | H | —Y² | —OCH₃ | H |
| 310 | H | H | —Y² | H | —OCH₃ |
| 311 | H | H | H | —Y² | —OCH₃ |
| 312 | —OCH₃ | —Y² | H | H | H |
| 313 | —OCH₃ | H | —Y² | H | H |
| 314 | —OCH₃ | H | H | —Y² | H |
| 315 | —OCH₃ | H | H | H | —Y² |
| 316 | H | —OCH₃ | —Y² | H | H |
| 317 | H | —OCH₃ | H | —Y² | H |
| 318 | H | —OCH₃ | H | H | —Y² |
| 319 | H | H | —OCH₃ | —Y² | H |
| 320 | H | H | —OCH₃ | H | —Y² |
| 321 | H | H | H | —OCH₃ | —Y² |
| 322 | —OCH₃ | —OCH₃ | H | H | H |
| 323 | —OCH₃ | H | —OCH₃ | H | H |
| 324 | —OCH₃ | H | H | —OCH₃ | H |
| 325 | —OCH₃ | H | H | H | —OCH₃ |
| 326 | H | —OCH₃ | —OCH₃ | H | H |
| 327 | H | —OCH₃ | H | —OCH₃ | H |
| 328 | H | —OCH₃ | H | H | —OCH₃ |
| 329 | H | H | —OCH₃ | —OCH₃ | H |
| 330 | H | H | —OCH₃ | H | —OCH₃ |
| 331 | H | H | H | —OCH₃ | —OCH₃ |
| 332 | —CH₃ | —OCH₃ | H | H | H |
| 333 | —CH₃ | H | —OCH₃ | H | H |
| 334 | —CH₃ | H | H | —OCH₃ | H |
| 335 | —CH₃ | H | H | H | —OCH₃ |
| 336 | H | —CH₃ | —OCH₃ | H | H |
| 337 | H | —CH₃ | H | —OCH₃ | H |
| 338 | H | —CH₃ | H | H | —OCH₃ |
| 339 | H | H | —CH₃ | —OCH₃ | H |
| 340 | H | H | —CH₃ | H | —OCH₃ |
| 341 | H | H | H | —CH₃ | —OCH₃ |
| 342 | —OCH₃ | —CH₃ | H | H | H |
| 343 | —OCH₃ | H | —CH₃ | H | H |
| 344 | —OCH₃ | H | H | —CH₃ | H |
| 345 | —OCH₃ | H | H | H | —CH₃ |
| 346 | H | —OCH₃ | —CH₃ | H | H |
| 347 | H | —OCH₃ | H | —CH₃ | H |
| 348 | H | —OCH₃ | H | H | —CH₃ |
| 349 | H | H | —OCH₃ | —CH₃ | H |
| 350 | H | H | —OCH₃ | H | —CH₃ |
| 351 | H | H | H | —OCH₃ | —CH₃ |
| 352 | —Y² | —Y² | H | H | H |
| 353 | —Y² | H | —Y² | H | H |
| 354 | —Y² | H | H | —Y² | H |
| 355 | —Y² | H | H | H | —Y² |
| 356 | H | —Y² | —Y² | H | H |
| 357 | H | —Y² | H | —Y² | H |
| 358 | H | —Y² | H | H | —Y² |
| 359 | H | H | —Y² | H | —Y² |
| 360 | —Y³ | —Y³ | H | H | H |
| 361 | —Y³ | H | —Y³ | H | H |
| 362 | —Y³ | H | H | —Y³ | H |
| 363 | —Y³ | H | H | H | —Y³ |
| 364 | H | —Y³ | —Y³ | H | H |
| 365 | H | —Y³ | H | —Y³ | H |
| 366 | H | —Y³ | H | H | —Y³ |
| 367 | H | H | —Y³ | H | —Y³ |
| 368 | —Y² | —Y³ | H | H | H |
| 369 | —Y² | H | —Y³ | H | H |
| 370 | —Y² | H | H | —Y³ | H |
| 371 | —Y² | H | H | H | —Y³ |
| 372 | H | —Y² | —Y³ | H | H |
| 373 | H | —Y² | H | —Y³ | H |
| 374 | H | —Y² | H | H | —Y³ |
| 375 | H | H | —Y² | —Y³ | H |
| 376 | —Y³ | —Y² | H | H | H |
| 377 | —Y³ | H | —Y² | H | H |
| 378 | —Y³ | H | H | —Y² | H |
| 379 | —Y³ | H | H | H | —Y² |
| 380 | H | —Y³ | —Y² | H | H |
| 381 | H | —Y³ | H | —Y² | H |

-continued

|  | R² | R³ | R⁴ | R⁵ | R⁶ |
|---|---|---|---|---|---|
| 382 | H | —Y³ | H | H | —Y² |
| 383 | H | H | —Y³ | H | —Y² |

In an exemplary embodiment, for any of the entries in the above table, $R^c$ is H. In an exemplary embodiment, for any of the entries in the above table, $R^c$ is methyl. In an exemplary embodiment, for any of the entries in the above table, $R^c$ is ethyl. In an exemplary embodiment, for any of the entries in the above table, $R^c$ is propyl.

In an exemplary embodiment, the compound of the invention has a structure according to the following formula:

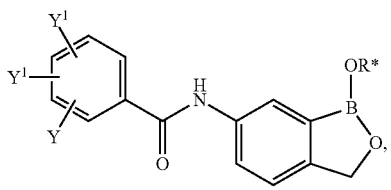

wherein each $Y^1$ is independently selected halogen, Y is halo-substituted $C_1$-$C_6$ alkyl, R* is H or a negative charge. In another exemplary embodiment, R* is H. In an exemplary embodiment, Y is fluoro-substituted $C_1$-$C_6$ alkyl, and each $Y^1$ is as described herein. In an exemplary embodiment, Y is trifluoro-substituted $C_1$-$C_6$ alkyl, and each $Y^1$ is as described herein. In an exemplary embodiment, Y is as described herein, and each $Y^1$ is as described herein. In an exemplary embodiment, Y is fluoro-substituted $C_1$-$C_6$ alkyl, and each $Y^1$ is chloro. In an exemplary embodiment, Y is fluoro-substituted $C_1$-$C_6$ alkyl, and each $Y^1$ is fluoro. In an exemplary embodiment, Y is fluoro-substituted $C_1$-$C_6$ alkyl, a $Y^1$ is fluoro, and another $Y^1$ is chloro. In an exemplary embodiment, Y is trifluoro-substituted $C_1$-$C_6$ alkyl, and each $Y^1$ is chloro. In an exemplary embodiment, Y is trifluoro-substituted $C_1$-$C_6$ alkyl, and each $Y^1$ is fluoro. In an exemplary embodiment, Y is trifluoro-substituted $C_1$-$C_6$ alkyl, a $Y^1$ is fluoro, and another $Y^1$ is chloro. In an exemplary embodiment, the compound of the invention has a structure which is selected from the group consisting of

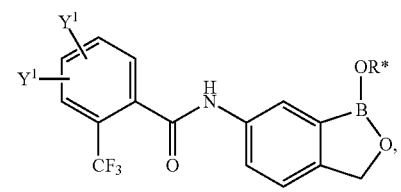

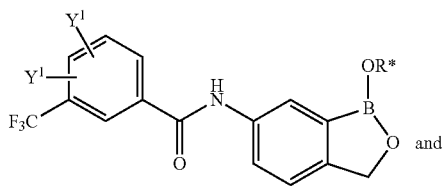
and

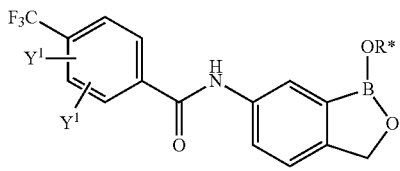

wherein each $Y^1$ and R* are as described herein.

In an exemplary embodiment, the compound of the invention has a structure which is selected from the group consisting of

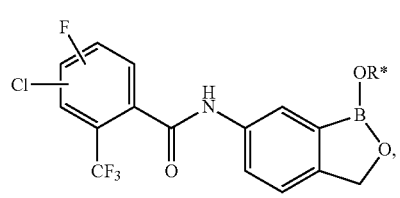

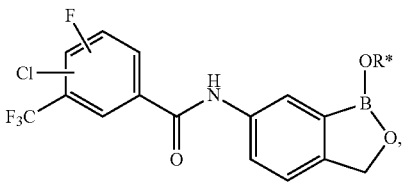

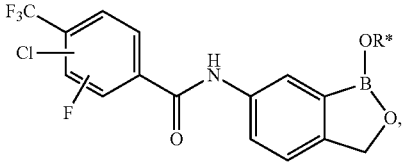

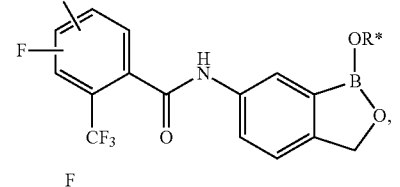

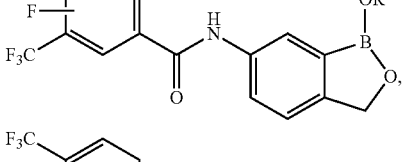

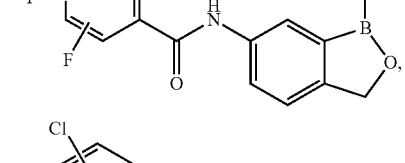

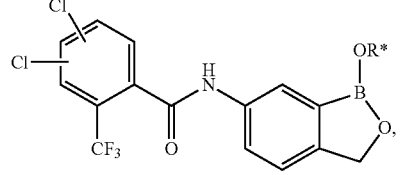

-continued

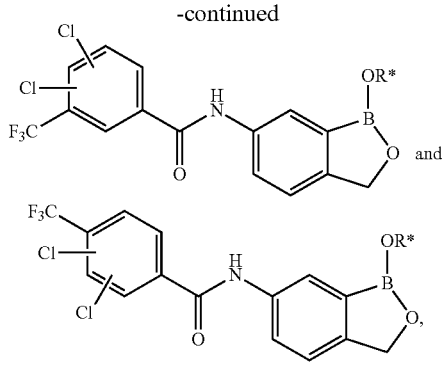

and or a salt thereof. In an exemplary embodiment, the compound is H24 or a salt thereof.

In an exemplary embodiment, the compound of the invention has a structure according to the following formula:

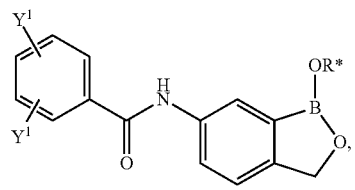

wherein each $Y^1$ is a halogen, R* is H or a negative charge. In another exemplary embodiment, R* is H. In an exemplary embodiment, each $Y^1$ is as described herein. In an exemplary embodiment, each $Y^1$ is fluoro. In an exemplary embodiment, each $Y^1$ is chloro. In an exemplary embodiment, one $Y^1$ is fluoro and another is $Y^1$ is chloro. In an exemplary embodiment, the compound of the invention is H11 or H12 or H13 or H14 or H15 or H16, or a salt thereof.

In an exemplary embodiment, the compound of the invention has a structure according to the following formula:

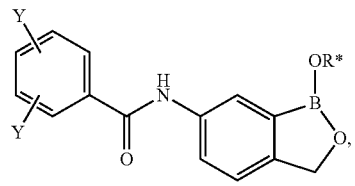

wherein each Y is an independently selected halo-substituted $C_1$-$C_6$ alkyl, R* is H or a negative charge. In another exemplary embodiment, R* is H. In an exemplary embodiment, each Y is as described herein. In an exemplary embodiment, one Y is fluoro-substituted $C_1$-$C_6$ alkyl, and the other Y is as described herein. In an exemplary embodiment, one Y is trifluoro-substituted $C_1$-$C_6$ alkyl and the other Y is as described herein. In an exemplary embodiment, each Y is fluoro-substituted $C_1$-$C_6$ alkyl. In an exemplary embodiment, each Y is trifluoro-substituted $C_1$-$C_6$ alkyl. In an exemplary embodiment, the compound of the invention is H25 or H26 or H27, or a salt thereof.

In an exemplary embodiment, the compound of the invention has a structure according to the following formula:

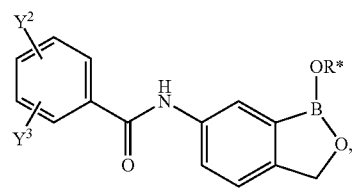

wherein $Y^2$ is unsubstituted alkyl and $Y^3$ is unsubstituted alkoxy, R* is H or a negative charge. In another exemplary embodiment, R* is H. In an exemplary embodiment, $Y^2$ is as described herein, and $Y^3$ is as described herein. In an exemplary embodiment, $Y^2$ is unsubstituted $C_1$-$C_6$ alkyl, and $Y^3$ is unsubstituted $C_1$-$C_6$ alkoxy. In an exemplary embodiment, $Y^2$ is methyl, $Y^3$ is as described herein. In an exemplary embodiment, $Y^2$ is as described herein, $Y^3$ is methoxy. In an exemplary embodiment, the compound of the invention is H43, or a salt thereof.

In an exemplary embodiment, the compound of the invention has a structure according to the following formula:

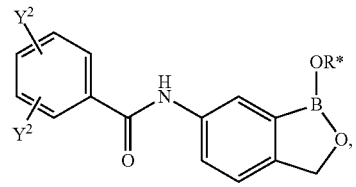

wherein each $Y^2$ is unsubstituted alkyl, and R* is H or a negative charge. In another exemplary embodiment, R* is H. In an exemplary embodiment, each $Y^2$ is as described herein. In an exemplary embodiment, $Y^2$ is unsubstituted $C_1$-$C_6$ alkyl. In an exemplary embodiment, one $Y^2$ is methyl, and the other $Y^2$ is an unsubstituted alkyl aside from methyl. In an exemplary embodiment, both $Y^2$ are methyl. In an exemplary embodiment, the compound of the invention is H43, or a salt thereof.

In an exemplary embodiment, the compound of the invention has a structure according to the following formula:

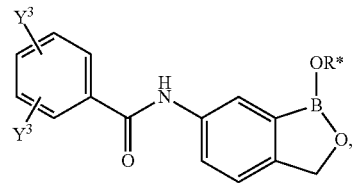

wherein each $Y^3$ is independently selected unsubstituted alkoxy, R* is H or a negative charge. In another exemplary embodiment, R* is H. In an exemplary embodiment, each $Y^3$ is as described herein. In an exemplary embodiment, $Y^3$ is unsubstituted $C_1$-$C_6$ alkoxy, and $Y^3$ is unsubstituted $C_1$-$C_6$ alkoxy. In an exemplary embodiment, a $Y^3$ is methoxy, and another $Y^3$ is as described herein. In an exemplary embodiment, the compound of the invention is H38 or H39 or H40, or a salt thereof.

In an exemplary embodiment, the compound has a structure according to the following formula:

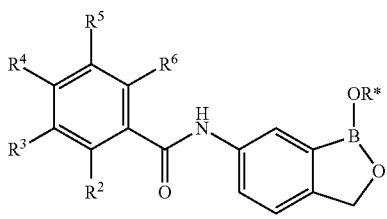

wherein R* is H or a negative charge, and R², R³, R⁴, R⁵ and R⁶ are according to the entries in the following table, or a salt thereof.

| | R² | R³ | R⁴ | R⁵ | R⁶ |
|---|---|---|---|---|---|
| 384 | —OCH₃ | —OCH₃ | —OCH₃ | H | H |
| 385 | —OCH₃ | —OCH₃ | H | —OCH₃ | H |
| 386 | —OCH₃ | —OCH₃ | H | H | —OCH₃ |
| 387 | —OCH₃ | H | —OCH₃ | H | —OCH₃ |
| 388 | —OCH₃ | H | —OCH₃ | —OCH₃ | H |
| 389 | H | —OCH₃ | —OCH₃ | —OCH₃ | H |
| 390 | H | —OCH₃ | H | —OCH₃ | —OCH₃ |
| 391 | H | H | —OCH₃ | —OCH₃ | —OCH₃ |
| 392 | —CF₃ | —Y¹ | —Y¹ | H | H |
| 393 | —CF₃ | —Y¹ | H | —Y¹ | H |
| 394 | —CF₃ | —Y¹ | H | H | —Y¹ |
| 395 | —CF₃ | H | —Y¹ | H | —Y¹ |
| 396 | —CF₃ | H | —Y¹ | —Y¹ | H |
| 397 | H | —CF₃ | —Y¹ | —Y¹ | H |
| 398 | H | —CF₃ | H | —Y¹ | —Y¹ |
| 399 | H | H | —CF₃ | —Y¹ | —Y¹ |
| 400 | —Y¹ | —CF₃ | —Y¹ | H | H |
| 401 | —Y¹ | —CF₃ | H | —Y¹ | H |
| 402 | —Y¹ | —CF₃ | H | H | —Y¹ |
| 403 | —Y¹ | H | —CF₃ | H | —Y¹ |
| 404 | —Y¹ | H | —CF₃ | —Y¹ | H |
| 405 | H | —Y¹ | —CF₃ | —Y¹ | H |
| 406 | H | —Y¹ | H | —CF₃ | —Y¹ |
| 407 | H | H | —Y¹ | —CF₃ | —Y¹ |
| 408 | —Y¹ | —Y¹ | —CF₃ | H | H |
| 409 | —Y¹ | —Y¹ | H | —CF₃ | H |
| 410 | —Y¹ | —Y¹ | H | H | —CF₃ |
| 411 | —Y¹ | H | —Y¹ | H | —CF₃ |
| 412 | —Y¹ | H | —Y¹ | —CF₃ | H |
| 413 | H | —Y¹ | —Y¹ | —CF₃ | H |
| 414 | H | —Y¹ | H | —Y¹ | —CF₃ |
| 415 | H | H | —Y¹ | —Y¹ | —CF₃ |
| 416 | —Y¹ | —Y¹ | —CF₃ | H | H |
| 417 | —Y¹ | —Y¹ | H | —CF₃ | H |
| 418 | —Y¹ | —Y¹ | H | H | —CF₃ |
| 419 | —Y¹ | H | —Y¹ | H | —CF₃ |
| 420 | —Y¹ | H | —Y¹ | —CF₃ | H |
| 421 | H | —Y¹ | —Y¹ | —CF₃ | H |
| 422 | H | —Y¹ | H | —Y¹ | —CF₃ |
| 423 | H | H | —Y¹ | —Y¹ | —CF₃ |

In an exemplary embodiment, the compound of the invention has the following structure:

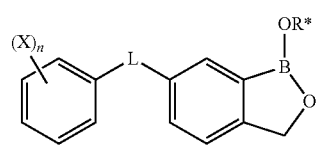

(I)

wherein n is an integer from 0 to 5, each X is an independently selected halogen, R* is selected from the group consisting of H, a negative charge and a positively charged counterion, and L is selected from the group consisting of —S—, —S(O)—, —SO₂—, —O—, —C(O)—, —C(OH)—, ''—CH₂O—', ''—CH₂NH—', ''—C(O)NH—', ''—NHC(O)—', ''—NHC(O)O—', and —CH₂—, wherein '' indicates a covalent linkage between L and the phenyl ring, and wherein ' indicates a covalent linkage between L and the boron-containing moiety, or a salt thereof.

In an exemplary embodiment, n is 0 and L is selected from the group consisting of —S(O)—, —SO₂—, —C(O)—, —C(OH)—, ''—CH₂O—', ''—NHC(O)O—' and —CH₂—, wherein '' indicates a covalent linkage between L and the phenyl ring, and wherein ' indicates a covalent linkage between L and the boron-containing moiety. In an exemplary embodiment, n is 0 and L is ''—NHC(O)—', wherein '' indicates a covalent linkage between L and the phenyl ring, and wherein ' indicates a covalent linkage between L and the boron-containing moiety. In another exemplary embodiment, R* is H.

In an exemplary embodiment, n is 1 and L is selected from the group consisting of —S—, —S(O)— and —SO₂—, and there is a proviso that the compound is not

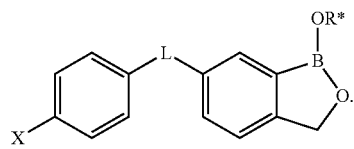

In an exemplary embodiment, there is a proviso that the compound is not

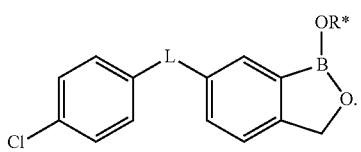

In an exemplary embodiment, n is 2 and L is selected from the group consisting of —S—, —S(O)— and —SO₂—. In an exemplary embodiment, n is 2, X is Cl and L is selected from the group consisting of —S—, —S(O)— and —SO₂—. In an exemplary embodiment, n is 2, X is F and L is selected from the group consisting of —S—, —S(O)— and —SO₂—. In an exemplary embodiment, n is 2, each X is F or Cl, wherein at least one X is Cl, and L is selected from the group consisting of —S—, —S(O)— and —SO₂—.

In an exemplary embodiment, n is 3 and L is selected from the group consisting of —S—, —S(O)— and —SO₂—. In an exemplary embodiment, n is 4 and L is selected from the group consisting of —S—, —S(O)— and —SO₂—. In an exemplary embodiment, n is 5 and L is selected from the group consisting of —S—, —S(O)— and —SO₂—.

In an exemplary embodiment, the compound has a structure according to the following formula:

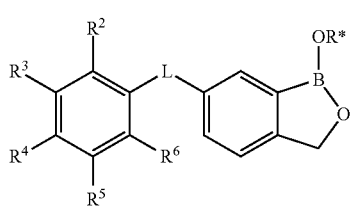

(II)

wherein R* is selected from the group consisting of H, a negative charge and a positively charged counterion, L is selected from the group consisting of —S—, —S(O)—, —SO$_2$—, —O—, —C(O)—, —C(OH)—, "—CH$_2$O—', "—CH$_2$NH—', "—C(O)NH—', "—NHC(O)—', "—NHC(O)O—', and —CH$_2$—, wherein " indicates a covalent linkage between L and the phenyl ring, and wherein ' indicates a covalent linkage between L and the boron-containing moiety, and R$^2$, R$^3$, R$^4$, R$^5$ and R$^6$ are members selected from the following table, or a salt thereof. In an exemplary embodiment, L is —S—, and R$^2$, R$^3$, R$^4$, R$^5$ and R$^6$ are members selected from the following table. In an exemplary embodiment, L is —S(O)—, and R$^2$, R$^3$, R$^4$, R$^5$ and R$^6$ are members selected from the following table. In an exemplary embodiment, L is —SO$_2$—, and R$^2$, R$^3$, R$^4$, R$^5$ and R$^6$ are according to the entries in the following table, or a salt thereof

|     | R$^2$ | R$^3$ | R$^4$ | R$^5$ | R$^6$ |
| --- | --- | --- | --- | --- | --- |
| 424 | Cl | H | H | H | H |
| 425 | H | Cl | H | H | H |
| 426 | H | H | Cl | H | H |
| 427 | Cl | Cl | H | H | H |
| 428 | Cl | H | Cl | H | H |
| 429 | Cl | H | H | Cl | H |
| 430 | Cl | H | H | H | Cl |
| 431 | H | Cl | Cl | H | H |
| 432 | H | Cl | H | Cl | H |
| 433 | Cl | Cl | Cl | H | H |
| 434 | Cl | Cl | H | Cl | H |
| 435 | Cl | Cl | H | H | Cl |
| 436 | Cl | H | Cl | H | Cl |
| 437 | H | Cl | Cl | Cl | H |
| 438 | Cl | Cl | Cl | Cl | H |
| 439 | Cl | Cl | Cl | H | Cl |
| 440 | Cl | Cl | H | Cl | Cl |
| 441 | Cl | Cl | Cl | Cl | Cl |
| 442 | F | H | H | H | H |
| 443 | H | F | H | H | H |
| 444 | H | H | F | H | H |
| 445 | F | F | H | H | H |
| 446 | F | H | F | H | H |
| 447 | F | H | H | F | H |
| 448 | F | H | H | H | F |
| 449 | H | F | F | H | H |
| 450 | H | F | H | F | H |
| 451 | F | F | F | H | H |
| 452 | F | F | H | F | H |
| 453 | F | F | H | H | F |
| 454 | F | H | F | H | F |
| 455 | H | F | F | F | H |
| 456 | F | F | F | F | H |
| 457 | F | F | F | H | F |
| 458 | F | F | H | F | F |
| 459 | F | F | F | F | F |
| 460 | Cl | F | H | H | H |
| 461 | F | Cl | H | H | H |
| 462 | Cl | H | F | H | H |
| 463 | F | H | Cl | H | H |
| 464 | Cl | H | H | F | H |
| 465 | F | H | H | Cl | H |
| 466 | Cl | H | H | H | F |
| 467 | F | H | H | H | Cl |
| 468 | H | Cl | F | H | H |
| 469 | H | F | Cl | H | H |
| 470 | H | Cl | H | F | H |
| 471 | H | F | H | Cl | H |
| 472 | Cl | F | F | H | H |
| 473 | F | Cl | F | H | H |
| 474 | F | F | Cl | H | H |
| 475 | Cl | Cl | F | H | H |
| 476 | F | Cl | Cl | H | H |
| 477 | Cl | F | Cl | H | H |
| 478 | Cl | F | H | F | H |
| 479 | F | Cl | H | F | H |
| 480 | F | F | H | Cl | H |
| 481 | Cl | Cl | H | F | H |
| 482 | Cl | F | H | Cl | H |
| 483 | F | Cl | H | Cl | H |
| 485 | Cl | F | H | H | F |
| 486 | F | Cl | H | H | F |
| 487 | F | F | H | H | Cl |
| 488 | Cl | Cl | H | H | F |
| 489 | Cl | F | H | H | Cl |
| 490 | F | Cl | H | H | Cl |
| 491 | Cl | H | F | H | F |
| 492 | F | H | Cl | H | F |
| 493 | Cl | H | Cl | H | F |
| 494 | Cl | H | F | H | Cl |
| 495 | H | Cl | F | F | H |
| 496 | H | F | Cl | F | H |
| 497 | H | Cl | Cl | F | H |
| 498 | H | Cl | F | Cl | H |
| 499 | Cl | F | F | F | H |
| 500 | F | Cl | F | F | H |
| 501 | F | F | Cl | F | H |
| 502 | F | F | F | Cl | H |
| 503 | Cl | Cl | F | F | H |
| 504 | Cl | F | Cl | F | H |
| 505 | Cl | F | F | Cl | H |
| 506 | F | Cl | Cl | F | H |
| 507 | F | Cl | Cl | Cl | H |
| 508 | Cl | F | Cl | Cl | H |
| 509 | Cl | Cl | F | Cl | H |
| 510 | Cl | Cl | Cl | F | H |
| 511 | F | F | F | F | H |
| 512 | Cl | F | F | H | F |
| 513 | F | Cl | F | H | F |
| 514 | F | F | Cl | H | F |
| 515 | F | F | F | H | Cl |
| 516 | Cl | Cl | F | H | F |
| 517 | Cl | F | Cl | H | F |
| 518 | Cl | F | F | H | Cl |
| 519 | F | Cl | Cl | H | F |
| 520 | F | F | Cl | H | Cl |
| 521 | Cl | Cl | Cl | H | F |
| 522 | Cl | Cl | F | H | Cl |
| 523 | Cl | F | Cl | H | Cl |
| 524 | F | Cl | Cl | H | Cl |
| 525 | Cl | F | H | F | F |
| 526 | F | Cl | H | F | F |
| 527 | Cl | Cl | H | F | F |
| 528 | Cl | F | H | Cl | F |
| 529 | Cl | F | H | F | Cl |
| 530 | F | Cl | H | Cl | F |
| 531 | Cl | Cl | H | Cl | F |
| 532 | Cl | Cl | H | F | Cl |
| 533 | F | Cl | Cl | Cl | Cl |
| 534 | Cl | F | Cl | Cl | Cl |
| 535 | Cl | Cl | F | Cl | Cl |
| 536 | F | F | Cl | Cl | Cl |
| 537 | F | Cl | F | Cl | Cl |
| 538 | F | Cl | Cl | F | Cl |
| 539 | F | Cl | Cl | Cl | F |
| 540 | Cl | F | Cl | F | Cl |
| 541 | Cl | Cl | F | F | Cl |
| 542 | F | F | F | Cl | Cl |
| 543 | F | F | Cl | F | Cl |
| 544 | F | Cl | F | F | Cl |
| 546 | Cl | F | F | F | Cl |
| 547 | F | Cl | F | Cl | F |
| 548 | F | Cl | Cl | F | F |
| 549 | Cl | F | F | F | F |
| 550 | F | Cl | F | F | F |
| 551 | F | F | Cl | F | F |

In an exemplary embodiment, the compound of the invention has the following structure:

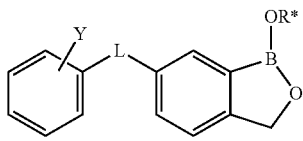

(III)

wherein Y is either halo-substituted $C_1$-$C_6$ alkyl or unsubstituted $C_1$-$C_6$ alkyl, and R* is selected from the group consisting of H, a negative charge and a positively charged counterion, L is selected from the group consisting of —S—, —S(O)—, —SO$_2$—, —O—, —C(O)—, —C(OH)—, "—CH$_2$O—', "—CH$_2$NH—', "—C(O)NH—', "—NHC(O)—', "—NHC(O)O—', and —CH$_2$—, wherein " indicates a covalent linkage between L and the phenyl ring, and wherein ' indicates a covalent linkage between L and the boron-containing moiety, or a salt thereof. In an exemplary embodiment, L is "—C(O)NH—' or "—NHC(O)—'.

In an exemplary embodiment, the compound has the following structure:

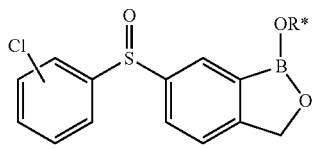

In an exemplary embodiment, the compound has the proviso that the compound is not

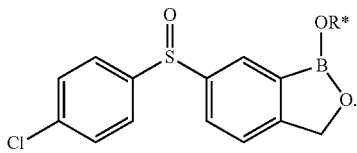

In an exemplary embodiment, the compound has structure which is

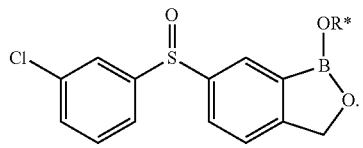

In an exemplary embodiment, the compound has structure which is

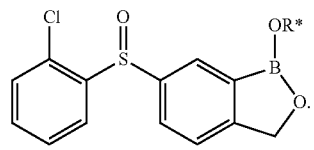

In an exemplary embodiment, the compound has a structure according to the following formula:

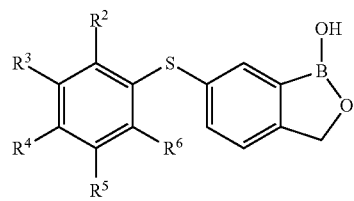

(II)

wherein $R^2$, $R^3$, $R^4$, $R^5$ and $R^6$ are members selected from the following table, or a salt thereof

|  | $R^2$ | $R^3$ | $R^4$ | $R^5$ | $R^6$ |
| --- | --- | --- | --- | --- | --- |
| 552 | H | H | H | H | H |
| 553 | NO$_2$ | H | H | H | H |
| 554 | H | NO$_2$ | H | H | H |
| 555 | H | H | NO$_2$ | H | H |
| 556 | H | H | H | NO$_2$ | H |
| 557 | H | H | H | H | NO$_2$ |
| 558 | C(O)OR$^{20}$ | H | H | H | H |
| 559 | H | C(O)OR$^{20}$ | H | H | H |
| 560 | H | H | C(O)OR$^{20}$ | H | H |
| 561 | H | H | H | C(O)OR$^{20}$ | H |
| 562 | H | H | H | H | C(O)OR$^{20}$ |
| 563 | C(O)OCH$_3$ | H | H | H | H |
|  | H | C(O)OCH$_3$ | H | H | H |
| 564 | H | H | C(O)OCH$_3$ | H | H |
| 565 | H | H | H | C(O)OCH$_3$ | H |
| 566 | H | H | H | H | C(O)OCH$_3$ |
| 567 | OR$^{20}$ | H | H | H | H |
| 568 | H | OR$^{20}$ | H | H | H |
| 569 | H | H | OR$^{20}$ | H | H |
| 570 | H | H | H | OR$^{20}$ | H |
| 571 | H | H | H | H | OR$^{20}$ |
| 572 | OCH$_3$ | H | H | H | H |
| 573 | H | OCH$_3$ | H | H | H |
| 574 | H | H | OCH$_3$ | H | H |
| 575 | H | H | H | OCH$_3$ | H |

-continued

| | R² | R³ | R⁴ | R⁵ | R⁶ |
|---|---|---|---|---|---|
| 576 | H | H | H | H | OCH₃ |
| 577 | NR²¹R²² | H | H | H | H |
| 578 | H | NR²¹R²² | H | H | H |
| 579 | H | H | NR²¹R²² | H | H |
| 580 | H | H | H | NR²¹R²² | H |
| 581 | H | H | H | H | NR²¹R²² |
| 582 | NHR²² | H | H | H | H |
| 583 | H | NHR²² | H | H | H |
| 584 | H | H | NHR²² | H | H |
| 585 | H | H | H | NHR²² | H |
| 586 | H | H | H | H | NHR²² |
| 587 | NHC(O)R¹⁵ | H | H | H | H |
| 588 | H | NHC(O)R¹⁵ | H | H | H |
| 589 | H | H | NHC(O)R¹⁵ | H | H |
| 590 | H | H | H | NHC(O)R¹⁵ | H |
| 591 | H | H | H | H | NHC(O)R¹⁵ |
| 592 | NH₂ | H | H | H | H |
| 593 | H | NH₂ | H | H | H |
| 594 | H | H | NH₂ | H | H |
| 595 | H | H | H | NH₂ | H |
| 596 | H | H | H | H | NH₂ |

For the respective entries in this table, R²⁰ is unsubstituted alkyl. For the respective entries in this table, R²¹ is H or unsubstituted alkyl. For the respective entries in this table, R²² is H or unsubstituted alkyl. In an exemplary embodiment, R¹⁵ in NHC(O)R¹⁵ is selected from the group consisting of substituted or unsubstituted alkyl, substituted or unsubstituted phenyl and substituted or unsubstituted cyclohexyl. In an exemplary embodiment, R¹⁵ in NHC(O)R¹⁵ is selected from the group consisting of unsubstituted alkyl, haloalkylsubstituted phenyl, unsubstituted phenyl and unsubstituted cyclohexyl. In an exemplary embodiment, R¹⁵ in NHC(O)R¹⁵ is selected from the group consisting of methyl, trifluoromethylsubstitutedphenyl, unsubstituted phenyl and unsubstituted cyclohexyl. In an exemplary embodiment, R¹⁵ in NHC(O)R¹⁵ is selected from the group consisting of methyl, halosubstitutedphenyl, alkoxy substitutedphenyl, trifluoromethylsubstitutedphenyl, unsubstituted phenyl and unsubstituted cyclohexyl.

In an exemplary embodiment, the compound has a structure according to the following formula:

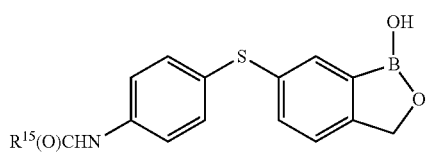

wherein R¹⁵ is selected from the group consisting of methyl, halosubstitutedphenyl, alkoxy substitutedphenyl, trifluoromethyl substitutedphenyl, unsubstituted phenyl and unsubstituted cyclohexyl. In an exemplary embodiment, R¹⁵ is selected from the group consisting of ortho-trifluoromethylsubstitutedphenyl, meta-trifluoromethylsubstitutedphenyl and para-trifluoromethylsubstitutedphenyl. In an exemplary embodiment, R¹⁵ is para-trifluoromethylsubstitutedphenyl. In an exemplary embodiment, R¹⁵ is selected from the group consisting of ortho-halosubstitutedphenyl, meta-halosubstitutedphenyl and para-halosubstitutedphenyl. In an exemplary embodiment, R¹⁵ is ortho-fluorophenyl. In an exemplary embodiment, R¹⁵ is meta-fluorophenyl. In an exemplary embodiment, R¹⁵ is para-fluorophenyl. In an exemplary embodiment, R¹⁵ is ortho-chlorophenyl. In an exemplary embodiment, R¹⁵ is meta-chlorophenyl. In an exemplary embodiment, R¹⁵ is para-chlorophenyl. In an exemplary embodiment, R¹⁵ is ortho-alkoxyphenyl. In an exemplary embodiment, R¹⁵ is meta-alkoxyphenyl. In an exemplary embodiment, R¹⁵ is para-alkoxyphenyl. In an exemplary embodiment, R¹⁵ is ortho-methoxyphenyl. In an exemplary embodiment, R¹⁵ is meta-methoxyphenyl. In an exemplary embodiment, R¹⁵ is para-methoxyphenyl.

In an exemplary embodiment, the compound of the invention is

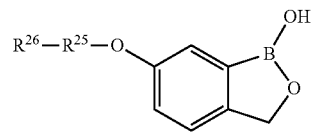

wherein R²⁵ is unsubstituted linear alkylene, and R²⁶ is halosubstituted aryl. In an exemplary embodiment, R²⁵ is unsubstituted linear alkylene, and R²⁶ is monohaloaryl. In an exemplary embodiment, R²⁵ is unsubstituted linear alkylene, and R²⁶ is 4-haloaryl. In an exemplary embodiment, R²⁵ is unsubstituted linear alkylene, and R²⁶ is 3-haloaryl. In an exemplary embodiment, R²⁵ is unsubstituted linear alkylene, and R²⁶ is 2-haloaryl. In an exemplary embodiment, R²⁵ is methylene, and R²⁶ is 4-haloaryl. In an exemplary embodiment, R²⁵ is methylene, and R²⁶ is 3-haloaryl. In an exemplary embodiment, R²⁵ is methylene, and R²⁶ is 2-haloaryl.

In an exemplary embodiment, the compound has a structure according to the following formula:

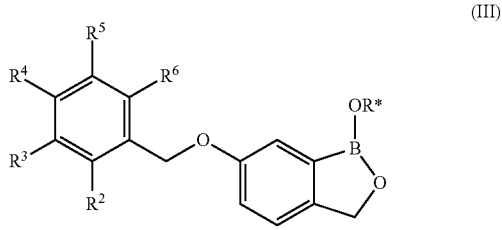

(III)

wherein R* is selected from the group consisting of H, a negative charge and a positively charged counterion, and R², R³, R⁴, R⁵ and R⁶ are members selected from the following table, or a salt thereof.

|     | R² | R³ | R⁴ | R⁵ | R⁶ |
|-----|----|----|----|----|----|
| 597 | Cl | H  | H  | H  | H  |
| 598 | H  | Cl | H  | H  | H  |
| 599 | H  | H  | Cl | H  | H  |
| 600 | Cl | Cl | H  | H  | H  |
| 601 | Cl | H  | Cl | H  | H  |
| 602 | Cl | H  | H  | Cl | H  |
| 603 | Cl | H  | H  | H  | Cl |
| 604 | H  | Cl | Cl | H  | H  |
| 605 | H  | Cl | H  | Cl | H  |
| 606 | Cl | Cl | Cl | H  | H  |
| 607 | Cl | Cl | H  | Cl | H  |
| 608 | Cl | Cl | H  | H  | Cl |
| 609 | Cl | H  | Cl | H  | Cl |
| 610 | H  | Cl | Cl | Cl | H  |
| 611 | Cl | Cl | Cl | Cl | H  |
| 612 | Cl | Cl | Cl | H  | Cl |
| 613 | Cl | Cl | H  | Cl | Cl |
| 614 | Cl | Cl | Cl | Cl | Cl |
| 615 | F  | H  | H  | H  | H  |
| 616 | H  | F  | H  | H  | H  |
| 617 | H  | H  | F  | H  | H  |
| 618 | F  | F  | H  | H  | H  |
| 619 | F  | H  | F  | H  | H  |
| 620 | F  | H  | H  | F  | H  |
| 621 | F  | H  | H  | H  | F  |
| 622 | H  | F  | F  | H  | H  |
| 623 | H  | F  | H  | F  | H  |
| 624 | F  | F  | F  | H  | H  |
| 625 | F  | F  | H  | F  | H  |
| 626 | F  | F  | H  | H  | F  |
| 627 | F  | H  | F  | H  | F  |
| 628 | H  | F  | F  | F  | H  |
| 629 | F  | F  | F  | F  | H  |
| 630 | F  | F  | F  | H  | F  |
| 631 | F  | F  | H  | F  | F  |
| 632 | F  | F  | F  | F  | F  |

In an exemplary embodiment, the compound has a structure which is

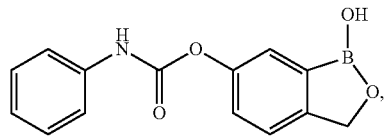 [SMILES: O=C(Nc1ccccc1)Oc1ccc2c(c1)B(O)OC2]

or a salt thereof. In an exemplary embodiment, the compound has a structure which is

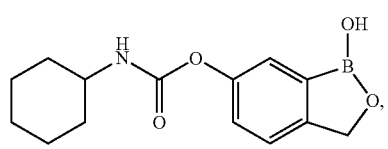 [SMILES: O=C(NC1CCCCC1)Oc1ccc2c(c1)B(O)OC2]

or a salt thereof.

In an exemplary embodiment, the compound of the invention has a structure which is

or salts thereof. In an exemplary embodiment, the compound of the invention has a structure which is

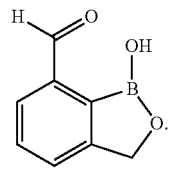

In an exemplary embodiment, the compound of the invention has a structure which is

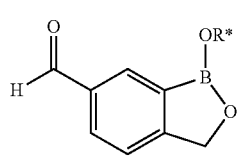

or salts thereof. In an exemplary embodiment, the compound of the invention has a structure which is

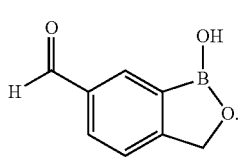

In an exemplary embodiment, the compound of the invention is

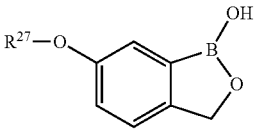

wherein R²⁷ is selected from the group consisting of unsubstituted indolyl, unsubstituted benzothiooxazolyl, and halo-substituted or unsubstituted pyrimidinyl.

In an exemplary embodiment, the compound of the invention is

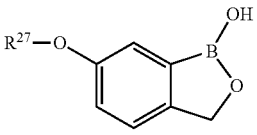

wherein R²⁷ is unsubstituted pyrimidinyl. In an exemplary embodiment, the compound is

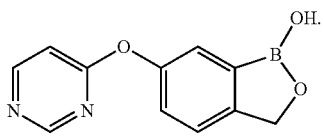 [SMILES: OB1OCc2ccc(Oc3ccncn3)cc21]

In an exemplary embodiment, the compound of the invention is

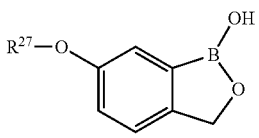

wherein $R^{27}$ is halosubstituted pyrimidinyl. In an exemplary embodiment, $R^{27}$ is monohalosubstituted pyrimidinyl. In an exemplary embodiment, $R^{27}$ is chlorosubstituted pyrimidinyl. In an exemplary embodiment, the compound is

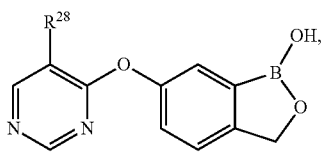

wherein $R^{28}$ is selected from the group consisting of F, Cl, Br and I. In an exemplary embodiment, the compound is

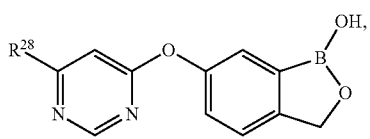

wherein $R^{28}$ is selected from the group consisting of F, Cl, Br and I. In an exemplary embodiment, the compound is

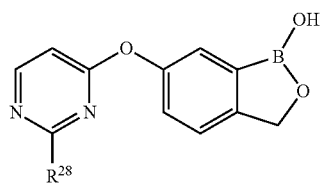

wherein $R^{28}$ is selected from the group consisting of F, Cl, Br and I. In an exemplary embodiment, $R^{28}$ is F. In an exemplary embodiment, the compound is

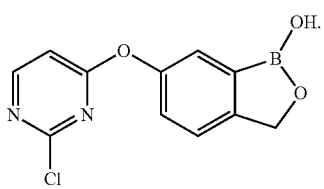 [SMILES: OB1OCc2ccc(Oc3ccnc(Cl)n3)cc21]

In an exemplary embodiment, the compound of the invention is

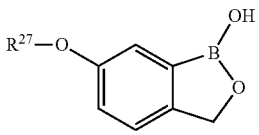

wherein $R^{27}$ is unsubstituted indolyl. In an exemplary embodiment, the compound is

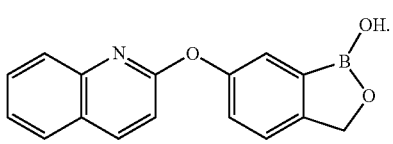 [SMILES: OB1OCc2ccc(Oc3ccc4ccccc4n3)cc21]

In an exemplary embodiment, the compound of the invention is

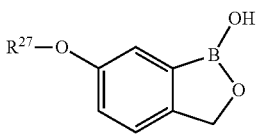

wherein $R^{27}$ is unsubstituted indolyl. In an exemplary embodiment, the compound is

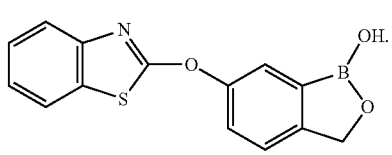 [SMILES: OB1OCc2ccc(Oc3nc4ccccc4s3)cc21]

In an exemplary embodiment, the cytotoxicity on murine L929 IC50 of a compound of the invention is a member selected from about 1 μM to 20 μM. In an exemplary embodiment, the cytotoxicity on murine L929 IC50 of a compound of the invention is a member selected from about 10 μM to 15 μM.

In an exemplary embodiment, the selectivity index (SI) of a compound of the invention is between about 50-150. In an exemplary embodiment, the selectivity index (SI) of N-(1-hydroxy-1,3-dihydrobenzo[c][1,2]oxaborol-6-yl)-2-(trifluoromethyl)benzamide is between about 75-100. In an exemplary embodiment, the selectivity index (SI) of 6-(4-chlorophenylsulfinyl)benzo[c][1,2]oxaborol-1(3H)-ol is greater than about 75-100.

In an exemplary embodiment, the in vitro metabolism T1/2 (Mouse/human liver microsomes) of a compound of the invention is a member selected from about 300 minutes to 400 minutes. In an exemplary embodiment, the in vitro metabolism T1/2 (Mouse/human liver microsomes) of a compound of the invention is a member selected from about 340 minutes to 360 minutes. In an exemplary embodiment, the in vitro metabolism T1/2 (Mouse/human liver microsomes) of N-(1-hydroxy-1,3-dihydrobenzo[c][1,2]oxaborol-6-yl)-2-(trifluoromethyl)benzamide is a member selected from about 340 minutes to 360 minutes. In an exemplary embodiment, the in vitro metabolism T1/2 (Mouse/human liver microsomes) of 6-(4-chlorophenyl sulfinyl)benzo[c][1,2]oxaborol-1(3H)-ol is greater than 350 minutes.

In an exemplary embodiment, the in vitro metabolism T1/2 (Mouse S9) of a compound of the invention is a member selected from about 100 minutes to 300 minutes. In an exemplary embodiment, the in vitro metabolism T1/2 (Mouse S9) of N-(1-hydroxy-1,3-dihydrobenzo[c][1,2]oxaborol-6-yl)-2-(trifluoromethyl)benzamide is a member selected from about 200 minutes to 225 minutes.

In an exemplary embodiment, a compound of the invention essentially does not inhibit a cytochrome P450 enzyme. In an exemplary embodiment, a compound of the invention does not inhibit a cytochrome P450 enzyme. In an exemplary embodiment, N-(1-hydroxy-1,3-dihydrobenzo[c][1,2]oxaborol-6-yl)-2-(trifluoromethyl)benzamide essentially does not inhibit a cytochrome P450 enzyme. In an exemplary embodiment, N-(1-hydroxy-1,3-dihydrobenzo[c][1,2]oxaborol-6-yl)-2-(trifluoromethyl)benzamide does not inhibit a cytochrome P450 enzyme. In an exemplary embodiment, 6-(4-chlorophenylsulfinyl)benzo[c][1,2]oxaborol-1(3H)-ol essentially does not inhibit a cytochrome P450 enzyme. In an exemplary embodiment, 6-(4-chlorophenylsulfinyl)benzo[c][1,2]oxaborol-1(3H)-ol does not inhibit a cytochrome P450 enzyme. In an exemplary embodiment, the cytochrome P450 enzyme is a member selected from CP1A2, 2C9, 2D6 and 3A4. In an exemplary embodiment, the cytochrome P450 enzyme is CYP2C19.

In an exemplary embodiment, a compound of the invention is essentially not a substrate for the P-gp transporter. In an exemplary embodiment, a compound of the invention is not a substrate for the P-gp transporter. In an exemplary embodiment, N-(1-hydroxy-1,3-dihydrobenzo[c][1,2]oxaborol-6-yl)-2-(trifluoromethyl)benzamide is essentially not a substrate for the P-gp transporter. In an exemplary embodiment, N-(1-hydroxy-1,3-dihydrobenzo[c][1,2]oxaborol-6-yl)-2-(trifluoromethyl)benzamide is not a substrate for the P-gp transporter.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

III.b) Compositions Involving Stereoisomers

As used herein, the term "chiral", "enantiomerically enriched" or "diastereomerically enriched" refers to a composition having an enantiomeric excess (ee) or a diastereomeric excess (de) of greater than about 50%, preferably greater than about 70% and more preferably greater than about 90%. In general, higher than about 90% enantiomeric or diastereomeric excess is particularly preferred, e.g., those compositions with greater than about 95%, greater than about 97% and greater than about 99% ee or de.

When a first compound and a second compound are present in a composition, and the first compound is a non-superimposable mirror image of the second compound, and the first compound is present in the composition in a greater amount than the second compound, then the first compound is referred to herein as being present in "enantiomeric excess".

The term "enantiomeric excess" of a compound z, as used herein, is defined as:

$$ee_z = \left(\frac{conc.\ of\ z - conc.\ of\ y}{conc.\ of\ z + conc.\ of\ y}\right) \times 100$$

wherein z is a first compound in a composition, y is a second compound in the composition, and the first compound is a non-superimposable mirror image of the second compound.

The term "enantiomeric excess" is related to the older term "optical purity" in that both are measures of the same phenomenon. The value of ee will be a number from 0 to 100, zero being racemic and 100 being enantiomerically pure. A composition which in the past might have been called 98% optically pure is now more precisely characterized by 96% ee. A 90% ee reflects the presence of 95% of one enantiomer and 5% of the other(s) in the material in question.

When a first compound and at least one additional compound are present in a composition, and the first compound and each of the additional compounds are stereoisomers, but not mirror images, of one another, and the first compound is present in the composition in a greater amount than each of the additional compounds, then the first compound is referred to herein as being present in "diastereomeric excess".

When dealing with mixtures of diastereomers, the term "diastereomeric excess" or "de" is defined analogously to enantiomeric excess. Thus:

$$de_w = \left(\frac{conc.\ of\ major\ diastereomer - conc.\ of\ minor\ diastereomer(s)}{conc.\ of\ major\ diastereomer + conc.\ of\ minor\ diastereomer(s)}\right) \times 100$$

wherein the major diastereomer is a first compound in a composition, and the minor diastereomer(s) is at least one additional compound in the composition, and the major diastereomer and minor diastereomer(s) are stereoisomers, but not mirror images, of one another.

The value of de will likewise be a number from 0 to 100, zero being an equal mixture of a first diastereomer and the remaining diastereomer(s), and 100 being 100% of a single diastereomer and zero % of the other(s)—i.e. diastereomerically pure. Thus, 90% de reflects the presence of 95% of one diastereomer and 5% of the other diastereomer(s) in the material in question.

Hence, in one embodiment, the invention provides a composition including a first compound of the invention, wherein the first compound of the invention has at least one stereocenter, and at least one stereoisomer of the first compound of the invention. In another embodiment, the invention provides a composition including a first compound of the invention, wherein the first compound of the invention has at least one stereocenter, and a second compound of the invention, wherein the first compound of the invention is a stereoisomer of the second compound of the invention. In another embodiment, the invention provides a composition including a first compound of the invention, wherein the first compound of the invention has at least one stereocenter, and only one stereoisomer of the first compound of the invention.

In another embodiment, the invention provides a composition including a first compound of the invention, wherein the first compound of the invention has only one stereocenter, and an enantiomer of the first compound of the invention. In another embodiment, the invention provides a composition including a first compound of the invention, wherein the first compound of the invention has two stereocenters, and an enantiomer of the first compound of the invention. In another embodiment, the invention provides a composition including a first compound of the invention, wherein the first compound of the invention has two stereocenters, and at least one diastereomer of the first compound of the invention. In another embodiment, the invention provides a composition including a first compound of the invention, wherein the first compound of the invention has two stereocenters, and only one diastereomer of the first compound of the invention.

In situations where the first compound of the invention and its enantiomer are present in a composition, the first compound of the invention can be present in an enantiomeric excess of at least about 80%, or at least about 90%, or at least about 92% or at least about 95%. In another embodiment, where the first compound of the invention and its enantiomer are present in a composition, the first compound of the invention can be present in an enantiomeric excess of at least about 96%, at least about 97%, at least about 98%, at least about 99% or at least about 99.5%. In another embodiment, the first compound of the invention has at least one stereocenter and is enantiomerically pure (enantiomeric excess is about 100%).

In situations where the first compound of the invention and at least one diastereomer of the first compound of the invention are present in a composition, the first compound of the invention can be present in a diastereomeric excess of at least about 80%, or at least about 90%, or at least about 92% or at least about 95%. In situations where the first compound of the invention and at least one diastereomer of the first compound of the invention are present in a composition, the first compound of the invention can be present in a diastereomeric excess of at least about 96%, at least about 97%, at least about 98%, at least about 99% or at least about 99.5%. In another embodiment, the first compound of the invention has at least two stereocenters and is diastereomerically pure (diastereomeric excess is about 100%).

Enantiomeric or diastereomeric excess can be determined relative to exactly one other stereoisomer, or can be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

As used herein, and unless otherwise indicated, a composition that is "substantially free" of a compound means that the composition contains less than about 20% by weight, or less than about 15% by weight, or less than about 10% by weight, or less than about 5% by weight, or less than about 3% by weight, or less than about 2% by weight, or less than about 1% by weight of the compound.

As used herein, the term "substantially free of the (or its) enantiomer" means that a composition contains a significantly greater proportion of a first compound of the invention than a second compound of the invention, wherein the first compound is a non-superimposable mirror image of the second compound. In one embodiment of the invention, the term "substantially free of the enantiomer" means that the composition is made up of at least about 90% by weight of a first compound of the invention, and about 10% by weight or less of a second compound of the invention, wherein the first compound is a non-superimposable mirror image of the second compound. In one embodiment of the invention, the term "substantially free of the (R) enantiomer" means that the composition is made up of at least about 90% by weight of a first compound of the invention which has only one stereocenter and the stereocenter is in an (S) configuration, and about 10% by weight or less of a second compound of the invention, wherein the second compound is the enantiomer of the first compound. In one embodiment of the invention, the term "substantially free of the enantiomer" means that the composition is made up of at least about 95% by weight of a first compound of the invention, and about 5% by weight or less of a second compound of the invention, wherein the first compound is a non-superimposable mirror image of the second compound. In one embodiment of the invention, the term "substantially free of the (R) enantiomer" means that the composition is made up of at least about 95% by weight of a first compound of the invention which has only one stereocenter and the stereocenter is in an (S) configuration, and about 5% by weight or less of a second compound of the invention, wherein the second compound is the enantiomer of the first compound. In one embodiment of the invention, the term "substantially free of the enantiomer" means that the composition is made up of at least about 98% by weight of a first compound of the invention, and about 2% by weight or less of a second compound of the invention, wherein the first compound is a non-superimposable mirror image of the second compound. In one embodiment of the invention, the term "substantially free of the (R) enantiomer" means that the composition is made up of at least about 98% by weight of a first compound of the invention which has only one stereocenter and the stereocenter is in an (S) configuration, and about 2% by weight or less of a second compound of the invention, wherein the second compound is the enantiomer of the first compound. In one embodiment of the invention, the term "substantially free of the enantiomer" means that the composition is made up of at least about 99% by weight of a first compound of the invention, and about 1% by weight or less of a second compound of the invention, wherein the first compound is a non-superimposable mirror image of the second compound. In one embodiment of the invention, the term "substantially free of the (R) enantiomer" means that the composition is made up of at least about 99% by weight of a first compound of the invention which has only one stereocenter and the stereocenter is in an (S) configuration, and about 1% by weight or less of a second compound of the invention, wherein the second compound is the enantiomer of the first compound.

III.b) Combinations Comprising Additional Therapeutic Agents

The compounds of the invention may also be used in combination with additional therapeutic agents. The invention thus provides, in a further aspect, a combination comprising a compound described herein or a pharmaceutically acceptable salt thereof together with at least one additional therapeutic agent. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom.

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. In an exemplary embodiment, the additional therapeutic agent is Berenil. In an exemplary embodiment, the additional therapeutic agent is an antiprotozoa. In an exemplary embodiment, the additional therapeutic agent is a member selected from Benznidazole, Buparvaquone, Carbarsone, Clioquinol, Disulfuram, Eflornithine, Emetine, Etofamide, Furazolidone, Meglumine antimonate, Melarsoprol, Metronidazole, Miltefosine, Nifurtimox, Nimorazole, Nitazoxanide, Ornidazole, Paromomycin sulfate, Pentamidine, Pyrimethamine, Secnidazole and Tinidazole. In an exemplary embodiment, the additional therapeutic agent is pentamidine. In an exemplary embodiment, the additional therapeutic agent is suramin. In an exemplary embodiment, the additional therapeutic agent is Eflornithine. In an exemplary embodiment, the additional therapeutic agent is Melarsoprol. In an exemplary embodiment, the additional therapeutic agent is Nifurtimox. In an exemplary embodiment, the additional therapeutic agent is an antiparasitic. In an exemplary embodiment, the additional therapeutic agent is a member selected from Amitraz, Avermectin, Carbadox, Diethylcarbamazine, Dimetridazole, Diminazene, Ivermectin, Macrofilaricide, Malathion, Mitaban, Organophosphate, Oxamniquine, Permethrin, Praziquantel, Pyrantel pamoate, Selamectin, Sodium stibogluconate and Thiabendazole. In an exemplary embodiment, the additional therapeutic agent is a member selected from antimony, meglumine antimonate, sodium stibogluconate, amphotericin, miltefosine and paromomycin.

The compounds of the invention, or pharmaceutical formulations thereof may also be used in combination with other therapeutic agents, for example immune therapies [e.g. interferon, such as interferon alfa-2a (ROFERON®-A; Hoffmann-La Roche), interferon alpha-2b (INTRON®-A; Schering-Plough), interferon alfacon-1 (INFERGEN®; Intermune), peginterferon alpha-2b (PEGINTRON™; Schering-Plough) or peginterferon alpha-2a (PEGASYS®; Hoffmann-La Roche)], therapeutic vaccines, antifibrotic agents, anti-inflammatory agents [such as corticosteroids or NSAIDs], bronchodilators [such as beta-2 adrenergic agonists and xanthines (e.g. theophylline)], mucolytic agents, anti-muscarinics, anti-leukotrienes, inhibitors of cell adhesion [e.g. ICAM antagonists], anti-oxidants [e.g. N-acetylcysteine], cytokine agonists, cytokine antagonists, lung surfactants and/or antimicrobial. The compositions according to the invention may also be used in combination with gene replacement therapy.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

It is to be understood that the present invention covers all combinations of aspects and/or embodiments, as well as suitable, convenient and preferred groups described herein.

III.c) Preparation of Boron-Containing Compounds

Compounds of use in the present invention can be prepared using commercially available starting materials or known intermediates. Compounds of use in the present invention can be prepared using synthetic methods known in the art or described herein.

The following general procedures were used as indicated in generating the examples and can be applied, using the knowledge of one of skill in the art, to other appropriate compounds to obtain additional analogues.

In one embodiment, the compound of the invention can be synthesized according to the following scheme:

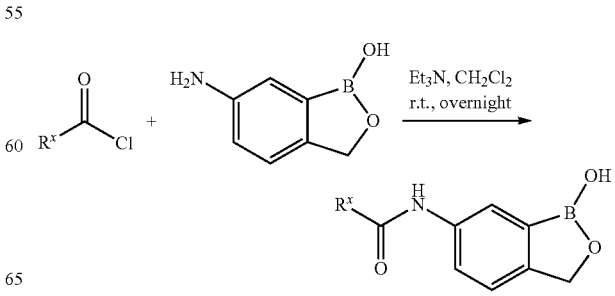

wherein $R^x$ is a member selected from substituted or unsubstituted aryl, substituted or unsubstituted heteroaryl, unsubstituted cycloalkyl, substituted or unsubstituted phenylalkyl, halosubstituted alkyl and unsubstituted alkyl, wherein the acid chloride is added to a mixture of 6-aminobenzo[c][1,2]oxaborol-1(3H)-ol and an agent such as $Et_3N$ in an appropriate solvent and is stirred for an appropriate period of time at an appropriate temperature to form the product.

In one embodiment, the compound of the invention can be synthesized according to the following scheme:

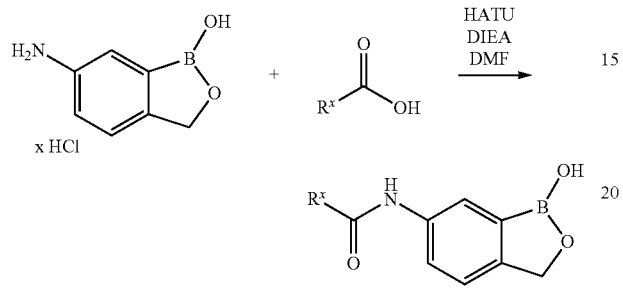

wherein $R^x$ is a member selected from substituted or unsubstituted aryl, substituted or unsubstituted heteroaryl, unsubstituted cycloalkyl, substituted or unsubstituted phenylalkyl, halosubstituted alkyl, and unsubstituted alkyl, wherein the mixture includes a carboxylic acid comprising molecule, a solvent such as DMF, and agents such as HATU and DIEA. The mixture can then be contacted with 5-amino-2-hydroxymethylphenylboronic acid hydrochloride, and stirred for an appropriate amount of time and temperature to form the product.

Method of preparation of
N-alkyl-oxaborole-6-carboxamides

In another embodiment, the compound of then invention (N.6) can be synthesized according to the following scheme:

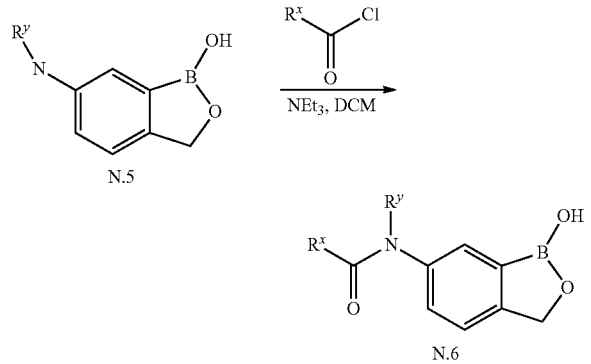

wherein $R^y$ is unsubstituted alkyl, and $R^x$ is a member selected from substituted or unsubstituted aryl, substituted or unsubstituted heteroaryl, unsubstituted cycloalkyl, substituted or unsubstituted phenylalkyl, halosubstituted alkyl and unsubstituted alkyl, wherein the acid chloride is added to a mixture of 6-aminobenzo[c][1,2]oxaborol-1(3H)-ol and an agent such as $Et_3N$ in an appropriate solvent and is stirred for an appropriate period of time at an appropriate temperature to form the product. The starting material, 6-alkylamino-3H-benzo[c][1,2]oxaborol-1-ol (N.5), can be synthesized by the following scheme:

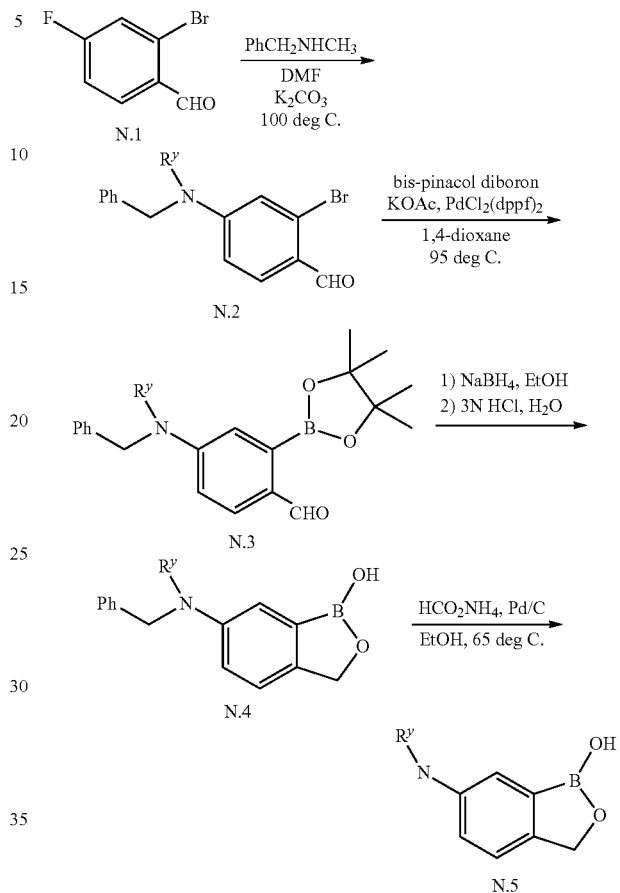

Reaction of 2-bromo-4-fluorobenzaldehyde (N.1) with an N-alkylbenzylamine in a polar aprotic solvent such as N,N-dimethylformamide in the presence of a base such as potassium carbonate affords the N-alkyl-N-benzyl derivative (N.2). Reaction of (N.2) with bis-pinacol diboron under the influence of a palladium (0) catalyst such as $PdCl_2(dppf)_2$ in a solvent such as 1,4-dioxane in the presence of a base such as potassium acetate provides (N.3). Reduction of the aldehyde functional group of (N.3) with a reagent such as sodium borohydride in a solvent such as ethanol, followed by hydrolysis of the boron pinacol ester under acidic conditions results in concomitant ring closure to provide the 6-substituted oxaborole derivative (N.4). Hydrogenolysis of the N-benzyl substituent by treatment with a hydrogen source such as ammonium formate in the presence of a catalyst such as palladium on carbon in a solvent such as ethanol affords 6-alkyl amino-3H-benzo[c][1,2]oxaborol-1-ol (N.5).

Additional Methods of Synthesis

Thioether, sulfoxide and sulfone derivatives such as B, C and D can be prepared by the following reactions. Thioethers such as B can be obtained by subjecting bromide A to boronylation conditions, such as treatment with n-butyl lithium and triisopropyl borate followed by addition of acid. Sulfoxides such as C can be obtained by subjecting B to oxidation conditions, such as sodium periodate or one equivalent of mCPBA. Sulfones such as D can be obtained by subjecting B to oxidation conditions such as sodium periodate over extended reaction time or two equivalents of mCPBA.

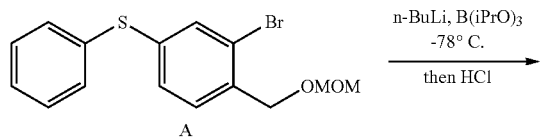

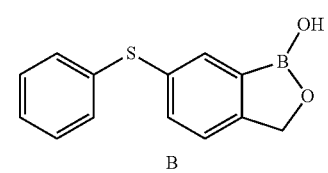

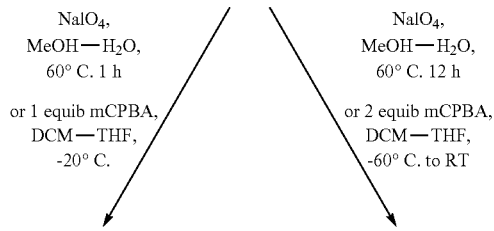

Carbamates such as F and G can be prepared by reacting compound E with corresponding isocyanate RNCO or ArNCO in the presence of base such as triethylamine.

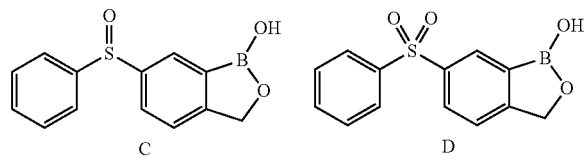

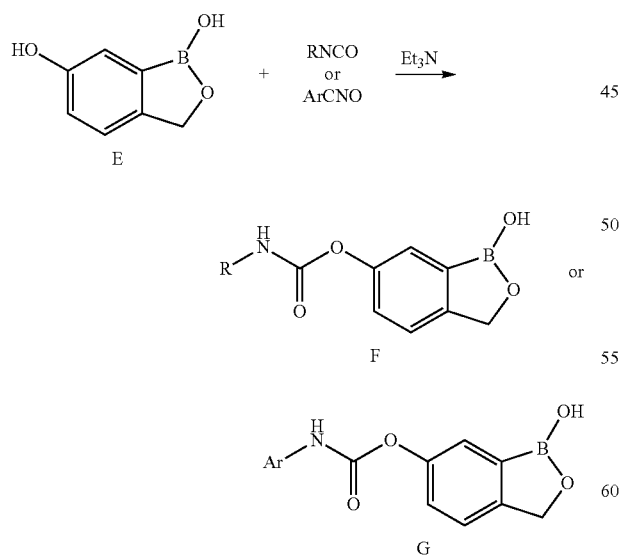

Ethers such as H and I can be obtained by reacting compound E under basic conditions with alkylbromide RBr or arylbromide ArBr.

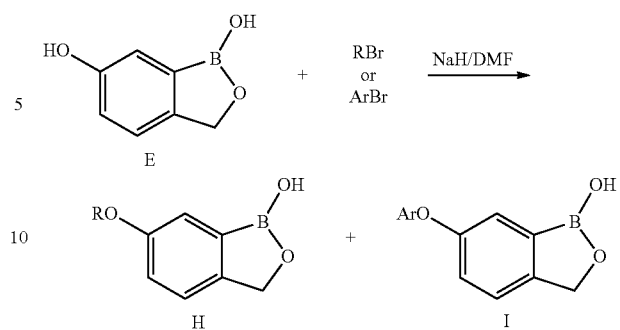

Benzylethers such as K can be obtained by reacting compound E under basic conditions with substituted benzyl bromide J.

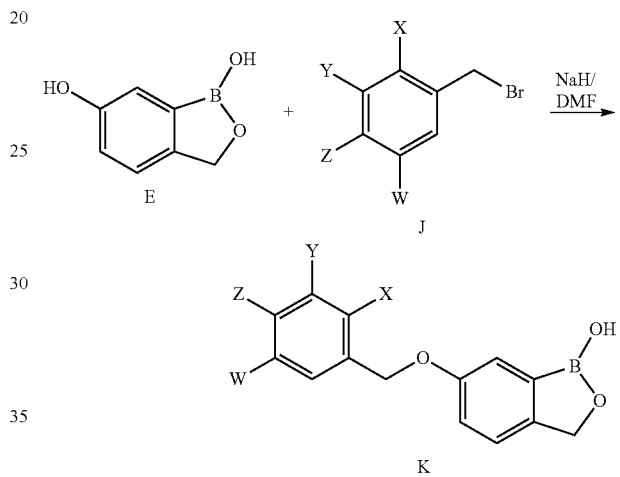

Carbinol derivatives such as M can be obtained by subjecting ketone L to reducing conditions such as sodium borohydride. Ketone derivatives such as N can be obtained by subjecting alcohol M to oxidation conditions such as PCC.

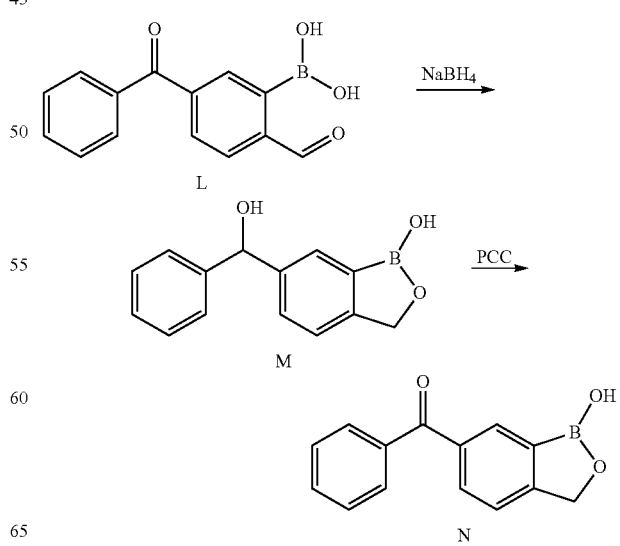

Amide derivatives such as P can be prepared from compound O and corresponding anilines by standard peptide coupling conditions as shown below.

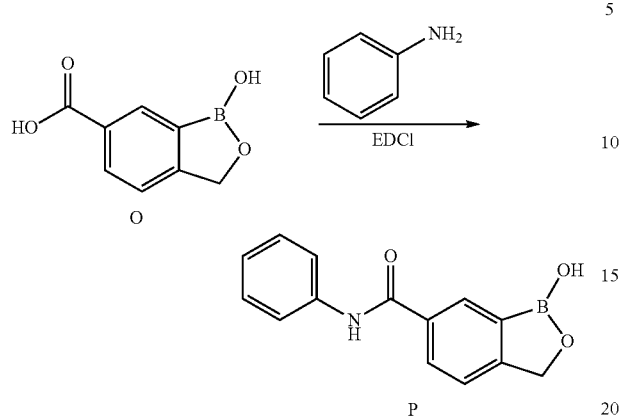

Amide derivatives such as S can be prepared from compound Q and corresponding acyl chlorides by standard peptide coupling conditions such as shown below.

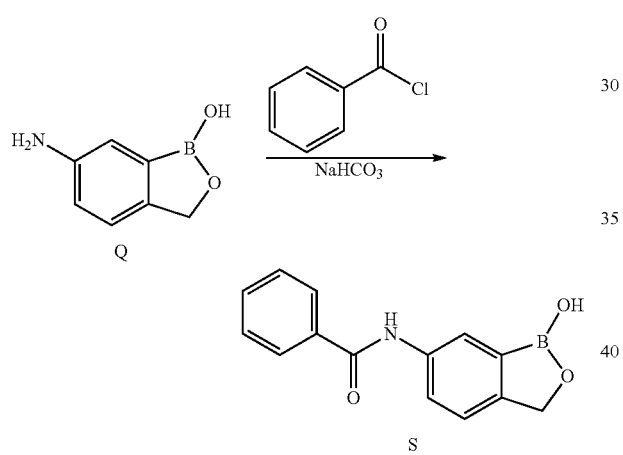

Benzylamine derivatives such as T can be obtained by reacting compound Q with corresponding benzyl bromides under basic conditions such as shown below.

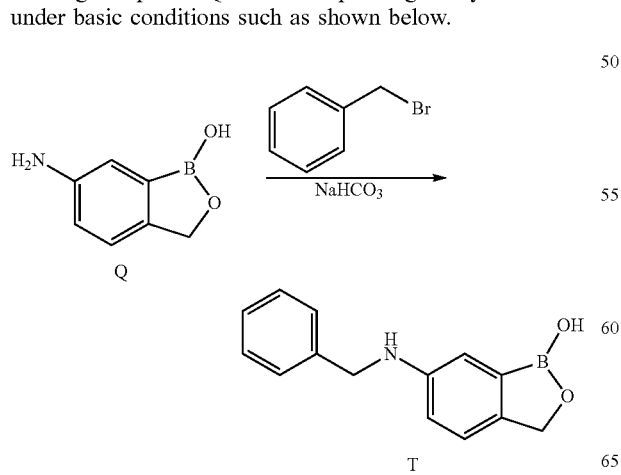

Sulfonamide derivatives such as U can be prepared from compound Q and corresponding sulfonyl chlorides under basic conditions such as shown below.

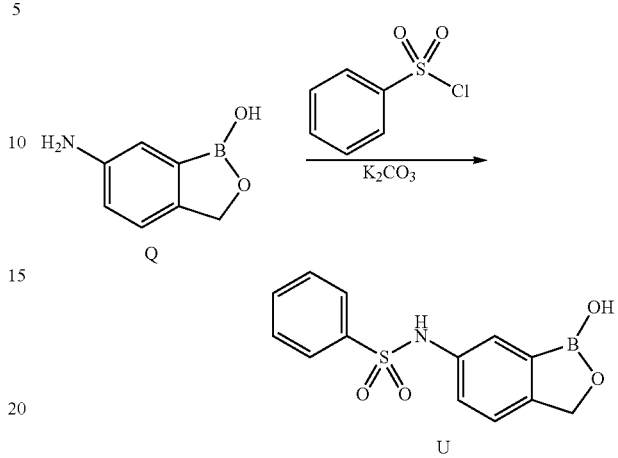

Compounds such as W can be prepared by subjecting protected amines such as V to acidic conditions such as shown below.

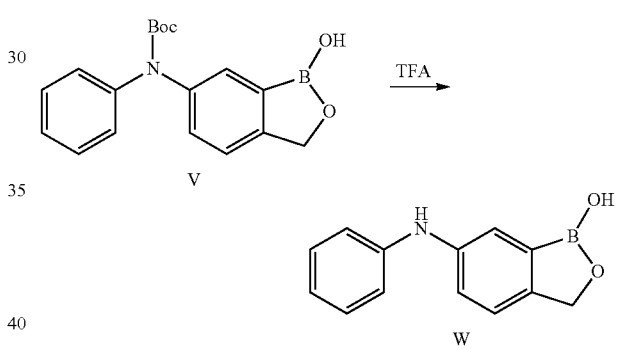

To make derivatives with a methylene linkage group such as Y, aldehyde X can be first subjected to reducing conditions such as sodium borohydride, then subjected to acidic conditions such as shown below.

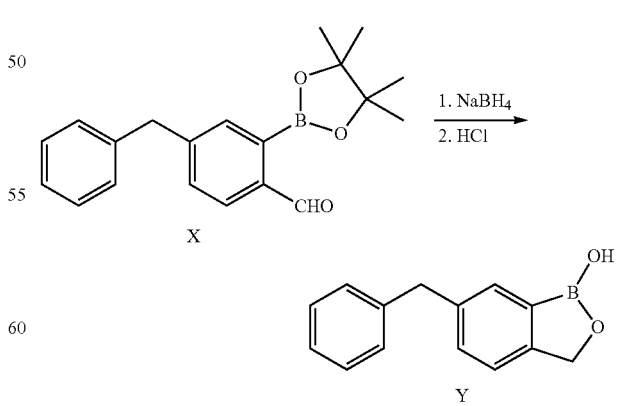

Compounds described herein can be converted into hydrates and solvates by methods similar to those described herein.

IV. Methods of Inhibiting Microorganism Growth or Killing Microorganisms

The compounds of the present invention exhibit potency against microorganisms, such as protozoa, and therefore have the potential to kill and/or inhibit the growth of microorganisms.

In a further aspect, the invention provides a method of killing and/or inhibiting the growth of a microorganism, said method comprising: contacting said microorganism with an effective amount of a compound of the invention, thereby killing and/or inhibiting the growth of the microorganism. In an exemplary embodiment, the microorganism is a protozoa. In an exemplary embodiment, the microorganism is a kinetoplastid. In another exemplary embodiment, the protozoa is a *Trypanosoma*. In an exemplary embodiment, the *Trypanosoma* is selected from the group consisting of *T. avium, T. boissoni, T. brucei, T. carassii, T. cruzi, T. congolense, T. equinum, T. equiperdum, T. evansi, T. hosei, T. levisi, T. melophagium, T. parroti, T. percae, T rangeli, T. rotatorium, T. rugosae, T. sergenti, T. simiae, T. sinipercae, T. suis, T. theileri, T. triglae* and *T. vivax*. In another exemplary embodiment, the protozoa is a *Trypanosoma brucei*. In another exemplary embodiment, the protozoa is *Trypanosoma brucei brucei*. In another exemplary embodiment, the protozoa is *Trypanosoma brucei rhodesiense*. In another exemplary embodiment, the protozoa is *Trypanosoma brucei gambiense*. In another exemplary embodiment, the protozoa is a member of the genus *Leishmania*. In another exemplary embodiment, the protozoa is a member of *Leishmania Viannia*. In an exemplary embodiment, the protozoa is selected from the group consisting of *L. donovani, L. infantum, L. chagasi; L. mexicana, L. amazonensis, L. venezuelensis, L. tropica, L. major, L. aethiopica, L. (V.) braziliensis, L. (V.) guyanensis, L. (V.) panamensis*, and *L. (V.) peruviana*. In an exemplary embodiment, the protozoa is *L. donovani*. In an exemplary embodiment, the protozoa is *L. infantum*. In another exemplary embodiment, the protozoa is a member of the genus *Plasmodium*. In another exemplary embodiment, the protozoa is selected from the group consisting of *Plasmodium falciparum, Plasmodium vivax, Plasmodium ovale, Plasmodium vivax, Plasmodium malariae* and *Plasmodium knowlesi*. In another exemplary embodiment, the protozoa is selected from the group consisting of *Plasmodium vivax, Plasmodium ovale, Plasmodium vivax* and *Plasmodium malariae*. In another exemplary embodiment, the protozoa is *Plasmodium falciparum*. In another exemplary embodiment, the protozoa is transmitted to the animal described herein by a mosquito infected with the protozoa. In another exemplary embodiment, wherein the protozoa is transmitted to the animal described herein by an *Anopheles* mosquito containing the protozoa. In an exemplary embodiment, the compound is selected from the group consisting of N-(1-hydroxy-1,3-dihydrobenzo[c][1,2]oxaborol-6-yl)-2-(chloro) benzamide, 5-fluoro-N-(1-hydroxy-1,3-dihydrobenzo[c][1,2]oxaborol-6-yl)-2-(trifluoromethyl)benzamide, 2-fluoro-N-(1-hydroxy-1,3-dihydrobenzo[c][1,2]oxaborol-6-yl)-2-(trifluoromethyl)benzamide, 4-fluoro-N-(1-hydroxy-1,3-dihydrobenzo[c][1,2]oxaborol-6-yl)-2-(trifluoromethyl)benzamide, 2-chloro-N-(1-hydroxy-1,3-dihydrobenzo[c][1,2]oxaborol-6-yl)-5-(trifluoromethyl)benzamide, 2-fluoro-N-(1-hydroxy-1,3-dihydrobenzo[c][1,2]oxaborol-6-yl)-5-(trifluoromethyl)benzamide, 2-fluoro-N-(1-hydroxy-1,3-dihydrobenzo[c][1,2]oxaborol-6-yl)-3-(trifluoromethyl)benzamide, 2-fluoro-N-(1-hydroxy-1,3-dihydrobenzo[c][1,2]oxaborol-6-yl)-4-(trifluoromethyl)benzamide, N-(1-hydroxy-1,3-dihydrobenzo[c][1,2]oxaborol-6-yl)-2-(trifluoromethyl)benzamide, N-(1-hydroxy-1,3-dihydrobenzo[c][1,2]oxaborol-6-yl)-3-(trifluoromethyl)benzamide, N-(1-hydroxy-1,3-dihydrobenzo[c][1,2]oxaborol-6-yl)-4-(trifluoromethyl)benzamide, 6-(2-chlorophenyl sulfinyl)benzo[c][1,2]oxaborol-1(3H)-ol, 6-(3-chlorophenylsulfinyl)benzo[c][1,2]oxaborol-1(3H)-ol and 6-(4-chlorophenylsulfinyl)benzo[c][1,2]oxaborol-1(3H)-ol, or a salt, prodrug, hydrate or solvate thereof, or a combination thereof. In an exemplary embodiment, the compound is a member selected from N-(1-hydroxy-1,3-dihydrobenzo[c][1,2]oxaborol-6-yl)-2-(trifluoromethyl)benzamide and 6-(4-chlorophenylsulfinyl)benzo[c][1,2]oxaborol-1(3H)-ol, or a salt, prodrug, hydrate or solvate thereof, or a combination thereof. In an exemplary embodiment, the compound is 6-(4-chlorophenylsulfinyl)benzo[c][1,2]oxaborol-1(3H)-ol. In an exemplary embodiment, the compound is 5-fluoro-N-(1-hydroxy-1,3-dihydrobenzo[c][1,2]oxaborol-6-yl)-2-(trifluoromethyl) benzamide. In an exemplary embodiment, the compound is 4-fluoro-N-(1-hydroxy-1,3-dihydrobenzo[c][1,2]oxaborol-6-yl)-2-(trifluoromethyl)benzamide. In an exemplary embodiment, the compound is N-(1-hydroxy-1,3-dihydrobenzo[c][1,2]oxaborol-6-yl)-2-(trifluoromethyl)benzamide. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another aspect, the microorganism is inside, or on the surface of an animal. In an exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism is killed or its growth is inhibited through oral administration of the compound of the invention. In an exemplary embodiment, the microorganism is killed or its growth is inhibited through intravenous administration of the compound of the invention. In an exemplary embodiment, the microorganism is killed or its growth is inhibited through topical administration of the compound of the invention. In an exemplary embodiment, the microorganism is killed or its growth is inhibited through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

V. Methods of Treating and/or Preventing Disease

The compounds of the present invention exhibit potency against microorganisms, such as protozoa, and therefore have the potential to achieve therapeutic efficacy in the animals described herein.

In another aspect, the invention provides a method of treating and/or preventing a disease. The method includes administering to the animal a therapeutically effective amount of the compound of the invention, sufficient to treat and/or prevent the disease. In an exemplary embodiment, the animal is not otherwise is need of treatment with the compound of the invention. In an exemplary embodiment, the compound of the invention can be used in human or veterinary medical therapy, particularly in the treatment or prophylaxis of protozoa-associated disease. In an exemplary embodiment, the compound of the invention can be used in human or veterinary medical therapy, particularly in the treatment or prophylaxis of kinetoplastid-associated disease. In an exemplary embodiment, the disease is associated with a *Trypanosoma*. In an exemplary embodiment, the *Trypanosoma* is selected from the group consisting of *T. avium, T. boissoni, T. brucei, T carassii, T. cruzi, T. congolense, T. equinum, T. equiperdum, T evansi, T. hosei, T levisi, T. melophagium, T. parroti, T. percae, T. rangeli, T. rotatorium, T. rugosae, T. sergenti, T. simiae, T. sinipercae, T. suis, T. theileri, T. triglae* and *T. vivax*. In an exemplary embodiment, the disease is associated with a *Trypanosoma brucei*. In an exemplary embodiment, the disease is associated with *Trypanosoma brucei brucei*. In an exemplary embodiment, the disease is associated with *Trypanosoma brucei rhodesiense*. In an exemplary embodiment, the disease is associated with *Trypanosoma brucei gambiense*. In an exemplary embodiment, the disease is a typanosomiasis. In an exemplary embodiment, the disease is a human typanosomiasis. In an exemplary embodiment, the disease is an animal typanosomiasis. In an exemplary embodiment, the disease is selected from the group consisting of nagana, surra, mal de caderas, murrina de caderas, dourine, cachexial fevers, Gambian horse sickness, baleri, kaodzera, tahaga, galziekte or galzietzke and peste-boba. In an exemplary embodiment, the disease is selected from the group consisting of Chagas disease (or Human American trypanosomiasis), nagana, surra, Covering sickness (or dourine) and sleeping sickness (or African sleeping sickness or Human African trypanosomiasis). In an exemplary embodiment, the disease is Chagas disease. In an exemplary embodiment, the disease is sleeping sickness (or African sleeping sickness). In an exemplary embodiment, the disease is acute phase sleeping sickness. In an exemplary embodiment, the disease is chronic phase sleeping sickness. In an exemplary embodiment, the disease is an acute phase of a typanosomiasis. In an exemplary embodiment, the disease is a chronic phase of a typanosomiasis. In an exemplary embodiment, the disease is the non-CNS form of a typanosomiasis. In an exemplary embodiment, the disease is the CNS form of a typanosomiasis. In an exemplary embodiment, the disease is the non-CNS form of sleeping sickness. In an exemplary embodiment, the disease is the CNS form of sleeping sickness. In an exemplary embodiment, the disease is early stage Human African trypanosomiasis. In an exemplary embodiment, the disease is late stage Human African trypanosomiasis. In another exemplary embodiment, the disease is associated with a member of the genus *Leishmania*. In another exemplary embodiment, the disease is associated with a member of *Leishmania Viannia*. In an exemplary embodiment, the disease is associated with a member selected from the group consisting of *L. donovani, L. infantum, L. chagasi; L. mexicana, L. amazonensis, L. venezuelensis, L. tropica, L. major, L. aethiopica, L. (V.) braziliensis, L. (V.) guyanensis, L. (V.) panamensis*, and *L. (V.) peruviana*. In an exemplary embodiment, the disease is associated with *L. donovani*. In an exemplary embodiment, the disease is associated with *L. infantum*. In an exemplary embodiment, the disease is leshmaniasis. In an exemplary embodiment, the disease is a member selected from visceral leshmaniasis and/or cutaneous leshmaniasis. In an exemplary embodiment, the disease is diffuse cutaneous leshmaniasis and/or mucocutaneous leshmaniasis. In another exemplary embodiment, the disease is associated with a member of the genus *Plasmodium*. In another exemplary embodiment, the disease is associated with a member selected from the group consisting of *Plasmodium falciparum, Plasmodium vivax, Plasmodium ovale, Plasmodium vivax, Plasmodium malariae* and *Plasmodium knowlesi*. In another exemplary embodiment, the disease is associated with a member selected from the group consisting of *Plasmodium vivax, Plasmodium ovale, Plasmodium vivax* and *Plasmodium malariae*. In another exemplary embodiment, the disease is associated with *Plasmodium falciparum*. In another exemplary embodiment, the disease is transmitted to the animal described herein by a mosquito infected with the protozoa. In another exemplary embodiment, the disease is transmitted to the animal described herein by an *Anopheles* mosquito containing the protozoa. In another exemplary embodiment, the disease is malaria. In another exemplary embodiment, the disease is cerebral malaria. In another exemplary embodiment, the disease is chronic malaria. In an exemplary embodiment, the compound is selected from the group consisting of N-(1-hydroxy-1,3-dihydrobenzo[c][1,2]oxaborol-6-yl)-2-(chloro)benzamide, 5-fluoro-N-(1-hydroxy-1,3-dihydrobenzo[c][1,2]oxaborol-6-yl)-2-(trifluoromethyl)benzamide, 2-fluoro-N-(1-hydroxy-1,3-dihydrobenzo[c][1,2]oxaborol-6-yl)-2-(trifluoromethyl)benzamide, 4-fluoro-N-(1-hydroxy-1,3-dihydrobenzo[c][1,2]oxaborol-6-yl)-2-(trifluoromethyl)benzamide, 2-chloro-N-(1-hydroxy-1,3-dihydrobenzo[c][1,2]oxaborol-6-yl)-5-(trifluoromethyl)benzamide, 2-fluoro-N-(1-hydroxy-1,3-dihydrobenzo[c][1,2]oxaborol-6-yl)-5-(trifluoromethyl)benzamide, 2-fluoro-N-(1-hydroxy-1,3-dihydrobenzo[c][1,2]oxaborol-6-yl)-3-(trifluoromethyl)benzamide, 2-fluoro-N-(1-hydroxy-1,3-dihydrobenzo[c][1,2]oxaborol-6-yl)-4-(trifluoromethyl)benzamide, N-(1-hydroxy-1,3-dihydrobenzo[c][1,2]oxaborol-6-yl)-2-(trifluoromethyl)benzamide, N-(1-hydroxy-1,3-dihydrobenzo[c][1,2]oxaborol-6-yl)-3-(trifluoromethyl)benzamide, N-(1-hydroxy-1,3-dihydrobenzo[c][1,2]oxaborol-6-yl)-4-(trifluoromethyl)benzamide, 6-(2-chlorophenylsulfinyl)benzo[c][1,2]oxaborol-1(3H)-ol, 6-(3-chlorophenylsulfinyl)benzo[c][1,2]oxaborol-1(3H)-ol and 6-(4-chlorophenylsulfinyl)benzo[c][1,2]oxaborol-1(3H)-ol, or a salt, prodrug, hydrate or solvate thereof, or a combination thereof. In an exemplary embodiment, the compound is N-(1-hydroxy-1,3-dihydrobenzo[c][1,2]oxaborol-6-yl)-2-(trifluoromethyl)benzamide or 6-(4-chlorophenylsulfinyl)benzo[c][1,2]oxaborol-1(3H)-ol, or a salt, prodrug, hydrate or solvate thereof, or a combination thereof. In an exemplary embodiment, the compound is 6-(4-chlorophenylsulfinyl)benzo[c][1,2]oxaborol-1(3H)-ol. In an exemplary embodiment, the compound is 5-fluoro-N-(1-hydroxy-1,3-dihydrobenzo[c][1,2]oxaborol-6-yl)-2-(trifluoromethyl)benzamide. In an exemplary embodiment, the compound is 4-fluoro-N-(1-hydroxy-1,3-dihydrobenzo[c][1,2]oxaborol-6-yl)-2-(trifluoromethyl)benzamide. In an exemplary embodiment, the compound is N-(1-hydroxy-1, 3-dihydrobenzo[c][1,2]oxaborol-6-yl)-2-(trifluoromethyl) benzamide. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a mouse. In another exemplary embodiment, the animal is selected from the group consisting of a human, cattle, goat, pig, sheep, horse, cow, bull, dog, guinea pig, gerbil, rabbit, cat, chicken and turkey.

In an exemplary embodiment, the disease is treated through oral administration of the compound of the invention. In an exemplary embodiment, the disease is treated through intravenous administration of the compound of the invention. In an exemplary embodiment, the disease is treated through topical administration of the compound of the invention. In an exemplary embodiment, the disease is treated through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

In an exemplary embodiment, the disease is associated with an infection by a microorganism described herein. In an exemplary embodiment, the disease is associated with an infection by a protozoa described herein.

VI. Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

In an exemplary embodiment, the invention is a pharmaceutical formulation which includes: (a) a pharmaceutically acceptable excipient; and (b) a compound which is

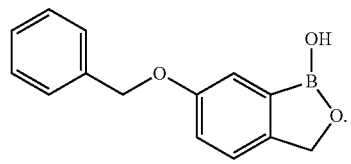 [SMILES: OB1OCc2ccc(OCc3ccccc3)cc21]

In an exemplary embodiment, the invention is a pharmaceutical formulation which includes: (a) a pharmaceutically acceptable excipient; and (b) a compound which is

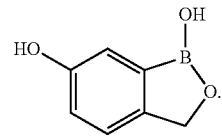 [SMILES: OB1OCc2ccc(O)cc21]

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered in a topically effective dose. In an exemplary embodiment, the pharmaceutical formulation is administered in a cosmetically effective dose. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 800 mg of a compound of the invention. In an exemplary embodiment, the unit dosage form contains from about 1 mg to about 500 mg of an active ingredient. In an exemplary embodiment, the unit dosage form contains from about 100 mg to about 800 mg of a compound of the invention. In an exemplary embodiment, the unit dosage form contains from about 200 mg to about 500 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocycles may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

VI. a) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat. B*677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between LD$_{50}$ and ED$_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the ED$_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

VI. b) Administration

For any compound used in the method of the invention, the therapeutically effective dose can be estimated initially from cell culture assays, as disclosed herein. For example, a dose can be formulated in animal models to achieve a circulating concentration range that includes the EC$_{50}$ (effective dose for 50% increase) as determined in cell culture, i.e., the concentration of the test compound which achieves a half-maximal inhibition of protozoa cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain protozoa cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m$^2$/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

Exemplary embodiments are summarized herein below.

In an exemplary embodiment, the invention provides a compound having a structure which is a member selected from:

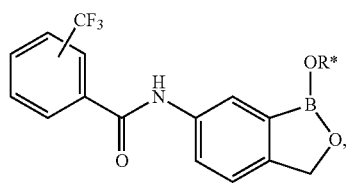

(I)

wherein R* is a member selected from H and a negative charge or a salt thereof.

In an exemplary embodiment, according to the above paragraph, the compound has a structure which is a member selected from:

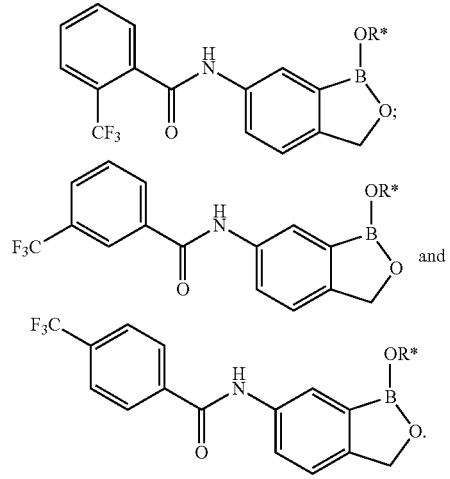

In an exemplary embodiment, according to any of the above paragraphs, the compound has a structure according to

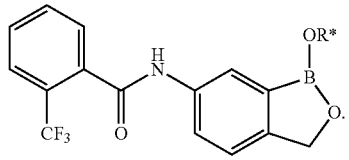

In an exemplary embodiment, according to any of the above paragraphs, R* is H.

In an exemplary embodiment, the invention provides a combination comprising the compound according to any of the above paragraphs, together with at least one other therapeutically active agent.

In an exemplary embodiment, the invention provides a pharmaceutical composition comprising the compound according to any of the above paragraphs, and a pharmaceutically acceptable excipient.

In an exemplary embodiment, according to any of the above paragraphs, the pharmaceutical formulation is a unit dosage form.

In an exemplary embodiment, according to any of the above paragraphs, the salt of the compound according to any of the above paragraphs is a pharmaceutically acceptable salt.

In an exemplary embodiment, the invention provides a method of killing and/or preventing the growth of a protozoa, comprising: contacting the protozoa with an effective amount of the compound according to any of the above paragraphs, thereby killing and/or preventing the growth of the protozoa.

In an exemplary embodiment, according to any of the above paragraphs, the protozoa is *Trypanosoma*.

In an exemplary embodiment, according to any of the above paragraphs, the protozoa is *Trypanosoma brucei*.

In an exemplary embodiment, according to any of the above paragraphs, the *Trypanosoma brucei* is a member selected from *Trypanosoma brucei brucei, Trypanosoma brucei gambiense* and *Trypanosoma brucei rhodesiense.*

In an exemplary embodiment, the invention provides a method of treating and/or preventing a disease in an animal, comprising: administering to the animal a therapeutically effective amount of the compound according to any of the above paragraphs, thereby treating and/or preventing the disease.

In an exemplary embodiment, according to any of the above paragraphs, the disease is sleeping sickness.

In an exemplary embodiment, according to any of the above paragraphs, the animal is a human.

The invention is further illustrated by the Examples that follow. The Examples are not intended to define or limit the scope of the invention.

EXAMPLES

The following Examples illustrate the synthesis of representative compounds used in the present invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

Abbreviations: DCM/CH$_2$Cl$_2$: dichloromethane; DIEA: diisopropylethylamine; DMAP: 4-dimethylaminopyridine; DMF: N,N-dimethylformamide; EtOAc: ethyl acetate; EDCI: 1-ethyl-3-(3'-dimethylaminopropyl)carbodiimide; ELS: evaporative light scattering; HATU: 2-(1H-7-azabenzotriazol-1-yl)-1,1,3,3-tetramethyl uronium; HOBt: N-hydroxybenzotriazole; HCO$_2$H: formic acid; MeOH: methanol; TEA: triethylamine; THF: tetrahydrofuran.

All temperatures are given in degrees Centigrade. Room temperature means 20 to 25° C. Reagents were purchased from commercial sources or prepared following standard literature procedures. Unless otherwise noted, reactions were carried out under a positive pressure of nitrogen. Reaction vessels were sealed with either rubber septa or Teflon screw caps. Nitrogen was introduced through Tygon tubing, fitted with a large bore syringe needle. Concentration under vacuum refers to the removal of solvent on a Büchi Rotary Evaporator.

Analytical HPLC was performed using a Supelco discovery C$_{18}$ 15 cm×4.6 mm/5 μm column coupled with an Agilent 1050 series VWD UV detector at 210 nm. Conditions: Solvent A: H$_2$O/1% acetonitrile/0.1% HCO$_2$H; Solvent B: methanol.

Proton magnetic resonance ($^1$H NMR) spectra were recorded on a Varian INOVA NMR spectrometer [400 MHz ($^1$H) or 500 MHz ($^1$H)]. All spectra were determined in the solvents indicated. Although chemical shifts are reported in ppm downfield of tetramethylsilane, they are referenced to the residual proton peak of the respective solvent peak for $^1$H NMR. Interproton coupling constants are reported in Hertz (Hz).

LCMS spectra were obtained using a ThermoFinnigan AQA MS ESI instrument utilizing a Phenomenex Aqua 5 micron C$_{18}$ 125 Å 50×4.60 mm column. The spray setting for the MS probe was at 350 μL/min with a cone voltage at 25 mV and a probe temperature at 450° C. The spectra were recorded using ELS and UV (254 nm) detection. Alternatively, LCMS spectra were obtained using an Agilent 1200SL HPLC equipped with a 6130 mass spectrometer operating with electrospray ionization.

Silica gel chromatography was carried out on either a Teledyne ISCO CombiFlash Companion or Companion Rf Flash Chromatography System with a variable flow rate from 5-100 mL/min. The columns used were Teledyne ISCO RediSep Disposable Flash Columns (4, 12, 40, 80, or 120 g prepacked silica gel), which were run with a maximum capacity of 1 g crude sample per 10 g silica gel. Samples were preloaded on Celite in Analogix Sample Loading Cartridges with fits (1/in, 1/out). The eluent was 0-100% EtOAc in heptane or 0-10% MeOH in CH$_2$Cl$_2$ as a linear gradient over the length of the run (14-20 minutes). Peaks were detected by variable wavelength UV absorption (200-360 nm). The resulting fractions were analyzed, combined as appropriate, and evaporated under reduced pressure to provide purified material.

HPLC purification was performed using a 50 mm Varian Dynamax HPLC 21.4 mm Microsorb Guard-8 C$_{18}$ column, Dyonex Chromeleon operating system coupled with a Varian Prostar 320 UV-vis detector (254 nm) and a Sedex55 ELS detector. Conditions: Solvent A: H$_2$O/1% acetonitrile/0.1% HCO$_2$H; Solvent B: MeOH. The appropriate solvent gradient for purification was determined based on the results of analytical HPLC experiments. The resulting fractions were analyzed, combined as appropriate, and evaporated under reduced pressure to provide purified material.

The following experimental sections illustrate procedures for the preparation of intermediates and methods for the preparation of products according to this invention. It should be evident to those skilled in the art that appropriate substitution of both the materials and methods disclosed herein will produce the examples illustrated below and those encompassed by the scope of the invention.

All solvents used were commercially available and were used without further purification. Reactions were typically run using anhydrous solvents under an inert atmosphere of N$_2$.

$^1$H, $^{13}$C, and $^{19}$F NMR spectra were recorded at 400 MHz for proton, 100 MHz for carbon-13, and 376 MHz for fluorine-19 on a Varian 300 MercuryPlus station with an Oxford AS400 Spectrometer equipped with a Varian 400 ATB PFG probe. All deuterated solvents typically contained 0.03% to 0.05% v/v tetramethylsilane, which was used as the reference signal (set at δ 0.00 for both $^1$H and $^{13}$C).

Compounds are named using ChemDraw 7.0 or their catalogue name if commercially available.

Mass spectra were recorded on a Waters MS consisting of an Alliance 2795 (LC) and Waters Micromass ZQ detector at 120° C. The mass spectrometer was equipped with an electrospray ion source (ESI) operated in a positive or negative mode. The mass spectrometer was scanned between m/z=100-1000 with a scan time of 0.3 s.

Elemental Analysis for C, H and N composition was performed using a Costech Instrument Elemental Combustion System ECS4010 with a helium flow of 100 mL/min (14 psi), oxygen 20 mL/min (10 psi), air 25 psi and purge of 50 mL/min. The reported analyses are an average of two runs.

HPLC analyses were performed on a Water 600 Controller system with a Waters 717 Plus Autosampler and a Waters 2996 Photodiode Array Detector. The column used was an ACE C$_{18}$, 5 μm, 4.6×150 mm. A linear gradient was applied, starting at 95% A (A: 0.1% H$_3$PO$_4$ in water) and ending at 90% B (B: MeCN) over 6 min and then maintained at 90% B until the 10 min mark. The column was then re-equilibrated over 3 min to 95:5 with a total run time of 20 min. The column temperature was at rt with the flow rate of 1.0 mL/min. The Diode Array Detector was scanned from 200-400 nm. For high purity samples requiring baseline subtraction, a linear gradient was applied, starting at 99% A (A: 0.1% $H_3PO_4$ in water) and ending at 90% B (B: MeCN) over 15 min. The column was then re-equilibrated over 3 min to 99% A with a total run time of 23 min. The column temperature was at rt with the flow rate of 1.0 mL/min. The Diode Array Detector was scanned from 200-400 nm. A blank MeOH sample was run immediately prior to the sample of which purity was to be determined: this was then subtracted to obtain the baseline subtracted chromatogram.

Thin layer chromatography (TLC) was performed on Alugram® (Silica gel 60 $F_{254}$) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), vanillin (generated by dissolving about 1 g vanillin in 100 mL 10% $H_2SO_4$), potassium permanganate (generated by dissolving 1.5 g $KMnO_4$ and 10 g $K_2CO_3$ in 1.25 mL NaOH and 200 mL $H_2O$), ninhydrin (available commercially from Aldrich), or Magic Stain (generated by thoroughly mixing 25 g $(NH_4)_6Mo_7O_{24}\cdot 4H_2O$, 5 g $(NH_4)_2Ce(IV)(NO_3)_6$ in 450 mL $H_2O$ and 50 mL conc $H_2SO_4$) to visualize the compound. Flash chromatography was preformed using typically 40-63 μm (230-400 mesh) silica gel from Silicycle following analogous techniques to those disclosed by Still et al. Typical solvents used for flash chromatography or thin layer chromatography (TLC) were mixtures of $CHCl_3$/MeOH, $CH_2Cl_2$/MeOH, EtOAc/MeOH and hexane/EtOAc. Reverse phase flash chromatography were performed on a Biotage® using a Biotage $C_{18}$ cartridges and a $H_2O$/MeOH gradient (typically eluting from 5% MeOH/$H_2O$ to 90% MeOH/$H_2O$).

Preparative chromatography was performed on either a Waters Prep LC 4000 System using a Waters 2487 Diode Array or on a Waters LC Module 1 plus. The column used were either a Waters×Terra Prep $C_{18}$, 5 μm, 30×100 mm, Phenomenex Luna $C_{18}$, 5 μm, 21.6×250 mm, or a Phenomenex Gemini $C_{18}$, 5 μm, 100×30 mm. Narrow gradients with MeCN/$H_2O$ (water containing either 0.1% TFA, 0.1% AcOH, 0.1% $HCO_2H$ or 0.1% $NH_4OAc$) were used to elute the compound at a flow rate of approximately 20 mL/min and a total run time between 20-30 min.

Starting materials used were either available from commercial sources or prepared according to literature procedures and had experimental data in accordance with those reported. 6-aminobenzo[c][1,2]oxaborol-1(3H)-ol, for example, can be synthesized according to the methods described in U.S. Pat. Pubs. US20060234981 and US20070155699.

Example 1

N-(1-hydroxy-1,3-dihydrobenzo[c][1,2]oxaborol-6-yl)-2-(trifluoromethyl)benzamide (H1)

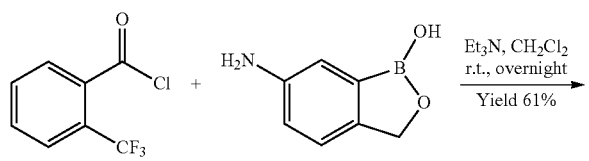

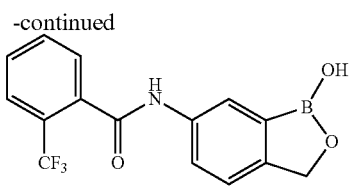

To a mixture of 6-aminobenzo[c][1,2]oxaborol-1(3H)-ol (50.0 mg, 0.335 mmol) and $Et_3N$ (50.9 mg, 0.503 mmol) in dry $CH_2Cl_2$ (5 mL) was added 2-(trifluoromethyl)benzoyl chloride (69.9 mg, 0.335 mmol) dropwise at 0° C., followed by stirring at room temperature overnight. Then the precipitate was collected by filtration and washed with $CH_2Cl_2$ to afford the title compound as pale yellow solid in 61% yield. $^1$H NMR (DMSO-$d_6$, 300 MHz): δ 10.56 (s, 1H), 9.24 (s, 1H), 8.13 (d, J=1.8 Hz, 1H), 7.85-7.63 (m, 5H), 7.36 (d, J=8.1 Hz, 1H), 4.95 (s, 2H). Purity: 100% at 220 nm and 100% at 254 nm. MS: m/z=322 (M+1, ESI+).

N-(1-hydroxy-1,3-dihydrobenzo[c][1,2]oxaborol-6-yl)-3-(trifluoromethyl)benzamide (H2)

This compound is produced by the similar method as H1 by substituting 2-(trifluoromethyl)benzoyl chloride with 3-(trifluoromethyl)benzoyl chloride.

$^1$H NMR (DMSO-$d_6$, 400 MHz): δ 10.51 (s, 1H), 9.24 (s, 1H), 8.24-8.35 (m, 2H), 8.17 (d, J=1.8 Hz, 1H), 7.97 (d, J=7.8 Hz, 1H), 7.72-7.84 (m, 2H), 7.41 (d, J=8.2 Hz, 1H), 4.98 (s, 2H). Purity: 94.1% at 220 nm and 93.4% at 254 nm. MS: m/z=322 (M+1, ESI+).

N-(1-hydroxy-1,3-dihydrobenzo[c][1,2]oxaborol-6-yl)-4-(trifluoromethyl)benzamide (H3)

This compound is produced by the similar method as H1 by substituting 2-(trifluoromethyl)benzoyl chloride with 4-(trifluoromethyl)benzoyl chloride.

$^1$H NMR (DMSO-$d_6$, 400 MHz): δ 10.51 (s, 1H), 9.24 (s, 1H), 8.09-8.20 (m, 3H), 7.92 (d, J=8.4 Hz, 1H), 7.77 (dd, J=8.2 & 2.0 Hz, 1H), 7.41 (d, J=8.4 Hz, 1H), 4.98 (s, 2H). Purity: 94.1% at 220 nm and 94.4% at 254 nm. MS: m/z=322 (M+1, ESI+).

2-Fluoro-N-(1-hydroxy-1,3-dihydro-benzo[c][1,2]oxaborol-6-yl)-benzamide (H4)

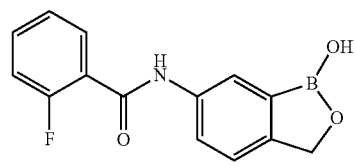

H4 was prepared using a procedure similar to that of H17 by substituting 5-fluoro-2-(trifluoromethyl)benzoyl chloride with 2-fluorobenzoyl chloride. LCMS (m/z): 272 (M+H); $^1$H NMR (400 MHz, DMSO-d6) δ ppm 4.97 (s, 2H) 7.30-7.42 (m, 3H) 7.54-7.62 (m, 1H) 7.63-7.75 (m, 2H) 8.15 (s, 1H) 9.24 (s, 1H) 10.43 (s, 1H).

3-Fluoro-N-(1-hydroxy-1,3-dihydro-benzo[c][1,2]oxaborol-6-yl)-benzamide (H5)

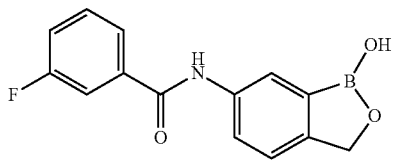 [SMILES: O=C(Nc1ccc2c(c1)B(O)OC2)c1cccc(F)c1]

H5 was prepared using a procedure similar to that of H17 by substituting 5-fluoro-2-(trifluoromethyl)benzoyl chloride with 3-fluorobenzoyl chloride. LCMS (m/z): 272 (M+H); $^1$H NMR (400 MHz, DMSO-d6) δ ppm 4.97 (s, 2H) 7.35-7.52 (m, 2H) 7.60 (td, J=8.0, 5.9 Hz, 1H) 7.71-7.88 (m, 3H) 8.17 (d, J=2.0 Hz, 1H) 9.24 (s, 1H) 10.35 (s, 1H).

4-Fluoro-N-(1-hydroxy-1,3-dihydro-benzo[c][1,2]oxaborol-6-yl)-benzamide (H6)

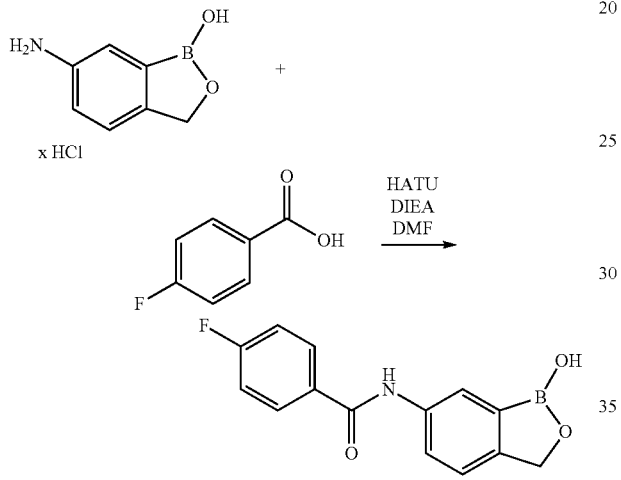

A 40 mL scintillation vial containing a mixture of 4-fluorobenzoic acid (275 mg 1.96 mmol, 1.1 eq), DMF (15 mL), HATU (710 mg, 1.9 mmol, 1.05 eq) and DIEA (460 μl, 2.7 mmol, 1.5 eq) was allowed to stir at room temperature for 2 hours. 5-amino-2-hydroxymethylphenylboronic acid hydrochloride (330 mg, 1.78 mmol, 1 eq) was then added in one portion. The reaction stirred at room temperature overnight. The solvent was removed under vacuum and the resulting oil was purified by silica gel chromatography to furnish H6. LCMS (m/z) 272 (M+H); $^1$H NMR (400 MHz, DMSO-d$_6$) δ ppm 4.97 (s, 2H) 7.32-7.44 (m, 3H) 7.76 (dd, J=8.2, 2.1 Hz, 1H) 8.05 (dd, J=8.8, 5.5 Hz, 2H) 8.16 (t, J=2.0 Hz, 1H) 9.22 (s, 1H) 10.30 (s, 1H).

2-Chloro-N-(1-hydroxy-1,3-dihydro-benzo[c][1,2]oxaborol-6-yl)-benzamide (H7)

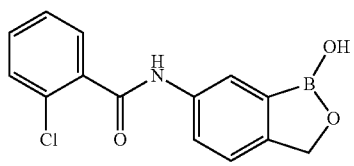 [SMILES: O=C(Nc1ccc2c(c1)B(O)OC2)c1ccccc1Cl]

H7 was prepared using a procedure similar to that of H17 by substituting 5-fluoro-2-(trifluoromethyl)benzoyl chloride with 2-chlorobenzoyl chloride. LCMS (m/z): 288 (M+H); $^1$H NMR (400 MHz, DMSO-d6) δ ppm 4.97 (s, 2H) 7.39 (d, J=8.2 Hz, 1H) 7.45-7.55 (m, 2H) 7.55-7.62 (m, 2H) 7.71 (dd, J=8.3, 2.1 Hz, 1H) 8.17 (d, J=1.8 Hz, 1H) 9.25 (s, 1H) 10.53 (s, 1H).

3-Chloro-N-(1-hydroxy-1,3-dihydro-benzo[c][1,2]oxaborol-6-yl)-benzamide (H8)

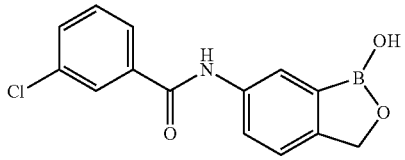 [SMILES: O=C(Nc1ccc2c(c1)B(O)OC2)c1cccc(Cl)c1]

H8 was prepared using a procedure similar to that of H17 by substituting 5-fluoro-2-(trifluoromethyl)benzoyl chloride with 3-chlorobenzoyl chloride. LCMS (m/z): 288 (M+H); $^1$H NMR (400 MHz, DMSO-d6) δ ppm 4.97 (s, 2H) 7.40 (d, J=8.6 Hz, 1H) 7.58 (t, J=7.8 Hz, 1H) 7.63-7.70 (m, 1H) 7.76 (dd, J=8.3, 2.0 Hz, 1H) 7.93 (ddd, J=8.0, 1.4, 1.2 Hz, 1H) 8.02 (t, J=1.9 Hz, 1H) 8.17 (d, J=1.8 Hz, 1H) 9.23 (s, 1H) 10.39 (s, 1H).

4-Chloro-N-(1-hydroxy-1,3-dihydro-benzo[c][1,2]oxaborol-6-yl)-benzamide (H9)

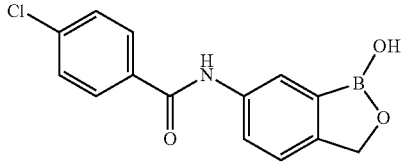 [SMILES: O=C(Nc1ccc2c(c1)B(O)OC2)c1ccc(Cl)cc1]

H9 was produced by a similar method as H63 by substituting thiophene-2-carbonyl chloride with 4-chlorobenzoyl chloride.

3-Bromo-N-(1-hydroxy-1,3-dihydro-benzo[c][1,2]oxaborol-6-yl)-benzamide (H10)

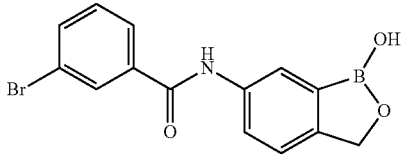

H10 was prepared using a procedure similar to that of H17 by substituting 5-fluoro-2-(trifluoromethyl)benzoyl chloride with 3-bromobenzoyl chloride. LCMS (m/z): 332 (M+H); $^1$H NMR (400 MHz, DMSO-d6) δ ppm 4.98 (s, 2H) 7.40 (d, J=8.2 Hz, 1H) 7.51 (t, J=7.8 Hz, 1H) 7.76 (dd, J=8.2, 2.1 Hz, 1H) 7.80 (ddd, J=8.0, 2.0, 1.0 Hz, 1H) 7.97 (ddd, J=8.0, 1.4, 1.2 Hz, 1H) 8.16 (ddd, J=3.5, 2.0, 1.8 Hz, 2H) 9.24 (s, 1H) 10.39 (s, 1H).

3,4-Dichloro-N-(1-hydroxy-1,3-dihydro-benzo[c][1,2]oxaborol-6-yl)-benzamide (H11)

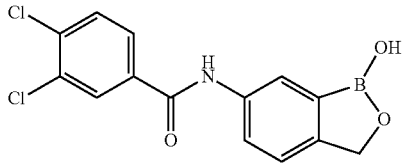 [SMILES: O=C(Nc1ccc2c(c1)B(O)OC2)c1ccc(Cl)c(Cl)c1]

H11 was prepared using a procedure similar to that of H17 by substituting 5-fluoro-2-(trifluoromethyl)benzoyl chloride with 3,4-dichlorobenzoyl chloride. LCMS (m/z): 322 (M+H); $^1$H NMR (400 MHz, DMSO-d6) δ ppm 4.97 (s, 2H) 7.40 (d, J=8.4 Hz, 1H) 7.75 (dd, J=8.3, 1.9 Hz, 1H) 7.83 (d, J=8.4 Hz, 1H) 7.95 (dd, J=8.3, 2.1 Hz, 1H) 8.16 (d, J=1.4 Hz, 1H) 8.23 (d, J=2.0 Hz, 1H) 9.24 (s, 1H) 10.43 (s, 1H).

3-Chloro-2-fluoro-N-(1-hydroxy-1,3-dihydro-benzo[c][1,2]oxaborol-6-yl)-benzamide (H12)

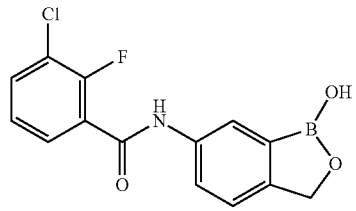 [SMILES: O=C(Nc1ccc2c(c1)B(O)OC2)c1cccc(Cl)c1F]

H12 was prepared using a procedure similar to that of H17 by substituting 5-fluoro-2-(trifluoromethyl)benzoyl chloride with 3-chloro-2-fluorobenzoyl chloride. LCMS (m/z): 306 (M+H); $^1$H NMR (400 MHz, DMSO-d6) δ ppm 4.97 (s, 2H) 7.33-7.43 (m, 2H) 7.65 (ddd, J=7.8, 6.2, 1.7 Hz, 1H) 7.71 (dd, J=8.2, 2.0 Hz, 1H) 7.74-7.80 (m, 1H) 8.14 (d, J=1.8 Hz, 1H) 9.26 (s, 1H) 10.58 (s, 1H).

5-Chloro-2-fluoro-N-(1-hydroxy-1,3-dihydro-benzo[c][1,2]oxaborol-6-yl)-benzamide (H13)

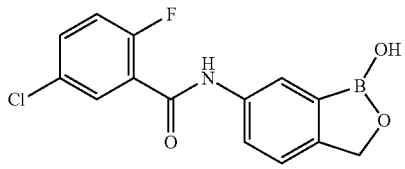 [SMILES: O=C(Nc1ccc2c(c1)B(O)OC2)c1cc(Cl)ccc1F]

H13 was prepared using a procedure similar to that of H17 by substituting 5-fluoro-2-(trifluoromethyl)benzoyl chloride with 3-chloro-6-fluorobenzoyl chloride. LCMS (m/z): 306 (M+H); $^1$H NMR (400 MHz, DMSO-d6) δ ppm 4.97 (s, 2H) 7.30-7.48 (m, 2H) 7.64 (ddd, J=8.8, 4.3, 2.8 Hz, 1H) 7.71 (dd, J=8.2, 2.0 Hz, 1H) 7.75 (dd, J=5.9, 2.7 Hz, 1H) 8.14 (d, J=1.8 Hz, 1H) 9.26 (s, 1H) 10.54 (s, 1H).

2-Chloro-4-fluoro-N-(1-hydroxy-1,3-dihydro-benzo[c][1,2]oxaborol-6-yl)-benzamide (H14)

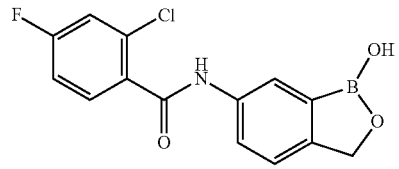 [SMILES: O=C(Nc1ccc2c(c1)B(O)OC2)c1ccc(F)cc1Cl]

H14 was prepared using a procedure similar to that of H17 by substituting 5-fluoro-2-(trifluoromethyl)benzoyl chloride with 2-chloro-4-fluorobenzoyl chloride. LCMS (m/z): 306 (M+H); $^1$H NMR (400 MHz, DMSO-d6) δ ppm 4.96 (s, 2H) 7.30-7.41 (m, 2H) 7.59 (dd, J=9.1, 2.4 Hz, 1H) 7.64-7.74 (m, 2H) 8.15 (d, J=2.0 Hz, 1H) 9.25 (s, 1H) 10.53 (s, 1H).

2,4-Difluoro-N-(1-hydroxy-1,3-dihydro-benzo[c][1,2]oxaborol-6-yl)-benzamide (H15)

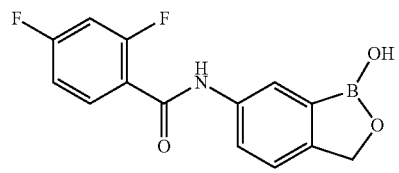 [SMILES: O=C(Nc1ccc2c(c1)B(O)OC2)c1ccc(F)cc1F]

H15 was prepared using a procedure similar to that of H17 by substituting 5-fluoro-2-(trifluoromethyl)benzoyl chloride with 2,4-difluorobenzoyl chloride. LCMS (m/z): 290 (M+H); $^1$H NMR (400 MHz, DMSO-d6) δ ppm 4.97 (s, 2H) 7.16-7.30 (m, 1H) 7.31-7.50 (m, 2H) 7.65-7.83 (m, 2H) 8.13 (s, 1H) 9.24 (s, 1H) 10.43 (s, 1H).

2,6-Difluoro-N-(1-hydroxy-1,3-dihydro-benzo[c][1,2]oxaborol-6-yl)-benzamide (H16)

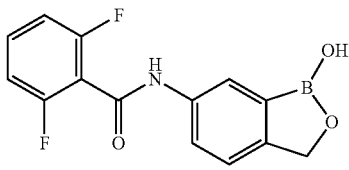 [SMILES: O=C(Nc1ccc2c(c1)B(O)OC2)c1c(F)cccc1F]

H16 was prepared using a procedure similar to that of H17 by substituting 5-fluoro-2-(trifluoromethyl)benzoyl chloride with 2,6-difluorobenzoyl chloride. LCMS (m/z): 290 (M+H); $^1$H NMR (400 MHz, DMSO-d6) δ ppm 4.97 (s, 2H) 7.15-7.32 (m, 2H) 7.40 (d, J=8.4 Hz, 1H) 7.59 (tt, J=8.5, 6.6 Hz, 1H) 7.68 (dd, J=8.2, 2.1 Hz, 1H) 8.14 (d, J=1.8 Hz, 1H) 10.81 (s, 1H).

5-Fluoro-N-(1-hydroxy-1,3-dihydro-benzo[c][1,2]
oxaborol-6-yl)-2-trifluoromethyl-benzamide (H17)

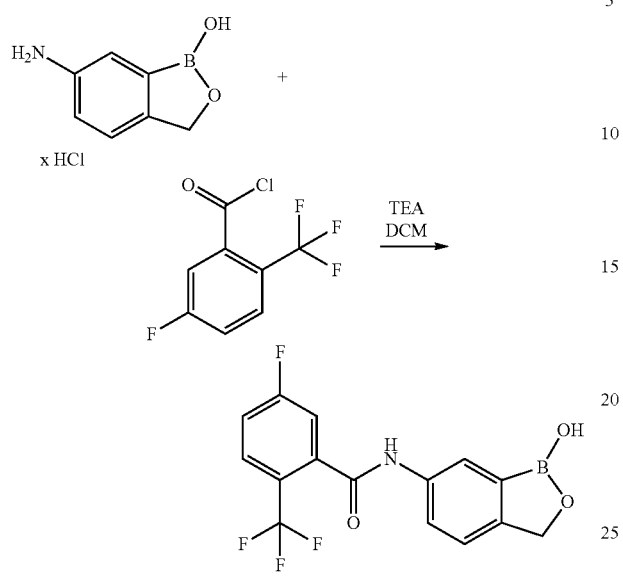

A 500 mL round bottom flask was charged with a mixture of 5-amino-2-hydroxymethylphenylboronic acid hydrochloride (2 g, 10.8 mmol, 1 eq), triethylamine (4.5 mL, 32.4 mmol, 3 eq) and dichloromethane (200 mL). 5-fluoro-2-(trifluoromethyl)benzoyl chloride (1.7 mL, 11.4 mmol, 1.05 eq) was then added and the reaction mixture was allowed to stair at room temperature overnight. Aqueous hydrochloric acid (1 M, 100 mL) was added to the mixture, and the reaction was stirred for an additional hour. The resulting precipitate was collected, and the resultant off-white powder was dried under vacuum.

LCMS (m/z) 340 (M+H); $^1$H NMR (400 MHz, DMSO-$d_6$) δ ppm 4.97 (s, 2H) 7.39 (d, J=8.4 Hz, 1H) 7.57 (td, J=8.7, 2.6 Hz, 1H) 7.65 (dd, J=8.3, 2.1 Hz, 1H) 7.71 (dd, J=8.7, 2.6 Hz, 1H) 7.94 (dd, J=8.8, 5.3 Hz, 1H) 8.13 (d, J=2.0 Hz, 1H) 9.26 (s, 1H) 10.63 (s, 1H). Amount Obtained: 2.44 g, 67% yield.

2-Fluoro-N-(1-hydroxy-1,3-dihydro-benzo[c][1,2]
oxaborol-6-yl)-6-trifluoromethyl-benzamide (H18)

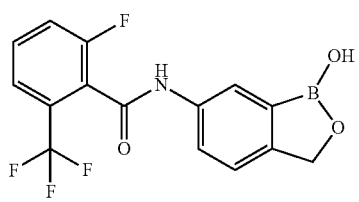 [SMILES: O=C(Nc1ccc2c(c1)B(O)OC2)c1c(F)cccc1C(F)(F)F]

H18 was prepared using a procedure similar to that of H17 by substituting 5-fluoro-2-(trifluoromethyl)benzoyl chloride with 2-fluoro-6-(trifluoromethyl)benzoyl chloride. LCMS (m/z): 340 (M+H); $^1$H NMR (400 MHz, DMSO-d6) δ ppm 4.97 (s, 2H) 7.40 (d, J=8.2 Hz, 1H) 7.63 (dd, J=8.2, 2.0 Hz, 1H) 7.67-7.85 (m, 3H) 8.12 (d, J=2.0 Hz, 1H) 9.26 (s, 1H) 10.81 (s, 1H).

4-Fluoro-N-(1-hydroxy-1,3-dihydro-benzo[c][1,2]
oxaborol-6-yl)-2-trifluoromethyl-benzamide (H19)

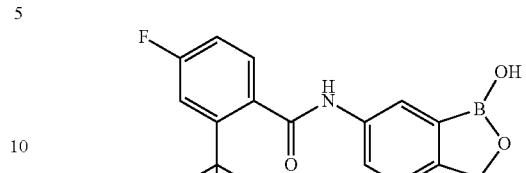

H19 was prepared using a procedure similar to that of H17 by substituting 5-fluoro-2-(trifluoromethyl)benzoyl chloride with 4-fluoro-2-(trifluoromethyl)-benzoyl chloride. LCMS (m/z): 339 (M+H); $^1$H NMR (400 MHz, DMSO-d6) δ ppm 4.96 (s, 2H) 7.39 (d, J=8.2 Hz, 1H) 7.61-7.73 (m, 2H) 7.74-7.89 (m, 2H) 8.13 (d, J=1.6 Hz, 1H) 9.25 (s, 1H) 10.59 (s, 1H).

2-Fluoro-N-(1-hydroxy-1,3-dihydro-benzo[c][1,2]
oxaborol-6-yl)-3-trifluoromethyl-benzamide (H20)

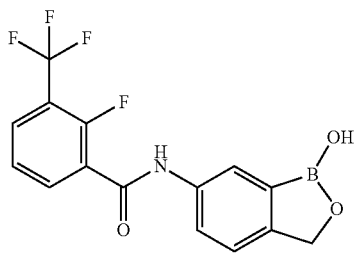 [SMILES: O=C(Nc1ccc2c(c1)B(O)OC2)c1cccc(C(F)(F)F)c1F]

H20 was prepared using a procedure similar to that of H17 by substituting 5-fluoro-2-(trifluoromethyl)benzoyl chloride with 2-fluoro-3-(trifluoromethyl)benzoyl chloride. LCMS (m/z): 362 (M+Na); $^1$H NMR (400 MHz, DMSO-d6) δ ppm 4.97 (s, 2H) 7.41 (d, J=8.4 Hz, 1H) 7.55 (t, J=7.8 Hz, 1H) 7.71 (dd, J=8.2, 2.0 Hz, 1H) 7.89-8.07 (m, 2H) 8.15 (d, J=2.0 Hz, 1H) 9.26 (s, 1H) 10.66 (s, 1H).

2-Fluoro-N-(1-hydroxy-1,3-dihydro-benzo[c][1,2]
oxaborol-6-yl)-4-trifluoromethyl-benzamide (H21)

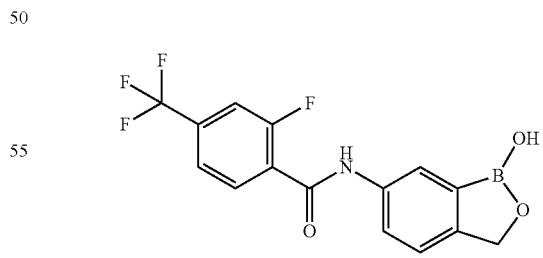

H21 was prepared using a procedure similar to that of H17 by substituting 5-fluoro-2-(trifluoromethyl)benzoyl chloride with 2-fluoro-4-(trifluoromethyl)benzoyl chloride. LCMS (m/z): 362 (M+Na); $^1$H NMR (400 MHz, DMSO-d6) δ ppm 4.97 (s, 2H) 7.41 (d, J=8.6 Hz, 1H) 7.67-7.80 (m, 2H) 7.83-7.98 (m, 2H) 8.14 (d, J=1.8 Hz, 1H) 9.26 (s, 1H) 10.64 (s, 1H).

2-Fluoro-N-(1-hydroxy-1,3-dihydro-benzo[c][1,2]oxaborol-6-yl)-5-trifluoromethyl-benzamide (H22)

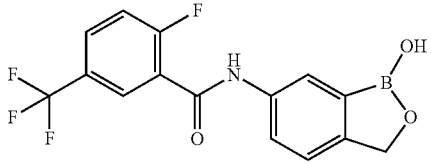 [SMILES: O=C(Nc1ccc2c(c1)B(O)OC2)c1cc(C(F)(F)F)ccc1F]

H22 was prepared using a procedure similar to that of H17 by substituting 5-fluoro-2-(trifluoromethyl)benzoyl chloride with 2-fluoro-5-(trifluoromethyl)benzoyl chloride. LCMS (m/z): 340 (M+H); $^1$H NMR (400 MHz, DMSO-d6) δ ppm 4.97 (s, 2H) 7.41 (d, J=8.4 Hz, 1H) 7.63 (t, J=9.1 Hz, 1H) 7.72 (dd, J=8.2, 2.0 Hz, 1H) 7.93-8.03 (m, 1H) 8.07 (dd, J=6.2, 2.3 Hz, 1H) 8.14 (d, J=2.0 Hz, 1H) 9.26 (s, 1H) 10.62 (s, 1H).

2-Chloro-N-(1-hydroxy-1,3-dihydro-benzo[c][1,2]oxaborol-6-yl)-5-trifluoromethyl-benzamide (H23)

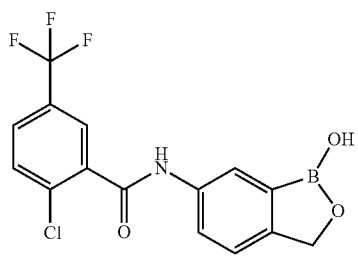 [SMILES: O=C(Nc1ccc2c(c1)B(O)OC2)c1cc(C(F)(F)F)ccc1Cl]

H23 was prepared using a procedure similar to that of H17 by substituting 5-fluoro-2-(trifluoromethyl)benzoyl chloride with 2-chloro-5-(trifluoromethyl)benzoyl chloride. LCMS (m/z): 356 (M+H); $^1$H NMR (400 MHz, DMSO-d6) δ ppm 4.97 (s, 2H) 7.40 (d, J=8.4 Hz, 1H) 7.70 (dd, J=8.2, 2.0 Hz, 1H) 7.76-7.94 (m, 2H) 8.04 (d, J=2.3 Hz, 1H) 8.16 (d, J=1.8 Hz, 1H) 9.26 (s, 1H) 10.66 (s, 1H).

3-Chloro-2-fluoro-N-(1-hydroxy-1,3-dihydro-benzo[c][1,2]oxaborol-6-yl)-6-trifluoromethyl-benzamide (H24)

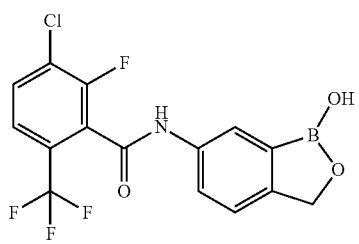 [SMILES: O=C(Nc1ccc2c(c1)B(O)OC2)c1c(C(F)(F)F)ccc(Cl)c1F]

H24 was prepared using a procedure similar to that of H17 by substituting 5-fluoro-2-(trifluoromethyl)benzoyl chloride with 3-chloro-2-fluoro-6-(trifluoromethyl)benzoyl chloride. LCMS (m/z): 374 (M+H); $^1$H NMR (400 MHz, DMSO-d6) δ ppm 4.97 (s, 2H) 7.41 (d, J=8.2 Hz, 1H) 7.61 (dd, J=8.3, 2.0 Hz, 1H) 7.77 (d, J=8.8 Hz, 1H) 7.98 (t, J=7.6 Hz, 1H) 8.10 (d, J=1.8 Hz, 1H) 9.27 (s, 1H) 10.89 (s, 1H).

N-(1-Hydroxy-1,3-dihydro-benzo[c][1,2]oxaborol-6-yl)-2,4-bis-trifluoromethyl-benzamide (H25)

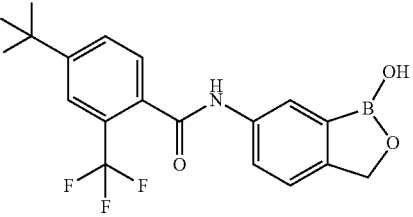

H25 was prepared using a procedure similar to that of H17 by substituting 5-fluoro-2-(trifluoromethyl)benzoyl chloride with 2,4-bis(trifluoromethyl)benzoyl chloride. LCMS (m/z): 412 (M+Na); $^1$H NMR (400 MHz, DMSO-d6) δ ppm 4.97 (s, 2H) 7.41 (d, J=8.4 Hz, 1H) 7.66 (dd, J=8.2, 2.0 Hz, 1H) 8.00 (d, J=8.0 Hz, 1H) 8.13 (d, J=1.8 Hz, 1H) 8.18-8.27 (m, 2H) 9.27 (s, 1H) 10.71 (s, 1H).

N-(1-Hydroxy-1,3-dihydro-benzo[c][1,2]oxaborol-6-yl)-2,5-bis-trifluoromethyl-benzamide (H26)

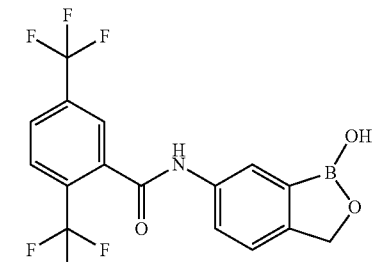

H26 was prepared using a procedure similar to that of H17 by substituting 5-fluoro-2-(trifluoromethyl)benzoyl chloride with 2,5-bis(trifluoromethyl)benzoyl chloride. LCMS (m/z): 390 (M+H); $^1$H NMR (400 MHz, DMSO-d6) δ ppm 4.97 (s, 2H) 7.40 (d, J=8.4 Hz, 1H) 7.66 (dd, J=8.2, 2.0 Hz, 1H) 8.11 (s, 2H) 8.13 (d, J=1.8 Hz, 1H) 8.19 (s, 1H) 9.26 (s, 1H) 10.71 (s, 1H).

N-(1-Hydroxy-1,3-dihydro-benzo[c][1,2]oxaborol-6-yl)-3,5-bis-trifluoromethyl-benzamide (H27)

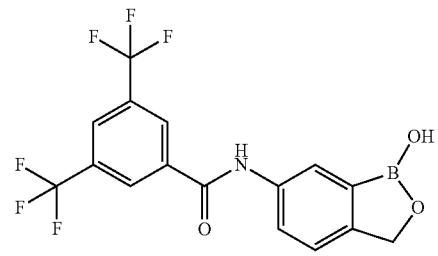 [SMILES: O=C(Nc1ccc2c(c1)B(O)OC2)c1cc(C(F)(F)F)cc(C(F)(F)F)c1]

H27 was prepared using a procedure similar to that of H17 by substituting 5-fluoro-2-(trifluoromethyl)benzoyl chloride with 2,5-bis(trifluoromethyl)benzoyl chloride. LCMS (m/z): 390 (M+H); $^1$H NMR (400 MHz, DMSO-d6) δ ppm 4.99 (s, 2H) 7.44 (d, J=8.2 Hz, 1H) 7.78 (dd, J=8.2, 2.0 Hz, 1H) 8.16 (d, J=1.8 Hz, 1H) 8.38 (s, 1H) 8.62 (s, 2H) 9.26 (br. s., 1H) 10.71 (s, 1H).

N-(1-Hydroxy-1,3-dihydro-benzo[c][1,2]oxaborol-6-yl)-2-methyl-benzamide (H28)

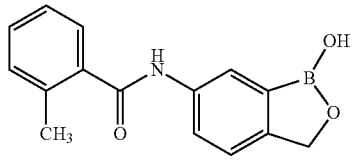 [SMILES: Cc1ccccc1C(=O)Nc1ccc2c(c1)B(O)OC2]

H28 was prepared using a procedure similar to that of H17 by substituting 5-fluoro-2-(trifluoromethyl)benzoyl chloride with 2-methylbenzoyl chloride. LCMS (m/z): 268 (M+H); $^1$H NMR (400 MHz, DMSO-d6) δ ppm 2.39 (s, 3H) 4.96 (s, 2H) 7.26-7.34 (m, 2H) 7.34-7.42 (m, 2H) 7.46 (d, J=7.6 Hz, 1H) 7.72 (dd, J=8.2, 1.8 Hz, 1H) 8.19 (d, J=1.2 Hz, 1H) 9.22 (s, 1H) 10.32 (s, 1H).

N-(1-Hydroxy-1,3-dihydro-benzo[c][1,2]oxaborol-6-yl)-3-methyl-benzamide (H29)

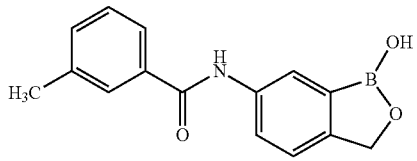 [SMILES: Cc1cccc(C(=O)Nc2ccc3c(c2)B(O)OC3)c1]

H29 was prepared using a procedure similar to that of H17 by substituting 5-fluoro-2-(trifluoromethyl)benzoyl chloride with 3-methylbenzoyl chloride. LCMS (m/z): 268 (M+H); $^1$H NMR (400 MHz, DMSO-d6) δ ppm 2.38 (s, 3H) 4.94 (s, 2H) 7.34-7.42 (m, 3H) 7.69-7.78 (m, 3H) 8.14 (s, 1H) 9.19 (s, 1H) 10.21 (s, 1H).

N-(1-Hydroxy-1,3-dihydro-benzo[c][1,2]oxaborol-6-yl)-4-methyl-benzamide (H30)

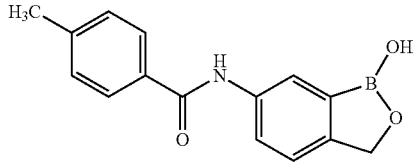

H30 was produced by a similar method as H63 by substituting thiophene-2-carbonyl chloride with 4-methyl-benzoyl chloride.

4-Ethyl-N-(1-hydroxy-1,3-dihydro-benzo[c][1,2]oxaborol-6-yl)-benzamide (H31)

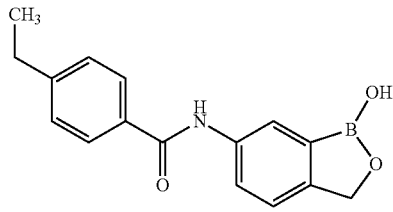 [SMILES: CCc1ccc(C(=O)Nc2ccc3c(c2)B(O)OC3)cc1]

H31 was prepared using a procedure similar to that of H17 by substituting 5-fluoro-2-(trifluoromethyl)benzoyl chloride with 4-ethyl benzoyl chloride. LCMS (m/z): 282 (M+H); $^1$H NMR (400 MHz, DMSO-d6) δ ppm 1.22 (t, J=7.6 Hz, 3H) 2.69 (q, J=7.6 Hz, 2H) 4.97 (s, 2H) 7.33-7.42 (m, 3H) 7.76 (dd, J=8.3, 2.1 Hz, 1H) 7.86-7.94 (m, 2H) 8.17 (d, J=1.8 Hz, 1H) 9.21 (s, 1H) 10.20 (s, 1H).

4-Butyl-N-(1-hydroxy-1,3-dihydro-benzo[c][1,2]oxaborol-6-yl)-benzamide (H32)

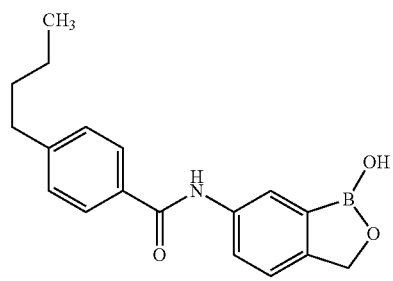 [SMILES: CCCCc1ccc(C(=O)Nc2ccc3c(c2)B(O)OC3)cc1]

H32 was prepared using a procedure similar to that of H17 by substituting 5-fluoro-2-(trifluoromethyl)benzoyl chloride with 4-n-butylbenzoyl chloride. LCMS (m/z): 310 (M+H); $^1$H NMR (400 MHz, DMSO-d6) δ ppm 0.83-0.97 (m, 3H) 1.32 (dq, J=14.9, 7.4 Hz, 2H) 1.52-1.67 (m, 2H) 2.66 (t, J=7.6 Hz, 2H) 4.97 (s, 2H) 7.30-7.43 (m, 3H) 7.76 (dd, J=8.3, 2.1 Hz, 1H) 7.84-7.93 (m, 2H) 8.17 (d, J=1.8 Hz, 1H) 9.21 (s, 1H) 10.20 (s, 1H).

4-tert-Butyl-N-(1-hydroxy-1,3-dihydro-benzo[c][1,2]oxaborol-6-yl)-benzamide (H33)

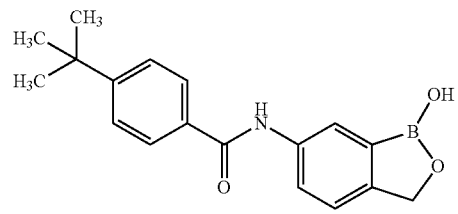 [SMILES: CC(C)(C)c1ccc(C(=O)Nc2ccc3c(c2)B(O)OC3)cc1]

H33 was prepared using a procedure similar to that of H17 by substituting 5-fluoro-2-(trifluoromethyl)benzoyl chloride with 4-(trifluoromethyl)benzoyl chloride. LCMS (m/z): 310 (M+H); $^1$H NMR (400 MHz, DMSO-d6) δ ppm 1.33 (s, 9H) 4.97 (s, 2H) 7.38 (d, J=8.4 Hz, 1H) 7.50-7.59 (m, 2H) 7.76

(dd, J=8.2, 2.0 Hz, 1H) 7.85-7.95 (m, 2H) 8.16 (d, J=1.8 Hz, 1H) 9.21 (s, 1H) 10.21 (s, 1H).

N-(1-Hydroxy-1,3-dihydro-benzo[c][1,2]oxaborol-6-yl)-3,5-dimethyl-benzamide (H34)

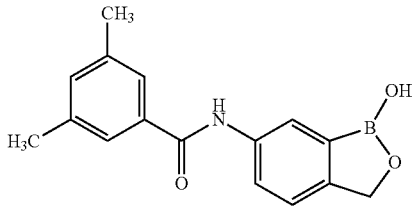 [SMILES: Cc1cc(C)cc(C(=O)Nc2ccc3c(c2)B(O)OC3)c1]

H34 was produced by a similar method as H75 by substituting pyrazine-2-carboxylic acid with 3,5-dimethyl-benzoic acid.

N-(1-Hydroxy-1,3-dihydro-benzo[c][1,2]oxaborol-6-yl)-2-methoxy-benzamide (H35)

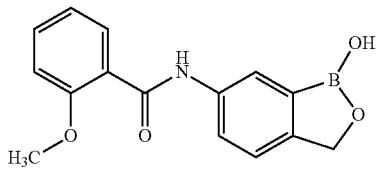 [SMILES: COc1ccccc1C(=O)Nc1ccc2c(c1)B(O)OC2]

H35 was prepared using a procedure similar to that of H17 by substituting 5-fluoro-2-(trifluoromethyl)benzoyl chloride with 2-methoxybenzoyl chloride. LCMS (m/z): 284 (M+H); $^1$H NMR (400 MHz, DMSO-d6) δ ppm 3.91 (s, 3H) 4.96 (s, 2H) 7.02-7.11 (m, 1H) 7.18 (d, J=8.4 Hz, 1H) 7.37 (d, J=8.2 Hz, 1H) 7.46-7.54 (m, 1H) 7.65 (dd, J=7.6, 1.8 Hz, 1H) 7.74 (dd, J=8.2, 2.0 Hz, 1H) 8.16 (d, J=1.8 Hz, 1H) 9.22 (s, 1H) 10.14 (s, 1H).

N-(1-Hydroxy-1,3-dihydro-benzo[c][1,2]oxaborol-6-yl)-3-methoxy-benzamide (H36)

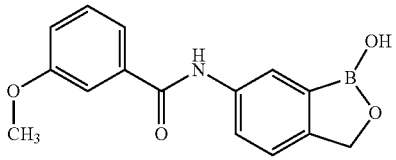 [SMILES: COc1cccc(C(=O)Nc2ccc3c(c2)B(O)OC3)c1]

H36 was prepared using a procedure similar to that of H17 by substituting 5-fluoro-2-(trifluoromethyl)benzoyl chloride with 3-methoxybenzoyl chloride. LCMS (m/z): 284 (M+H); $^1$H NMR (400 MHz, DMSO-d6) δ ppm 3.84 (s, 3H) 4.97 (s, 2H) 7.12-7.19 (m, 1H) 7.35-7.59 (m, 4H) 7.77 (dd, J=8.3, 2.0 Hz, 1H) 8.15 (d, J=1.8 Hz, 1H) 9.22 (s, 1H) 10.25 (s, 1H).

N-(1-Hydroxy-1,3-dihydro-benzo[c][1,2]oxaborol-6-yl)-4-methoxy-benzamide (H37)

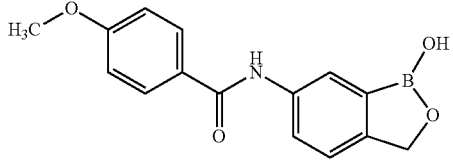 [SMILES: COc1ccc(C(=O)Nc2ccc3c(c2)B(O)OC3)cc1]

H37 was prepared using a procedure similar to that of H17 by substituting 5-fluoro-2-(trifluoromethyl)benzoyl chloride with 4-methoxybenzoyl chloride. LCMS (m/z): 284 (M+H); $^1$H NMR (400 MHz, DMSO-d6) δ ppm 3.84 (s, 3H) 4.96 (s, 2H) 6.96-7.12 (m, 2H) 7.37 (d, J=8.6 Hz, 1H) 7.76 (dd, J=8.3, 2.0 Hz, 1H) 7.91-8.03 (m, 2H) 8.15 (d, J=2.0 Hz, 1H) 9.20 (s, 1H) 10.12 (s, 1H).

N-(1-Hydroxy-1,3-dihydro-benzo[c][1,2]oxaborol-6-yl)-2,4-ditnethoxy-benzamide (H38)

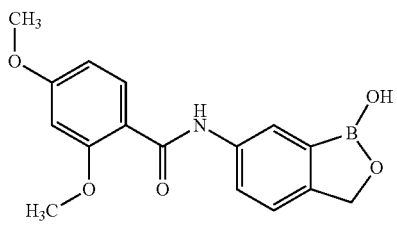 [SMILES: COc1ccc(C(=O)Nc2ccc3c(c2)B(O)OC3)c(OC)c1]

H38 was prepared using a procedure similar to that of H17 by substituting 5-fluoro-2-(trifluoromethyl)benzoyl chloride with 3,5-dimethoxybenzoyl chloride. LCMS (m/z): 314 (M+H); $^1$H NMR (400 MHz, DMSO-d6) δ ppm 3.85 (s, 3H) 3.96 (s, 3H) 4.96 (s, 2H) 6.67 (dd, J=8.6, 2.3 Hz, 1H) 6.71 (d, J=2.3 Hz, 1H) 7.36 (d, J=8.4 Hz, 1H) 7.74 (dd, J=8.1, 1.9 Hz, 1H) 7.77 (d, J=8.6 Hz, 1H) 8.13 (d, J=1.8 Hz, 1H) 9.20 (br. s., 1H) 9.95 (s, 1H).

N-(1-Hydroxy-1,3-dihydro-benzo[c][1,2]oxaborol-6-yl)-3,4-ditnethoxy-benzamide (H39)

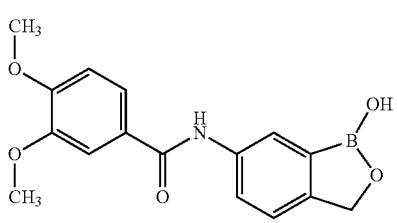 [SMILES: COc1ccc(C(=O)Nc2ccc3c(c2)B(O)OC3)cc1OC]

H39 was produced by a similar method as H75 by substituting pyrazine-2-carboxylic acid with 3,4-dimethoxy-benzoic acid.

N-(1-Hydroxy-1,3-dihydro-benzo[c][1,2]oxaborol-6-yl)-2,6-dimethoxy-benzamide (H40)

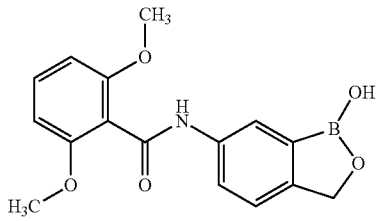 [SMILES: COc1cccc(OC)c1C(=O)Nc1ccc2c(c1)B(O)OC2]

H40 was produced by a similar method as H63 by substituting thiophene-2-carbonyl chloride with 2,6-dimethoxybenzoyl chloride.

N-(1-Hydroxy-1,3-dihydro-benzo[c][1,2]oxaborol-6-yl)-2,4,6-trimethoxy-benzamide (H41)

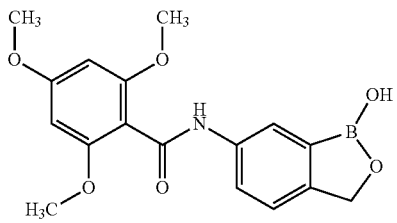 [SMILES: COc1cc(OC)c(C(=O)Nc2ccc3c(c2)B(O)OC3)c(OC)c1]

H41 was produced by a similar method as H63 by substituting thiophene-2-carbonyl chloride with 3,4,5-trimethoxybenzoyl chloride.

N-(1-Hydroxy-1,3-dihydro-benzo[c][1,2]oxaborol-6-yl)-4-isopropoxy-benzamide (H42)

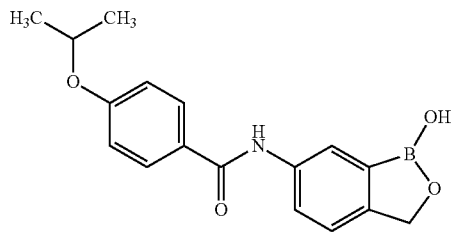 [SMILES: CC(C)Oc1ccc(C(=O)Nc2ccc3c(c2)B(O)OC3)cc1]

H42 was prepared using a procedure similar to that of H6 by substituting 4-fluorobenzoic acid with 4-isopropoxybenzoic acid. LCMS (m/z): 312 (M+H); $^1$H NMR (400 MHz, DMSO-d6) δ ppm 1.30 (d, J=6.1 Hz, 7H) 4.74 (spt, J=6.0 Hz, 1H) 4.96 (s, 2H) 6.98-7.09 (m, 2H) 7.37 (d, J=8.2 Hz, 1H) 7.75 (dd, J=8.2, 2.0 Hz, 1H) 7.90-7.98 (m, 2H) 8.15 (d, J=1.6 Hz, 1H) 9.23 (br. s., 1H) 10.11 (s, 1H).

N-(1-Hydroxy-1,3-dihydro-benzo[c][1,2]oxaborol-6-yl)-4-methoxy-3-methyl-benzamide (H43)

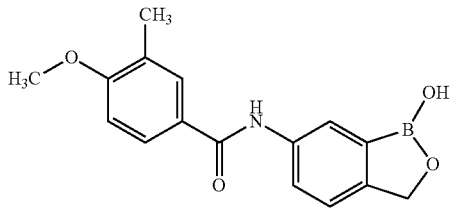 [SMILES: COc1ccc(C(=O)Nc2ccc3c(c2)B(O)OC3)cc1C]

H43 was prepared using a procedure similar to that of H6 by substituting 4-fluorobenzoic acid with 4-methoxy-3-methylbenzoic acid. LCMS (m/z): 298 (M+H); $^1$H NMR (400 MHz, DMSO-d6) δ ppm 2.22 (s, 3H) 3.87 (s, 3H) 4.96 (s, 2H) 7.06 (d, J=8.6 Hz, 1H) 7.37 (d, J=8.2 Hz, 1H) 7.75 (dd, J=8.3, 1.9 Hz, 1H) 7.81 (d, J=1.8 Hz, 1H) 7.86 (dd, J=8.5, 2.2 Hz, 1H) 8.14 (d, J=1.6 Hz, 1H) 10.09 (s, 1H).

N-(1-Hydroxy-1,3-dihydro-benzo[c][1,2]oxaborol-6-yl)-2-trifluoromethoxy-benzamide (H44)

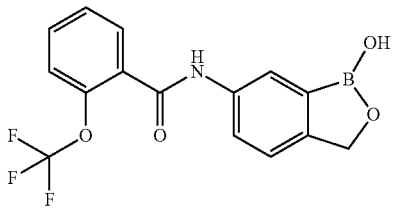 [SMILES: O=C(Nc1ccc2c(c1)B(O)OC2)c1ccccc1OC(F)(F)F]

H44 was prepared using a procedure similar to that of H17 by substituting 5-fluoro-2-(trifluoromethyl)benzoyl chloride with 2-(trifluoromethoxy)benzoyl chloride. LCMS (m/z): 338 (M+H); $^1$H NMR (400 MHz, DMSO-d6) δ ppm 4.96 (s, 2H) 7.38 (d, J=8.2 Hz, 1H) 7.47-7.60 (m, 2H) 7.60-7.77 (m, 4H) 8.15 (d, J=1.8 Hz, 1H) 9.25 (s, 1H) 10.51 (s, 1H).

N-(1-Hydroxy-1,3-dihydro-benzo[c][1,2]oxaborol-6-yl)-3-trifluoromethoxy-benzamide (H45)

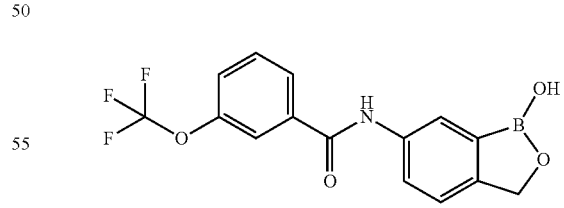

H45 was prepared using a procedure similar to that of H17 by substituting 5-fluoro-2-(trifluoromethyl)benzoyl chloride with 3-(trifluoromethoxy)benzoyl chloride. LCMS (m/z): 338 (M+H); $^1$H NMR (400 MHz, DMSO-d6) δ ppm 4.98 (s, 2H) 7.41 (d, J=8.4 Hz, 1H) 7.58-7.66 (m, 1H) 7.69 (t, J=8.0 Hz, 1H) 7.76 (dd, J=8.2, 2.0 Hz, 1H) 7.93 (s, 1H) 8.03 (dt, J=7.8, 1.3 Hz, 1H) 8.15 (d, J=2.0 Hz, 1H) 9.24 (s, 1H) 10.43 (s, 1H).

111

N-(1-Hydroxy-1,3-dihydro-benzo[c][1,2]oxaborol-6-yl)-4-trifluoromethoxy-benzamide (H46)

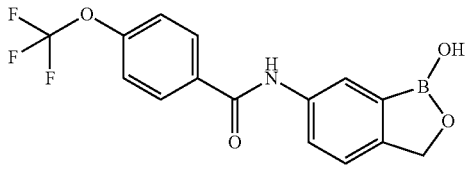 [SMILES: O=C(Nc1ccc2c(c1)B(O)OC2)c1ccc(OC(F)(F)F)cc1]

H46 was prepared using a procedure similar to that of H17 by substituting 5-fluoro-2-(trifluoromethyl)benzoyl chloride with 4-(trifluoromethoxy)benzoyl chloride. LCMS (m/z): 338 (M+H); $^1$H NMR (400 MHz, DMSO-d6) δ ppm 4.97 (s, 2H) 7.40 (d, J=8.2 Hz, 1H) 7.54 (d, J=8.0 Hz, 2H) 7.76 (dd, J=8.2, 2.0 Hz, 1H) 8.05-8.13 (m, 2H) 8.16 (d, J=1.8 Hz, 1H) 9.24 (s, 1H) 10.39 (s, 1H).

N-(1-Hydroxy-1,3-dihydro-benzo[c][1,2]oxaborol-6-yl)-4-trifluoromethylsulfanyl-benzamide (H47)

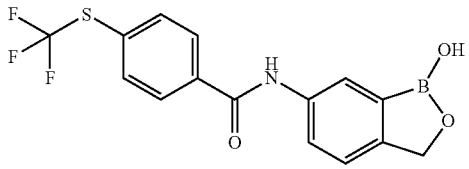 [SMILES: O=C(Nc1ccc2c(c1)B(O)OC2)c1ccc(SC(F)(F)F)cc1]

H47 was prepared using a procedure similar to that of H17 by substituting 5-fluoro-2-(trifluoromethyl)benzoyl chloride with 4-(trifluoromethylsulfanyl)benzoyl chloride. LCMS (m/z): 354 (M+H); $^1$H NMR (400 MHz, DMSO-d6) δ ppm 4.98 (s, 2H) 7.41 (d, J=8.2 Hz, 1H) 7.77 (dd, J=8.3, 2.0 Hz, 1H) 7.89 (d, J=8.2 Hz, 2H) 8.03-8.13 (m, 2H) 8.18 (d, J=2.0 Hz, 1H) 9.25 (s, 1H) 10.48 (s, 1H).

N-(1-Hydroxy-1,3-dihydro-benzo[c][1,2]oxaborol-6-yl)-2-nitro-benzamide (H48)

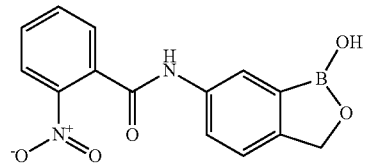

H48 was prepared using a procedure similar to that of H17 by substituting 5-fluoro-2-(trifluoromethyl)benzoyl chloride with 2-nitrobenzoyl chloride. LCMS (m/z): 299 (M+H); $^1$H NMR (400 MHz, DMSO-d6) δ ppm 4.97 (s, 2H) 7.40 (d, J=8.8 Hz, 1H) 7.66 (dd, J=8.3, 2.1 Hz, 1H) 7.72-7.82 (m, 2H) 7.84-7.92 (m, 1H) 8.09-8.20 (m, 2H) 9.26 (s, 1H) 10.69 (s, 1H).

112

4-Cyano-N-(1-hydroxy-1,3-dihydro-benzo[c][1,2]oxaborol-6-yl)-benzamide (H49)

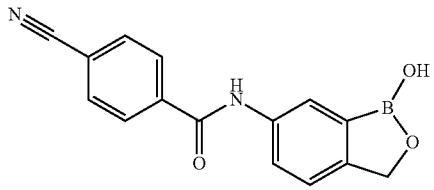 [SMILES: N#Cc1ccc(C(=O)Nc2ccc3c(c2)B(O)OC3)cc1]

H49 was prepared using a procedure similar to that of H17 by substituting 5-fluoro-2-(trifluoromethyl)benzoyl chloride with 4-cyanobenzoyl chloride. LCMS (m/z): 279 (M+H); $^1$H NMR (400 MHz, DMSO-d6) δ ppm 4.98 (s, 2H) 7.41 (d, J=8.2 Hz, 1H) 7.77 (dd, J=8.2, 2.0 Hz, 1H) 7.99-8.08 (m, 2H) 8.08-8.16 (m, 2H) 8.18 (d, J=1.8 Hz, 1H) 9.25 (s, 1H) 10.53 (s, 1H).

4-Dimethylamino-N-(1-hydroxy-1,3-dihydro-benzo[c][1,2]oxaborol-6-yl)-benzamide (H50)

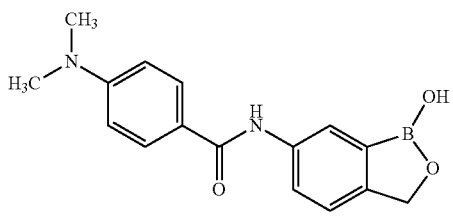 [SMILES: CN(C)c1ccc(C(=O)Nc2ccc3c(c2)B(O)OC3)cc1]

H50 was produced by a similar method as H63 by substituting thiophene-2-carbonyl chloride with 4-(dimethylamino)benzoyl chloride.

4-Acetylamino-N-(1-hydroxy-1,3-dihydro-benzo[c][1,2]oxaborol-6-yl)-benzamide (H51)

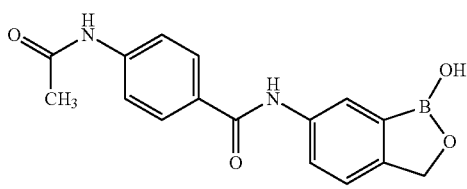 [SMILES: CC(=O)Nc1ccc(C(=O)Nc2ccc3c(c2)B(O)OC3)cc1]

H51 was prepared using a procedure similar to that of H17 by substituting 5-fluoro-2-(trifluoromethyl)benzoyl chloride with 4-(N-acetylamino)benzoyl chloride. LCMS (m/z): 311 (M+H); $^1$H NMR (400 MHz, DMSO-d6) δ ppm 2.09 (s, 3H) 4.96 (s, 2H) 7.37 (d, J=8.2 Hz, 1H) 7.65-7.81 (m, 3H) 7.89-8.00 (m, 2H) 8.15 (d, J=2.0 Hz, 1H) 9.21 (s, 1H) 10.15 (s, 1H) 10.22 (s, 1H).

4-{[1-Dimethylamino-meth-(E)-ylidene]-sulfa-moyl}-N-(1-hydroxy-1,3-dihydro-benzo[c][1,2]oxa-borol-6-yl)-benzamide (H52)

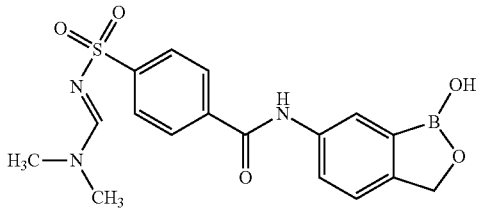 [SMILES: CN(C)/C=N/S(=O)(=O)c1ccc(C(=O)Nc2ccc3c(c2)B(O)OC3)cc1]

H52 was prepared using a procedure similar to that of H17 by substituting 5-fluoro-2-(trifluoromethyl)benzoyl chloride with the dimethylformamide complex of 4-(sulfamido)be-nozyl chloride. LCMS (m/z): 388 (M+H); $^1$H NMR (400 MHz, Acetone-d6) δ ppm 3.02 (s, 3H) 3.26 (s, 3H) 5.01 (s, 2H) 7.41 (d, J=8.2 Hz, 1H) 7.85 (dt, J=8.3, 1.8 Hz, 1H) 7.89-7.97 (m, 2H) 8.08-8.14 (m, 3H) 8.21 (s, 1H) 8.25 (t, J=2.1 Hz, 1H) 9.79 (br. s., 1H).

4-Phenyl-N-(1-hydroxy-1,3-dihydro-benzo[c][1,2]oxaborol-6-yl)-benzamide (H53)

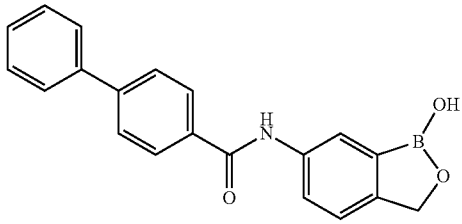 [SMILES: O=C(Nc1ccc2c(c1)B(O)OC2)c1ccc(-c2ccccc2)cc1]

This compound was produced by a similar method as H75 by substituting pyrazine-2-carboxylic acid with biphenyl-4-carboxylic acid.

Naphthalene-1-carboxylic acid (1-hydroxy-1,3-dihydro-benzo[c][1,2]oxaborol-6-yl)-amide (H54)

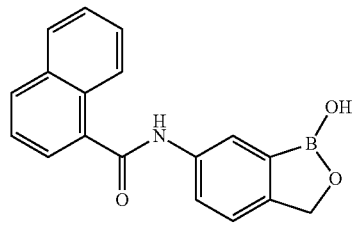 [SMILES: O=C(Nc1ccc2c(c1)B(O)OC2)c1cccc2ccccc12]

H54 was prepared using a procedure similar to that of H17 by substituting 5-fluoro-2-(trifluoromethyl)benzoyl chloride with 1-naphthoyl chloride. LCMS (m/z) δ 304 (M+H); $^1$H NMR (400 MHz, DMSO-d6) δ ppm 4.99 (s, 2H) 7.41 (d, J=8.2 Hz, 1H) 7.56-7.66 (m, 3H) 7.72-7.85 (m, 2H) 8.00-8.06 (m, 1H) 8.08 (d, J=8.4 Hz, 1H) 8.15-8.22 (m, 1H) 8.26 (d, J=1.8 Hz, 1H) 9.25 (s, 1H) 10.60 (s, 1H).

Naphthalene-2-carboxylic acid (1-hydroxy-1,3-dihydro-benzo[c][1,2]oxaborol-6-yl)-amide (H55)

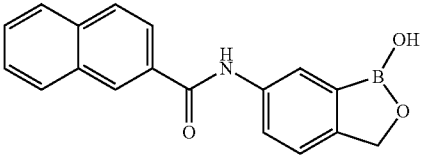 [SMILES: O=C(Nc1ccc2c(c1)B(O)OC2)c1ccc2ccccc2c1]

H55 was prepared using a procedure similar to that of H17 by substituting 5-fluoro-2-(trifluoromethyl)benzoyl chloride with 2-naphthoyl chloride. LCMS (m/z): 304 (M+H); $^1$H NMR (400 MHz, DMSO-d6) δ ppm 4.99 (s, 2H) 7.41 (d, J=8.0 Hz, 1H) 7.58-7.69 (m, 2H) 7.82 (dd, J=8.3, 2.1 Hz, 1H) 7.99-8.13 (m, 4H) 8.23 (d, J=1.8 Hz, 1H) 8.60 (s, 1H) 9.24 (s, 1H) 10.47 (s, 1H).

Benzo[1,3]dioxole-5-carboxylic acid (1-hydroxy-1,3-dihydro-benzo[c][1,2]oxaborol-6-yl)-amide (H56)

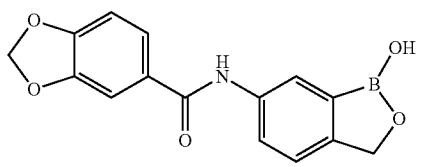 [SMILES: O=C(Nc1ccc2c(c1)B(O)OC2)c1ccc2c(c1)OCO2]

H56 was prepared using a procedure similar to that of H17 by substituting 5-fluoro-2-(trifluoromethyl)benzoyl chloride with piperonyloyl chloride. LCMS (m/z): 298 (M+H); $^1$H NMR (400 MHz, DMSO-d6) δ ppm 4.96 (s, 2H) 6.13 (s, 2H) 7.06 (d, J=8.2 Hz, 1H) 7.37 (d, J=8.4 Hz, 1H) 7.53 (d, J=1.8 Hz, 1H) 7.59 (dd, J=8.2, 1.8 Hz, 1H) 7.74 (dd, J=8.2, 2.1 Hz, 1H) 8.14 (d, J=1.8 Hz, 1H) 9.21 (s, 1H).

Cyclopropanecarboxylic acid (1-hydroxy-1,3-dihydro-benzo[c][1,2]oxaborol-6-yl)-amide (H57)

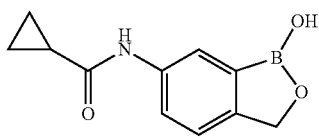 [SMILES: O=C(Nc1ccc2c(c1)B(O)OC2)C1CC1]

H57 was prepared using a procedure similar to that of H17 by substituting 5-fluoro-2-(trifluoromethyl)benzoyl chloride with cyclopropanecarbonyl chloride. LCMS (m/z): 218 (M+H); $^1$H NMR (400 MHz, DMSO-d6) δ ppm 0.73-0.86 (m, 4H) 1.71-1.88 (m, 1H) 4.93 (s, 2H) 7.31 (d, J=8.2 Hz, 1H) 7.62 (dd, J=8.2, 2.0 Hz, 1H) 7.97 (d, J=1.8 Hz, 1H) 9.17 (s, 1H) 10.19 (s, 1H).

Cyclohexanecarboxylic acid (1-hydroxy-1,3-dihydro-benzo[c][1,2]oxaborol-6-yl)-amide (H58)

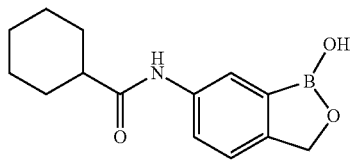 [SMILES: O=C(Nc1ccc2c(c1)B(O)OC2)C1CCCCC1]

H58 was prepared using a procedure similar to that of H17 by substituting 5-fluoro-2-(trifluoromethyl)benzoyl chloride with cyclohexanecarbonyl chloride. LCMS (m/z): 260 (M+H); $^1$H NMR (400 MHz, DMSO-d6) δ ppm 1.09-1.35 (m, 3H) 1.34-1.50 (m, 2H) 1.65 (d, J=12.5 Hz, 1H) 1.78 (t, J=14.3 Hz, 4H) 2.27-2.40 (m, 1H) 4.92 (s, 2H) 7.30 (d, J=8.4 Hz, 1H) 7.61 (dd, J=8.2, 2.0 Hz, 1H) 8.00 (d, J=2.0 Hz, 1H) 9.16 (s, 1H) 9.80 (s, 1H).

N-(1-Hydroxy-1,3-dihydro-benzo[c][1,2]oxaborol-6-yl)-nicotinamide (H59)

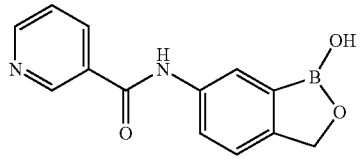 [SMILES: O=C(Nc1ccc2c(c1)B(O)OC2)c1cccnc1]

H59 was prepared using a procedure similar to that of H17 by substituting 5-fluoro-2-(trifluoromethyl)benzoyl chloride with nicotinoyl chloride hydrochloride. LCMS (m/z): 255 (M+H); $^1$H NMR (400 MHz, DMSO-d6) δ ppm 4.98 (s, 2H) 7.41 (d, J=8.2 Hz, 1H) 7.58 (ddd, J=8.0, 4.8, 0.9 Hz, 1H) 7.77 (dd, J=8.2, 2.0 Hz, 1H) 8.17 (d, J=1.8 Hz, 1H) 8.31 (dt, J=7.9, 2.0 Hz, 1H) 8.76 (dd, J=4.8, 1.7 Hz, 1H) 9.07-9.15 (m, 1H) 9.24 (s, 1H) 10.48 (s, 1H).

N-(1-Hydroxy-1,3-dihydro-benzo[c][1,2]oxaborol-6-yl)-isonicotinamide (H60)

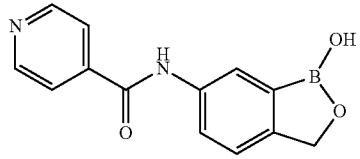 [SMILES: O=C(Nc1ccc2c(c1)B(O)OC2)c1ccncc1]

H60 was prepared using a procedure similar to that of H17 by substituting 5-fluoro-2-(trifluoromethyl)benzoyl chloride with isonicotinoyl chloride hydrochloride. LCMS (m/z): 256 (M+H); $^1$H NMR (400 MHz, DMSO-d6) δ ppm 4.98 (s, 2H) 7.41 (d, J=8.2 Hz, 1H) 7.74-7.83 (m, 1H) 7.89 (d, J=5.9 Hz, 2H) 8.18 (d, J=1.8 Hz, 1H) 8.79 (d, J=6.1 Hz, 2H) 9.26 (s, 1H) 10.58 (br. s., 1H).

Furan-2-carboxylic acid (1-hydroxy-1,3-dihydro-benzo[c][1,2]oxaborol-6-yl)-amide (H61)

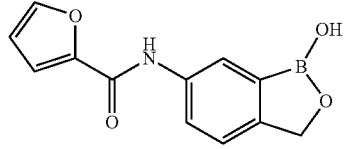 [SMILES: O=C(Nc1ccc2c(c1)B(O)OC2)c1ccco1]

H61 was prepared using a procedure similar to that of H17 by substituting 5-fluoro-2-(trifluoromethyl)benzoyl chloride with 2-furoyl chloride. LCMS (m/z): 244 (M+H); $^1$H NMR (400 MHz, DMSO-d6) δ ppm 4.96 (s, 2H) 6.70 (dd, J=3.4, 1.7 Hz, 1H) 7.34 (dd, J=3.5, 0.8 Hz, 1H) 7.37 (d, J=8.2 Hz, 1H) 7.74 (dd, J=8.3, 2.1 Hz, 1H) 7.93 (dd, J=1.8, 0.8 Hz, 1H) 8.13 (d, J=1.8 Hz, 1H) 9.22 (s, 1H) 10.20 (s, 1H).

3-Methyl-furan-2-carboxylic acid (1-hydroxy-1,3-dihydro-benzo[c][1,2]oxaborol-6-yl)-amide (H62)

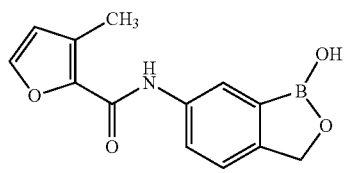 [SMILES: Cc1ccoc1C(=O)Nc1ccc2c(c1)B(O)OC2]

H62 was prepared using a procedure similar to that of H17 by substituting 5-fluoro-2-(trifluoromethyl)benzoyl chloride with 3-methylfuran-2-carbonyl chloride. LCMS (m/z): 258 (M+H); $^1$H NMR (400 MHz, DMSO-d6) δ ppm 2.35 (s, 3H) 4.95 (s, 2H) 6.59 (d, J=1.8 Hz, 1H) 7.35 (d, J=8.2 Hz, 1H) 7.73 (dd, J=8.3, 2.1 Hz, 1H) 7.78 (d, J=1.8 Hz, 1H) 8.18 (d, J=2.0 Hz, 1H) 9.19 (s, 1H) 10.06 (s, 1H).

Thiophene-2-carboxylic acid (1-hydroxy-1,3-dihydro-benzo[c][1,2]oxaborol-6-yl)-amide (H63)

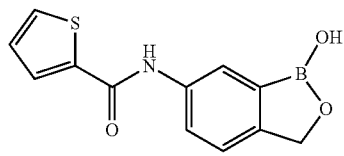 [SMILES: O=C(Nc1ccc2c(c1)B(O)OC2)c1cccs1]

To a suspension of 6-aminobenzo[c][1,2]oxaborol-1(3H)-ol (50.0 mg, 0.335 mmol) and Et$_3$N (50.9 mg, 0.503 mmol) in dry CH$_2$Cl$_2$ (5 mL) was added thiophene-2-carbonyl chloride (49.1 mg, 0.335 mmol) dropwise at 0° C., followed by stirring at room temperature overnight. Then the precipitate was collected by filtration and washed with CH$_2$Cl$_2$ to afford H63.

LCMS (m/z): 260 (M+H); $^1$H NMR (400 MHz, DMSO-d6) δ ppm 4.97 (s, 2H) 7.23 (dd, J=4.9, 3.7 Hz, 1H) 7.39 (d, J=8.2 Hz, 1H) 7.73 (dd, J=8.3, 2.0 Hz, 1H) 7.85 (dd, J=5.1, 1.0 Hz, 1H) 8.03 (dd, J=3.8, 1.1 Hz, 1H) 8.09 (d, J=2.0 Hz, 1H) 9.22 (s, 1H) 10.27 (s, 1H).

117

3-Methyl-thiophene-2-carboxylic acid (1-hydroxy-1,3-dihydro-benzo[c][1,2]oxaborol-6-yl)-amide (H64)

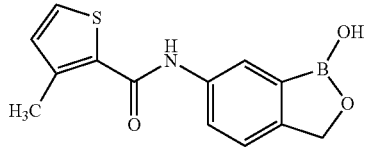

H64 was prepared using a procedure similar to that of H17 by substituting 5-fluoro-2-(trifluoromethyl)benzoyl chloride with 3-methylthiophene-2-carbonyl chloride. LCMS (m/z): 274 (M+H); $^1$H NMR (400 MHz, DMSO-d6) δ ppm 2.46 (s, 3H) 4.96 (s, 2H) 7.03 (d, J=4.9 Hz, 1H) 7.37 (d, J=8.2 Hz, 1H) 7.66 (d, J=4.9 Hz, 1H) 7.69 (dd, J=8.2, 2.1 Hz, 1H) 8.08 (d, J=2.0 Hz, 1H) 9.21 (s, 1H) 9.99 (s, 1H).

4-Methyl-thiophene-2-carboxylic acid (1-hydroxy-1,3-dihydro-benzo[c][1,2]oxaborol-6-yl)-amide (H65)

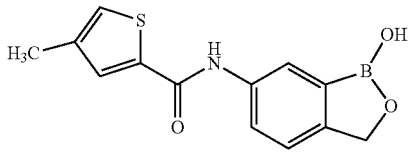 [SMILES: Cc1csc(C(=O)Nc2ccc3c(c2)B(O)OC3)c1]

H65 was prepared using a procedure similar to that of H17 by substituting 5-fluoro-2-(trifluoromethyl)benzoyl chloride with 4-methylthiophene-2-carbonyl chloride. LCMS (m/z): 274 (M+H); $^1$H NMR (400 MHz, DMSO-d6) δ ppm 2.2121 (d, J=1.0 Hz, 3H) 4.96 (s, 2H) 7.38 (d, J=8.6 Hz, 1H) 7.44 (t, J=1.2 Hz, 1H) 7.72 (dd, J=8.2, 2.1 Hz, 1H) 7.85 (d, J=1.4 Hz, 1H) 8.10 (d, J=1.8 Hz, 1H) 9.22 (s, 1H) 10.19 (s, 1H).

Benzo[b]thiophene-2-carboxylic acid (1-hydroxy-1,3-dihydro-benzo[c][1,2]oxaborol-6-yl)-amide (H66)

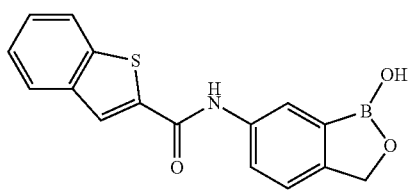 [SMILES: O=C(Nc1ccc2c(c1)B(O)OC2)c1cc2ccccc2s1]

H66 was prepared using a procedure similar to that of H17 by substituting 5-fluoro-2-(trifluoromethyl)benzoyl chloride with benzo[b]thiophene-2-carbonyl chloride. LCMS (m/z): 310 (M+H); $^1$H NMR (400 MHz, DMSO-d6) δ ppm 4.98 (s, 2H) 7.42 (d, J=8.2 Hz, 1H) 7.44-7.54 (m, 2H) 7.78 (dd, J=8.2, 2.0 Hz, 1H) 7.99-8.04 (m, 1H) 8.04-8.09 (m, 1H) 8.16 (d, J=2.0 Hz, 1H) 8.38 (s, 1H) 9.25 (s, 1H) 10.57 (s, 1H).

118

3-Chloro-benzo[b]thiophene-2-carboxylic acid (1-hydroxy-1,3-dihydro-benzo[c][1,2]oxaborol-6-yl)-amide (H67)

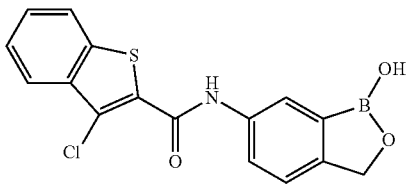 [SMILES: O=C(Nc1ccc2c(c1)B(O)OC2)c1sc2ccccc2c1Cl]

H67 was prepared using a procedure similar to that of H17 by substituting 5-fluoro-2-(trifluoromethyl)benzoyl chloride with 3-chlorobenzo[b]thiophene-2-carbonyl chloride. LCMS (m/z): 344 (M+H); $^1$H NMR (400 MHz, DMSO-d6) δ ppm 4.99 (s, 2H) 7.43 (d, J=8.2 Hz, 1H) 7.59-7.66 (m, 2H) 7.76 (dd, J=8.3, 2.0 Hz, 1H) 7.92-7.98 (m, 1H) 8.11-8.20 (m, 2H) 9.27 (br. s., 1H) 10.58 (s, 1H).

3-Chloro-6-fluoro-benzo[b]thiophene-2-carboxylic acid (1-hydroxy-1,3-dihydro-benzo[c][1,2]oxaborol-6-yl)-amide (H68)

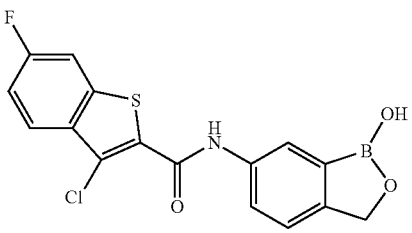 [SMILES: O=C(Nc1ccc2c(c1)B(O)OC2)c1sc2cc(F)ccc2c1Cl]

H68 was prepared using a procedure similar to that of H17 by substituting 5-fluoro-2-(trifluoromethyl)benzoyl chloride with 3-chloro-6-fluorobenzo[b]thiophene-2-carbonyl chloride. LCMS (m/z): 362 (M+H); $^1$H NMR (400 MHz, DMSO-d6) δ ppm 4.99 (s, 2H) 7.43 (d, J=8.6 Hz, 1H) 7.52 (td, J=9.0, 2.4 Hz, 1H) 7.75 (dd, J=8.2, 2.0 Hz, 1H) 7.98 (dd, J=9.0, 5.1 Hz, 1H) 8.07-8.19 (m, 2H) 9.27 (br. s., 1H) 10.57 (s, 1H).

1-Methyl-1H-pyrrole-2-carboxylic acid (1-hydroxy-1,3-dihydro-benzo[c][1,2]oxaborol-6-yl)-amide (H69)

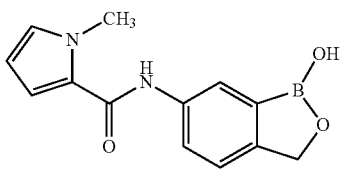 [SMILES: Cn1cccc1C(=O)Nc1ccc2c(c1)B(O)OC2]

H69 was produced by a similar method as H75 by substituting pyrazine-2-carboxylic acid with 1-methyl-1H-pyrrole-2-carboxylic acid.

Isoxazole-5-carboxylic acid (1-hydroxy-1,3-di-hydro-benzo[c][1,2]oxaborol-6-yl)-amide (H70)

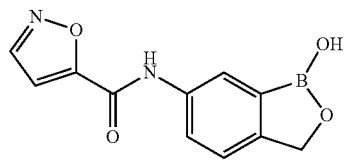 [SMILES: O=C(Nc1ccc2c(c1)B(O)OC2)c1ccno1]

H70 was prepared using a procedure similar to that of H17 by substituting 5-fluoro-2-(trifluoromethyl)benzoyl chloride with isoxazole-5-carbonyl chloride. LCMS (m/z): 245 (M+H); $^1$H NMR (400 MHz, DMSO-d6) δ ppm 4.98 (s, 2H) 7.28 (d, J=2.0 Hz, 1H) 7.42 (d, J=8.2 Hz, 1H) 7.76 (dd, J=8.2, 2.0 Hz, 1H) 8.15 (d, J=1.8 Hz, 1H) 8.82 (d, J=1.8 Hz, 1H) 10.78 (s, 1H).

4-Methyl-oxazole-5-carboxylic acid (1-hydroxy-1,3-dihydro-benzo[c][1,2]oxaborol-6-yl)-amide (H71)

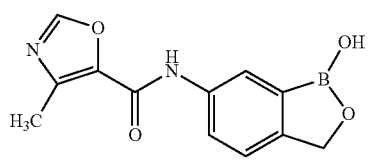 [SMILES: Cc1ncoc1C(=O)Nc1ccc2c(c1)B(O)OC2]

H71 was produced by a similar method as H63 by substituting thiophene-2-carbonyl chloride with 4-methyl-oxazole-5-carbonyl chloride.

3-Methyl-thiazolyl-phene-2-carboxylic acid (1-hydroxy-1,3-dihydro-benzo[c][1,2]oxaborol-6-yl)-amide (H72)

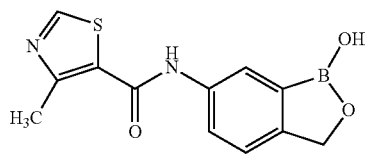 [SMILES: Cc1ncsc1C(=O)Nc1ccc2c(c1)B(O)OC2]

This compound was produced by a similar method as H75 by substituting pyrazine-2-carboxylic acid with 4-methyl-thiazole-5-carboxylic acid.

1-Methyl-1H-pyrazole-3-carboxylic acid (1-hydroxy-1,3-dihydro-benzo[c][1,2]oxaborol-6-yl)-amide (H73)

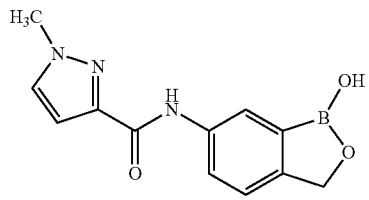 [SMILES: Cn1ccc(C(=O)Nc2ccc3c(c2)B(O)OC3)n1]

H73 was produced by a similar method as H75 by substituting pyrazine-2-carboxylic acid with 1-methyl-1H-pyrazole-3-carboxylic acid.

5-Methyl-1-phenyl-1H-pyrazole-4-carboxylic acid (1-hydroxy-1,3-dihydro-benzo[c][1,2]oxaborol-6-yl)-amide (H74)

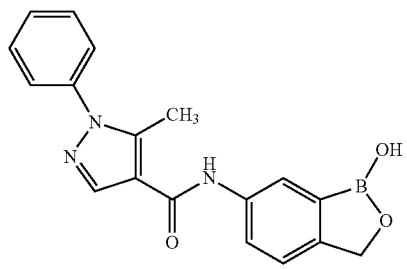 [SMILES: Cc1c(C(=O)Nc2ccc3c(c2)B(O)OC3)cnn1-c1ccccc1]

This compound was produced by a similar method as H75 by substituting pyrazine-2-carboxylic acid with 5-methyl-1-phenyl-1H-pyrazole-4-carboxylic acid.

Pyrazine-2-carboxylic acid (1-hydroxy-1,3-dihydro-benzo[c][1,2]oxaborol-6-yl)-amide (H75)

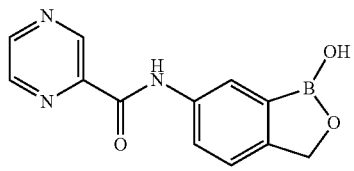 [SMILES: O=C(Nc1ccc2c(c1)B(O)OC2)c1cnccn1]

To a solution of 6-aminobenzo[c][1,2]oxaborol-1(3H)-ol (52.1 mg, 0.35 mmol), pyrazine-2-carboxylic acid (47.8 mg, 0.385 mmol) and HATU (199.5 mg, 0.525 mmol) in DMF (5 mL) was added DIEA (67.85 mg, 0.525 mmol) one portion, then the mixture was stirred at room temperature overnight. The solvent was removed under vacuum and the resulting yellow oil was purified by prep-HPLC to afford H75.

3,6-Dichloro-pyridazine-4-carboxylic acid (1-hydroxy-1,3-dihydro-benzo[c][1,2]oxaborol-6-yl)-amide (H76)

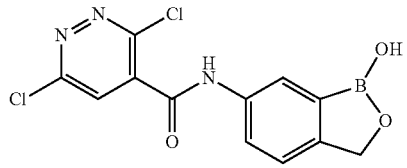 [SMILES: O=C(Nc1ccc2c(c1)B(O)OC2)c1cc(Cl)nnc1Cl]

H76 was obtained by a similar procedure to H75 by substituting pyrazine-2-carboxylic acid with 3,6-dichloro-pyridazine-4-carboxylic acid.

4-Hydroxy-2-mercapto-pyrimidine-5-carboxylic acid (1-hydroxy-1,3-dihydro-benzo[c][1,2]oxaborol-6-yl)-amide (H77)

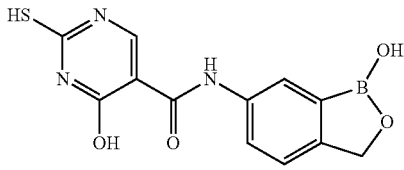 [SMILES: O=C(Nc1ccc2c(c1)B(O)OC2)c1cnc(S)nc1O]

H77 was obtained by a similar procedure to H75 by substituting pyrazine-2-carboxylic acid with 4-hydroxy-2-mercaptopyrimidine-5-carboxylic acid.

N-(1-Hydroxy-1,3-dihydro-benzo[c][1,2]oxaborol-6-yl)-acetamide (H78)

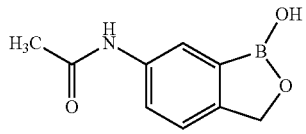

H78 was prepared using a procedure similar to that of H17 by substituting 5-fluoro-2-(trifluoromethyl)benzoyl chloride with acetyl chloride. LCMS (m/z): 192 (M+H); $^1$H NMR (400 MHz, DMSO-d6) δ ppm 2.05 (s, 3H) 4.92 (s, 2H) 7.31 (d, J=8.4 Hz, 1H) 7.59 (dd, J=8.2, 2.0 Hz, 1H) 7.98 (d, J=1.8 Hz, 1H) 9.18 (s, 1H) 9.93 (s, 1H).

N-(1-Hydroxy-1,3-dihydro-benzo[c][1,2]oxaborol-6-yl)-2,2-dimethyl-propionamide (H79)

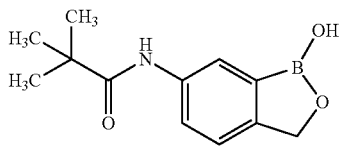

H79 was prepared using a procedure similar to that of H17 by substituting 5-fluoro-2-(trifluoromethyl)benzoyl chloride with trimethylacetyl chloride. LCMS (m/z): 234 (M+H); $^1$H NMR (400 MHz, DMSO-d6) δ ppm 1.23 (s, 9H) 7.31 (d, J=8.2 Hz, 1H) 7.61 (dd, J=8.2, 2.0 Hz, 1H) 8.00 (d, J=1.8 Hz, 1H) 9.23 (s, 1H).

2-Ethoxy-N-(1-hydroxy-1,3-dihydro-benzo[c][1,2]oxaborol-6-yl)-benzamide (H80)

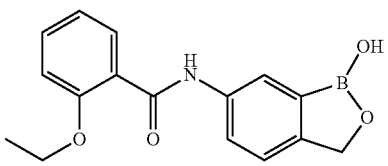 [SMILES: CCOc1ccccc1C(=O)Nc1ccc2c(c1)B(O)OC2]

H80 was prepared using a procedure similar to that of H17 by substituting 5-fluoro-2-(trifluoromethyl)benzoyl chloride with 2-ethoxybenzoyl chloride. LCMS (m/z): 298 (M+H); $^1$H NMR (400 MHz, DMSO-d$_6$) δ ppm 1.43 (t, J=6.9 Hz, 3H) 4.20 (q, J=6.9 Hz, 2H) 4.96 (s, 2H) 7.01-7.12 (m, 1H) 7.18 (d, J=8.2 Hz, 1H) 7.38 (d, J=8.4 Hz, 1H) 7.45-7.55 (m, 1H) 7.74 (dt, J=8.0, 1.9 Hz, 2H) 8.15 (d, J=1.8 Hz, 1H) 9.24 (s, 1H) 10.17 (s, 1H).

2-Iodo-N-(1-hydroxy-1,3-dihydro-benzo[c][1,2]oxaborol-6-yl)-benzamide (H81)

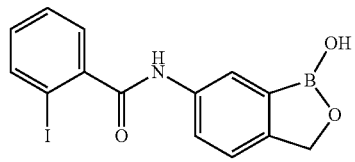 [SMILES: O=C(Nc1ccc2c(c1)B(O)OC2)c1ccccc1I]

H81 was prepared using a procedure similar to that of H17 by substituting 5-fluoro-2-(trifluoromethyl)benzoyl chloride with 2-iodobenzoyl chloride. LCMS (m/z): 380 (M+H); $^1$H NMR (400 MHz, DMSO-d$_6$) δ ppm 4.96 (s, 2H) 7.23 (ddd, J=7.9, 6.2, 2.8 Hz, 1H) 7.38 (d, J=8.4 Hz, 1H) 7.44-7.58 (m, 2H) 7.70 (dd, J=8.2, 2.0 Hz, 1H) 7.94 (d, J=7.8 Hz, 1H) 8.17 (d, J=1.8 Hz, 1H) 9.25 (s, 1H) 10.44 (s, 1H).

N-(1-Hydroxy-1,3-dihydro-benzo[c][1,2]oxaborol-6-yl)-4-nitro-benzamide (H82)

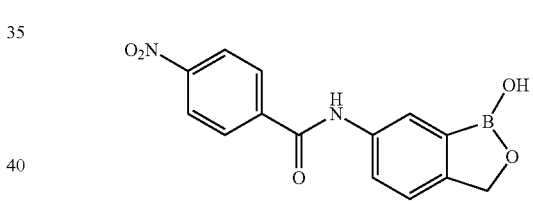

H82 was prepared using a procedure similar to that of H17 by substituting 5-fluoro-2-(trifluoromethyl)benzoyl chloride with 4-nitrobenzoyl chloride. LCMS (m/z): 299 (M+H); $^1$H NMR (400 MHz, DMSO-d$_6$) δ ppm 4.98 (s, 2H) 7.30-7.51 (m, 1H) 7.70-7.86 (m, 1H) 8.20 (d, J=8.93 Hz, 3H) 8.38 (d, J=8.79 Hz, 2H) 9.25 (s, 1H) 10.61 (s, 1H).

4-Amino-N-(1-hydroxy-1,3-dihydro-benzo[c][1,2]oxaborol-6-yl)-benzamide (H83)

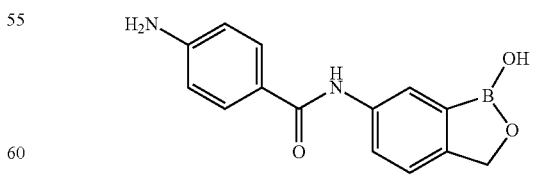

In a 50 mL round bottom flask, 5% palladium on carbon was suspended in 3 mL of clean, dry THF under nitrogen. H82 (63 mg) was taken up in 2 mL of dry THF and added slowly to the stirred suspension of catalyst. Glacial acetic acid was added to the reaction mixture, and the system was degassed for 1 minute. Hydrogen gas was introduced to the reaction vessel, and the reaction stirred at room temperature for 18 h. The hydrogen gas was then removed and the system was flushed with $N_2$. This was repeated three times. The suspension was then diluted with 40 mL of acetone and the reaction mixture was filtered through Celite. An additional 50 mL of acetone was used to wash the Celite. The collected mixture was then concentrated under reduced pressure, and the resultant yellow oil was then purified using silica gel column chromatography (eluting 100% DCM to 3.5% MeOH in DCM). H83 was isolated as a pale yellow solid. LCMS (m/z)=269 (M+H); $^1$H NMR (400 MHz, DMSO-d6) δ ppm 4.95 (s, 2H) 5.73 (s, 2H) 6.60 (d, J=8.6 Hz, 2H) 7.34 (d, J=8.2 Hz, 1H) 7.72 (d, J=8.5 Hz, 3H) 8.13 (s, 1H) 9.17 (s, 1H) 9.79 (s, 1H).

4-Fluoro-N-(1-hydroxy-1,3-dihydro-benzo[c][1,2]oxaborol-6-yl)-N-methyl-benzamide (H84)

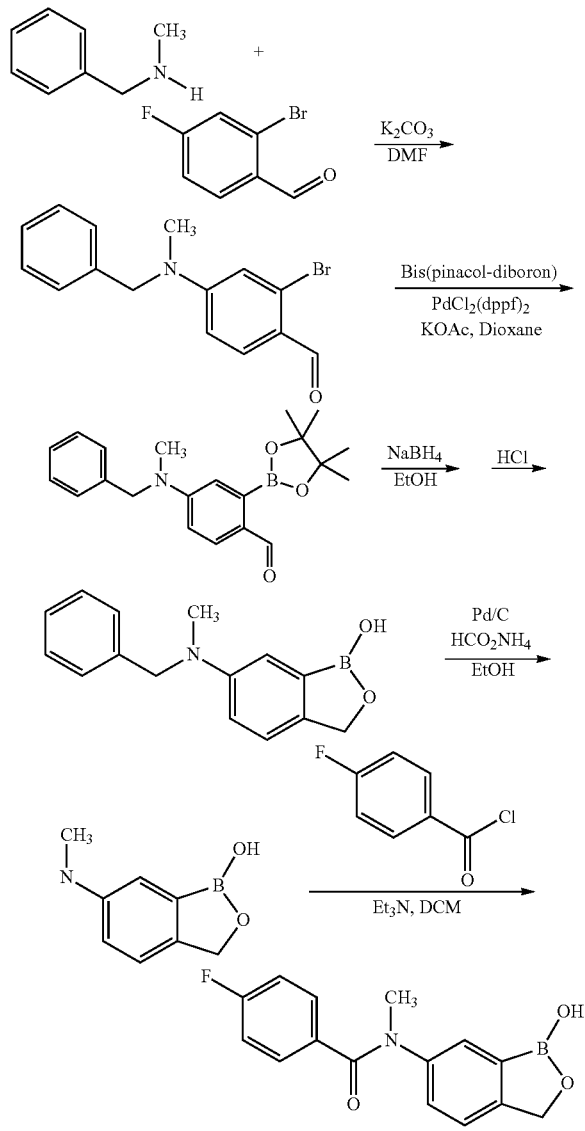

To a solution of benzylmethylamine (3.8 mL, 30.0 mmol, 1.0 eq.) and 2-bromo-4-fluoro-benzaldehyde (6.1 g, 30.0 mmol, 1.0 eq.) in DMF (100.0 mL) was added $K_2CO_3$ (8.3 g, 60.0 mmol, 2.0 eq.) under nitrogen atmosphere. The mixture was heated at 100° C. overnight. After cooling to room temperature, the mixture was filtered through a short pack of Celite to remove the solid residue. The filtrate was concentrated under reduced pressure and the residue was purified by silica gel chromatography eluting with EtOAc/heptanes (0:100 to 100:0) to give 4-(benzyl-methyl-amino)-2-bromo-benzaldehyde as a fine yellow powder. $^1$H NMR (400 MHz, CHLOROFORM-d) δ 10.06 (d, J=0.7 Hz, 1H), 7.76 (d, J=8.9 Hz, 1H), 7.30-7.35 (m, 2H), 7.27 (d, J=7.2 Hz, 1H), 7.14 (d, J=7.3 Hz, 2H), 6.85 (d, J=2.5 Hz, 1H), 6.67 (dd, J=8.9, 2.5 Hz, 1H), 4.61 (s, 2H), 3.11 (s, 3H). Amount obtained, 7.2 g, 79.0% yield.

To a solution of 4-(benzyl-methyl-amino)-2-bromo-benzaldehyde (7.2 g, 23.7 mmol, 1.0 eq.) in 1,4-dioxane (125 mL) was added bis-pinacol-diboron (6.61 g, 26.0 mmol, 1.1 eq.), KOAc (6.98 g, 71.1 mmol, 3.0 eq.) and $PdCl_2(dppf)_2$ (520 mg, 0.7 mmol, 0.03 eq.). The mixture was degassed with $N_2$ and heated at 95° C. overnight. After cooling to room temperature, the mixture was filtered though a short pack of Celite and the filtrate was concentrated under reduced pressure. The residue was purified by silica gel chromatography eluting with EtOAc/Heptanes (0:100 to 100:0) to give 4-(benzyl-ethyl-amino)-2-(4,4,5,5-tetramethyl-[1,3,2]dioxaborolan-2-yl)-benzaldehyde as a yellow solid. $^1$H NMR (400 MHz, CHLOROFORM-d) δ 10.16 (s, 1H), 7.78 (d, J=8.8 Hz, 1H), 7.27-7.32 (m, 2H), 7.25 (s, 1H), 7.15 (d, J=7.1 Hz, 2H), 7.06 (d, J=2.7 Hz, 1H), 6.74 (dd, J=8.8, 2.6 Hz, 1H), 4.64 (s, 2H), 3.12 (s, 3H), 1.36 (s, 12H).

To a suspension of 4-(benzyl-ethyl-amino)-2-(4,4,5,5-tetramethyl-[1,3,2]dioxaborolan-2-yl)-benzaldehyde (3.5 g, 10.0 mmol, 1.0 eq.) in EtOH (60 mL) at 0° C. was added $NaBH_4$ (378.3 mg, 10.0 mmol, 1.0 eq.) in small portions. The mixture was stirred at this temperature for 20 minutes, and then allowed to warm to room temperature over 1 h. After cooling to 0° C., the clear solution was carefully treated with $H_2O$ (1 mL), followed by slow addition of HCl (30 mL, 3N). The resulting yellow suspension was allowed to warm to room temperature gradually and stirred for 2 h. The mixture was then treated with sat. $NaHCO_3$ dropwise until the solution reached a final pH of 7. The resultant precipitate was collected by filtration and washed with $H_2O$ to give 6-(benzyl-methyl-amino)-3H-benzo[c][1,2]oxaborol-1-ol as a white solid. $^1$H NMR (400 MHz, DMSO-d$_6$) δ 8.95 (s, 1H), 7.28-7.34 (m, 2H), 7.20 (q, J=8.9 Hz, 4H), 7.07 (d, J=2.4 Hz, 1H), 6.90 (dd, J=8.4, 2.5 Hz, 1H), 4.86 (s, 2H), 4.58 (s, 2H), 3.01 (s, 3H).

To a solution of 6-(benzyl-methyl-amino)-3H-benzo[c][1,2]oxaborol-1-ol (506.2 mg, 2.0 mmol, 1.0 eq.) in EtOH (30 mL) was added $HCO_2NH_4$ (1.2 g, 20.0 mmol, 10.0 eq.) and Pd/C (80 mg, 5 mol %). The mixture was heated to 65° C. in a preheated oil bath under $N_2$. Upon complete consumption of the starting material by TLC, the mixture was cooled to room temperature and filtered. The filtrate was concentrated under reduced pressure to give 6-methylamino-3H-benzo[c][1,2]oxaborol-1-ol a light yellow solid. The yellow solid was carried forward to the next step without further purification. $^1$H NMR (400 MHz, acetone) δ 7.80 (s, 1H), 7.09-7.14 (m, 1H), 6.90 (d, J=2.2 Hz, 1H), 6.73-6.78 (m, 1H), 4.87 (s, 2H), 3.79 (s, 1H), 2.77 (s, 3H).

To a 20 mL scintillation vial containing 6-methylamino-3H-benzo[c][1,2]oxaborol-1-ol (80.9 mg, 0.5 mmol, 1.0 eq.) in DCM (8.0 mL) was added Et$_3$N (140 μL, 1.0 mmol, 2.0 eq.), followed by 4-fluoro-benzoyl chloride (66.9 μL, 0.55 mmol, 1.1 eq.). The resulting white suspension was stirred at room temperature over 8 hours before being concentrated under reduced pressure. The residue was purified by silica gel chromatography, eluting with MeOH/DCM (0:100 to 10:90) to give 4-Fluoro-N-(1-hydroxy-1,3-dihydro-benzo[c][1,2]oxaborol-6-yl)-N-methyl-benzamide H84 as a white solid. LCMS (m/z) 286 (M+H); $^1$H NMR (400 MHz, DMSO-d$_6$) δ 9.19 (s, 1H), 7.46 (d, J=1.6 Hz, 1H), 7.30-7.35 (m, 3H), 7.29 (d, J=2.0 Hz, 1H), 7.06 (t, J=8.9 Hz, 2H), 4.93 (s, 2H), 3.37 (s, 3H).

N-(1-Hydroxy-1,3-dihydro-benzo[c][1,2]oxaborol-6-yl)-4-methoxy-N-methyl-benzamide (H85)

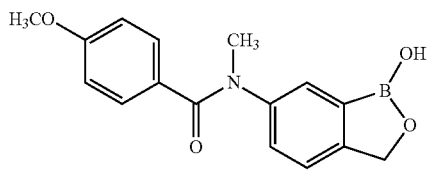 [SMILES: COc1ccc(C(=O)N(C)c2ccc3c(c2)B(O)OC3)cc1]

H85 was prepared using a procedure similar to that of H84 by substituting 4-fluorobenzoyl chloride with 4-methoxybenzoyl chloride. LCMS (m/z): 298 (M+H); $^1$H NMR (400 MHz, acetone) δ 8.09 (br. s., 1H), 7.46 (d, J=1.9 Hz, 1H), 7.29-7.34 (m, 1H), 7.21-7.27 (m, 3H), 6.67-6.72 (m, 2H), 4.96 (s, 2H), 3.71 (s, 3H), 3.39 (s, 3H).

4-Chloro-N-(1-hydroxy-1,3-dihydro-benzo[c][1,2]oxaborol-6-yl)-N-methyl-benzamide (H86)

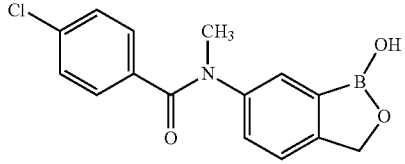 [SMILES: CN(C(=O)c1ccc(Cl)cc1)c1ccc2c(c1)B(O)OC2]

H86 was prepared using a procedure similar to that of H84 by substituting 4-fluorobenzoyl chloride with 4-chlorobenzoyl chloride. LCMS (m/z): 302 (M+H); $^1$H NMR (400 MHz, acetone) δ 8.02 (d, J=8.6 Hz, 1H), 7.53 (d, J=8.5 Hz, 1H), 7.48 (d, J=1.6 Hz, 1H), 7.27-7.33 (m, 3H), 7.18-7.24 (m, 2H), 4.95 (s, 2H), 3.42 (s, 3H).

N-(1-Hydroxy-1,3-dihydro-benzo[c][1,2]oxaborol-6-yl)-4,N-dimethyl-benzamide (H87)

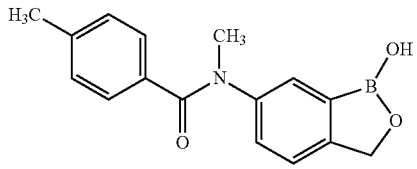 [SMILES: Cc1ccc(C(=O)N(C)c2ccc3c(c2)B(O)OC3)cc1]

H87 was prepared using a procedure similar to that of H84 by substituting 4-fluorobenzoyl chloride with 4-methylbenzoyl chloride. LCMS (m/z): 282 (M+H); $^1$H NMR (400 MHz, acetone) δ 7.91 (d, J=8.2 Hz, 1H), 7.46 (d, J=1.8 Hz, 1H), 7.28-7.33 (m, 1H), 7.22-7.27 (m, 1H), 7.18 (d, J=8.2 Hz, 2H), 6.97 (d, J=7.9 Hz, 2H), 4.95 (s, 2H), 3.40 (s, 3H), 2.20 (s, 3H).

2,4-Difluoro-N-(1-hydroxy-1,3-dihydro-benzo[c][1,2]oxaborol-6-yl)-N-methyl-benzamide (H88)

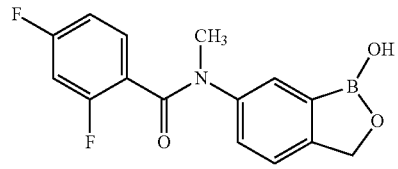 [SMILES: CN(C(=O)c1ccc(F)cc1F)c1ccc2c(c1)B(O)OC2]

H88 was prepared using a procedure similar to that of H84 by substituting 4-fluorobenzoyl chloride with 2,4-difluorobenzoyl chloride. LCMS (m/z): 304 (M+H); $^1$H NMR (400 MHz, DMSO-d$_6$) δ 9.17 (s, 1H), 7.42-7.49 (m, 2H), 7.18-7.30 (m, 2H), 6.89-7.10 (m, 2H), 4.87 (s, 2H), 3.33 (s, 3H).

2-(4-Chlorophenyl)-N-(1-hydroxy-1,3-dihydro-benzo[c][1,2]oxaborol-6-yl)-acetamide (H89)

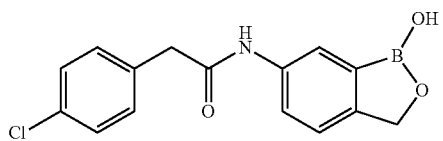 [SMILES: O=C(Cc1ccc(Cl)cc1)Nc1ccc2c(c1)B(O)OC2]

H89 was prepared using a procedure similar to that of H17 by substituting 5-fluoro-2-(trifluoromethyl)benzoyl chloride with 4-chlorophenylacetyl chloride. LCMS (m/z) 302 [M+H]; $^1$H NMR (400 MHz, DMSO-d$_6$) δ ppm 3.66 (s, 2H) 4.93 (s, 2H) 7.20-7.48 (m, 5H) 7.61 (dd, J=8.3, 2.0 Hz, 1H) 7.98 (d, J=1.8 Hz, 1H) 9.18 (s, 1H) 10.20 (s, 1H).

N-(1-Hydroxy-1,3-dihydro-benzo[c][1,2]oxaborol-6-yl)-2-(4-methoxy-phenyl)-acetamide (H90)

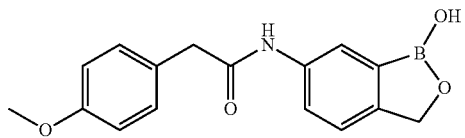 [SMILES: COc1ccc(CC(=O)Nc2ccc3c(c2)B(O)OC3)cc1]

H90 was prepared using a procedure similar to that of H17 by substituting 5-fluoro-2-(trifluoromethyl)benzoyl chloride with 4-methoxyphenylacetyl chloride. LCMS (m/z) 298 [M+H]; $^1$H NMR (400 MHz, acetone) δ ppm 3.30 (s, 1H) 3.61 (s, 2H) 3.77 (s, 3H) 4.96 (s, 2H) 6.88 (d, J=8.8 Hz, 2H) 7.18-7.39 (m, 3H) 7.63 (d, J=2.0 Hz, 1H) 8.03 (d, J=0.6 Hz, 1H) 9.22 (br. s., 1H).

N-(1-Hydroxy-1,3-dihydro-benzo[c][1,2]oxaborol-6-yl)-2-phenyl-butyramide (H91)

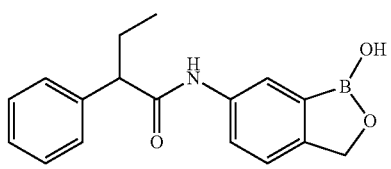 [SMILES: CCC(C(=O)Nc1ccc2c(c1)B(O)OC2)c1ccccc1]

H91 was prepared using a procedure similar to that of H17 by substituting 5-fluoro-2-(trifluoromethyl)benzoyl chloride with 2-phenylbutyroyl chloride. LCMS (m/z) 296 [M+H]; $^1$H NMR (400 MHz, DMSO-$d_6$) δ ppm 0.87 (t, J=7.3 Hz, 3H) 1.46-1.87 (m, 1H) 1.94-2.20 (m, 1H) 3.58 (dd, J=8.6, 6.4 Hz, 1H) 4.91 (s, 2H) 7.17-7.28 (m, 1H) 7.27-7.36 (m, 3H) 7.40 (d, J=7.2 Hz, 2H) 7.57 (dd, J=8.2, 2.0 Hz, 1H) 8.00 (dd, J=1.7, 0.5 Hz, 1H) 9.16 (s, 1H) 10.09 (s, 1H).

N-(1-Hydroxy-1,3-dihydro-benzo[c][1,2]oxaborol-6-yl)-2-phenyl-acetamide (H92)

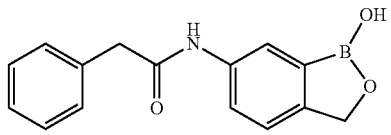 [SMILES: O=C(Cc1ccccc1)Nc1ccc2c(c1)B(O)OC2]

H92 was prepared using a procedure similar to that of H17 by substituting 5-fluoro-2-(trifluoromethyl)benzoyl chloride with phenylacetyl chloride. LCMS (m/z) 268 [M+H]; $^1$H NMR (400 MHz, DMSO-$d_6$) d ppm 3.64 (s, 2H) 4.93 (s, 2H) 7.17-7.29 (m, 1H) 7.27-7.44 (m, 5H) 7.61 (dd, J=8.2, 2.0 Hz, 1H) 7.98 (d, J=1.8 Hz, 1H) 9.17 (s, 1H) 10.17 (s, 1H).

2-(4-Fluoro-phenyl)-N-(1-hydroxy-1,3-dihydro-benzo[c][1,2]oxaborol-6-yl)-acetamide (H93)

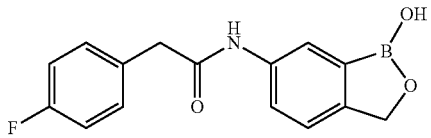 [SMILES: O=C(Cc1ccc(F)cc1)Nc1ccc2c(c1)B(O)OC2]

H93 was prepared using a procedure similar to that of H17 by substituting 5-fluoro-2-(trifluoromethyl)benzoyl chloride with 4-fluorophenylacetyl chloride. LCMS (m/z) 286 [M+H]; $^1$H NMR (400 MHz, DMSO-$d_6$) δ ppm 3.64 (s, 2H) 4.93 (s, 2H) 7.15 (t, J=8.9 Hz, 2H) 7.24-7.45 (m, 3H) 7.61 (dd, J=8.2, 2.1 Hz, 1H) 7.98 (d, J=1.8 Hz, 1H) 9.17 (s, 1H) 10.17 (s, 1H).

N-(1-Hydroxy-1,3-dihydro-benzo[c][1,2]oxaborol-6-yl)-3-phenyl-propionamide (H94)

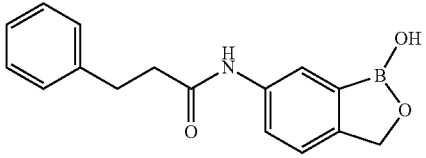 [SMILES: O=C(CCc1ccccc1)Nc1ccc2c(c1)B(O)OC2]

H94 was prepared using a procedure similar to that of H17 by substituting 5-fluoro-2-(trifluoromethyl)benzoyl chloride with hydrocinnamoyl chloride. LCMS (m/z) 282 [M+H]; $^1$H NMR (400 MHz, DMSO-$d_6$) δ ppm 2.63 (t, J=7.7 Hz, 2H) 2.92 (t, J=7.6 Hz, 2H) 4.92 (s, 2H) 7.14-7.22 (m, 1H) 7.23-7.35 (m, 5H) 7.59 (dd, J=8.3, 2.1 Hz, 1H) 7.99 (d, 1H) 9.18 (s, 1H) 9.91 (s, 1H).

N-(1-Hydroxy-1,3-dihydro-benzo[c][1,2]oxaborol-6-yl)-2-p-tolyl-acetamide (H95)

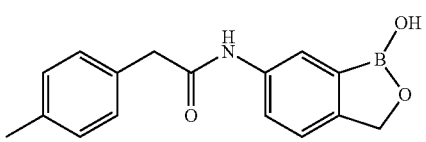 [SMILES: Cc1ccc(CC(=O)Nc2ccc3c(c2)B(O)OC3)cc1]

H95 was prepared using a procedure similar to that of H6 by substituting 4-fluorobenzoic acid with 4-methylphenylacetic acid. LCMS (m/z) 282 [M+H]; $^1$H NMR (400 MHz, DMSO-$d_6$) δ ppm 2.25 (s, 3H) 3.57 (s, 2H) 4.90 (s, 2H) 7.11 (d, J=7.8 Hz, 2H) 7.21 (d, 2H) 7.30 (d, J=8.4 Hz, 1H) 7.59 (dd, J=8.2, 2.0 Hz, 1H) 7.96 (d, J=1.6 Hz, 1H) 9.15 (s, 1H) 10.11 (s, 1H).

N-(1-Hydroxy-1,3-dihydro-benzo[c][1,2]oxaborol-6-yl)-2-(7-methoxy-2-oxo-2H-chromen-4-yl)-acetamide (H96)

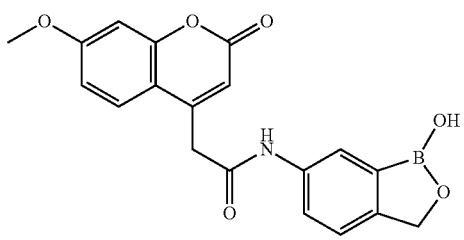 [SMILES: COc1ccc2c(CC(=O)Nc3ccc4c(c3)B(O)OC4)cc(=O)oc2c1]

H96 was prepared using a procedure similar to that of H6 by substituting 4-fluorobenzoic acid with 7-methoxycoumarin-4-acetic acid. LCMS (m/z): 366 (M+H); $^1$H NMR (400 MHz, Acetone-d6) δ ppm 3.92 (s, 3H) 3.99 (s, 2H) 4.97 (s, 2H) 6.32 (s, 1H) 6.90 (d, J=2.3 Hz, 1H) 6.94 (dd, J=8.8, 2.5 Hz, 1H) 7.34 (d, J=8.2 Hz, 1H) 7.64 (dt, J=8.3, 1.6 Hz, 1H) 7.82 (d, J=9.0 Hz, 2H) 8.01-8.05 (m, 1H) 9.53 (br. s., 1H).

4-Benzyloxy-N-(1-hydroxy-1,3-dihydro-benzo[c][1,2]oxaborol-6-yl)-butyramide (H97)

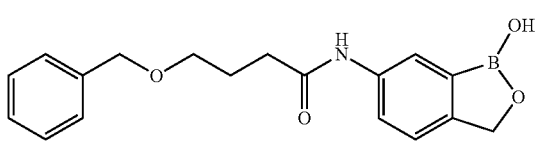 [SMILES: O=C(CCCOCc1ccccc1)Nc1ccc2c(c1)B(O)OC2]

To a solution of 6-aminobenzo[c][1,2]oxaborol-1(3H)-ol (74.5 mg, 0.5 mmol), 4-(benzyloxy)butanoic acid (128.2 mg, 0.55 mmol) and HATU (285 mg, 0.75 mmol) in DMF (8 mL) was added DIEA (96.93 mg, 0.75 mmol) one portion, then the mixture was stirred at room temperature overnight. The solvent was removed under vacuum and the resulting yellow oil was purified by prep-HPLC to afford H97 as a yellow powder (103.7 mg, yield 63.8%).

4-Hydroxy-N-(1-hydroxy-1,3-dihydro-benzo[c][1,2] oxaborol-6-yl)-butyramide (H98)

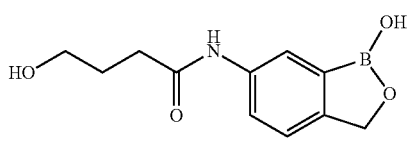 [SMILES: O=C(CCCO)Nc1ccc2c(c1)B(O)OC2]

A suspension of H97 (60 mg, 0.185 mmol) and 10% Pd—C (12 mg) in EtOH (8 mL) was stirred under an atmosphere of hydrogen at room temperature overnight. Then the catalyst was filtered off and the filtrate was then concentrated in vacuum to afford the title compound.

6-N-phenylformamide-1,3-dihydro-1-hydroxy-2,1-benzoxaborole (H99)

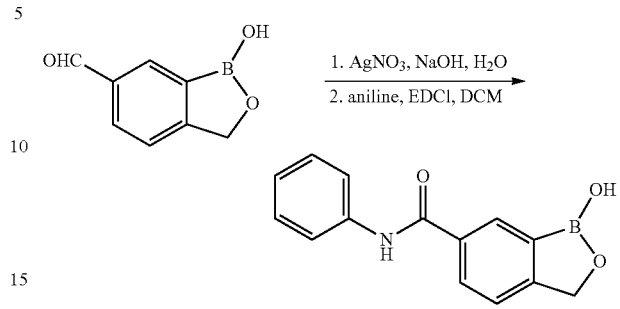

To a solution of NaOH (2.32 g, 58.0 mmol) in water (10 mL) was added silver nitrate (416 mg, 2.46 mmol) in water (3 mL). The mixture was stirred for 5 minutes at room temperature and cooled to 0° C. To the mixture under stirring was added compound 123 (200 mg, 1.33 mmol) in portions. The reaction was conducted at 0° C. for 2 hours before filtration. The filtrate was acidified with 1 M HCl to pH 3 and extracted with ethyl acetate. The extracts were dried over $Na_2SO_4$ and evaporated to give the carboxylic acid intermediate (175 mg, 0.98 mmol, 79.6% yield).

To a mixture of the carboxylic acid intermediate (175 mg, 0.98 mmol) and aniline (1084, 1.18 mmol, 1.2 eq) in DCM (8 mL) were added EDCI (377 mg, 1.97 mmol, 2.0 eq) and DMAP (5 mg, 0.04 mmol, 0.04 eq). The mixture was stirred at room temperature for 60 hours before evaporation. The residue was dissolved in ethyl acetate, and washed with 1 M HCl and brine. The residue after evaporation was purified by column chromatography over silica gel to give the title compound (128 mg, 51.6% yield). $^1$H NMR (400 MHz, DMSO-$d_6$): δ 10.29 (s, 1H), 9.34 (s, 1H), 8.30 (d, J=0.8 Hz, 1H), 8.03 (dd, J=8 & 1.6 Hz, 1H), 7.77 (dd, J=8 & 0.8 Hz, 2H), 7.54 (d, J=8 Hz, 1H), 7.34 (t, J=8 Hz, 1H), 7.08 (t, J=8 Hz, 1H) and 5.06 (s, 2H) ppm.

Alternate synthesis of 1-hydroxy-N-phenyl-1,3-dihydrobenzo[c][1,2]oxaborole-6-carboxamide

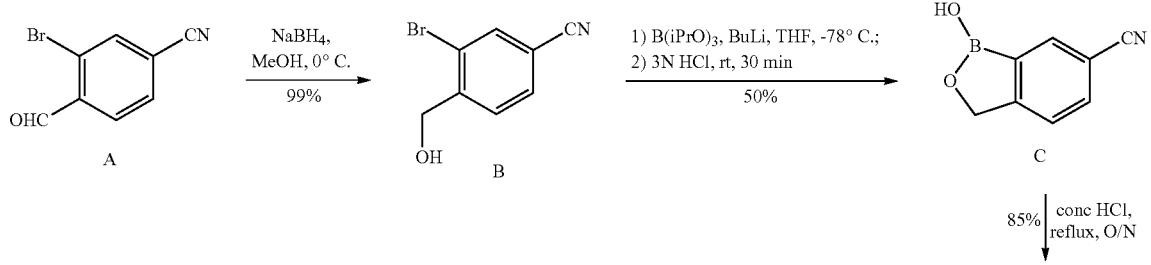

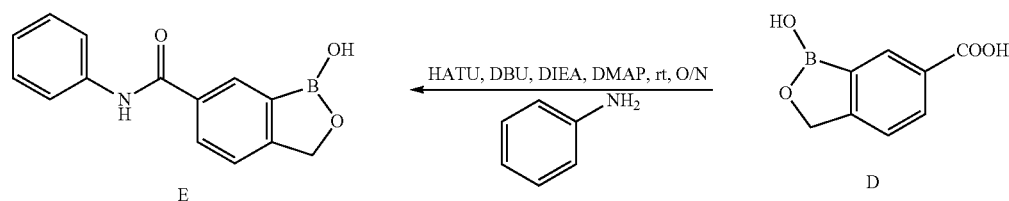

Synthesis of 3-bromo-4-(hydroxymethyl)benzonitrile (B)

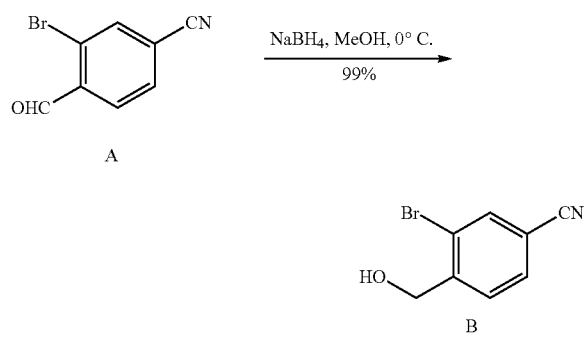

A solution of 3-bromo-4-formylbenzonitrile A (1.0 g, 4.8 mmol) in CH$_3$OH (30 mL) was cooled to 0° C. NaBH$_4$ (180 mg, 4.8 mmol) was added portionwise. The mixture was allowed to warm to room temperature and stir at room temperature for 1 h. The mixture was quenched with 1N HCl and concentrated under vacuum. The residue was extracted with ethyl acetate (25 mL*3). The combined organic layers were washed with brine (20 mL), dried (Na$_2$SO$_4$) and concentrated under vacuum to give a white solid of the desired compound B (1.0 g, 99%). $^1$H NMR (300 MHz, CDCl$_3$): δ 7.82 (s, 1H), 7.49-7.71 (m, 2H), 4.75 (s, 2H). LC-MS: 212 (M+1)$^+$.

Synthesis of 1-hydroxy-1,3-dihydrobenzo[c][1,2]oxaborole-6-carbonitrile (C)

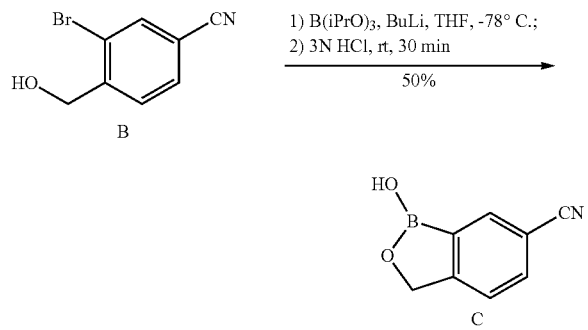

A solution of compound B (211 mg, 1.0 mmol) and triisopropyl borate (282 mg, 1.5 mmol) in anhydrous THF (10 mL) at N$_2$ atmosphere was cooled to −78° C. n-BuLi (0.9 mL, 2.25 mmol) was added dropwise at −78° C. Then the mixture was allowed to warm to room temperature and stir at room temperature for 1 h. The mixture was quenched with 1N HCl and extracted with ethyl acetate (25 mL*3). The combined organic layers were washed with brine (20 mL), dried (Na$_2$SO$_4$) and concentrated under vacuum. The residue was purified by column chromatography (eluting with CH$_3$OH and EtOAc=1:1) on silica gel to give the desired compound C as a yellow solid (80 mg, 50%). $^1$H NMR (300 MHz, CDCl$_3$): δ 9.50 (s, 1H), 8.08 (s, 1H), 7.83-7.92 (m, 1H), 7.61-7.66 (m, 1H), 5.06 (s, 2H). LC-MS: 160 (M+1)$^+$.

Synthesis of 1-hydroxy-1,3-dihydrobenzo[c][1,2]oxaborole-6-carboxylic acid (D)

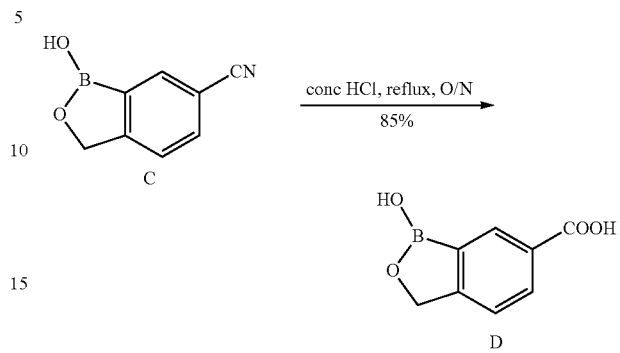

A solution of compound C (100 mg, 0.63 mmol) in conc. HCl (10 mL) was refluxed for 3 h and cooled to RT. The mixture was filtrated. The solid was washed with water, dried to give the product D as a white solid (95 mg, 85%). $^1$H NMR (300 MHz, DMSO-d$_6$): δ 12.92 (s, 1H), 9.36 (s, 1H), 8.10 (s, 1H), 8.05 (d, 1H), 7.54 (d, 1H), 5.08 (s, 2H). LC-MS: 177 (M−1)$^+$. Purity on HPLC: 50.5% (214 nm).

Synthesis of 1-hydroxy-N-phenyl-1,3-dihydrobenzo[c][1,2]oxaborole-6-carboxamide

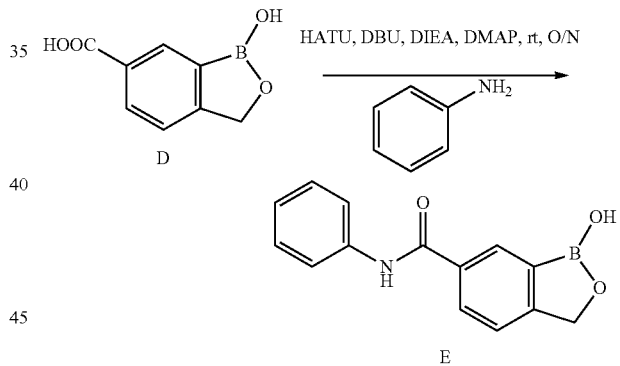

A solution of compound C (20 mg, 0.11 mmol), HATU (46.5 mg, 0.12 mmol) and DIEA (52.4 mg, 0.40 mmol) in dry DMF (2 mL) is stirred for 1 h before the addition of a solution of aniline (0.10 mmol), DMAP (50 mg, 0.40 mmol) and DBU (62 mg, 0.40 mmol) in dry DMF (1 mL). The reaction mixture is stirred at room temperature overnight and diluted with EtOAc (100 mL) and is washed with aqueous NaOAc buffer (30 mL*2), 5% NaHCO$_3$ (30 mL) and brine (50 mL). The organic layer is dried over Na$_2$SO$_4$ and is concentrated. The residue is purified by prep-HPLC to give the title compound.

6-(4-chlorophenylsulfinyl)benzo[c][1,2]oxaborol-1(3H)-ol (H100)

The title compound was synthesized as shown in the scheme.

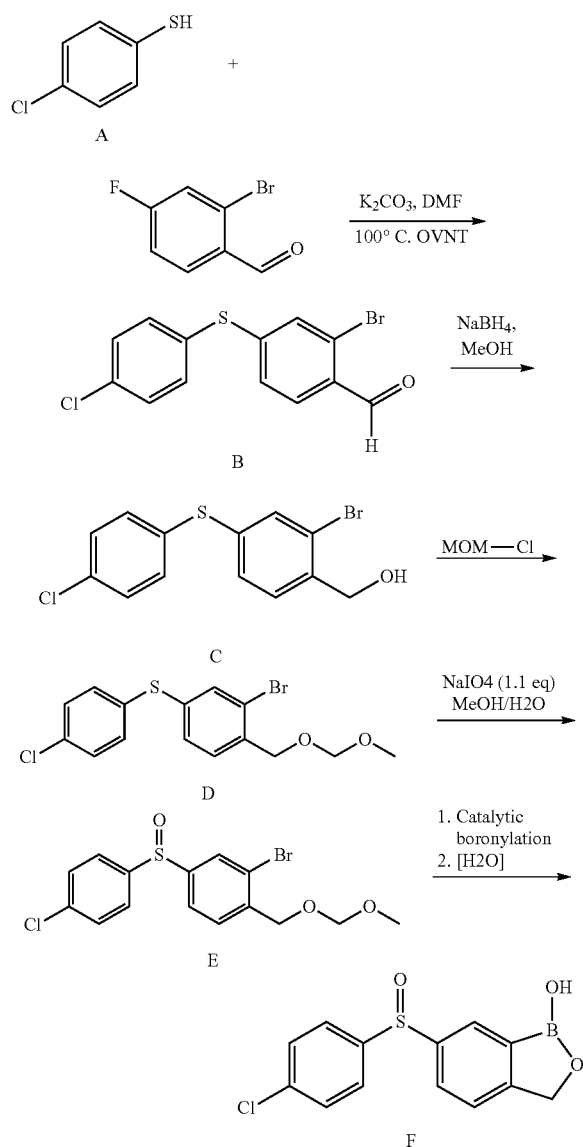

Synthesis of 2-bromo-4-(4-chlorophenylthio)benzaldehyde (B)

A mixture of 4-chlorophenylthiol (10 g, 69.15 mmol), 2-bromo-4-fluorobenzaldehyde (14.04 g, 69.15 mmol) and K$_2$CO$_3$ (19 g) in dry DMF (150 mL) was heated to 100° C. and stirred for 4 h. The mixture was filtered and the filtrate was evaporated to remove the solvent. The residue was dissolved in Et$_2$O and filtered to remove insoluble solid. Again, the filtrate was evaporated to give a brown liquid that became solid after being pumped on vacuum (22.17 g, yield 97.9%). $^1$H NMR (300 Hz, DMSO-d$_6$): δ 10.08 (s, 1H), 7.72 (d, 1H), 7.57 (s, 4H), 7.43 (s, 1H) and 7.21 (d, 1H) ppm.

Synthesis of (2-bromo-4-(4-chlorophenylthio)phenyl)methanol (C)

2-Bromo-4-(4-chlorophenylthio)benzaldehyde (22.1 g, 67.45 mmol) in methanol (300 mL) was reduced with NaBH$_4$ (3.1 g) at 0° C. for 20 min after the completion of NaBH$_4$ addition. A normal work-up and purification by silica gel column chromatography (hexane:EtOAc=5; 1, v/v) provided the desired alcohol (19.8 g, yield 89%) as a white solid. $^1$H NMR (300 Hz, DMSO-d$_6$): δ 7.54-7.50 (m, 2H), 7.43 (d, 2H), 7.37 (dd, 1H), 7.32 (d, 2H), 5.49 (t, 1H) and 4.48 (d, 2H) ppm.

Synthesis of (3-bromo-4-((methoxymethoxy)methyl)phenyl)(4-chlorophenyl)sulfane (D)

To a solution of (2-bromo-4-(4-chlorophenylthio)phenyl)methanol (20 g, 61.3 mmol) and N,N-diisopropyl-N-ethyl amine (184 mmol) in DCM (200 mL) was added dropwise methoxymethyl chloride (MOM-Cl, 14.7 g, 184 mmol) at 0° C. under N$_2$. The mixture was stirred at r.t. for 2 days. The mixture was washed with water and concentrated under vacuum to give a crude residue, which was purified by column to afford the desired product as a white solid (16 g, yield 70%).

Synthesis of 2-bromo-4-(4-chlorophenylsulfinyl)-1-((methoxymethoxy)methyl)benzene (E)

To a solution of (3-bromo-4-((methoxymethoxy)methyl)phenyl)(4-chlorophenyl)sulfane (16 g, 43 mmol) in DCM (100 mL) was added NaIO$_4$ (10.1 g, 47.3 mmol) at 0° C. under N$_2$. The mixture was stirred at r.t. for 1 hour. The mixture was washed with water and the organic layer was concentrated under vacuum to give the crude residue that was purified by column chromatography to afford the desired product as a white solid (10 g, yield 64%). $^1$H NMR (300 MHz, CDCl$_3$) δ 7.81 (d, J=1.5 Hz, 1H), 7.60-7.55 (m, 4H), 7.44 (d, J=8.7 Hz, 2H), 4.75 (s, 2H), 4.63 (s, 2H), 4.00 (s, 3H) ppm.

Synthesis of 6-(4-chlorophenylsulfinyl)benzo[c][1,2]oxaborol-1(3H)-ol (F) from compound E To a solution of 2-bromo-4-(4-chlorophenylsulfinyl)-1-((methoxymethoxy)methyl)-benzene (10 g, 37.5 mmol) in dioxane (100 mL) was added 4,4,4',4',5,5,5',5'-octamethyl-2,2'-bi(1,3,2-dioxaborolane) (11.4 g, 45 mmol), Pd(dppf)$_2$Cl$_2$ (765 mg, 2.5 mol %), and KOAc (11 g, 112.5 mmol) at r.t. under N$_2$. The mixture was stirred at 70° C. for 10 hours. The mixture was filtered and the filtrate was extracted with EtOAc. The combined organic layers were concentrated in vacuo to give the crude residue, which was purified by column chromatography to provide 2-(5-(4-chlorophenylsulfinyl)-2-((methoxymethoxy)methyl)phenyl)-4,4,5,5-tetramethyl-1,3,2-dioxaborolane as a white solid (10 g, yield 70%). $^1$H NMR (300 MHz, CDCl$_3$) δ 8.05 (d, J=1.8 Hz, 1H), 7.70-7.56 (m, 4H), 7.31 (d, J=8.4 Hz, 2H), 4.84 (s, 2H), 4.72 (s, 2H), 3.38 (s, 3H), 1.33 (s, 12H) ppm.

This pinacol-boron intermediate (10 g, 22.3 mmol) and 6N HCl (200 mL) were stirred at rt overnight. The precipitate was filtered and the solid was dried to give the desired title compound as a white power (6 g, 89.5%). $^1$H NMR (300 MHz, DMSO-d$_6$) δ 9.40 (s, 1H), 8.08 (s, 1H), 7.80 (dd, J=7.8, 1.2 Hz, 1H), 7.72 (d, 2H), 7.61 (d, 2H), 7.56 (d, 1H) and 5.01 (s, 2H) ppm. The data are consistent with the NMR of the compound generated with another method described above.

6-(3-chlorophenylsulfinyl)benzo[c][1,2]oxaborol-1(3H)-ol (H101)

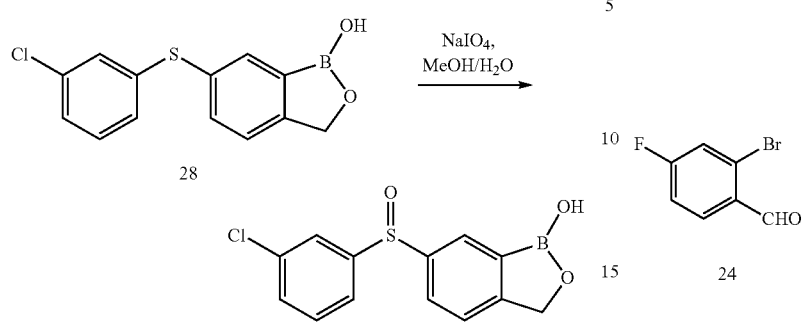

Compound 28 (1.45 mmol) was dissolved in 10% (v/v) H₂O in MeOH (30 mL). To this solution was added sodium periodate (3.2 g, 14.5 mmol, 10.0 eq). The reaction mixture was stirred for 12 hours then treated with 1 M HCl (10 ml). After extraction with ethyl acetate, the organic layer was washed with water and brine, and dried over anhydrous Na₂SO₄. After rotary evaporation the residue was purified by crystallization to give the title compound (275 mg, 65% yield). ¹H NMR (300 MHz, DMSO-d₆): δ 9.39 (s, 1H), 8.11 (s, 1H), 7.85 (dd, J=8.1 & 1.8 Hz, 1H), 7.78 (s, 1H), 7.69-7.63 (m, 1H), 7.59-7.56 (m, 3H) and 5.01 (s, 2H) ppm. Mp 152-153° C.

6-(2-chlorophenylsulfinyl)benzo[c][1,2]oxaborol-1(3H)-ol (H102)

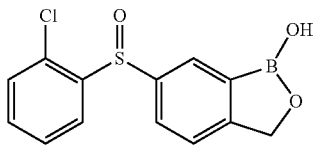 [SMILES: O=S(c1ccc2c(c1)B(O)OC2)c1ccccc1Cl]

This compound was produced by the same method as H101 by substituting 4-chlorophenylthiol with 2-chlorophenylthiol. ¹H NMR (300 MHz, DMSO-d₆): δ 9.41 (s, 1H), 8.09 (d, J=1.2 Hz, 1H), 8.01-7.97 (m, 1H), 7.83 (dd, J=8.1 & 1.8 Hz, 1H), 7.71-7.65 (m, 1H), 7.61-7.51 (m, 3H) and 5.02 (s, 2H) ppm. MS: found: 315 (M+Na)⁺, 347 (M+Na+MeOH)⁺. Mp 174-175° C.

6-(4'-chlorophenylsulfanyl)-1,3-dihydro-1-hydroxy-2,1-benzoxaborole (H103)

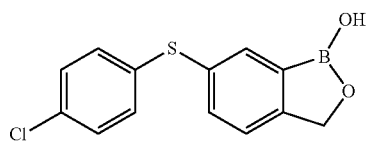 [SMILES: OB1OCc2ccc(Sc3ccc(Cl)cc3)cc21]

The synthesis of the title compound has been described previously in U.S. patent application Ser. Nos. 11/357,687; 11/505,591 and 11/676,120.

6-(3'-chlorophenylsulfanyl)-1,3-dihydro-1-hydroxy-2,1-benzoxaborole (H104)

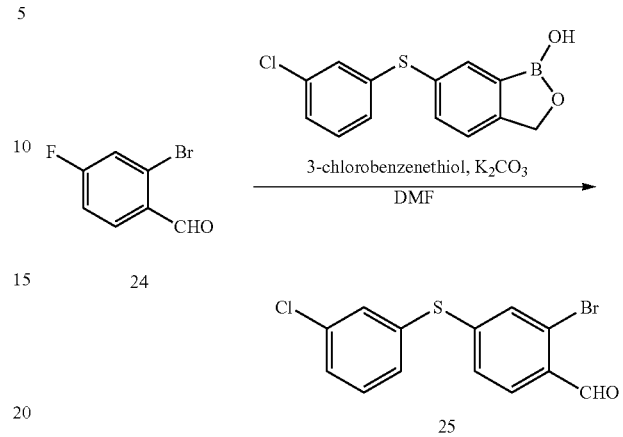

2-bromo-4-(3-chlorophenylsulfanyl)benzaldehyde (25)

Compound 24 (7.39 mmol) was dissolved in DMF (25 mL) and cooled to 0° C. with ice bath. To this solution under nitrogen were added in sequence potassium carbonate (2.04 g, 14.78 mmol, 2.0 eq) and 3-chlorobenzenethiol (0.835 ml, 7.39 mmol, 1.0 eq). The reaction mixture was stirred for 0.5 hour then treated with cooled water (50 ml). After extraction with ethyl acetate, the organic layer was washed with water and brine, and dried over anhydrous Na₂SO₄. The residue after rotary evaporation was purified by column chromatography over silica gel to give compound 25 (1.92 g, 80% yield). ¹H NMR (400 MHz, CDCl₃): δ 10.25 (s, 1H), 7.78 (d, J=8 Hz, 1H) and 7.52-7.12 (m, 6H) ppm.

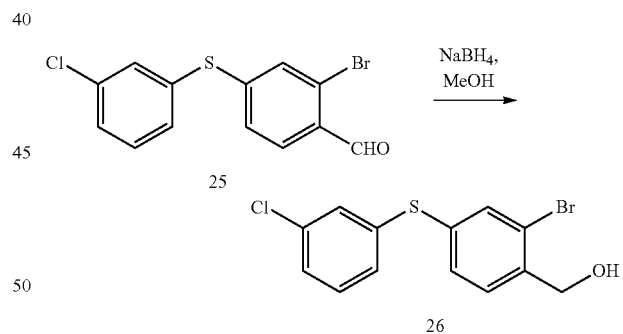

2-bromo-4-(3'-chlorophenylthio)benzyl alcohol (26)

Compound 25 (6.08 mmol) was dissolved in MeOH (25 mL) and cooled to 0° C. with ice bath. To this solution was added NaBH₄ (459.6 mg, 12.16 mmol, 2.0 eq). The reaction mixture was stirred for 0.5 hour then treated with saturated NaHCO₃. After evaporation, the residue was extracted with ethyl acetate, washed with water and brine, and dried over anhydrous Na₂SO₄. The residue after rotary evaporation was purified by column chromatography over silica gel to give compound 26 (1.8 g, 90% yield). ¹H NMR (400 MHz, DMSO-d₆): δ 7.60-7.23 (m, 7H), 5.53 (t, J=5.2 Hz, 1H) and 4.51 (d, J=5.2 Hz, 2H) ppm.

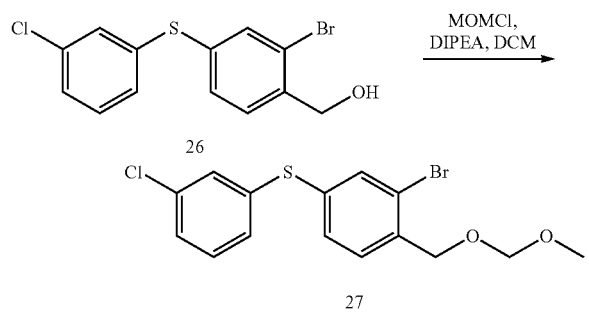

(3-bromo-4-((methoxymethoxy)methyl)phenyl)(3-chlorophenyl)sulfane (27)

Compound 26 (5.94 mmol) was dissolved in anhydrous $CH_2Cl_2$ (25 mL). To this solution under nitrogen were added in sequence N,N-diisopropylethylamine (3.67 ml, 20.79 mmol, 3.5 eq) and chloromethyl methyl ether (0.96 mL, 13.07 mmol, 2.2 eq). The reaction mixture was stirred for 14 hours then treated with water (10 ml). After extraction with dichloromethane, the organic layer was washed with water and brine, and dried over anhydrous $Na_2SO_4$. After rotary evaporation, the residue was purified by column chromatography over silica gel to give compound 27 (1.79 g, 80% yield). $^1$H NMR (400 MHz, CDCl$_3$): δ 7.56 (d, J=1.6 Hz, 1H), 7.46 (d, J=8.0 Hz, 1H), 7.32-7.17 (m, 5H), 4.77 (s, 2H), 4.64 (s, 2H) and 3.43 (s, 3H) ppm.

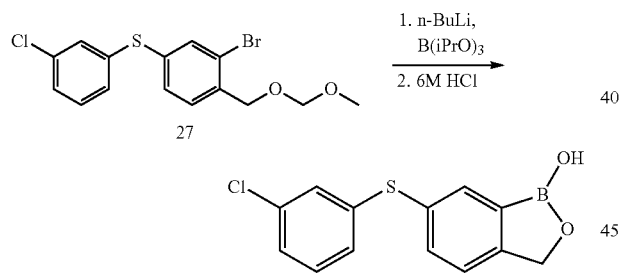

6-(3'-chlorophenylsulfanyl)-1,3-dihydro-1-hydroxy-2,1-benzoxaborole

Compound 27 (1.0 g, 2.67 mmol) was dissolved in anhydrous THF (20 mL) and cooled to −80° C. To this solution under nitrogen was added dropwise 1.6M n-BuLi (1.84 mL, 2.94 mmol, 1.1 eq) over 20 minutes. After stirring for another 20 minutes at −80° C., B(iPrO)$_3$ (0.68 mL, 2.94 mmol, 1.1 eq) was added dropwise over 8 minutes. The reaction mixture was allowed to warm to room temperature gradually and stirred overnight at room temperature. After 6M HCl (10 mL) was added and stirred for 2 hours, the mixture was evaporated and extracted with ethyl acetate (25 mL×5) and dried over anhydrous $Na_2SO_4$. The residue after rotary evaporation was purified by column chromatography over silica gel to give the title compound (380 mg, 51.5% yield). $^1$H NMR (400 MHz, DMSO-d$_6$): δ 9.30 (s, 1H), 7.81 (d, J=1.6 Hz, 1H), 7.58 (dd, J=8 & 1.6 Hz, 1H), 7.5 (d, J=8 Hz, 1H), 7.45-7.15 (m, 4H) and 5.02 (s, 2H) ppm.

6-(2'-chlorophenylsulfanyl)-1,3-dihydro-1-hydroxy-2,1-benzoxaborole (H105)

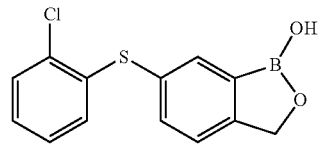 [SMILES: OB1OCc2ccc(Sc3ccccc3Cl)cc21]

This compound was produced by the same method as H104 by substituting 3-chlorobenzenethiol with 2-chlorobenzenethiol. $^1$H NMR (300 MHz, DMSO-d$_6$): δ 9.30 (s, 1H), 7.80 (d, J=0.9 Hz, 1H), 7.50-7.59 (m, 3H), 7.25 (m, 2H), 6.91 (m, 1H) and 5.03 (s, 2H) ppm. MS: found: 275 (M−H)$^-$. Mp 116-118° C.

6-(4'-chlorophenylsulfanyl)-1,3-dihydro-1-hydroxy-2,1-benzoxaborole (H106)

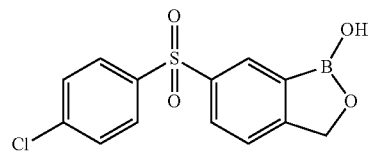 [SMILES: O=S(=O)(c1ccc(Cl)cc1)c1ccc2c(c1)B(O)OC2]

The synthesis of the title compound has been described previously in U.S. patent application Ser. Nos. 11/357,687; 11/505,591 and 11/676,120.

6-(3'-chloro)phenylsulfonyl-1,3-dihydro-1-hydroxy-2,1-benzoxaborole (H107)

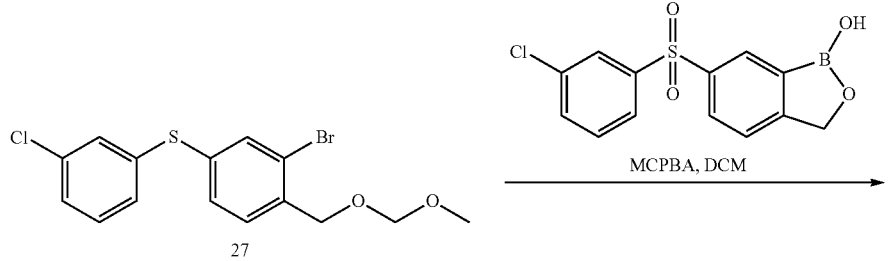

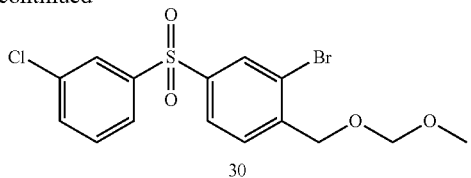

1-(3'-bromo-4'-((methoxymethoxy)methyl)phenyl-sulfonyl)-3-chlorobenzene (30)

Compound 27 (4.78 mmol) was dissolved in CH$_2$Cl$_2$ (45 mL) and cooled to 0° C. with ice bath. To this solution was added meta-chloroperoxybenzoic acid (2.48 g, 14.36 mmol, 3.0 eq). The reaction mixture was stirred for 18 hours then treated with 1.25M NaOH (20 ml). After evaporation the residue was extracted with ethyl acetate, washed with water and brine, and dried over anhydrous Na$_2$SO$_4$. The residue after rotary evaporation was purified by column chromatography over silica gel to give compound 30 (1.5 g, 77% yield). $^1$H NMR (300 MHz, DMSO-d$_6$): δ 8.24 (d, J=1.8 Hz, 1H), 8.11-7.97 (m, 6H), 4.72 (s, 2H), 4.60 (s, 2H) and 3.29 (s, 3H) ppm.

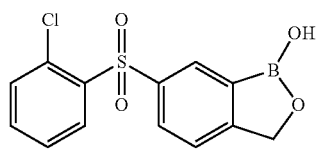 [SMILES: O=S(=O)(c1ccc2c(c1)B(O)OC2)c1ccccc1Cl]

6-(3'-chloro)phenylsulfonyl-1,3-dihydro-1-hydroxy-2,1-benzoxaborole

Compound 30 (1.0 g, 2.46 mmol) was dissolved in anhydrous THF (16 mL) and cooled to -80° C. To this solution under nitrogen was added dropwise 1.6M n-BuLi (1.69 mL, 2.71 mmol, 1.1 eq) over 20 minutes. After stirring for 20 minutes at -80° C., B(iPrO)$_3$ (0.62 mL, 2.71 mmol, 1.1 eq) was added dropwise over 8 minutes. The reaction mixture was allowed to warm to room temperature gradually and stirred overnight at room temperature. After 6M HCl (10 mL) was added and stirred for 2 hours, the mixture was evaporated, extracted with ethyl acetate (25 mL×5) and dried over anhydrous Na$_2$SO$_4$. The residue after rotary evaporation was purified by crystallization to give the title compound (123 mg, 16.2% yield). $^1$H NMR (300 MHz, DMSO-d$_6$): δ 9.48 (s, 1H), 8.35-7.63 (m, 7H), and 5.06 (s, 2H) ppm.

6-(2'-chlorophenylsulfanyl)-1,3-dihydro-1-hydroxy-2,1-benzoxaborole (H108)

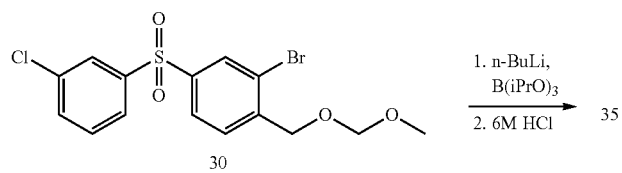

This compound was produced by the same method as H104 by substituting 3-chlorobenzenethiol with 2-chlorobenzenethiol. $^1$H NMR (300 MHz, DMSO-d$_6$): δ 9.50 (s, 1H), 8.35-8.30 (m, 2H), 8.00 (dd, J=8.1 & 1.8 Hz, 1H), 7.78-7.62 (m, 4H) and 5.08 (s, 2H) ppm. MS: found: 331 (M+Na)$^+$, 363 (M+Na+MeOH)$^+$. Mp 130-132° C.

6-(3',4'-dichlorophenyl)sulfenyl-1,3-dihydro-1-hydroxy-2,1-benzoxaborole (H109)

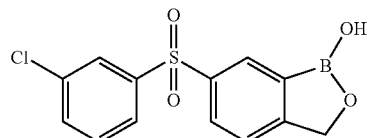

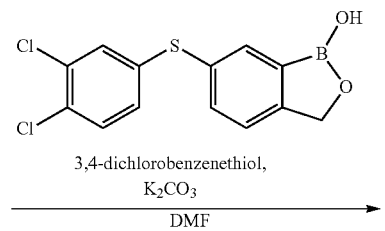

2-bromo-4-(3',4'-dichlorophenylsulfanyl)benzaldehyde (32)

Compound 24 (14.78 mmol) was dissolved in DMF (70 mL) and cooled to 0° C. with ice bath. To this solution under nitrogen were added in sequence potassium carbonate (4.08 g, 29.55 mmol, 2.0 eq) and 3,4-dichlorobenzenethiol (1.88 ml, 14.78 mmol, 1.0 eq). The reaction mixture was stirred for 0.5 hour then treated with cooled water (100 ml). After extraction with ethyl acetate the organic layer was washed with water and brine, and dried over anhydrous Na$_2$SO$_4$. The residue was evaporated to give compound 32 (4.49 g, 84% yield).

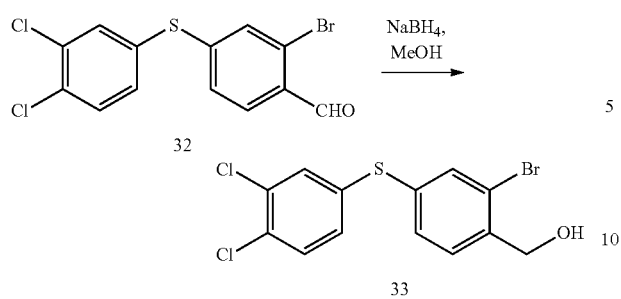

(2-bromo-4-(3',4'-dichlorophenylsulfanyl)benzyl alcohol (33)

Compound 32 (12.46 mmol) was dissolved in MeOH (50 mL) and cooled to 0° C. with ice bath. To this solution was added NaBH$_4$ (942 mg, 24.93 mmol, 2.0 eq). The reaction mixture was stirred for 0.5 hour then treated with saturated NaHCO$_3$. After evaporation the residue was extracted with ethyl acetate, washed with water and brine, and dried over anhydrous Na$_2$SO$_4$. The residue was evaporated to give compound 33 (4.3 g, 95% yield).

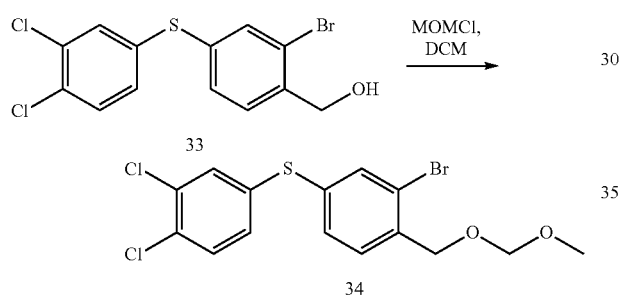

(3-bromo-4-((methoxymethoxy)methyl)phenyl)(3,4-dichlorophenyl)sulfane (34)

Compound 33 (11.84 mmol) was dissolved in anhydrous CH$_2$Cl$_2$ (50 mL). To this solution under nitrogen were added in sequence N,N-Diisopropylethylamine (7.32 ml, 41.45 mmol, 3.5 eq) and chloromethyl methyl ether (1.91 mL, 26.05 mmol, 2.2 eq). The reaction mixture was stirred for 14 hours then treated with water (15 ml). After extraction with dichloromethane, the organic layer was washed with water and brine, and dried over anhydrous Na$_2$SO$_4$. After rotary evaporation the residue was purified by column chromatography over silica gel to give compound 34 (4.04 g, 83% yield). $^1$H NMR (400 MHz, DMSO-d$_6$): δ 7.66-7.58 (m, 3H), 7.53 (d, J=8.4 Hz, 1H), 7.43 (dd, J=8.4 & 2 Hz, 1H), 7.28-7.25 (m, 1H), 4.71 (s, 2H), 4.55 (s, 2H) and 3.31 (s, 3H) ppm

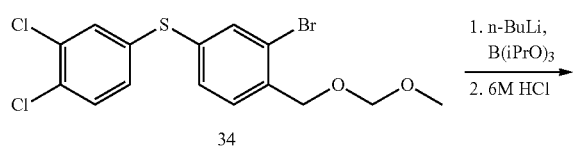

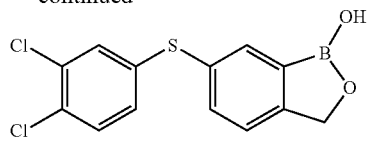

6-(3',4'-dichlorophenyl)sulfenyl-1,3-dihydro-1-hydroxy-2,1-benzoxaborole

Compound 34 (2.39 g, 5.86 mmol) was dissolved in anhydrous THF (25 mL) and cooled to −80° C. To this solution under nitrogen was added dropwise 1.6M n-BuLi (4.03 mL, 6.45 mmol, 1.1 eq) over 20 minutes. After stirred for another 20 minutes at −80° C., B(iPrO)$_3$ (1.48 mL, 6.45 mmol, 1.1 eq) was added dropwise over 8 minutes. The reaction mixture was allowed to warm to room temperature gradually and stirred overnight at room temperature. After 6M HCl (20 mL) was added and stirred overnight, the mixture was evaporated and extracted with ethyl acetate (25 mL×5) and dried over anhydrous Na$_2$SO$_4$. The residue after rotary evaporation was purified by column chromatography over silica gel to give the title compound (607.5 mg, 33.3% yield). $^1$H NMR (400 MHz, DMSO-d$_6$): δ 9.28 (s, 1H), 7.81 (s, 1H), 7.60-7.45 (m, 4H), 7.15 (dd, J=8.4 & 2 Hz, 1H) and 5.03 (s, 2H) ppm.

6-(2',3'-dichlorophenyl)sulfenyl-1,3-dihydro-1-hydroxy-2,1-benzoxaborole (H110)

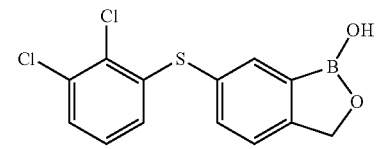 [SMILES: OB1OCc2ccc(Sc3cccc(Cl)c3Cl)cc21]

This compound can be produced by the same method as H109 by substituting 3,4-dichlorobenzenethiol with 2,3-dichlorobenzenethiol.

6-(2',4'-dichlorophenyl)sulfenyl-1,3-dihydro-1-hydroxy-2,1-benzoxaborole (H111)

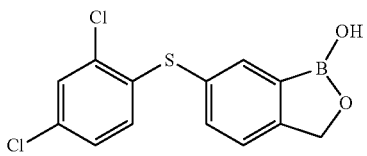 [SMILES: OB1OCc2ccc(Sc3ccc(Cl)cc3Cl)cc21]

This compound was produced by the same method as H109 by substituting 3,4-dichlorobenzenethiol with 2,4-dichlorobenzenethiol. $^1$H NMR (400 MHz, DMSO-d$_6$): δ 9.30 (s, 1H), 7.79 (s, 1H), 7.70 (d, J=2.0 Hz, 1H), 7.54 (m, 2H), 7.33 (dd, J=8.4 & 2.0 Hz, 1H), 6.86 (d, J=8.4 Hz, 1H) and 5.02 (s, 2H) ppm. MS: found: 309 (M+1)$^+$. Mp 125-127° C.

6-(2',5'-dichlorophenyl)sulfenyl-1,3-dihydro-1-hydroxy-2,1-benzoxaborole (H112)

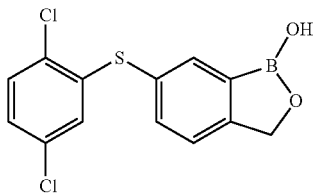 [SMILES: OB1OCc2ccc(Sc3cc(Cl)ccc3Cl)cc21]

This compound can be produced by the same method as H109 by substituting 3,4-dichlorobenzenethiol with 2,5-dichlorobenzenethiol.

6-(2',6'-dichlorophenyl)sulfenyl-1,3-dihydro-1-hydroxy-2,1-benzoxaborole (H113)

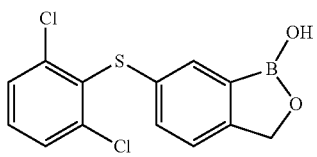 [SMILES: OB1OCc2ccc(Sc3c(Cl)cccc3Cl)cc21]

This compound can be produced by the same method as H109 by substituting 3,4-dichlorobenzenethiol with 2,6-dichlorobenzenethiol.

6-(3',4'-dichlorophenyl)sulfinyl-1,3-dihydro-1-hydroxy-2,1-benzoxaborole (H114)

6-(3',4'-dichlorophenyl)sulfinyl-1,3-dihydro-1-hydroxy-2,1-benzoxaborole (36)

Compound 35 (0.64 mmol) was dissolved in 10% (v/v) $H_2O$ in MeOH (15 mL). To this solution was added sodium periodate (688 mg, 3.21 mmol, 5.0 eq). The reaction mixture was stirred for 12 hours then evaporated and extracted with ethyl acetate. The organic layer was washed with water and brine, and dried over anhydrous $Na_2SO_4$. After rotary evaporation the residue was purified by crystallization to give the title compound (112.4 mg, 53.5% yield). $^1$H NMR (400 MHz, DMSO-$d_6$): δ 9.39 (s, 1H), 8.11 (s, 1H), 7.99 (d, J=2 Hz, 1H), 7.88-7.81 (m, 2H), 7.69-7.60 (m, 2H) and 5.02 (s, 2H) ppm.

6-(2',3'-dichlorophenyl)sulfinyl-1,3-dihydro-1-hydroxy-2,1-benzoxaborole (H115)

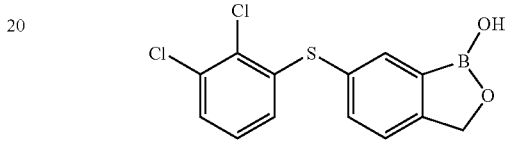

This compound can be produced by the same method as H114 by substituting 3,4-dichlorobenzenethiol used in making compound 35 with 2,3-dichlorobenzenethiol.

6-(2',4'-dichlorophenyl)sulfinyl-1,3-dihydro-1-hydroxy-2,1-benzoxaborole (H116)

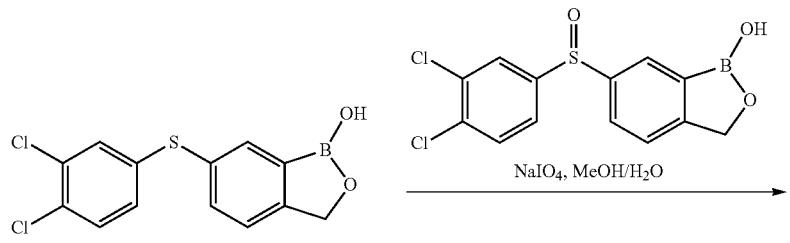

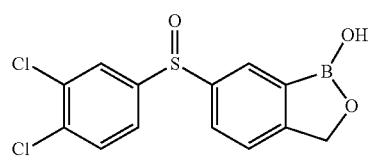 [SMILES: O=S(c1ccc2c(c1)B(O)OC2)c1ccc(Cl)cc1Cl]

This compound was produced by the same method as H114 by substituting 3,4-dichlorobenzenethiol used in making compound 35 with 2,4-dichlorobenzenethiol. ¹H NMR (300 MHz, DMSO-d₆): δ 9.41 (s, 1H), 8.07 (d, J=1.5 Hz, 1H), 7.97 (m, 1H), 7.83 (dd, J=8.1 & 1.8 Hz, 1H), 7.78 (m, 2H), 7.58 (d, J=8.1 Hz, 1H) and 5.03 (s, 2H) ppm. MS: found: 327 (M−1)⁻. Mp 155-157° C.

6-(2',5'-dichlorophenyl)sulfinyl-1,3-dihydro-1-hydroxy-2,1-benzoxaborole (H117)

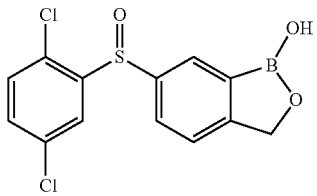 [SMILES: O=S(c1ccc2c(c1)B(O)OC2)c1cc(Cl)ccc1Cl]

This compound can be produced by the same method as H114 by substituting 3,4-dichlorobenzenethiol used in making compound 35 with 2,5-dichlorobenzenethiol.

6-(2',6'-dichlorophenyl)sulfinyl-1,3-dihydro-1-hydroxy-2,1-benzoxaborole (H118)

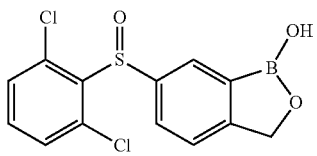 [SMILES: O=S(c1ccc2c(c1)B(O)OC2)c1c(Cl)cccc1Cl]

This compound can be produced by the same method as H114 by substituting 3,4-dichlorobenzenethiol used in making compound 35 with 2,6-dichlorobenzenethiol.

6-(3',4'-dichlorophenyl)sulfonyl-1,3-dihydro-1-hydroxy-2,1-benzoxaborole (H119)

6-(3',4'-dichlorophenyl)sulfonyl-1,3-dihydro-1-hydroxy-2,1-benzoxaborole

Compound 35 (0.83 mmol) was dissolved in 10% (v/v) H₂O in MeOH (20 mL). To this solution was added sodium periodate (894 mg, 4.17 mmol, 6.5 eq). The mixture was stirred for 2 days at 65° C. then evaporated and extracted with ethyl acetate, the organic layer was washed with water and brine, and dried over anhydrous Na₂SO₄. After rotary evaporation, the residue was purified by crystallization to give the title compound (86 mg, 30% yield). ¹H NMR (400 MHz, DMSO-d₆): δ 9.49 (s, 1H), 8.35 (s, 1H), 8.20 (s, 1H), 8.12 (dd, J=8.4 & 2 Hz, 1H), 7.90 (d, J=1.2 Hz, 2H), 7.68 (d, J=8.4 Hz, 1H), and 5.06 (s, 2H) ppm.

6-(2',3'-dichlorophenyl)sulfonyl-1,3-dihydro-1-hydroxy-2,1-benzoxaborole (H120)

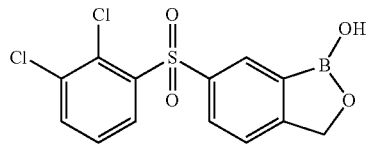 [SMILES: O=S(=O)(c1ccc2c(c1)B(O)OC2)c1cccc(Cl)c1Cl]

This compound can be produced by the same method as H119 by substituting 3,4-dichlorobenzenethiol used in making compound 35 with 2,3-dichlorobenzenethiol.

6-(2',4'-dichlorophenyl)sulfonyl-1,3-dihydro-1-hydroxy-2,1-benzoxaborole (H121)

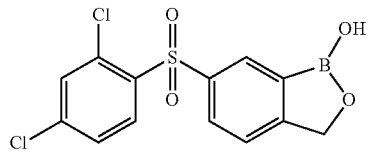 [SMILES: O=S(=O)(c1ccc2c(c1)B(O)OC2)c1ccc(Cl)cc1Cl]

This compound was produced by the same method as H119 by substituting 3,4-dichlorobenzenethiol used in making compound 35 with 2,4-dichlorobenzenethiol. ¹H NMR (300 MHz, DMSO-d₆): δ 9.49 (s, 1H), 8.31 (d, J=8.7 Hz, 2H), 8.00 (dd, J=8.4 & 2.1 Hz, 1H), 7.87 (d, J=1.8 Hz, 1H),

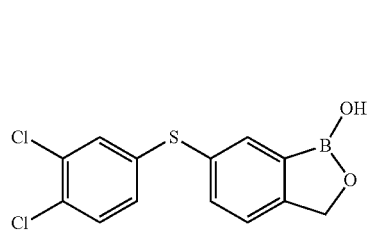

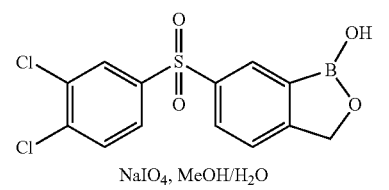

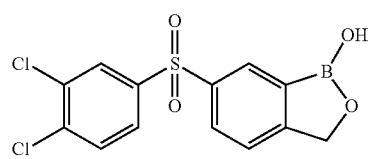

7.80 (dd, J=8.7 & 2.1 Hz, 1H), 7.67 (d, J=8.4 Hz, 1H) and 5.09 (s, 2H) ppm. Mp 169-171° C.

6-(2',5'-dichlorophenyl)sulfonyl-1,3-dihydro-1-hydroxy-2,1-benzoxaborole (H122)

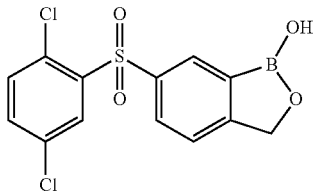 [SMILES: O=S(=O)(c1ccc2c(c1)B(O)OC2)c1cc(Cl)ccc1Cl]

This compound can be produced by the same method as H119 by substituting 3,4-dichlorobenzenethiol used in making compound 35 with 2,5-dichlorobenzenethiol.

6-(2',6'-dichlorophenyl)sulfonyl-1,3-dihydro-1-hydroxy-2,1-benzoxaborole (H123)

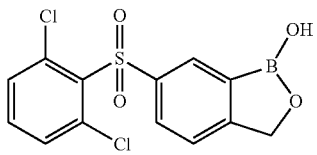 [SMILES: O=S(=O)(c1ccc2c(c1)B(O)OC2)c1c(Cl)cccc1Cl]

This compound can be produced by the same method as H119 by substituting 3,4-dichlorobenzenethiol used in making compound 35 with 2,6-dichlorobenzenethiol.

6-(phenylthio)benzo[c][1,2]oxaborol-1(3H)-ol (H124)

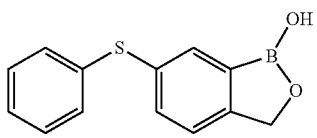 [SMILES: OB1OCc2ccc(Sc3ccccc3)cc21]

The synthesis of the title compound has been described previously in U.S. patent application Ser. Nos. 11/357,687; 11/505,591 and 11/676,120.

6-(phenoxy)benzo[c][1,2]oxaborol-1(3H)-ol (H125)

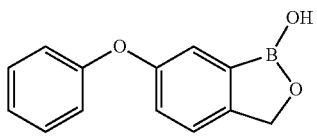 [SMILES: OB1OCc2ccc(Oc3ccccc3)cc21]

The synthesis of the title compound has been described previously in U.S. patent application Ser. Nos. 11/357,687; 11/505,591 and 11/676,120.

N-(1-hydroxy-1,3-dihydrobenzo[c][1,2]oxaborol-6-yl)-benzamide (H126)

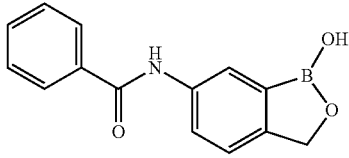 [SMILES: O=C(Nc1ccc2c(c1)B(O)OC2)c1ccccc1]

The synthesis of the title compound has been described previously in U.S. patent application Ser. Nos. 11/357,687; 11/505,591 and 11/676,120. Alternatively, the title compound can be synthesized according to the methods described above by using benzoyl chloride in place of 2-(trifluoromethyl)benzoyl chloride.

N-(1-hydroxy-1,3-dihydrobenzo[c][1,2]oxaborol-6-yl)-benzamine (H127)

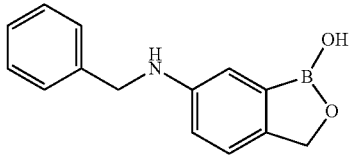 [SMILES: OB1OCc2ccc(NCc3ccccc3)cc21]

The synthesis of the title compound has been described previously in U.S. patent application Ser. Nos. 11/357,687; 11/505,591 and 11/676,120.

6-(phenylsulfonamido)benzo[c][1,2]oxaborol-1(3H)-ol (H128)

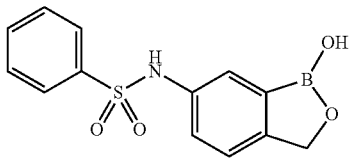 [SMILES: O=S(=O)(Nc1ccc2c(c1)B(O)OC2)c1ccccc1]

The synthesis of the title compound has been described previously in U.S. patent application Ser. Nos. 11/357,687; 11/505,591 and 11/676,120.

6-(phenylsulfinyl)benzo[c][1,2]oxaborol-1(3H)-ol (H129)

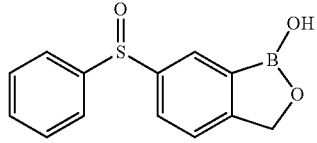 [SMILES: O=S(c1ccccc1)c1ccc2c(c1)B(O)OC2]

The title compound was synthesized according to the methods above by using phenylthiol in place of 4-chlorophenylthiol.

6-(phenylsulfonyl)benzo[c][1,2]oxaborol-1(3H)-ol (H130)

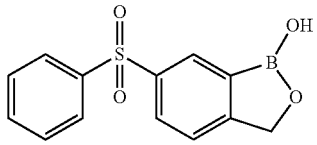 [SMILES: O=S(=O)(c1ccccc1)c1ccc2c(c1)B(O)OC2]

The title compound was synthesized according to the methods described above by using phenylthiol in place of 4-chlorophenylthiol.

[6-(1-phenyl-1-hydroxylmethyl)]-1,3-dihydro-1-hydroxy-2,1-benzoxaborole (H131)

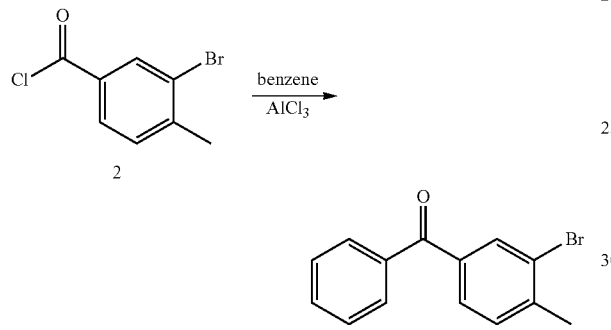

(2-bromo-4-benzoyl)toluene (15)

To a mixture of AlCl$_3$ (1.46 g, 11.0 mmol, 1.1 eq) in benzene (16 mL) was added a solution of compound 2 (2.33 g, 10.0 mmol) in benzene (8 mL) dropwise at room temperature. This mixture was stirred for 2 hours at 50° C. The mixture was washed with 3M HCl (20 mL) and saturated brine (20 mL), and dried over anhydrous Na$_2$SO$_4$. The residue after rotary evaporation was purified by column chromatography over silica gel to give compound 15 (2.7 g, 98% yield). $^1$H NMR (300 MHz, CDCl$_3$): δ 7.98 (d, J=1.8 Hz, 1H), 7.78 (d, J=6.9 Hz, 2H), 7.65 (dd, J=7.8 & 1.5 Hz, 1H), 7.59 (d, J=7.5 Hz, 1H), 7.49 (t, J=7.5 Hz, 2H), 7.35 (d, J=8.1 Hz, 2H) and 2.49 (s, 3H) ppm.

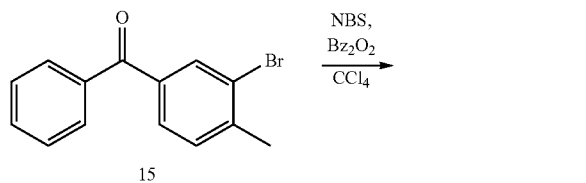

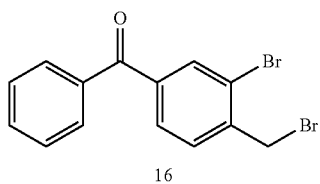

(2-bromomethyl-5-benzoyl)bromobenzene (16)

To a solution of compound 15 (2.7 g, 9.8 mmol) in CCl$_4$ (50 mL) was added NBS (1.75 g, 9.8 mmol, 1.0 eq) and Bz$_2$O$_2$ (0.12 g, 0.5 mmol, 0.05 eq). This mixture was heated to reflux and stirred overnight. The residue after rotary evaporation was purified by column chromatography over silica gel to give compound 16 (1.71 g, 49.3% yield). $^1$H NMR (300 MHz, CDCl$_3$): δ 8.01 (d, J=1.5 Hz, 1H), 7.79 (d, J=7.8 Hz, 2H), 7.71 (dd, J=8.1 & 1.5 Hz, 1H) and 4.64 (s, 2H) ppm.

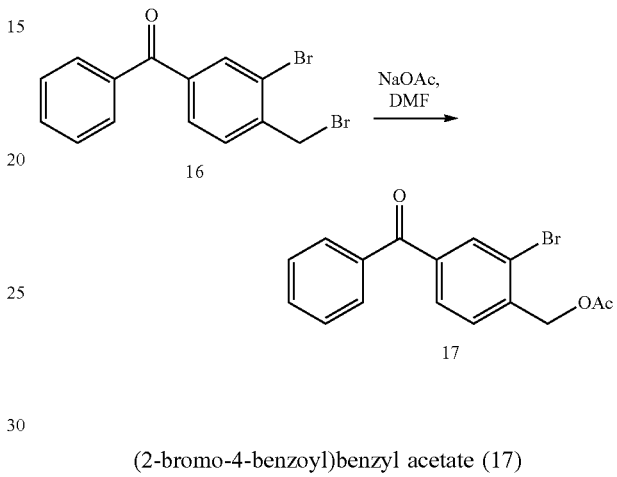

(2-bromo-4-benzoyl)benzyl acetate (17)

To a solution of compound 16 (1.71 g, 4.83 mmol) in DMF (30 mL) was added sodium acetate (1.98 g, 24.15 mmol, 5.0 eq). This mixture was heated to 60° C. and stirred overnight. The mixture was poured into ice-water (50 g). The precipitate was filtered, washed with water and dried under vacuum to give compound 17 (1.63 g, 100% yield).

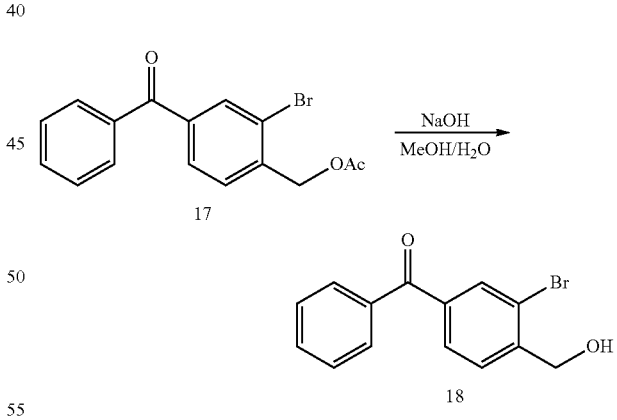

(2-bromo-4-benzoyl)benzyl alcohol (18)

To a solution of compound 17 (1.63 g, 4.9 mmol) in methanol (25 mL) was added 15% aq NaOH (5 mL). This mixture was heated to reflux and stirred for 1 hour. After methanol was evaporated the mixture was extracted with ethyl acetate, dried over anhydrous Na$_2$SO$_4$. The residue after rotary evaporation was purified by crystallization to give compound 18 (1.50 g, 100% yield).

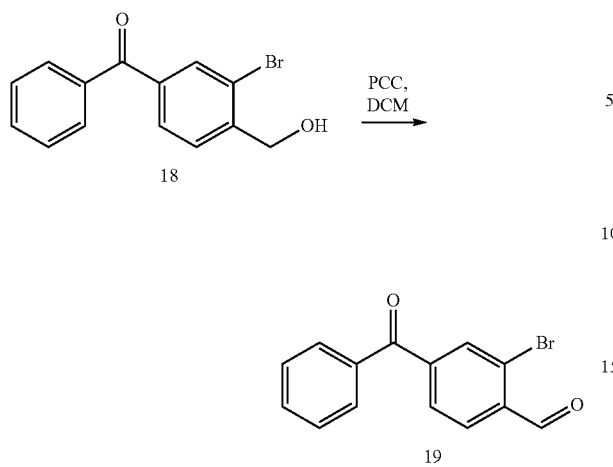

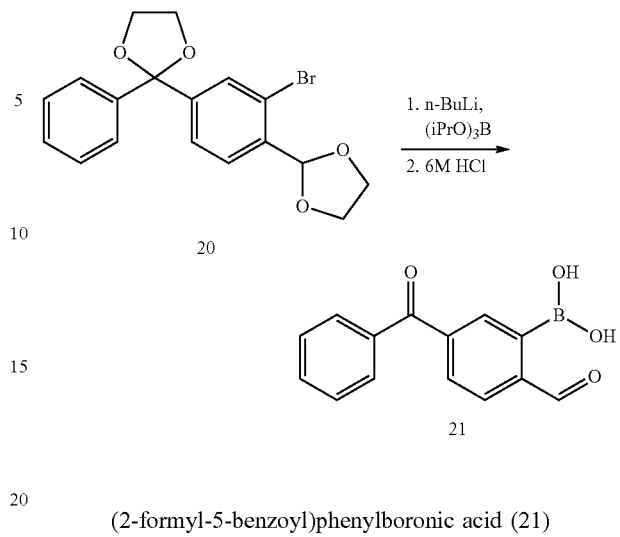

(2-bromo-4-benzoyl)benzaldehyde (19)

To a solution of compound 18 (1.50 g, 5.15 mmol) in DCM (30 mL) was added PCC (2.22 g, 10.3 mmol, 2.0 eq) and celite (2.5 g). This mixture was stirred overnight at room temperature. Then the mixture was filtered and the residue after rotary evaporation was purified by crystallization to give compound 19 (1.32 g, 88.7% yield).

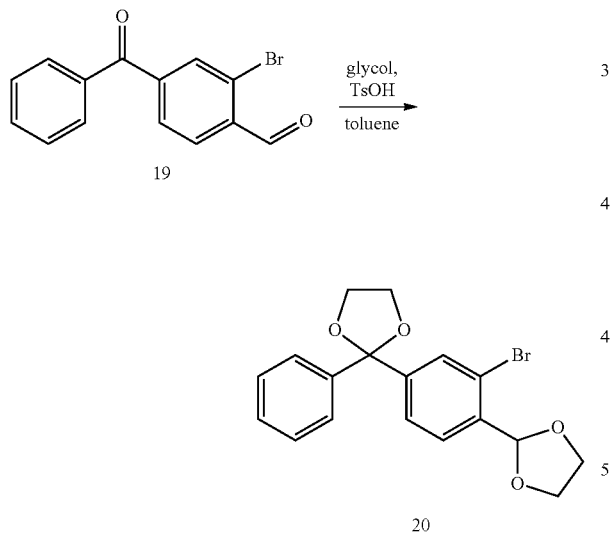

[2-(3-bromo-4-(1,3-dioxolan-2-yl)phenyl)-2-phenyl]-1,3-dioxolane (20)

To a solution of compound 19 (1.32 g, 4.57 mmol) in toluene (50 mL) was added ethylene glycol (2.83 g, 45.70 mmol, 10.0 eq) and p-toluenesulfonate monohydrate (69 mg, 0.36 mmol, 0.08 eq). This mixture was heated to reflux and stirred for 96 hours. The mixture was washed with saturated NaHCO$_3$, water and brine, dried over anhydrous Na$_2$SO$_4$. The solvent was evaporated to give compound 20 (1.51 g, 98% yield).

(2-formyl-5-benzoyl)phenylboronic acid (21)

Compound 20 (0.50 g, 1.23 mmol) was dissolved in anhydrous THF (10 mL) and cooled to −80° C. To this solution under nitrogen was added dropwise 1.6M n-BuLi (0.88 mL, 1.41 mmol, 1.15 eq) over 15 minutes. After stirred for another 20 minutes at −80° C., B(iPrO)$_3$ (0.33 mL, 1.41 mmol, 1.15 eq) was added dropwise over 10 minutes. The reaction mixture was allowed to warm to room temperature gradually and stirred overnight at room temperature. After 6M HCl (6 mL) was added and stirred for 2 hours, the mixture was evaporated and extracted with ethyl acetate (25 mL×5) and dried over anhydrous Na$_2$SO$_4$. The residue after rotary evaporation was purified by column chromatography over silica gel to give compound 21 (0.31 g, 88% yield).

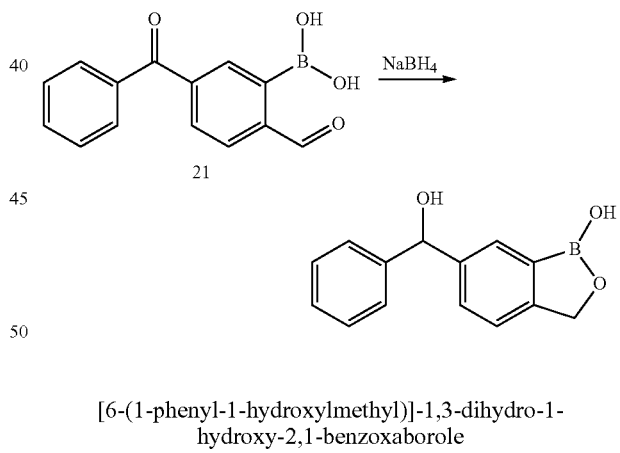

[6-(1-phenyl-1-hydroxylmethyl)]-1,3-dihydro-1-hydroxy-2,1-benzoxaborole

Compound 21 (0.75 g, 2.95 mmol) was dissolved in THF (8 mL) and water (0.5 mL). To this solution under stirring was added NaBH$_4$ (217 mg, 5.90 mmol, 2.0 eq) at room temperature. After stirred for 3 hours, 3M HCl (10 mL) was added to quench the reaction, and the mixture was evaporated and extracted with ethyl acetate (30 mL×3), dried over anhydrous Na$_2$SO$_4$. The residue after rotary evaporation was purified by crystallization to give the title compound (0.35 g, 50% yield). $^1$H NMR (300 MHz, DMSO-d$_6$): δ 9.1 (s, 1H), 7.71 (s, 1H), 7.46 (dd, J=8.1 & 1.8 Hz, 1H), 7.31 (m, 5H), 7.18 (d, J=7.5 Hz, 1H), 5.89 (d, J=3.9 Hz, 1H), 5.72 (d, J=3.6 Hz, 1H) and 4.91 (s, 2H) ppm.

6-Benzoyl-1,3-dihydro-1-hydroxy-2,1-benzoxaborole (H132)

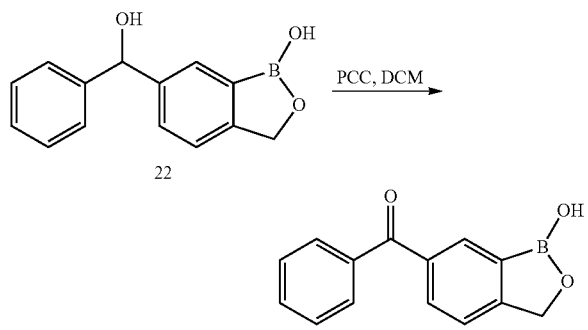

To a solution of compound 22 (0.2 g, 0.83 mmol) in 15 mL DCM was added PCC (0.45 g, 2.08 mmol, 2.5 eq) and celite (0.45 g). This mixture was stirred for 3 hours at room temperature before filtration. The residue after rotary evaporation was purified by crystallization to give the title compound (0.15 g, 76% yield). $^1$H NMR (400 MHz, DMSO-$d_6$): δ 9.35 (s, 1H), 8.12 (s, 1H), 7.87 (dd, J=8 & 1.6 Hz, 1H), 7.69 (m, 3H), 7.57 (m, 3H) and 5.08 (s, 2H) ppm.

6-Benzyloxy-1,3-dihydro-1-hydroxy-2,1-benzoxaborole (H133)

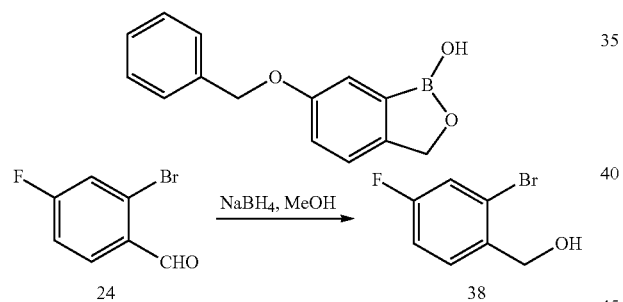

2-bromo-4-fluorobenzyl alcohol (38)

Compound 24 (49 mmol) was dissolved in MeOH (100 mL) and cooled to 0° C. with ice bath. To this solution was added NaBH$_4$ (3.7 g, 98 mmol, 2.0 eq). The reaction mixture was stirred for 1 hour then treated with saturated NaHCO$_3$. After evaporation, the residue was extracted with ethyl acetate and the organic layer was washed with water and brine. The residue after rotary evaporation was purified by column chromatography over silica gel to give compound 38 (9.04 g, 90% yield).

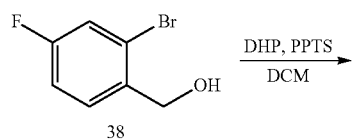

[3-fluoro-6-(((tetrahydro-2H-pyran-2-yl)oxy)methyl)]bromobenzene (39)

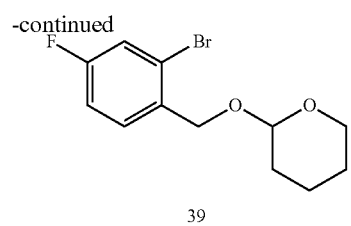

Compound 38 (4.88 mmol) and 3,4-dihydro-2H-pyran (24.4 mmol, 5.0 eq) was dissolved in DCM (20 mL). To this solution were added in sequence pyridinium p-toluenesulfonate (0.5 mmol, 0.1 eq). The reaction mixture was stirred overnight at room temperature then treated with saturated NaHCO$_3$. After extraction with ethyl acetate, the organic layer was washed with water and brine. The residue after rotary evaporation was purified by column chromatography over silica gel to give compound 39 (1.2 g, 85.1% yield).

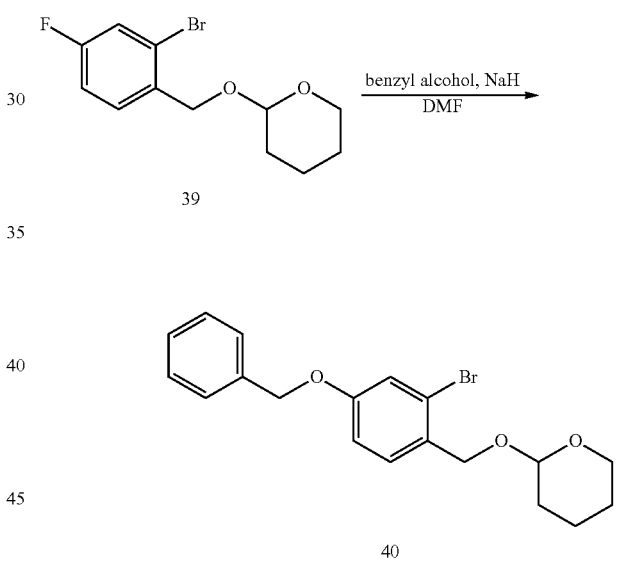

[3-benzyloxy-6-(((tetrahydro-2H-pyran-2-yl)oxy)methyl)]bromobenzene (40)

Compound 39 (1 mmol) was dissolved in DMF (20 mL) and cooled to 0° C. with ice bath. To this solution under nitrogen were added in sequence sodium hydride (353 mg, 8.8 mmol, 2.5 eq) and benzyl alcohol (0.76 g, 7.06 mmol, 2.0 eq). The reaction mixture was stirred for 1 hour at 100° C. then treated with cold water (30 ml). After extraction with ethyl acetate, the organic layer was washed with water and brine. The residue after rotary evaporation was purified by column chromatography over silica gel to give compound 40 (0.86 g, 64.8% yield). $^1$H NMR (300 MHz, CDCl$_3$): δ 7.39 (m, 6H), 7.20 (dd, J=3.2 Hz, 1H), 6.92 (dd, J=11.2 & 3.2 Hz, 1H), 5.04 (s, 2H), 4.79 (s, 0.5H), 4.75 (s, 1.5H), 4.52 (s, 1H), 3.93 (m, 1H), 3.55 (m, 1H) and 1.70 (m, 6H) ppm.

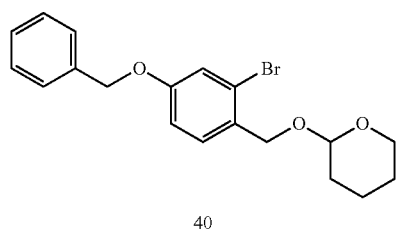

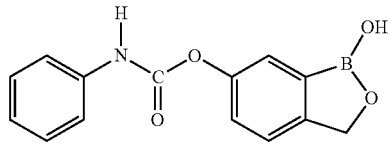 [SMILES: O=C(Nc1ccccc1)Oc1ccc2c(c1)B(O)OC2]

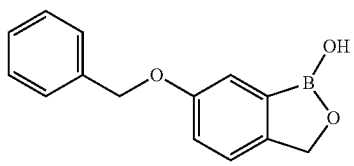

Compound 40 (0.86 g, 2.28 mmol) was dissolved in anhydrous THF (200 mL) and cooled to −80° C. To this solution under nitrogen was added dropwise 1.6M n-BuLi (1.64 mL, 2.62 mmol, 1.15 eq) over 20 minutes. After the mixture was stirred for another 20 minutes at −80° C., B(iPrO)₃ (0.61 mL, 2.62 mmol, 1.15 eq) was added dropwise over 8 minutes. The mixture was allowed to warm to room temperature gradually and stirred overnight at room temperature. After 6M HCl (6 mL) was added and stirred for 2 hours, the mixture was evaporated and extracted with ethyl acetate (25 mL×5) and dried over anhydrous Na₂SO₄. The residue after rotary evaporation was purified by crystallization to give the title compound (0.36 g, 66% yield). ¹H NMR (300 MHz, DMSO-d₆): δ 9.12 (s, 1H), 7.38 (m, 7H), 7.11 (dd, J=7.2 & 3.2 Hz, 1H), 5.10 (s, 2H) and 4.90 (s, 2H) ppm.

6-Hydroxyl-1,3-dihydro-1-hydroxy-2,1-benzoxaborole (H134)

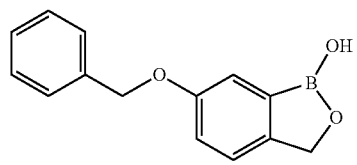

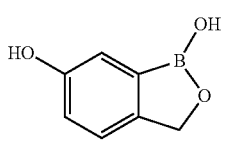

H134 (13 mmol) was dissolved in MeOH (300 mL). To this solution under nitrogen was added 10% Pd/C (200 mg). The reaction mixture was vacuumed and backfilled hydrogen for 3 times, then stirred overnight at room temperature. After filtration and rotary evaporation, the residue was purified by recrystallization to give the title compound (1.98 mg, 98% yield). ¹H NMR (300 MHz, DMSO-d₆): δ 9.29 (s, 1H), 9.04 (s, 1H), 7.18 (d, J=8.4 Hz, 2H), 6.87 (dd, J=8.1 & 2.4 Hz, 1H) and 4.86 (s, 2H) ppm. Mp 133-135° C.

1,3-dihydro-1-hydroxy-2,1-benzoxaborol-6-yl N-phenylcarbamate (H135)

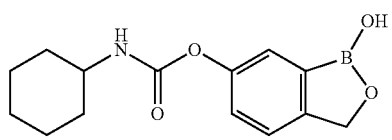 [SMILES: O=C(NC1CCCCC1)Oc1ccc2c(c1)B(O)OC2]

6-Hydroxyl-1,3-dihydro-1-hydroxy-2,1-benzoxaborole (0.667 mmol) was dissolved in DMF (10 mL) and cooled to 0° C. with ice bath. To this solution under nitrogen were added in sequence triethylamine (0.28 ml, 2 mmol, 3.0 eq) and isocyanatobenzene (0.852 mL, 6.67 mmol, 10.0 eq). The reaction mixture was stirred for 2 days at room temperature then treated with 1 M HCl (10 ml). After extraction with ethyl acetate, the organic layer was washed with water and brine. The residue after rotary evaporation was purified by column chromatography over silica gel to give the title compound (32 mg, 18% yield). ¹H NMR (300 MHz, DMSO-d₆): δ 10.23 (s, 1H), 9.25 (s, 1H), 7.53-7.02 (m, 8H) and 5.00 (s, 2H) ppm.

1,3-Dihydro-1-hydroxy-2,1-benzoxaborol-6-yl N-cyclohexylcarbamate (H136)

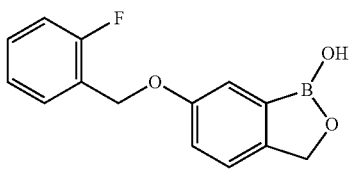 [SMILES: OB1OCc2ccc(OCc3ccccc3F)cc21]

6-Hydroxyl-1,3-dihydro-1-hydroxy-2,1-benzoxaborole (0.667 mmol) was dissolved in toluene (10 mL) and cooled to 0° C. with ice bath. To this solution under nitrogen were added in sequence triethylamine (0.28 ml, 2 mmol, 3.0 eq) and isocyanatocyclohexane (0.852 mL, 6.67 mmol, 10.0 eq). The reaction mixture was stirred for 2 days at room temperature then treated with 1 M HCl (10 ml). The white solid was filtrated then purified by column chromatography over silica gel and recrystallization to give the title compound (24 mg, 13% yield). ¹H NMR (300 MHz, Acetone-d₆): δ 8.09 (s, 1H), 7.42-7.37 (m, 2H), 7.19 (dd, J=8.4 & 2.1 Hz, 1H), 6.65 (m, 1H), 5.00 (s, 2H), 3.46 (m, 1H) and 1.98-1.15 (m, 10H) ppm. Mp 198-200° C.

6-(2'-Fluoro)benzyloxy-1,3-dihydro-1-hydroxy-2,1-benzoxaborole (H137)

6-Hydroxyl-1,3-dihydro-1-hydroxy-2,1-benzoxaborole (1 mmol) was dissolved in DMF (10 mL) and cooled to 0° C. with ice bath. To this solution under nitrogen were added in sequence sodium hydride (160 mg, 4 mmol, 4.0 eq) and 1-(chloromethyl)-2-fluorobenzene (0.485 mL, 4 mmol, 4.0 eq). The reaction mixture was stirred for 2 hours then treated with 1 M HCl (10 ml). After extraction with ethyl acetate, the organic layer was washed with water and brine. The residue after rotary evaporation was purified by column chromatography over silica gel to give the title compound (143.6 mg, 55.7% yield). $^1$H NMR (300 MHz, DMSO-$d_6$): δ 9.13 (s, 1H), 7.58-7.12 (m, 7H), 5.16 (s, 2H) and 4.92 (s, 2H) ppm. Mp 129-131° C.

6-(4'-Fluoro)benzyloxy-1,3-dihydro-1-hydroxy-2,1-benzoxaborole (H138)

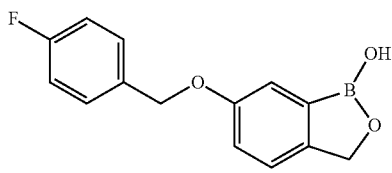 [SMILES: OB1OCc2ccc(OCc3ccc(F)cc3)cc21]

6-Hydroxyl-1,3-dihydro-1-hydroxy-2,1-benzoxaborole (1 mmol) was dissolved in DMF (10 mL) and cooled to 0° C. with ice bath. To this solution under nitrogen were added in sequence sodium hydride (160 mg, 4 mmol, 4.0 eq) and 1-(chloromethyl)-4-fluorobenzene (0.485 mL, 4 mmol, 4.0 eq). The reaction mixture was stirred for 2 hours then treated with 1 M HCl (10 ml). After extraction with ethyl acetate, the organic layer was washed with water and saturated brine. After rotary evaporation, the residue was purified by column chromatography over silica gel to give the title compound (228.2 mg, 88.4% yield). $^1$H NMR (300 MHz, DMSO-$d_6$): δ 9.13 (s, 1H), 7.53-7.11 (m, 7H), 5.10 (s, 2H) and 4.91 (s, 2H) ppm. Mp 136-137° C.

6-(2-Nitrobenzyloxy)-1,3-dihydro-1-hydroxy-2,1-benzoxaborole (H139)

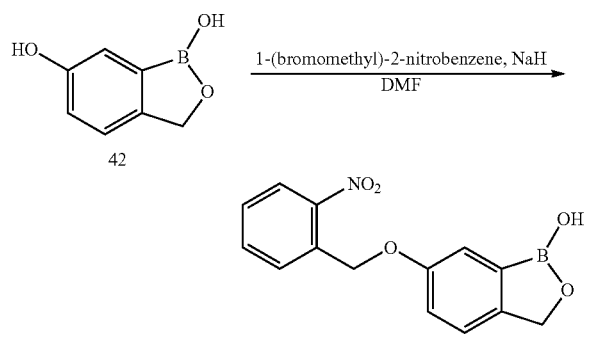

Compound 42 (200 mg, 1.33 mmol) was dissolved in DMF (9.0 mL) and cooled to 0° C. with ice bath. To this solution under nitrogen were added in sequence NaH (60% in mineral oil, 133 mg, 3.33 mmol) and 1-(bromomethyl)-2-nitrobenzene (432 mg, 2.00 mmol). The reaction mixture was stirred for 1 h then treated with 1.0 M HCl (10.0 mL). After extraction with ethyl acetate, the organic phase was washed with water and saturated brine. After rotary evaporation, the residue was purified by column chromatography over silica gel to give the title compound (153 mg, 40% yield). $^1$H NMR (300 MHz, DMSO-$d_6$): δ 9.17 (s, 1H), 8.15 (d, J=7.2 Hz, 1H), 7.83-7.76 (m, 2H), 7.66-7.59 (m, 1H), 7.37-7.30 (m, 2H), 7.15 (dd, J=8.1 & 2.4 Hz, 1H), 5.48 (s, 2H) and 4.92 (s, 2H) ppm; Mp: 135-138° C.

6-(Benzyl)benzo[c][1,2]oxaborol-1(3H)-ol (H140)

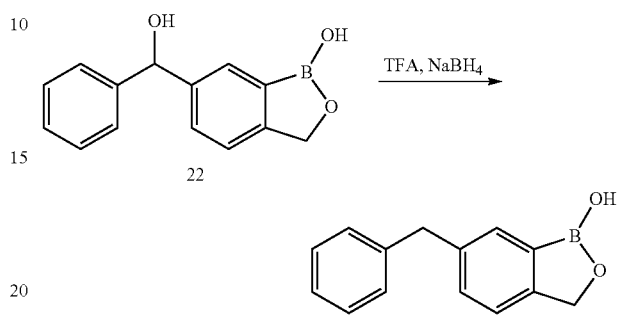

Compound 22 (125 mg, 0.5 mmol) and NaBH$_4$ (190 mg, 5 mmol) was slowly added in portions with vigorous stirring to trifluoroacetic acid (20 mL) at 0° C. under nitrogen. After 15 min, aqueous NaHCO$_3$ was slowly added and the solution was extracted with CH$_2$Cl$_2$. The organic layer was washed with brine, dried over Na$_2$SO$_4$, and evaporated under vacuum to a solid residue. The crude product was recrystallized from hexane and ethyl acetate to give 105 mg of the product (90%).

6-Formyl-1-hydroxy-1,3-dihydro-2,1-benzoxaborole (H141)

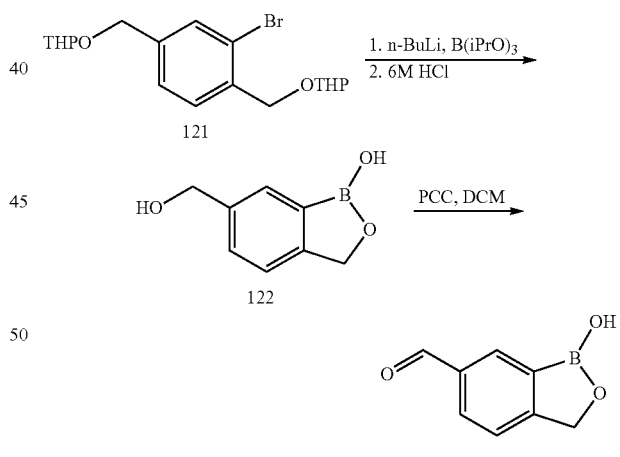

To a solution of compound 121 (24.0 g, 62.3 mmol) in THF (250 mL) under nitrogen at −78° C. was added dropwise n-BuLi solution (1.6M in hexane, 42.9 mL, 68.6 mmol, 1.1 eq) over 30 minutes. After the mixture was stirred at −78° C. for another 20 minutes, triisopropyl borate (15.7 mL, 68.6 mmol, 1.1 eq) was added over 10 minutes. The mixture was allowed to warm to room temperature gradually and stirred overnight before quenched with 6M HCl (100 mL). The mixture was stirred for another 6 hours at room temperature. All of solvents were evaporated under reduced pressure to give crude product 122 which was used to oxidative reaction without purification.

To a mixture of crude product 122 in CH$_2$Cl$_2$ (250 mL) were added PCC (26.8 g, 124.6 mmol, 2.0 eq) and Celite (40.2 g). The mixture was stirred overnight at room temperature. The reaction mixture was filtered through celite and silica gel pad and the filtrate was washed with 1 M HCl and 1 M NaOH. The aqueous phase was acidified by concentrated HCl to pH 2 and extracted with ethyl acetate. The organic phase was washed with brine, dried over anhydrous Na$_2$SO$_4$, and evaporated to give crude product (4.70 g) which was purified by column chromatography and recrystallization to give the title compound (1.60 g, 15.8% yield). $^1$H NMR (300 MHz, DMSO-d$_6$): δ 10.06 (s, 1H), 9.44 (s, 1H), 8.28 (s, 1H), 8.01 (m, 1H), 7.63 (m, 1H) and 5.09 (s, 2H) ppm. Mp 133-135° C.

7-Formyl-1-hydroxy-1,3-dihydro-2,1-benzoxaborole (H142)

H142 can be synthesized using the following procedure:

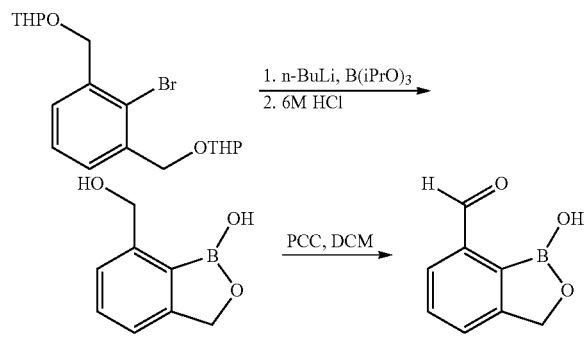

6-(4-Nitro-phenylsulfanyl)-3H-benzo[c][1,2]oxaborol-1-ol (H143)

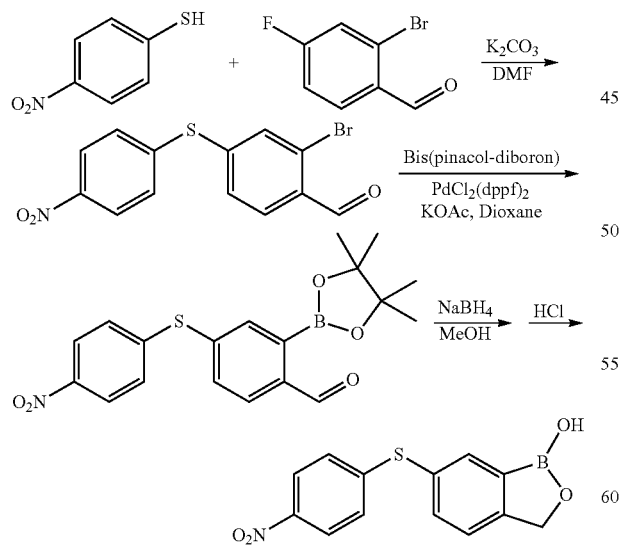

To a solution of 4-nitro-benzenethiol (3.1 g, 20.0 mmol, 1.0 eq.), 2-bromo-4-fluoro-benzaldehyde (4.1 g, 20.0 mmol, 1.0 eq.) in DMF (40.0 mL) was added K$_2$CO$_3$ (5.5 g, 40.0 mmol, 2.0 eq.) under nitrogen atmosphere. The mixture was heated at 100° C. overnight. After cooling to room temperature, the mixture was filtered through a short pack of celite to remove the solid residue. The filtrate was concentrated under reduced pressure to ⅕ volume and poured into DCM (30 mL) and H$_2$O (30 mL). The aqueous phase as slightly acidified by adding a couple drop of HCl (3N) and the layers were separated and the aqueous phase was extracted with DCM (3×30 mL). Combined organic extracts was washed with brine (30 mL), dried over MgSO$_4$, filtered and the filtrate was concentrated under reduced pressure. The residue was applied to silica chromatography eluting with EtOAc/heptanes (0:100 to 100:0) to give 2-bromo-4-(4-nitro-phenylsulfanyl)-benzaldehyde as a fine yellow powder. $^1$H NMR(CHLOROFORM-d) δ: 10.35 (s, 1H), 8.43 (dd, J=2.3, 0.6 Hz, 1H), 7.98 (dd, J=8.6, 2.3 Hz, 1H), 7.69-7.77 (m, 2H), 7.30 (dd, J=8.6, 3.0 Hz, 1H), 7.12 (dd, J=8.6, 0.8 Hz, 1H). Amount obtained, 4.3, 71.2% yield.

To a solution of 2-bromo-4-(4-nitro-phenylsulfanyl)-benzaldehyde (2.7 g, 8.0 mmol, 1.0 eq.) in 1,4-dioxane (50 mL) was added bis-pinacol-diboron (2.23 g, 8.8 mmol, 1.1 eq.), KOAc (2.35 g, 24.0 mmol, 3.0 eq.) and PdCl$_2$(dppf)$_2$ (175 mg, 0.24 mmol, 0.03 eq.). The mixture was degassed with N$_2$ and heated at 80° C. overnight. After cooling to room temperature, the mixture was filtered though a short pack of celite and the filtrate was concentrated under reduced pressure. The residue was applied to silica chromatography eluting with EtOAc/Heptanes (0:100 to 50:50) to give 4-(4-nitro-phenylsulfanyl)-2-(4,4,5,5-tetramethyl-[1,3,2]dioxaborolan-2-yl)-benzaldehyde as a yellow solid. $^1$H NMR (CHLOROFORM-d) δ: 10.56 (s, 1H), 8.20-8.25 (m, 2H), 8.11-8.17 (m, 1H), 7.94-8.00 (m, 2H), 7.47-7.53 (m, 1H), 7.33-7.38 (m, 1H), 1.27 (s, 12H).

To a suspension of 4-(4-nitro-phenylsulfanyl)-2-(4,4,5,5-tetramethyl-1,3,2]dioxaborolan-2-yl)-benzaldehyde (1.3 g, 3.4 mmol, 1.0 eq.) in EtOH (30 mL) at 0° C. was added NaBH$_4$ (127.7 mg, 3.4 mmol, 1.0 eq.) in small portions. The mixture was stirred at 0° C. for 20 minutes and allowed to warm to room temperature in another 1 h. After cooling to 0° C., the clear solution was carefully treated with H$_2$O (1 mL), followed by slow addition of HCl (10 mL, 3N). The resulting yellow suspension was allowed to ward to room temperature gradually and stirred for 2 h. The mixture was then treated with sat. NaHCO$_3$ drop wise until PH reaching 7. The precipitate was collected by filtration and applied to silica chromatography eluting with MeOH/DCM (0:100 to 10:90) to give 6-(4-nitro-phenylsulfanyl)-3H-benzo[c][1,2] oxaborol-1-ol as a white solid. LCMS (m/z) 310 (M+23); $^1$H NMR (DMSO-d$_6$) δ: 9.32 (s, 1H), 8.08-8.14 (m, 2H), 7.91 (d, J=1.2 Hz, 1H), 7.67 (dd, J=7.9, 1.8 Hz, 1H), 7.57 (dd, J=7.9, 0.6 Hz, 1H), 7.22-7.28 (m, 2H), 5.05 (s, 2H).

6-(Pyridin-4-ylsulfanyl)-3H-benzo[c][1,2]oxaborol-1-ol (H144)

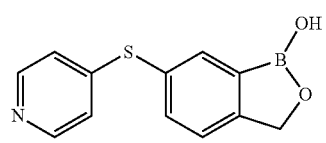 [SMILES: OB1OCc2ccc(Sc3ccncc3)cc21]

H144 was prepared using a procedure similar to compound H143 by substituting 4-nitro-benzenethiol with 4-mercaptopyridine. LCMS (m/z) 244 (M+H); $^1$H NMR (DMSO-d$_6$) δ: 9.32 (s, 1H), 8.34 (d, J=6.0 Hz, 2H), 7.91 (s, 1H), 7.66 (d, J=9.3 Hz, 1H), 7.57 (d, J=8.0 Hz, 1H), 6.98 (d, J=6.0 Hz, 2H), 5.05 (s, 2H).

6-(3-Methoxy-phenylsulfanyl)-3H-benzo[c][1,2]oxaborol-1-ol (H145)

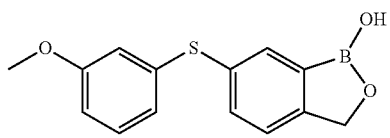 [SMILES: COc1cccc(Sc2ccc3c(c2)B(O)OC3)c1]

H145 was prepared using a procedure similar to compound H143 by substituting 4-nitrobenzenethiol with 3-methoxybenzenethiol. LCMS (m/z) 273 (M+H); $^1$H NMR (DMSO-d$_6$) δ: 9.24 (s, 1H), 7.74 (d, J=1.2 Hz, 1H), 7.46-7.51 (m, 1H), 7.40-7.46 (m, 1H), 7.25 (t, J=8.2 Hz, 1H), 6.82 (ddd, J=8.2, 2.4, 0.9 Hz, 1H), 6.75-6.80 (m, 2H), 4.98 (s, 2H), 3.69 (s, 3H).

2-(1-Hydroxy-1,3-dihydro-benzo[c][1,2]oxaborol-6-ylsulfanyl)-benzoic acid methyl ester (H146)

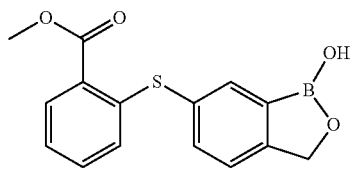 [SMILES: COC(=O)c1ccccc1Sc1ccc2c(c1)B(O)OC2]

H146 was prepared using a procedure similar to compound H143 by substituting 4-nitrobenzenethiol with methyl thiosalicylate. LCMS (m/z) 323 (M+23); $^1$H NMR (DMSO-d$_6$) δ: 9.29 (s, 1H), 7.90 (dd, J=7.8, 1.5 Hz, 1H), 7.86 (d, J=1.2 Hz, 1H), 7.58-7.64 (m, 1H), 7.50-7.57 (m, 1H), 7.38 (td, J=7.7, 1.6 Hz, 1H), 7.22 (td, J=7.6, 1.1 Hz, 1H), 6.73 (dd, J=8.1, 0.8 Hz, 1H), 5.04 (s, 2H), 3.86 (s, 3H).

6-(3-Methoxy-benzenesulfinyl)-3H-benzo[c][1,2]oxaborol-1-ol (H147)

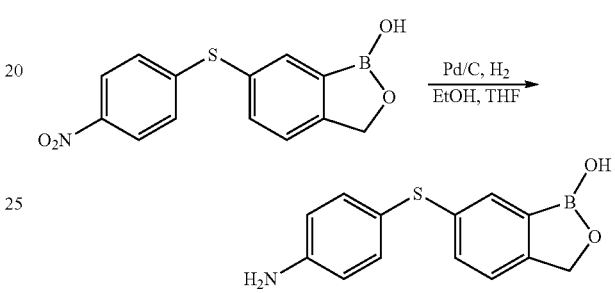

To a 20 mL scintillation vial containing 6-(3-methoxyphenylsulfanyl)-3H-benzo[c][1,2]oxaborol-1-ol (200 mg, 0.73 mmol, 1.0 in MeOH (9.0 mL) was added a solution of NaIO$_4$ (172.9 mg, 0.81 mmol, 1.1 eq.) in H$_2$O (1.0 mL. The mixture was stirred at room temperature overnight. The mixture was treated with H$_2$O (10 mL) and was extracted with EtOAc (3×10 mL), combined organic phase was washed with brine (10 mL), dried over MgSO$_4$, filtered and the filtrate was concentrated under reduced pressure. The residue was applied to silica chromatography eluting with MeOH/DCM (0:100 to 10:90) to give 6-(3-methoxy-benzenesulfinyl)-3H-benzo[c][1,2]oxaborol-1-ol as a white solid. LCMS (m/z) 289 (M+H); $^1$H NMR (DMSO-d$_6$) δ: 9.35 (s, 1H), 8.07 (d, J=1.1 Hz, 1H), 7.79 (dd, J=8.0, 1.8 Hz, 1H), 7.53 (dd, J=8.0, 0.6 Hz, 1H), 7.42 (t, J=8.0 Hz, 1H), 7.18-7.28 (m, 2H), 6.99-7.05 (m, 1H), 4.98 (s, 2H), 3.76 (s, 3H).

6-(4-Amino-phenylsulfanyl)-3H-benzo[c][1,2]oxaborol-1-ol (H148)

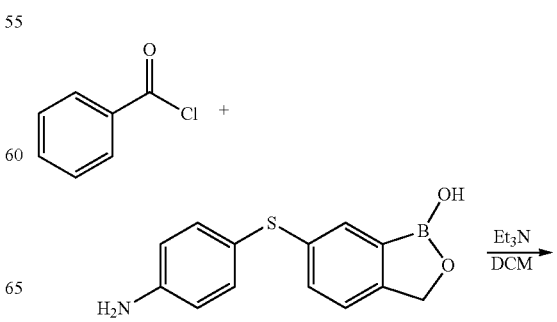

To a 25 mL round-bottom flask fitted with magnetic stirring bar was added 4-nitro-phenylsulfanyl)-3H-benzo[c][1,2]oxaborol-1-ol (120 mg, 0.42 mmol, 1.0 eq.), followed by addition of EtOH (4 mL) and THF (1 mL). The flask was evacuated and recharged with N$_2$ twice. To the stirring solution was added 5% Pd/C (20 mg) and the flask was evacuated and recharged with H$_2$ three times. The resulting suspension was stirred under a H$_2$ balloon at room temperature overnight. The mixture was filtered through a short pack of celite and washed with MeOH (3×10 mL). The combined filtrate was concentrated under reduced pressure to give a white solid. The solid was dissolved in minimum amount of MeOH and carefully treated with HCl (conc.). The precipitate was collected by filtration, washed with heptanes to give 6-(4-amino-phenylsulfanyl)-3H-benzo[c][1,2]oxaborol-1-ol hydrochloride salt as a white solid. LCMS (m/z) 258 (M+H); $^1$H NMR (DMSO-d$_6$) δ: 7.72 (d, J=3.9 Hz, 1H), 7.40-7.48 (m, 2H), 7.27-7.32 (m, 2H), 7.21 (t, J=8.8 Hz, 2H), 4.97 (s, 2H).

N-[4-(1-Hydroxy-1,3-dihydro-benzo[c][1,2]oxaborol-6-ylsulfanyl)-phenyl]-benzamide (H149)

-continued

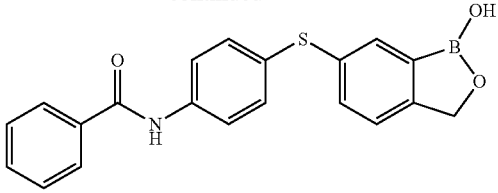

To a 20 mL scintillation vial containing 6-(4-aminophenylsulfanyl)-3H-benzo[c][1,2]oxaborol-1-ol (77.1 mg, 0.3 mmol, 1.0 eq.) in DCM (4.0 mL) was added Et$_3$N (58.5 μL, 0.42 mmol, 1.4 eq.), followed by benzoyl chloride (42.7 μL, 0.36 mmol, 1.2 eq.). The resulting white suspension was diluted with DCM (5 mL). The precipitate was collected by filtration and washed with DCM to give N-[4-(1-hydroxy-1,3-dihydro-benzo[c][1,2]oxaborol-6-ylsulfanyl)-phenyl]-benzamide as a white solid. LCMS (m/z) 362 (M+H); $^1$H NMR (DMSO-d$_6$) δ: 10.36 (s, 1H), 9.21 (s, 1H), 7.93 (d, J=7.0 Hz, 2H), 7.81 (t, J=4.7 Hz, 1H), 7.81 (d, J=8.7 Hz, 1H), 7.62 (s, 1H), 7.55-7.61 (m, 1H), 7.48-7.55 (m, 1H), 7.52 (d, J=7.7 Hz, 1H), 7.33-7.43 (m, 4H), 4.96 (s, 2H).

N-[4-(1-Hydroxy-1,3-dihydro-benzo[c][1,2]oxaborol-6-ylsulfanyl)-phenyl]-2-trifluoromethyl-benzamide (H150)

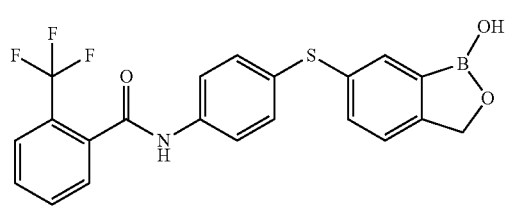 [SMILES: O=C(Nc1ccc(Sc2ccc3c(c2)B(O)OC3)cc1)c1ccccc1C(F)(F)F]

H150 was prepared using a procedure similar to that of H149 by substituting benzoyl chloride with 2-trifluoromethylbenzoyl chloride. LCMS (m/z) 452 (M+23); $^1$H NMR (DMSO-d$_6$) δ: 10.68 (s, 1H), 9.22 (s, 1H), 7.83 (d, J=7.9 Hz, 1H), 7.77 (d, J=7.5 Hz, 1H), 7.66-7.73 (m, 4H), 7.63 (s, 1H), 7.35-7.42 (m, 4H), 4.96 (s, 2H).

Cyclohexanecarboxylic acid [4-(1-hydroxy-1,3-dihydro-benzo[c][1,2]oxaborol-6-ylsulfanyl)-phenyl]-amide (H151)

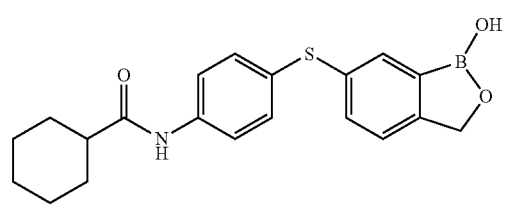 [SMILES: O=C(Nc1ccc(Sc2ccc3c(c2)B(O)OC3)cc1)C1CCCCC1]

H151 was prepared using a procedure similar to that of H149 by substituting benzoyl chloride with cyclohexanecarbonyl chloride. LCMS (m/z) 390 (M+23); $^1$H NMR (DMSO-d$_6$) δ: 9.92 (s, 1H), 9.19 (s, 1H), 7.63 (d, J=8.7 Hz, 1H), 7.63 (q, J=4.6 Hz, 1H), 7.56 (s, 1H), 7.29-7.38 (m, 4H), 4.94 (s, 2H), 2.30 (t, J=2.7 Hz, 1H), 2.25-2.35 (m, 1H), 1.75 (t, J=13.7 Hz, 4H), 1.59-1.66 (m, 1H), 1.38 (d, J=11.9 Hz, 1H), 1.31-1.44 (m, 1H), 1.23 (quin, J=12.4 Hz, 2H), 1.11-1.31 (m, 1H).

N-[4-(1-Hydroxy-1,3-dihydro-benzo[c][1,2]oxaborol-6-ylsulfanyl)-phenyl]-acetamide (H152)

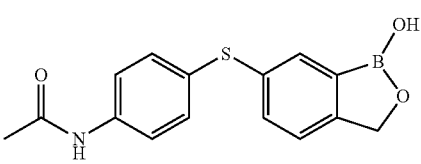 [SMILES: CC(=O)Nc1ccc(Sc2ccc3c(c2)B(O)OC3)cc1]

H152 was prepared using a procedure similar to that of H149 by substituting benzoyl chloride with acetyl chloride. LCMS (m/z) 300 (M+H); $^1$H NMR (DMSO-d$_6$) δ: 10.05 (s, 1H), 7.55-7.59 (m, 3H), 7.28-7.38 (m, 4H), 4.94 (s, 2H), 2.02 (s, 3H).

N-[4-(1-Hydroxy-1,3-dihydro-benzo[c][1,2]oxaborol-6-ylsulfanyl)-phenyl]-4-methoxy-benzamide (H153)

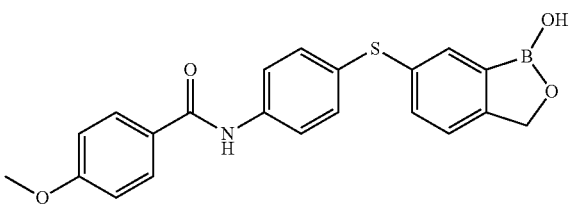 [SMILES: COc1ccc(C(=O)Nc2ccc(Sc3ccc4c(c3)B(O)OC4)cc2)cc1]

H153 was prepared using a procedure similar to that of H149 by substituting benzoyl chloride with 4-methoxybenzoyl chloride. LCMS (m/z) 392 (M+H); $^1$H NMR (DMSO-d$_6$) δ: 10.19 (s, 1H), 9.21 (s, 1H), 7.90-7.97 (m, 2H), 7.77-7.83 (m, 2H), 7.62 (s, 1H), 7.32-7.41 (m, 4H), 7.01-7.08 (m, 2H), 4.95 (s, 2H), 3.82 (s, 3H).

4-Chloro-N-[4-(1-hydroxy-1,3-dihydro-benzo[c][1,2]oxaborol-6-ylsulfanyl)-phenyl]-benzamide (H154)

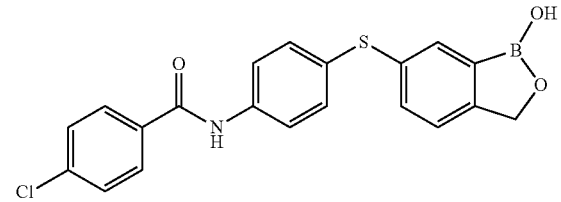 [SMILES: O=C(Nc1ccc(Sc2ccc3c(c2)B(O)OC3)cc1)c1ccc(Cl)cc1]

H154 was prepared using a procedure similar to that of H149 by substituting benzoyl chloride with 4-chlorobenzoyl chloride. LCMS (m/z) 418 (M+23); $^1$H NMR (DMSO-d$_6$) δ: 10.41 (s, 1H), 9.21 (s, 1H), 7.96 (d, J=8.6 Hz, 2H), 7.79 (d, J=8.7 Hz, 2H), 7.57-7.62 (m, 3H), 7.33-7.42 (m, 4H), 4.96 (s, 2H).

H155

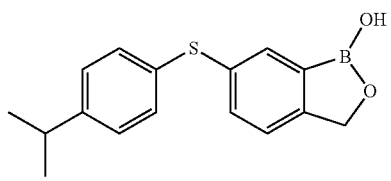 [SMILES: CC(C)c1ccc(Sc2ccc3c(c2)B(O)OC3)cc1]

This compound was prepared using a procedure similar to that of H104 by substituting 3-chlorophenyl sulfide with 4-isopropylphenyl sulfide. $^1$H NMR (400 MHz, DMSO-d$_6$): δ 9.26 (s, 1H), 7.70 (d, J=0.8 Hz, 1H), 7.43 (m, 2H), 7.25 (s, 4H), 4.98 (s, 2H), 2.85 (m, 1H), 1.19 (s, 3H) and 1.17 (s, 3H) ppm.

Example 2

Trypanosoma brucei brucei High-Throughput Screening Assay Procedure

Experiments were conducted with the bloodstream-form trypanosome T. brucei brucei S427 strain and the T. brucei brucei STIB 795 strain. Parasites were cultured in T-25 vented cap flasks and kept in humidified incubators at 37° C. and 5% CO$_2$. The parasite culture media was complete HMI-9 medium (c.f. Hirumi, Journal of Parasitology, 40:75, 985-989 (1989)) containing 10% FBS, 10% Serum Plus medium and penicillin/streptomycin. To ensure log growth phase, trypanosomes were sub-cultured at appropriate dilutions every 2-3 days.

In Vitro Drug Sensitivity Assays

Log phase cultures were diluted 1:10 in HMI-9 and 10 uL was counted using hemocytometer to determine parasite concentration. Parasites were diluted to 2×10$^5$/mL in HMI-9 to generate a 2-fold working concentration for assay. Compounds to be tested were serially diluted in DMSO and 0.5 uL added to 49.5 uL HMI-9 in triplicate 96-well plates using a Biomek NX liquid handler. Parasites from the diluted stock were added to each well (50 uL) using a Multidrop 384 dispenser to give a final concentration of 1.0×10$^5$/ml parasites in 0.4% for DMSO. Trypanosomes were incubated with compounds for 72 hrs at 37° C. with 5% CO$_2$. Resazurin (20 uL of 12.5 mg/ml stock) from Sigma-Aldrich was added to each well and plates were incubated for an additional 2-4 hrs. Assay plates were read using an EnVision plate reader at an excitation wavelength of 544 nm and emission of 590 nm. Triplicate data points were averaged to generate sigmoidal dose response curve and determine IC$_{50}$ values using XLfit curve fitting software from IDBS (Guildford, UK).

Results from the S427 strain and the STIB 795 strain are provided in FIG. 1.

Example 3

Trypanosoma cruzi C2C4 Screening Assay Procedure

Rat skeletal myoblasts (L-6 cells) were seeded in 96-well microtitre plates at 2×10$^3$ cells/well in 100 μL RPMI 1640 medium with 10% FBS and 2 mM L-glutamine. After 24 h the medium was removed and replaced by 100 μl per well containing 5×10$^3$ trypomastigote forms of T. cruzi Tulahuen strain C2C4 containing the β-galactosidase (Lac Z) gene (Buckner, et al., Antimicrobial Agents and Chemotherapy, 40: 2592-2597 (1996)). After 48 h the medium was removed from the wells and replaced by 100 μl fresh medium with or without a serial drug dilution of seven 3-fold dilution steps covering a range from 90 to 0.123 μg/ml. After 96 h of incubation the plates were inspected under an inverted microscope to assure growth of the controls and sterility. The substrate (50 μl) chlorophenol red-β-D-galactopyranoside (CPRG, Roche Diagnostics Ltd) in 0.25% Nonidet P-40/PBS was added to all wells and a color reaction developed within 2-6 h. which was read photometrically at 540 nm. Data were transferred into the graphic programme Softmax Pro (Molecular Devices), which calculated IC50 values.

Results from this assay are provided in FIG. 1.

Example 4

Trypanosoma cruzi CL2 Screening Assay Procedure

Parasite and cell cultures. Trypanosoma cruzi, Tulahuen CL2, β galactosidase strain (nifurtimox-sensitive) was used (Buckner et al., Antimicrob Agents Chemother. 40: 2592-2597 (1996)). The strain was maintained in MRC-5SV2 (human lung fibroblast) cells. A SV-40 transformed cell line was available to obtain unlimited subcultivation characteristics in MEM medium, supplemented with 200 mM. L-glutamine, 16.5 mM NaHCO$_3$, and 5% inactivated fetal calf serum. All cultures and assays were conducted at 37° C. with 5% CO$_2$.

Compound Solutions/Dilutions.

Compound stock solutions were prepared in 100% DMSO at 20 mM or mg/ml for natural products, drug mixtures and if the molecular weight was not known. The compounds were serially pre-diluted (2-fold or 4-fold) in DMSO followed by a further (intermediate) dilution in demineralized water to assure a final in-test DMSO concentration of <1%.

Drug Sensitivity Assays.

Assays were performed in sterile 96-well microtiter plates, each well containing 10 μl of the watery compound dilutions together with 190 μl of MRC-5 cell/parasite inoculum (4×10$^3$ cells/well+4×10$^4$ parasites/well). Parasite growth was compared to untreated-infected controls (100% growth) and noninfected controls (0% growth) after 7 days incubation at 37° C. and 5% CO$_2$. Parasite burdens were assessed after adding the substrate CPRG (chlorophenolred β-D-galactopyranoside): 50 μl/well of a stock solution containing 15.2 mg CPRG+250 μl Nonidet in 100 ml PBS. The change in color was measured spectrophotometrically at 540 nm after 4 hours incubation at 37° C. The results were expressed as % reduction in parasite burdens compared to control wells and an 1050 (50% inhibitory concentration) was calculated.

Primary Screen.

Trypanosoma cruzi β galactosidase strain was used. Compounds were tested at 5 concentrations (64-16-4-1 and 0.25 μM or ug/ml). Nifurtimox or benznidazole were included as the reference drugs. The test compound was classified as inactive when the IC$_{50}$ was higher than 30 μM. When the IC50 was between 30 and 5 μM, the compound was regarded as being moderate active. When the IC$_{50}$ was lower than 5 μM, the compound was classified as highly active on the condition that it also demonstrated selective action (absence of cytotoxicity). A final recommendation for activity was given after confirmatory evaluation in a secondary screening.

Secondary Screen.

*Trypanosoma cruzi* β galactosidase strain was used and IC50-values were determined using an extended dose range (2-fold compound dilutions). Nifurtimox or benznidazole was included as reference drugs. Advanced selectivity evaluation was performed against a panel of unrelated organisms (bacteria, yeasts, fungi and other protozoan parasites).

Results from this assay are provided in FIG. 1.

Example 5

*Trypanosoma brucei gambiense* Screening Assay Procedure

The following *T. b. gambiense* strains were isolated from sleeping sickness patients as described, and were subsequently propagated in mice at Swiss Tropical Institute.

*T. b. gambiense* 40R, 108R were isolated by Pati Pyana in Mbuji Mayi (D.R Congo) in 2005 and then propagated in STI (Swiss Tropical Institute, Basel, Switzerland) in different mice in winter 2006.

40R is a relapse 6 months after a 10 days melarsoprol treatment.

108R is a relapse 8 months after a 10 days melarsoprol treatment

*T. b. gambiense* DAL 1402 was obtained from the cryobank of the "Project de Recherches Cliniques Sur la Trypanosomiase," in Daloa. It was isolated in 1990 from a human patient in Cote d'Ivoire.

*T. b. gambiense* ITMAP 141267 was isolated in Bandundu/Lac Mai-Ndombe, DRC, 1960

*T. b. gambiense* Drani was isolated from a patient in Uganda; West Nile, 1995; original stabilate ID: UTRO 210396 A.

In Vitro Culture and Assay Procedure:

50 µl HMI-9 medium (Hirumi et al., *J. Parasitology*, 75: 985-989 (1989)) supplemented 10% heat inactivated fetal calf serum and 5% heat inactivated human serum was added to each well of a 96-well microtiter plate. Serial drug dilutions of seven 3-fold dilution steps covering a range from 90 to 0.123 µg/ml were prepared. Then $2 \times 10^5$ bloodstream forms of *T. b. gambiense* in 50 µl medium was added to each well and the plate incubated at 37° C. under a 5% $CO_2$ atmosphere for 72 h. 10 µl Alamar Blue (resazurin, 12.5 mg in 100 ml double-distilled water) was then added to each well and incubation continued for a further 2-4 h (Räz et al, *Acta Trop* 68:139-47 (1997)). Then the plates were read with a Spectramax Gemini XS microplate fluorometer (Molecular Devices Cooperation, Sunnyvale, Calif., USA) using an excitation wave length of 536 nm and an emission wave length of 588 nm. Data were analyzed using the microplate reader software Softmax Pro (Molecular Devices Cooperation, Sunnyvale, Calif., USA).

Results from the 108R, 40R, DAL1402, DRANI, and ITMAP strains are provided in FIG. 1.

Example 6

*Trypanosoma brucei rhodesiense* STIB 900 Screening Assay Procedure

The *Trypanosoma brucei rhodesiense* STIB900 strain was isolated in 1982 from a human patient in Tanzania and after several mouse passages cloned and adapted to axenic culture conditions (Baltz, et al., *EMBO Journal* 4:1273-1277 (1985); Thuita, et al., *Acta Tropica* 108:6-10 (2008)). Minimum Essential Medium (50 µl) supplemented with 25 mM HEPES, 1 g/L additional glucose, 1% MEM non-essential amino acids (100×), 0.2 mM 2-mercaptoethanol, 1 mM Na-pyruvate and 15% heat inactivated horse serum was added to each well of a 96-well microtiter plate. Serial drug dilutions of seven 3-fold dilution steps covering a range from 90 to 0.123 µg/ml were prepared. Then $10^4$ bloodstream forms of *T. b. rhodesiense* STIB 900 in 50 µl was added to each well and the plate incubated at 37° C. under a 5% $CO_2$ atmosphere for 72 h. 10 µl Alamar Blue (resazurin, 12.5 mg in 100 ml double-distilled water) was then added to each well and incubation continued for a further 2-4 h (Räz, et al., *Acta Trop* 68:139-47 (1997)). Then the plates were read with a Spectramax Gemini XS microplate fluorometer (Molecular Devices Cooperation, Sunnyvale, Calif., USA) using an excitation wave length of 536 nm and an emission wave length of 588 nm. Data were analyzed using the microplate reader software Softmax Pro (Molecular Devices Cooperation, Sunnyvale, Calif., USA).

Results from this assay are provided in FIG. 1.

Example 7

*Leishmania donovani* Axenic Amastigote Screening Assay Procedure

Amastigotes of *L. donovani* strain MHOM/ET/67/L82 were grown in axenic culture at 37° C. in SM medium (Cunningham, I. *J Protozol.* 24:325-329 (1977)) at pH 5.4 supplemented with 10% heat-inactivated fetal bovine serum under an atmosphere of 5% $CO_2$ in air. One hundred microliters of culture medium with $10^5$ amastigotes from axenic culture with or without a serial drug dilution were seeded in 96-well microtitre plates. Serial drug dilutions of seven 3-fold dilution steps covering a range from 90 to 0.123 µg/ml were prepared. After 72 h of incubation the plates were inspected under an inverted microscope to assure growth of the controls and sterile conditions. 10 µl of Alamar Blue (12.5 mg resazurin dissolved in 100 ml distilled water) (Mikus and Steverdig, *Parasitology International* 48:265-269 (2000)) were then added to each well and the plates incubated for another 2 h. Then the plates were read with a Spectramax Gemini XS microplate fluorometer (Molecular Devices Cooperation, Sunnyvale, Calif., USA) using an excitation wave length of 536 nm and an emission wave length of 588 nm. Data were analyzed using the software Softmax Pro (Molecular Devices Cooperation, Sunnyvale, Calif., USA). Decrease of fluorescence (=inhibition) was expressed as percentage of the fluorescence of control cultures and plotted against the drug concentrations. From the sigmoidal inhibition curves the $IC_{50}$ values were calculated.

Example 8

*Leishmania donovani* Macrophage and *Leishmania infantum* Macrophage Screening Assay Procedure Parasite and cell cultures. Two *Leishmania* species (*L. infantum* MHOM/MA(BE)/67 and *L. donovani* MHOM/ET/67/L82) were used. The strains were maintained in the Golden Hamster (*Mesocricetus auratus*). Amastigotes were collected from the spleen of an infected donor hamster using three centrifugation purification steps (300 rpm, keeping the supernatant, 2200 rpm, keeping the supernatants and 3500 rpm, keeping the pellet) and spleen parasite burdens were assessed using the Stauber technique (Stauber L A., *Exp*

*Parasitol.* 18: 1-11 (1966)). Primary peritoneal mouse macrophages were used as host cell and were collected 2 days after peritoneal stimulation with a 2% potato starch suspension. All cultures and assays were conducted at 37° C. under an atmosphere of 5% $CO_2$.

Compound Solutions/Dilutions.

Compound stock solutions were prepared in 100% DMSO at 20 mM or mg/ml. Concentrations were standard and expressed in molar concentrations, except for natural products, drug mixtures and if the molecular weight was not known. The compounds were serially pre-diluted (2-fold or 4-fold) in DMSO followed by a further (intermediate) dilution in demineralized water to assure a final in-test DMSO concentration of <1%.

Drug Sensitivity Assays.

Assays were performed in 96-well microtiter plates, each well contained 10 μl of the compound dilutions together with 190 μl of macrophage/parasite inoculum ($3\times10^3$ cells+ $4.5\times10^5$ parasites/well). The inoculum was prepared in RPMI-1640 medium, supplemented with 200 mM L-glutamine, 16.5 mM $NaHCO_3$, and 5% heat-inactivated fetal calf serum. Parasite multiplication was compared to untreated-infected controls (100% growth) and uninfected controls (0% growth). After 5 days incubation, parasite burdens (mean number of amastigotes/macrophage) were microscopically assessed after staining the cells with a 10% Giemsa solution. The results were expressed as % reduction in parasite burden compared to untreated control wells and an $IC_{50}$ (50% inhibitory concentration) was calculated.

Primary Screen.

*Leishmania infantum* MHOM/MA(BE)/67 strain was used. The compounds were tested at 5 concentrations (64-16-4-1 and 0.25 μM or μg/ml). Sodium-stibogluconate ($IC_{50}$=8.7+2.1 μM) and miltefosin ($IC_{50}$=4.3+1.1 μM) were included as the reference drugs. A test compound was classified as inactive when the $IC_{50}$ was higher than 30 μM. When the $IC_{50}$ was between 30 and 10 μM, the compound was regarded as moderately active. If the $IC_{50}$ is lower than 10 μM, the compound was classified as highly active on the condition that it also demonstrates selective action (absence of cytotoxicity against primary peritoneal macrophages). A final recommendation for activity was given after confirmatory evaluation in a secondary screening.

Secondary Screen.

*Leishmania infantum* MHOM/MA(BE)/67 and *L. donovani* MHOM/ET/67/L82 strains were used and the $IC_{50}$-values were determined using an extended dose range (2-fold compound dilutions). Pentostam®, miltefosine, fungizone and PX-6518 were included as reference drugs. Advanced selectivity evaluations were performed against a panel of unrelated organisms (bacteria, yeasts, fungi and other protozoan parasites).

Results from this assay are provided in FIG. 1.

Example 9

*Plasmodium falciparum* Screening Assay Procedure

In vitro activity against erythrocytic stages of *P. falciparum* was determined using a $^3$H-hypoxanthine incorporation assay (Desjardins et al., Antimicrobial Agents and Chemotherapy 16:710-718 (1979), Matiel and Pink. *Plasmodium falciparum* malaria parasite cultures and their use in immunology. In I. Lefkovits and B. Pernis (ed.), Immunological Methods. Academic Press, San Diego (1990)), using the chloroquine and pyrimethamine resistant K1 strain that originate from Thailand (Thaitong et al. Transactions of the Royal Society of Tropical Medicine and Hygiene 77:228-231 (1983)) and the standard drug chloroquine (Sigma C6628). Compounds were dissolved in DMSO at 10 mg/ml and added to parasite cultures incubated in RPMI 1640 medium without hypoxanthine, supplemented with HEPES (5.94 g/l), $NaHCO_3$ (2.1 g/l), neomycin (100 U/ml), Albumax$^R$ (5 g/l) and washed human red cells A$^+$ at 2.5% haematocrit (0.3% parasitaemia). Serial drug dilutions of seven 2-fold dilution steps covering a range from 5 to 0.156 μg/ml were prepared. The 96-well plates were incubated in a humidified atmosphere at 37 C; 4% $CO_2$, 3% $O_2$, 93% $N_2$. After 48 h 50 μl of $^3$H-hypoxanthine (=0.5 μCi) was added to each well of the plate. The plates were incubated for a further 24 h under the same conditions. The plates were then harvested with a Betaplate™ cell harvester (Wallac, Zurich, Switzerland), and the red blood cells transferred onto a glass fibre filter then washed with distilled water. The dried filters were inserted into a plastic foil with 10 ml of scintillation fluid, and counted in a Betaplate™ liquid scintillation counter (Wallac, Zurich, Switzerland). $IC_{50}$ values were calculated from sigmoidal inhibition curves using Microsoft Excel.

Results from this assay are provided in FIG. 1.

Example 10

In vitro *Trypanosoma* PDE assays

A solution can be formed including a compound described herein, 40 mM Mops, pH 7.5, 0.8 mM EGTA, 15 mM magnesium acetate, 0.2 mg/ml bovine serum albumin (BSA) and 100000 c.p.m. of [$^3$H]cAMP, in a final volume of 250 μl at 30° C. The assay reaction can be started with the addition of the *trypanosoma* PDE (the amount will be in the linear hydrolysis vs. time zone as determined in a preliminary experiment) to this mixture. If the *trypanosoma* PDE source is a cell lysate or protein homogenate, then an inhibitor of endogenous PDEs, such as, but not limited to, IBMX (3-isobutylmethylxanthine), may be added. The reaction can be terminated by boiling the mixture for 2 minutes and the resulting AMP can be converted to adenosine by the addition of 10 mg/ml snake venom nucleotidase and further incubation at 37° C. for 10 minutes. Unhydrolyzed cAMP can be bound to AG1-X2 resin, and the remaining [$^3$H]Adenosine in the aqueous phase can be quantitated by scintillation counting. Compounds described herein can be tested at concentrations varying from 0.001 to 100 μM for $IC_{50}$ determination. *Trypanosoma brucei* PDEA (TbrPDEA, formerly known as TbPDE1) can be obtained through the methods described in Kunz, et al., Eur. J. Biochem. 271: 637-647 (2004). *Trypanosoma brucei* PDEB1 (TbrPDEB1, formerly known as TbPDE2C) can be obtained through the methods described in Zoraghi, et al., Proc. Natl. Acad. Sci. U.S.A. 99: 4343-4348 (2002). *Trypanosoma brucei* PDEB2 (TbrPDEB2, formerly known as TbPDE2B) can be obtained through the methods described in Rascon, et al., *Proc. Natl. Acad. Sci. U.S.A.* 99: 4714-4719 (2002). *Trypanosoma brucei* PDE2A (TbPDE2A) can be obtained through the methods described in Zoraghi, et al., J. Biol. Chem., 276: 11559-11566 (2001).

Example 11

Acute Murine Model A

Female Swiss Webster mice were inoculated with 250,000 parasites of the LAB 110 EATRO strain of *T. b. brucei*. 24 hrs post-infection, treatment was initiated BID for 4 days with 20 mg/kg/dose (40 mg/kg/day) intraperitoneally (IP) or orally (PO), 5 mg/kg BID or 10 mg/kg BID orally (PO). N=3 mice/group. Mice were monitored for 30 days for survival. Pentamidine at 2 mg/kg IP was used as the positive control. After 10 days, 0% of the untreated mice were parasite free. After 10 days, 100% of mice treated with 20 mg/kg, ip, BID of 6-(4-chlorophenylsulfinyl)benzo[c][1,2]oxaborol-1(3H)-ol were parasite free. After 30 days, 100% of mice treated with 10 mg/kg, ip, BID of N-(1-hydroxy-1,3-dihydrobenzo[c][1,2]oxaborol-6-yl)-2-(trifluoromethyl)benzamide were parasite free. These results indicate that N-(1-hydroxy-1,3-dihydrobenzo[c][1,2]oxaborol-6-yl)-2-(trifluoromethyl)benzamide, 2-Chloro-N-(1-hydroxy-1,3-dihydro-benzo[c][1,2]oxaborol-6-yl)-benzamide, 5-Fluoro-N-(1-hydroxy-1,3-dihydro-benzo[c][1,2]oxaborol-6-yl)-2-trifluoromethyl-benzamide and 4-Fluoro-N-(1-hydroxy-1,3-dihydro-benzo[c][1,2]oxaborol-6-yl)-2-trifluoromethyl-benzamide can prevent the development of diseases associated with *T. b. brucei*. These results indicate that N-(1-hydroxy-1,3-dihydrobenzo[c][1,2]oxaborol-6-yl)-2-(trifluoromethyl)benzamide, 2-Chloro-N-(1-hydroxy-1,3-dihydro-benzo[c][1,2]oxaborol-6-yl)-benzamide, 5-Fluoro-N-(1-hydroxy-1,3-dihydro-benzo[c][1,2]oxaborol-6-yl)-2-trifluoromethyl-benzamide and 4-Fluoro-N-(1-hydroxy-1,3-dihydro-benzo[c][1,2]oxaborol-6-yl)-2-trifluoromethyl-benzamide has potential for development to treat early-stage HAT.

| Compound | Route | *T. brucei* Minimum Effective Dose |
|---|---|---|
| H1 | ip | 10 mg/kg, bid × 4 days |
| H7 | po | 10 mg/kg, bid × 4 days |
| H17 | po | 5 mg/kg, bid × 4 days |
| H19 | po | 5 mg/kg, bid × 4 days |

Acute Murine Model B

Female BALB/C mice were inoculated with 600 parasites of *T. b. brucei* or $10^4$ parasites of *T. b. rhodesiense*. 24 hrs post-infection, treatment with 6-(4-chlorophenylsulfinyl)benzo[c][1,2]oxaborol-1(3H)-ol was initiated BID for 5 days at 50 mg/kg BID intraperitoneally (IP). Mice were monitored for 40-60 days for survival. After 10 days, 20% of the untreated mice were parasite free and at 20 days, 0% of the untreated mice were parasite free. After 55 days, 100% of mice treated with 6-(4-chlorophenylsulfinyl)benzo[c][1,2]oxaborol-1(3H)-ol were parasite free. These results indicate that 6-(4-chlorophenylsulfinyl)benzo[c][1,2]oxaborol-1(3H)-ol can prevent the development of diseases associated with *T. b. brucei* or *T. b. rhodesiense*.

Example 12

Chronic CNS Model

Mice were infected with 10,000 parasites of the TREU 667 strain of *T. b. brucei*. Twenty one days post-infection mice were treated with 50 mg/kg of the compound BID for 7 days intraperitoneally (IP). Positive control mice were treated with Berenil on Day 4 post-infection. Negative control mice were treated with Berenil on Day 21. Since Berenil is not able to penetrate the CNS, mice treated at Day 21 are not able to cure the infection. Starting 1 week after the end of treatment, mice are monitored for parasitemia and sacrificed if parasites are detected in the blood. Mice that survive 6 months are considered "cured."

Treatment with 50 mg/kg of N-(1-hydroxy-1,3-dihydrobenzo[c][1,2]oxaborol-6-yl)-2-(trifluoromethyl)benzamide BID for 7 days, starting at Day 21 post-infection, resulted in absence of blood parasites through Day 91 in 70% of the mice. In contrast, all animals treated on Day 21 with the non-CNS penetrant drug Diminazene relapsed to exhibit blood parasitemia by Day 53. These results indicate that N-(1-hydroxy-1,3-dihydrobenzo[c][1,2]oxaborol-6-yl)-2-(trifluoromethyl)benzamide has potential for development to treat late-stage HAT.

Additional Results: 100% of mice treated with H17 were parasite free for at least 60 days. 100% of mice treated with H7 or H19 were parasite free for at least 100 days.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound, or a salt thereof, having a structure according to the following formula:

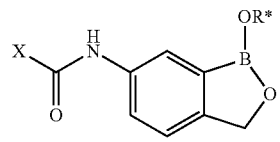

wherein
R* is H or negative charge; and
X is selected from the group consisting of substituted phenyl, unsubstituted heteroaryl, substituted heteroaryl, and unsubstituted cycloalkyl;
wherein said substituted phenyl is phenyl, substituted with at least one member selected from the group consisting of halogen, cyano, nitro, OR, SR, NRR, unsubstituted alkyl, substituted alkyl, unsubstituted heteroalkyl, substituted heteroalkyl, unsubstituted cycloalkyl, substituted cycloalkyl, unsubstituted heterocycloalkyl, substituted heterocycloalkyl, unsubstituted aryl, substituted aryl, unsubstituted heteroaryl, and substituted heteroaryl,
wherein each R is independently selected from the group consisting of unsubstituted alkyl, substituted alkyl, unsubstituted heteroalkyl, substituted heteroalkyl, unsubstituted cycloalkyl, substituted cycloalkyl, unsubstituted heterocycloalkyl, substituted heterocycloalkyl, unsubstituted aryl, substituted aryl, unsubstituted heteroaryl, and substituted heteroaryl.

2. The compound of claim 1, or a salt thereof, wherein X is phenyl, substituted with at least one member selected from the group consisting of: halogen, cyano, nitro, OR, SR, NRR, unsubstituted alkyl, substituted alkyl, unsubstituted heteroalkyl, substituted heteroalkyl, unsubstituted cycloalkyl, substituted cycloalkyl, unsubstituted heterocycloalkyl, substituted heterocycloalkyl, unsubstituted aryl, substituted aryl, unsubstituted heteroaryl, and substituted heteroaryl,
wherein each R is independently selected from the group consisting of unsubstituted alkyl, substituted alkyl, unsubstituted heteroalkyl, substituted heteroalkyl, unsubstituted cycloalkyl, substituted cycloalkyl, unsubstituted heterocycloalkyl, substituted heterocycloalkyl, unsubstituted aryl, substituted aryl, unsubstituted heteroaryl, and substituted heteroaryl.

3. The compound of claim 1, or a salt thereof, having a structure according to the following formula:

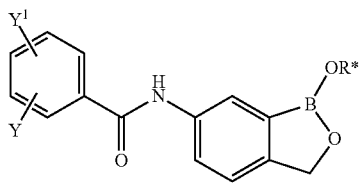

wherein
$Y^1$ is a halogen;
Y is halo-substituted $C_1$-$C_6$ alkyl.

4. The compound of claim 3, or a salt thereof, wherein said $Y^1$ is a halogen, and said halogen is fluoro.

5. The compound of claim 3, or a salt thereof, wherein said Y is halo-substituted $C_1$-$C_6$ alkyl, and said halo-substituted $C_1$-$C_6$ alkyl is trifluoromethyl.

6. The compound of claim 3, or a salt thereof, having a structure according to the following formula:

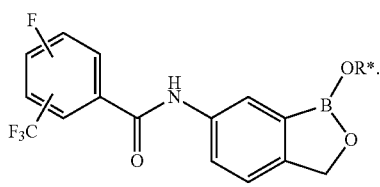

7. The compound of claim 3, or a salt thereof, having a structure according to the following formula:

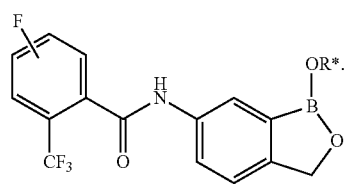

8. The compound of claim 3, or a salt thereof, having a structure according to the following formula:

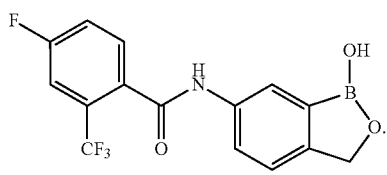 [SMILES: O=C(Nc1ccc2c(c1)B(O)OC2)c1ccc(F)cc1C(F)(F)F]

9. A combination comprising the compound of claim 1, or a salt thereof, together with at least one other therapeutically active agent.

10. A pharmaceutical formulation comprising:
a) the compound of claim 1, or a pharmaceutically acceptable salt thereof; and
b) a pharmaceutically acceptable excipient.

11. The pharmaceutical formulation of claim 10, wherein the pharmaceutical formulation is a unit dosage form.

12. The compound of claim 1, wherein the salt of said compound is a pharmaceutically acceptable salt.

13. A method of killing and/or inhibiting the growth of a protozoa, comprising: contacting the protozoa with an effective amount of the compound of claim 1, or a salt thereof, thereby killing and/or preventing the growth of the protozoa, wherein the protozoa is of a genus selected from the group consisting of *Trypanosoma*, *Leishmania*, and *Plasmodium*.

14. The method of claim 13, wherein the compound is according to claim 1, or a salt thereof.

15. The method of claim 13, wherein the protozoa is of the genus *Trypanosoma*.

16. The method of claim 13, wherein the protozoa is *Trypanosoma brucei*.

17. The method of claim 16, wherein the *Trypanosoma brucei* is selected from the group consisting of *Trypanosoma brucei brucei*, *Trypanosoma brucei gambiense* and *Trypanosoma brucei rhodesiense*.

18. A method of treating a disease in an animal, comprising: administering to the animal a therapeutically effective amount of the compound of claim 1, or a salt thereof, thereby treating the disease, wherein the disease is associated with a protozoa of a genus selected from the group consisting of *Trypanosoma*, *Leishmania*, and *Plasmodium*.

19. The method of claim 18, wherein the compound is according to claim 1.

20. The method of claim 18, wherein the disease is sleeping sickness.

21. The method of claim 18, wherein the animal is a human.

22. The compound of claim 2, or a salt thereof, wherein X is phenyl, substituted with at least one member which is halosubstituted alkyl.

23. The compound of claim 2, or a salt thereof, wherein X is phenyl, substituted with at least one member which is trifluoromethyl.

24. The compound of claim 1, or a salt thereof, having a structure according to the following formula:

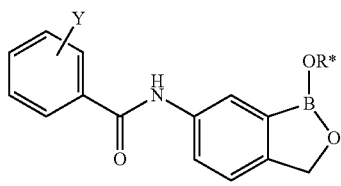

wherein Y is halo-substituted $C_1$-$C_6$ alkyl.

25. The compound of claim 24, or a salt thereof, wherein Y is $C_1$-$C_6$ alkyl, substituted with one, two, three, or four halogens.

26. The compound of claim 24, or a salt thereof, wherein Y is $C_1$-$C_6$ alkyl, substituted with one, two, three, or four fluorines.

27. The compound of claim 24, or a salt thereof, wherein Y is $C_1$-$C_6$ alkyl, substituted with one, two, three, or four chlorines.

28. The compound of claim 24, or a salt thereof, wherein Y is trifluoromethyl.

29. The compound of claim 24, or a salt thereof, which is N-(1-hydroxy-1,3-dihydrobenzo[c][1,2]oxaborol-6-yl)-2-(trifluoromethyl)benzamide.

30. The compound of claim 24, or a salt thereof, which is N-(1-hydroxy-1,3-dihydrobenzo[c][1,2]oxaborol-6-yl)-3-(trifluoromethyl)benzamide.

31. The compound of claim 24, or a salt thereof, which is N-(1-hydroxy-1,3-dihydrobenzo[c][1,2]oxaborol-6-yl)-4-(trifluoromethyl)benzamide.

32. The compound of claim 1, or a salt thereof, having a structure according to the following formula:

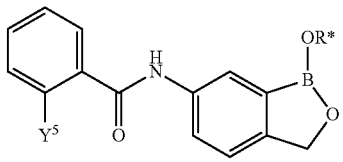

wherein $Y^5$ is halosubstituted $C_1$-$C_6$ alkoxy.

33. The compound of claim 32, or a salt thereof, wherein $Y^5$ is substituted with one or two or three halogens.

34. The compound of claim 32, or a salt thereof, wherein said $Y^5$ is halosubstituted $C_1$-$C_6$ alkoxy, and said halosubstituted $C_1$-$C_6$ alkoxy is fluoro-substituted $C_1$-$C_6$ alkoxy.

35. The compound of claim 32, or a salt thereof, wherein said $Y^5$ is halosubstituted $C_1$-$C_6$ alkoxy, and said halosubstituted $C_1$-$C_6$ alkoxy is trifluoro-substituted $C_1$-$C_6$ alkoxy.

36. The compound of claim 1, or a salt thereof, which is N-(1-hydroxy-1,3-dihydrobenzo[c][1,2]oxaborol-6-yl)-2-(trifluoromethoxy)benzamide.

37. The compound of claim 1, or a salt thereof, having a structure according to the following formula:

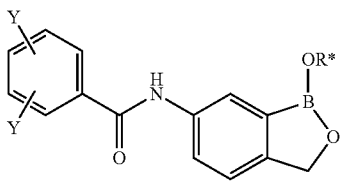

wherein each Y is an independently selected halo-substituted $C_1$-$C_6$ alkyl.

38. The compound of claim 37, or a salt thereof, wherein one Y is fluoro-substituted $C_1$-$C_6$ alkyl.

39. The compound of claim 37, or a salt thereof, wherein one Y is trifluoro-substituted $C_1$-$C_6$ alkyl.

40. The compound of claim 37, or a salt thereof, wherein each Y is fluoro-substituted $C_1$-$C_6$ alkyl.

41. The compound of claim 37, or a salt thereof, wherein each Y is trifluoro-substituted $C_1$-$C_6$ alkyl.

42. The compound of claim 1, or a salt thereof, which is N-(1-Hydroxy-1,3-dihydro-benzo[c][1,2]oxaborol-6-yl)-2,4-bis-trifluoromethyl-benzamide.

43. The compound of claim 1, or a salt thereof, which is N-(1-Hydroxy-1,3-dihydro-benzo[c][1,2]oxaborol-6-yl)-2,5-bis-trifluoromethyl-benzamide.

44. The compound of claim 1, or a salt thereof, which is N-(1-Hydroxy-1,3-dihydro-benzo[c][1,2]oxaborol-6-yl)-3,5-bis-trifluoromethyl-benzamide.

45. The compound of claim 1, or a salt thereof, having a structure according to the following formula:

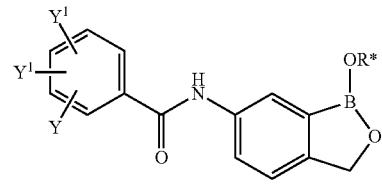

wherein each $Y^1$ is independently selected halogen, Y is halo-substituted $C_1$-$C_6$ alkyl, R* is H or a negative charge.

46. The compound of claim 5, or a salt thereof, wherein Y is fluoro-substituted $C_1$-$C_6$ alkyl.

47. The compound of claim 45, or a salt thereof, wherein Y is trifluoro-substituted $C_1$-$C_6$ alkyl.

48. The compound of claim 45, or a salt thereof, wherein Y is fluoro-substituted $C_1$-$C_6$ alkyl, and each $Y^1$ is chloro.

49. The compound of claim 45, or a salt thereof, wherein Y is fluoro-substituted $C_1$-$C_6$ alkyl, and each $Y^1$ is fluoro.

50. The compound of claim 45, or a salt thereof, wherein Y is fluoro-substituted $C_1$-$C_6$ alkyl, a $Y^1$ is fluoro, and another $Y^1$ is chloro.

51. The compound of claim 45, or a salt thereof, wherein Y is trifluoro-substituted $C_1$-$C_6$ alkyl, and each $Y^1$ is chloro.

52. The compound of claim 45, or a salt thereof, wherein Y is trifluoro-substituted $C_1$-$C_6$ alkyl, and each $Y^1$ is fluoro.

53. The compound of claim 45, or a salt thereof, wherein Y is trifluoro-substituted $C_1$-$C_6$ alkyl, a $Y^1$ is fluoro, and another $Y^1$ is chloro.

54. The compound of claim 45, or a salt thereof, having a structure which is

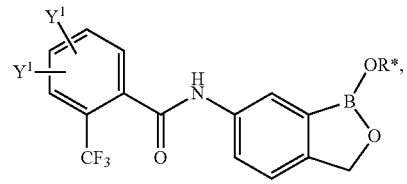

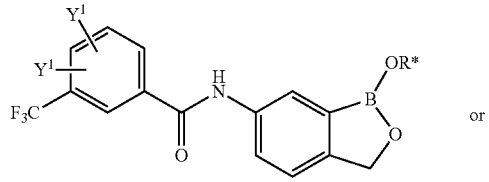

or

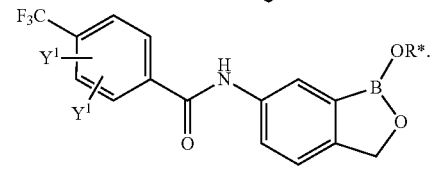

55. The compound of claim 45, or a salt thereof, having a structure which is

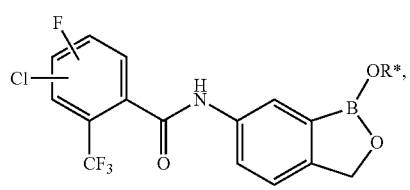

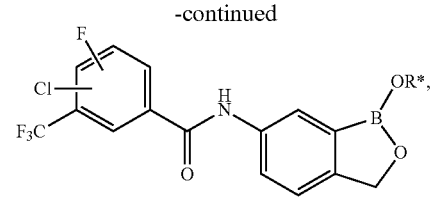
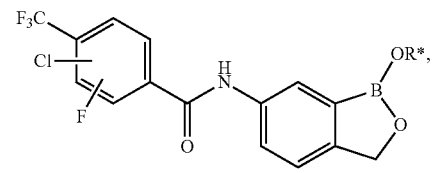
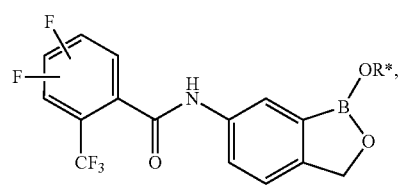
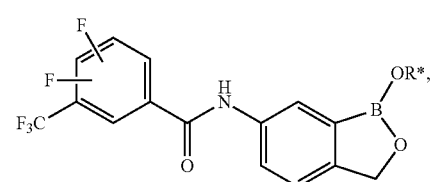
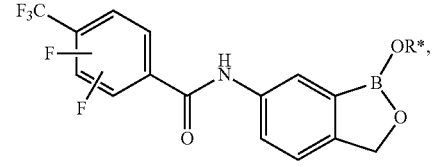
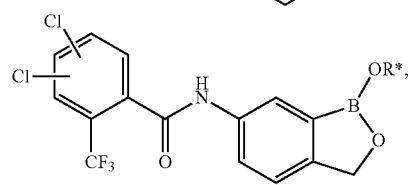
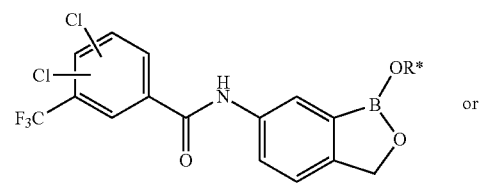
or
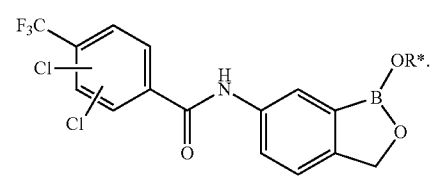
56. The compound of claim 45, or a salt thereof, having a structure which is
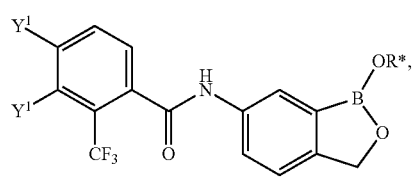
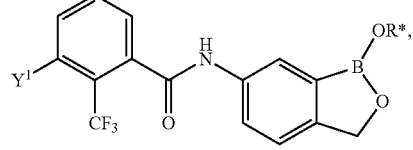
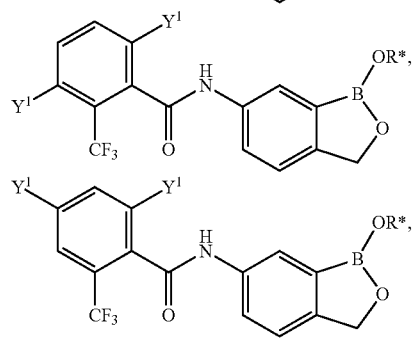
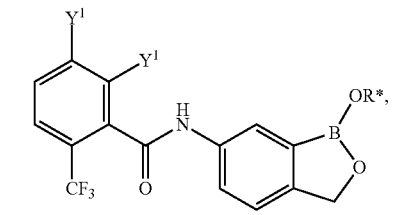
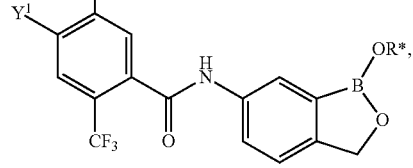
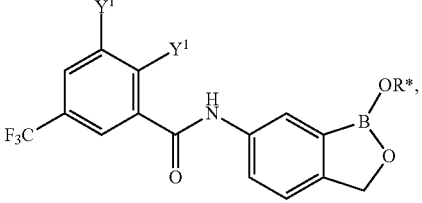
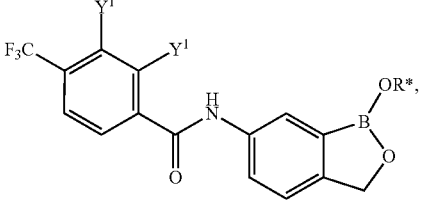
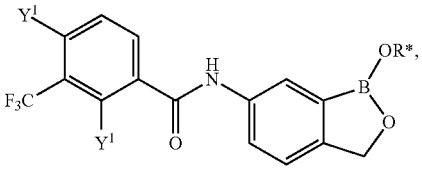

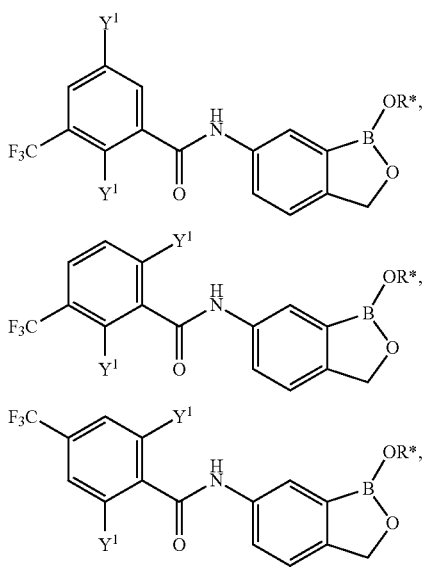
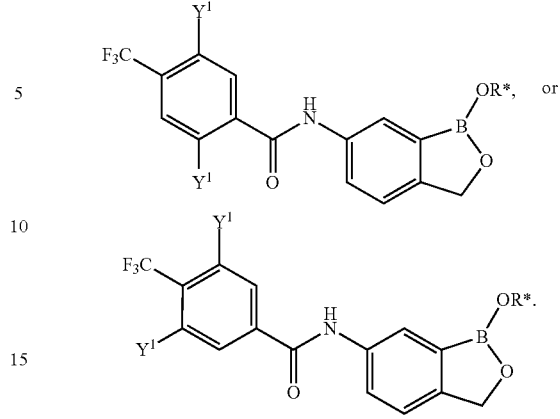
57. The compound of claim 1, or a salt thereof, wherein said compound is 3-chloro-2-fluoro-N-(1-hydroxy-1,3-dihydro-benzo[c][1,2]oxaborol-6-yl)-6-trifluoromethyl-benzamide.
* * * * *